(12) United States Patent
Poltorak

(10) Patent No.: US 12,251,201 B2
(45) Date of Patent: Mar. 18, 2025

(54) DEVICE AND METHOD FOR MEDICAL DIAGNOSTICS

(71) Applicant: Poltorak Technologies, LLC, Suffern, NY (US)

(72) Inventor: Alexander Poltorak, Monsey, NY (US)

(73) Assignee: Poltorak Technologies LLC, Pomona, NY (US)

( * ) Notice: Subject to any disclaimer, the term of this patent is extended or adjusted under 35 U.S.C. 154(b) by 475 days.

(21) Appl. No.: 16/995,749

(22) Filed: Aug. 17, 2020

(65) Prior Publication Data

US 2021/0045640 A1   Feb. 18, 2021

Related U.S. Application Data

(60) Provisional application No. 62/888,213, filed on Aug. 16, 2019.

(51) Int. Cl.
*G16H 50/30* (2018.01)
*A61B 5/00* (2006.01)
(Continued)

(52) U.S. Cl.
CPC ........ *A61B 5/02055* (2013.01); *A61B 5/0022* (2013.01); *A61B 5/029* (2013.01); *A61B 5/0533* (2013.01); *A61B 5/369* (2021.01); *A61B 5/389* (2021.01); *A61B 5/6802* (2013.01); *A61B 5/6847* (2013.01); *A61B 5/7264* (2013.01); *A61B 5/7275* (2013.01); *A61B 5/746* (2013.01); *G16H 50/30* (2018.01); *A61B 5/021* (2013.01); *A61B 5/024* (2013.01); *A61B 5/02416* (2013.01); *A61B 5/0816* (2013.01); *A61B 5/091* (2013.01); *A61B 5/7239* (2013.01); *A61B 2503/40* (2013.01); *A61B 2560/0257* (2013.01); *A61B 2562/0247* (2013.01); *A61B 2562/0257* (2013.01); *A61B 2562/0271* (2013.01); *G16H 50/50* (2018.01); *G16H 50/70* (2018.01)

(58) Field of Classification Search
CPC ........ G16H 50/30; G16H 50/50; G16H 50/70; A61B 5/7275; A61B 5/7239; A61B 2503/40
USPC ............................................................ 705/2
See application file for complete search history.

(56) References Cited

U.S. PATENT DOCUMENTS

| 2,269,385 A | 1/1942 | Lee |
| 2,342,944 A | 2/1944 | Kretske |

(Continued)

OTHER PUBLICATIONS

US 7,233,149, 12/1901, Edwards (withdrawn).

(Continued)

*Primary Examiner* — Jay M. Patel
(74) *Attorney, Agent, or Firm* — Hoffberg & Associates; Steven M Hoffberg

(57) ABSTRACT

A method and device for analysis of sampled physiological parameters according to at least a second-order process over time, e.g., second-order differential equation or model, for use in therapeutic, diagnostic, or predictive health applications. The system may generate an alert regarding a present or predicted health abnormality. The biometric device may be implantable, wearable, contact or non-contact, and may communicate through a network, to send an alert. The system may further comprise an actuator or therapeutic device to perform an action based on the at least second-order process.

17 Claims, 9 Drawing Sheets

(51) Int. Cl.
*A61B 5/0205* (2006.01)
*A61B 5/029* (2006.01)
*A61B 5/0533* (2021.01)
*A61B 5/369* (2021.01)
*A61B 5/389* (2021.01)
*G16H 50/50* (2018.01)
*G16H 50/70* (2018.01)
*A61B 5/021* (2006.01)
*A61B 5/024* (2006.01)
*A61B 5/08* (2006.01)
*A61B 5/091* (2006.01)

(56) References Cited

U.S. PATENT DOCUMENTS

| | | |
|---|---|---|
| 2,865,116 A | 12/1958 | Messer |
| 3,966,877 A | 6/1976 | Kalach et al. |
| 4,209,871 A | 7/1980 | Ernest et al. |
| 4,589,078 A | 5/1986 | Rosenberg |
| 4,660,242 A | 4/1987 | Vornberger et al. |
| 4,679,269 A | 7/1987 | Becka et al. |
| 4,763,282 A | 8/1988 | Rosenberg |
| 4,829,932 A | 5/1989 | Bennett |
| 4,866,802 A | 9/1989 | Stein et al. |
| 5,216,594 A | 6/1993 | White et al. |
| 5,341,229 A | 8/1994 | Rowan |
| 5,373,651 A | 12/1994 | Wood |
| 5,615,111 A | 3/1997 | Raskas et al. |
| 5,626,140 A | 5/1997 | Feldman et al. |
| 5,629,848 A | 5/1997 | Repperger et al. |
| 5,642,096 A | 6/1997 | Leyerer et al. |
| 5,694,142 A | 12/1997 | Dumoulin et al. |
| 5,720,200 A | 2/1998 | Anderson et al. |
| 5,764,518 A | 6/1998 | Collins |
| 5,794,361 A | 8/1998 | Sadler |
| 5,850,352 A | 12/1998 | Moezzi et al. |
| 6,001,067 A | 12/1999 | Shults et al. |
| 6,157,850 A | 12/2000 | Diab et al. |
| 6,230,501 B1 | 5/2001 | Bailey, Sr. et al. |
| 6,236,872 B1 | 5/2001 | Diab et al. |
| 6,379,669 B1 | 4/2002 | Sinha |
| 6,424,847 B1 | 7/2002 | Mastrototaro et al. |
| 6,453,195 B1 | 9/2002 | Thompson |
| 6,477,395 B2 | 11/2002 | Schulman et al. |
| 6,484,046 B1 | 11/2002 | Say et al. |
| 6,512,939 B1 | 1/2003 | Colvin et al. |
| 6,558,351 B1 | 5/2003 | Steil et al. |
| 6,563,423 B2 | 5/2003 | Smith |
| 6,565,509 B1 | 5/2003 | Say et al. |
| 6,567,259 B2 | 5/2003 | Stevenson et al. |
| 6,572,545 B2 | 6/2003 | Knobbe et al. |
| 6,575,905 B2 | 6/2003 | Knobbe et al. |
| 6,579,690 B1 | 6/2003 | Bonnecaze et al. |
| 6,595,929 B2 | 7/2003 | Stivoric et al. |
| 6,675,049 B2 | 1/2004 | Thompson et al. |
| 6,768,246 B2 | 7/2004 | Pelrine et al. |
| 6,788,200 B1 | 9/2004 | Jamel et al. |
| 6,817,979 B2 | 11/2004 | Nihtila |
| 6,833,039 B2 | 12/2004 | Andersen et al. |
| 6,843,578 B1 | 1/2005 | Cheung |
| 6,865,825 B2 | 3/2005 | Bailey, Sr. et al. |
| 6,931,327 B2 | 8/2005 | Goode, Jr. et al. |
| 6,949,066 B2 | 9/2005 | Bearnson et al. |
| 7,010,869 B1 | 3/2006 | Ellis, III |
| 7,020,508 B2 | 3/2006 | Stivoric et al. |
| 7,044,911 B2 | 5/2006 | Drinan et al. |
| 7,059,070 B2 | 6/2006 | Omstead et al. |
| 7,070,398 B2 | 7/2006 | Olsen et al. |
| 7,097,662 B2 | 8/2006 | Evans, III et al. |
| 7,107,706 B1 | 9/2006 | Bailey, Sr. et al. |
| 7,108,659 B2 | 9/2006 | Ross et al. |
| 7,149,320 B2 | 12/2006 | Haykin et al. |
| 7,167,743 B2 | 1/2007 | Heruth et al. |
| 7,172,897 B2 | 2/2007 | Blackburn et al. |
| 7,188,439 B2 | 3/2007 | DiBenedetto et al. |
| 7,204,041 B1 | 4/2007 | Bailey, Sr. et al. |
| 7,215,986 B2 | 5/2007 | Diab et al. |
| 7,219,449 B1 | 5/2007 | Hoffberg et al. |
| 7,225,565 B2 | 6/2007 | DiBenedetto et al. |
| 7,231,254 B2 | 6/2007 | DiLorenzo |
| 7,261,690 B2 | 8/2007 | Teller et al. |
| 7,265,666 B2 | 9/2007 | Daniel |
| 7,267,665 B2 | 9/2007 | Steil et al. |
| 7,273,457 B2 | 9/2007 | Penner |
| 7,280,870 B2 | 10/2007 | Nurmikko et al. |
| 7,285,090 B2 | 10/2007 | Stivoric et al. |
| 7,291,114 B2 | 11/2007 | Mault |
| 7,310,544 B2 | 12/2007 | Brister et al. |
| 7,312,087 B2 | 12/2007 | Duong et al. |
| 7,313,440 B2 | 12/2007 | Miesel |
| 7,330,760 B2 | 2/2008 | Heruth et al. |
| 7,333,013 B2 | 2/2008 | Berger |
| 7,334,350 B2 | 2/2008 | Ellis, III |
| 7,354,420 B2 | 4/2008 | Steil et al. |
| 7,366,572 B2 | 4/2008 | Heruth et al. |
| 7,371,825 B2 | 5/2008 | Das et al. |
| 7,392,079 B2 | 6/2008 | Donoghue et al. |
| 7,395,113 B2 | 7/2008 | Heruth et al. |
| 7,395,614 B1 | 7/2008 | Bailey, Sr. et al. |
| 7,402,153 B2 | 7/2008 | Steil et al. |
| 7,404,263 B2 | 7/2008 | Guzman |
| 7,407,484 B2 | 8/2008 | Korman |
| 7,409,256 B2 | 8/2008 | Lin et al. |
| 7,414,534 B1 | 8/2008 | Kroll et al. |
| 7,414,611 B2 | 8/2008 | Liberty |
| 7,426,873 B1 | 9/2008 | Kholwadwala et al. |
| 7,447,545 B2 | 11/2008 | Heruth et al. |
| 7,463,142 B2 | 12/2008 | Lindsay |
| 7,489,298 B2 | 2/2009 | Liberty et al. |
| 7,489,299 B2 | 2/2009 | Liberty et al. |
| 7,491,181 B2 | 2/2009 | Heruth et al. |
| 7,493,230 B2 | 2/2009 | Schwartz et al. |
| 7,497,037 B2 | 3/2009 | Vick et al. |
| 7,506,460 B2 | 3/2009 | DiBenedetto et al. |
| 7,519,406 B2 | 4/2009 | Blank et al. |
| 7,519,512 B2 | 4/2009 | Spence et al. |
| 7,535,456 B2 | 5/2009 | Liberty et al. |
| 7,542,803 B2 | 6/2009 | Heruth et al. |
| 7,561,919 B2 | 7/2009 | Shalev et al. |
| 7,562,468 B2 | 7/2009 | Ellis, III |
| RE40,879 E | 8/2009 | Jamel et al. |
| 7,577,475 B2 | 8/2009 | Cosentino et al. |
| 7,579,946 B2 | 8/2009 | Case, Jr. |
| 7,590,453 B2 | 9/2009 | Heruth et al. |
| 7,590,455 B2 | 9/2009 | Heruth et al. |
| 7,598,878 B2 | 10/2009 | Goldreich |
| 7,607,243 B2 | 10/2009 | Berner, Jr. et al. |
| 7,610,094 B2 | 10/2009 | Stahmann et al. |
| 7,614,166 B2 | 11/2009 | Vick et al. |
| 7,616,991 B2 | 11/2009 | Mann et al. |
| 7,621,876 B2 | 11/2009 | Hoctor et al. |
| 7,623,919 B2 | 11/2009 | Goetz et al. |
| 7,623,928 B2 | 11/2009 | DiLorenzo |
| 7,630,755 B2 | 12/2009 | Stahmann et al. |
| 7,631,382 B2 | 12/2009 | DiBenedetto et al. |
| RE41,087 E | 1/2010 | Jamel et al. |
| 7,641,619 B2 | 1/2010 | Penner |
| RE41,102 E | 2/2010 | Jamel et al. |
| RE41,122 E | 2/2010 | Jamel et al. |
| 7,671,599 B1 | 3/2010 | Tan et al. |
| 7,676,960 B2 | 3/2010 | DiBenedetto et al. |
| 7,676,961 B2 | 3/2010 | DiBenedetto et al. |
| 7,695,512 B2 | 4/2010 | Lashinski et al. |
| 7,697,994 B2 | 4/2010 | VanDanacker |
| 7,707,742 B2 | 5/2010 | Ellis, III |
| 7,713,923 B2 | 5/2010 | Genove et al. |
| 7,716,008 B2 | 5/2010 | Ohta |
| 7,717,848 B2 | 5/2010 | Heruth et al. |
| 7,727,143 B2 | 6/2010 | Birk et al. |
| 7,735,351 B2 | 6/2010 | Profit et al. |
| 7,758,523 B2 | 7/2010 | Collings et al. |
| 7,761,261 B2 | 7/2010 | Shmueli et al. |
| 7,765,005 B2 | 7/2010 | Stevenson |

(56) References Cited

U.S. PATENT DOCUMENTS

| | | |
|---|---|---|
| 7,765,012 B2 | 7/2010 | Gerber |
| 7,774,155 B2 | 8/2010 | Sato et al. |
| 7,775,993 B2 | 8/2010 | Heruth et al. |
| 7,780,590 B2 | 8/2010 | Birk et al. |
| 7,782,192 B2 | 8/2010 | Jeckelmann et al. |
| 7,783,442 B2 | 8/2010 | Mueller, Jr. et al. |
| 7,787,946 B2 | 8/2010 | Stahmann et al. |
| 7,787,958 B2 | 8/2010 | Stevenson |
| 7,792,583 B2 | 9/2010 | Miesel et al. |
| 7,793,430 B2 | 9/2010 | Ellis |
| 7,794,101 B2 | 9/2010 | Galica et al. |
| 7,801,591 B1 | 9/2010 | Shusterman |
| 7,805,196 B2 | 9/2010 | Miesel et al. |
| 7,806,886 B2 | 10/2010 | Kanderian, Jr. et al. |
| 7,813,778 B2 | 10/2010 | Benaron et al. |
| 7,816,632 B2 | 10/2010 | Bourke, III et al. |
| 7,819,909 B2 | 10/2010 | Goetz et al. |
| 7,825,794 B2 | 11/2010 | Janetis et al. |
| 7,842,092 B2 | 11/2010 | Otto et al. |
| 7,848,819 B2 | 12/2010 | Goetz et al. |
| 7,853,329 B2 | 12/2010 | DiLorenzo |
| 7,859,540 B2 | 12/2010 | Dariush |
| 7,860,676 B2 | 12/2010 | Sheng et al. |
| 7,876,228 B2 | 1/2011 | Kroll et al. |
| 7,877,224 B2 | 1/2011 | Ohta |
| 7,881,798 B2 | 2/2011 | Miesel et al. |
| 7,885,712 B2 | 2/2011 | Goetz et al. |
| 7,890,055 B1 | 2/2011 | Stein |
| 7,904,149 B2 | 3/2011 | Gerber |
| 7,908,000 B2 | 3/2011 | Shalev |
| 7,908,013 B2 | 3/2011 | Miesel et al. |
| 7,916,013 B2 | 3/2011 | Stevenson |
| 7,927,216 B2 | 4/2011 | Ikeda et al. |
| 7,930,035 B2 | 4/2011 | DiLorenzo |
| 7,930,131 B2 | 4/2011 | Ridenour et al. |
| 7,931,535 B2 | 4/2011 | Ikeda et al. |
| 7,932,825 B2 | 4/2011 | Berger |
| 7,942,745 B2 | 5/2011 | Ikeda et al. |
| 7,953,488 B2 | 5/2011 | Casavant et al. |
| 7,956,162 B2 | 6/2011 | Chahal et al. |
| 7,959,567 B2 | 6/2011 | Stivoric et al. |
| 7,966,075 B2 | 6/2011 | Johnson et al. |
| 7,970,470 B2 | 6/2011 | Hartley et al. |
| 7,974,696 B1 | 7/2011 | DiLorenzo |
| 7,978,062 B2 | 7/2011 | LaLonde et al. |
| 7,981,025 B2 | 7/2011 | Pool et al. |
| 7,983,435 B2 | 7/2011 | Moses |
| 7,983,763 B2 | 7/2011 | Stevenson et al. |
| 7,996,158 B2 | 8/2011 | Hayter et al. |
| 8,000,801 B2 | 8/2011 | Stevenson et al. |
| 8,005,539 B2 | 8/2011 | Burnes et al. |
| 8,010,189 B2 | 8/2011 | Shalev |
| 8,015,732 B2 | 9/2011 | Berner, Jr. et al. |
| 8,021,299 B2 | 9/2011 | Miesel et al. |
| 8,028,443 B2 | 10/2011 | Case, Jr. |
| 8,032,224 B2 | 10/2011 | Miesel et al. |
| 8,033,999 B2 | 10/2011 | Xi |
| 8,036,736 B2 | 10/2011 | Snyder et al. |
| 8,038,613 B2 | 10/2011 | Stupp et al. |
| 8,041,536 B2 | 10/2011 | Ohta |
| 8,055,330 B2 | 11/2011 | Egozi |
| 8,055,334 B2 | 11/2011 | Savage et al. |
| 8,055,348 B2 | 11/2011 | Heruth et al. |
| 8,056,268 B2 | 11/2011 | DiBenedetto et al. |
| 8,072,424 B2 | 12/2011 | Liberty |
| 8,078,278 B2 | 12/2011 | Penner |
| 8,078,282 B2 | 12/2011 | Nycz |
| 8,079,518 B2 | 12/2011 | Turner et al. |
| 8,081,925 B2 | 12/2011 | Parramon et al. |
| 8,086,250 B2 | 12/2011 | Janetis et al. |
| 8,086,302 B2 | 12/2011 | Kracker |
| 8,089,458 B2 | 1/2012 | Barney et al. |
| 8,093,991 B2 | 1/2012 | Stevenson et al. |
| 8,103,471 B2 | 1/2012 | Hayter |
| 8,103,802 B2 | 1/2012 | Lay et al. |
| 8,114,021 B2 | 2/2012 | Robertson et al. |
| 8,114,345 B2 | 2/2012 | Dlugos, Jr. et al. |
| 8,114,964 B2 | 2/2012 | Das et al. |
| 8,115,618 B2 | 2/2012 | Robertson et al. |
| 8,121,691 B2 | 2/2012 | Gerber et al. |
| 8,121,694 B2 | 2/2012 | Molnar et al. |
| 8,123,696 B2 | 2/2012 | Childre et al. |
| 8,127,470 B2 | 3/2012 | Connor |
| 8,135,473 B2 | 3/2012 | Miesel et al. |
| 8,137,195 B2 | 3/2012 | Penzias |
| 8,137,269 B2 | 3/2012 | Sheikhzadeh-Nadjar et al. |
| 8,140,161 B2 | 3/2012 | Willerton et al. |
| 8,141,276 B2 | 3/2012 | Ellis |
| 8,152,710 B2 | 4/2012 | Dlugos, Jr. et al. |
| 8,157,651 B2 | 4/2012 | Ohta et al. |
| 8,157,731 B2 | 4/2012 | Teller et al. |
| 8,160,273 B2 | 4/2012 | Visser et al. |
| 8,160,669 B2 | 4/2012 | Brauker et al. |
| 8,160,695 B2 | 4/2012 | Dacey, Jr. et al. |
| 8,160,702 B2 | 4/2012 | Mann et al. |
| 8,164,567 B1 | 4/2012 | Barney et al. |
| 8,165,691 B2 | 4/2012 | Ellingson et al. |
| 8,165,893 B1 | 4/2012 | Goldberg et al. |
| 8,169,406 B2 | 5/2012 | Barney et al. |
| 8,172,459 B2 | 5/2012 | Abreu |
| 8,174,378 B2 | 5/2012 | Richman et al. |
| 8,174,395 B2 | 5/2012 | Samuelsson et al. |
| 8,180,446 B2 | 5/2012 | Dacey, Jr. et al. |
| 8,180,447 B2 | 5/2012 | Dacey, Jr. et al. |
| 8,180,591 B2 | 5/2012 | Yuen et al. |
| 8,180,592 B2 | 5/2012 | Yuen et al. |
| 8,184,097 B1 | 5/2012 | Barney et al. |
| 8,185,181 B2 | 5/2012 | Feldman et al. |
| 8,186,081 B2 | 5/2012 | Wilson, III et al. |
| 8,190,253 B2 | 5/2012 | Heruth et al. |
| 8,192,406 B2 | 6/2012 | Wells et al. |
| 8,197,454 B2 | 6/2012 | Mann et al. |
| 8,200,342 B2 | 6/2012 | Stevenson et al. |
| 8,202,260 B2 | 6/2012 | Mann et al. |
| 8,204,590 B2 | 6/2012 | Sambelashvili et al. |
| 8,204,597 B2 | 6/2012 | Gerber et al. |
| 8,205,356 B2 | 6/2012 | Ellis |
| 8,207,316 B1 | 6/2012 | Bentwich |
| 8,214,045 B2 | 7/2012 | Kronich et al. |
| 8,216,139 B2 | 7/2012 | Brauker et al. |
| 8,217,946 B2 | 7/2012 | Halpern et al. |
| 8,226,493 B2 | 7/2012 | Briggs et al. |
| 8,233,958 B2 | 7/2012 | Brauker et al. |
| 8,233,959 B2 | 7/2012 | Kamath et al. |
| 8,233,976 B2 | 7/2012 | Dacey, Jr. et al. |
| 8,234,798 B2 | 8/2012 | DiBenedetto et al. |
| 8,237,657 B2 | 8/2012 | Liberty et al. |
| 8,239,166 B2 | 8/2012 | Hayter et al. |
| 8,246,533 B2 | 8/2012 | Chang et al. |
| 8,246,563 B2 | 8/2012 | Wariar |
| 8,248,367 B1 | 8/2012 | Barney et al. |
| 8,249,708 B2 | 8/2012 | Krause et al. |
| 8,250,782 B2 | 8/2012 | Callahan et al. |
| 8,251,061 B2 | 8/2012 | Lee et al. |
| 8,251,903 B2 | 8/2012 | LeBoeuf et al. |
| 8,251,906 B2 | 8/2012 | Brauker et al. |
| 8,251,946 B2 | 8/2012 | Bardy |
| 8,257,259 B2 | 9/2012 | Brauker et al. |
| 8,257,729 B2 | 9/2012 | Schmitz et al. |
| 8,258,941 B2 | 9/2012 | Case, Jr. |
| 8,260,393 B2 | 9/2012 | Kamath et al. |
| 8,260,412 B2 | 9/2012 | Krause et al. |
| 8,260,422 B2 | 9/2012 | Ellingson et al. |
| 8,260,558 B2 | 9/2012 | Hayter et al. |
| 8,261,468 B2 | 9/2012 | Ellis, III |
| 8,265,723 B1 | 9/2012 | McHale et al. |
| 8,265,725 B2 | 9/2012 | Brauker et al. |
| 8,265,771 B2 | 9/2012 | Donofrio et al. |
| 8,267,786 B2 | 9/2012 | Ikeda |
| 8,269,635 B2 | 9/2012 | Kroll et al. |
| 8,269,636 B2 | 9/2012 | Kroll et al. |
| 8,270,938 B2 | 9/2012 | Flippo et al. |
| 8,271,072 B2 | 9/2012 | Houben et al. |
| 8,273,032 B2 | 9/2012 | Carney et al. |

(56) References Cited

U.S. PATENT DOCUMENTS

| | | |
|---|---|---|
| 8,275,437 B2 | 9/2012 | Brauker et al. |
| 8,277,741 B2 | 10/2012 | McCabe |
| 8,280,475 B2 | 10/2012 | Brister et al. |
| 8,282,549 B2 | 10/2012 | Brauker et al. |
| 8,287,520 B2 | 10/2012 | Drew et al. |
| 8,290,561 B2 | 10/2012 | Brauker et al. |
| 8,290,596 B2 | 10/2012 | Wei et al. |
| 8,291,614 B2 | 10/2012 | Ellis |
| 8,295,933 B2 | 10/2012 | Gerber et al. |
| 8,301,219 B2 | 10/2012 | Chen et al. |
| 8,301,243 B2 | 10/2012 | Stevenson et al. |
| 8,306,610 B2 | 11/2012 | Mirow |
| 8,306,766 B2 | 11/2012 | Mueller, Jr. et al. |
| 8,308,563 B2 | 11/2012 | Ikeda et al. |
| 8,308,661 B2 | 11/2012 | Miesel et al. |
| 8,310,336 B2 | 11/2012 | Muhsin et al. |
| 8,311,749 B2 | 11/2012 | Brauker et al. |
| 8,311,769 B2 | 11/2012 | Yuen et al. |
| 8,311,770 B2 | 11/2012 | Yuen et al. |
| 8,313,379 B2 | 11/2012 | Ikeda et al. |
| 8,321,003 B2 | 11/2012 | Zhang et al. |
| 8,321,032 B2 | 11/2012 | Frysz et al. |
| 8,321,149 B2 | 11/2012 | Brauker et al. |
| 8,323,232 B2 | 12/2012 | Bardy |
| 8,326,435 B2 | 12/2012 | Stevenson |
| 8,328,420 B2 | 12/2012 | Abreu |
| 8,332,038 B2 | 12/2012 | Heruth et al. |
| 8,335,568 B2 | 12/2012 | Heruth et al. |
| 8,337,431 B2 | 12/2012 | Heruth et al. |
| 8,348,882 B2 | 1/2013 | Bardy |
| 8,348,886 B2 | 1/2013 | Kanderian, Jr. et al. |
| 8,348,923 B2 | 1/2013 | Kanderian, Jr. et al. |
| 8,355,783 B2 | 1/2013 | Goetz et al. |
| 8,359,095 B2 | 1/2013 | Hedberg et al. |
| 8,359,545 B2 | 1/2013 | Pixley et al. |
| 8,368,648 B2 | 2/2013 | Barney et al. |
| 8,373,556 B2 | 2/2013 | LaLonde et al. |
| 8,373,659 B2 | 2/2013 | Barney et al. |
| 8,374,667 B2 | 2/2013 | Brauker et al. |
| 8,374,697 B2 | 2/2013 | Berger |
| 8,376,943 B2 | 2/2013 | Kovach et al. |
| 8,384,668 B2 | 2/2013 | Barney et al. |
| 8,385,971 B2 | 2/2013 | Rhoads et al. |
| 8,386,004 B2 | 2/2013 | Kamath et al. |
| 8,386,008 B2 | 2/2013 | Yuen et al. |
| 8,388,347 B2 | 3/2013 | Beville |
| 8,388,530 B2 | 3/2013 | Shusterman |
| 8,388,544 B2 | 3/2013 | Hoctor et al. |
| 8,389,286 B2 | 3/2013 | Chahal et al. |
| 8,395,498 B2 | 3/2013 | Gaskill et al. |
| 8,396,554 B2 | 3/2013 | Miesel et al. |
| 8,396,557 B2 | 3/2013 | DiLorenzo |
| 8,398,546 B2 | 3/2013 | Pacione et al. |
| 8,406,893 B2 | 3/2013 | Krause et al. |
| 8,407,022 B2 | 3/2013 | Sheng et al. |
| 8,409,003 B2 | 4/2013 | Ikeda |
| 8,410,940 B2 | 4/2013 | Samuelsson et al. |
| 8,412,352 B2 | 4/2013 | Griswold et al. |
| 8,417,311 B2 | 4/2013 | Rule |
| 8,419,650 B2 | 4/2013 | Cosentino et al. |
| 8,421,822 B2 | 4/2013 | Odland et al. |
| 8,428,744 B2 | 4/2013 | Stancer et al. |
| 8,430,753 B2 | 4/2013 | Ikeda et al. |
| 8,433,395 B1 | 4/2013 | Brockway et al. |
| 8,435,186 B2 | 5/2013 | Hettrick et al. |
| 8,435,738 B2 | 5/2013 | Holmes |
| 8,436,810 B2 | 5/2013 | Langereis et al. |
| 8,437,980 B2 | 5/2013 | Yuen et al. |
| 8,438,038 B2 | 5/2013 | Cosentino et al. |
| 8,444,560 B2 | 5/2013 | Hayter et al. |
| 8,444,653 B2 | 5/2013 | Nycz et al. |
| 8,447,265 B2 | 5/2013 | Flippo et al. |
| 8,447,401 B2 | 5/2013 | Miesel et al. |
| 8,447,403 B2 | 5/2013 | Sharma et al. |
| 8,447,404 B2 | 5/2013 | Sharma et al. |
| 8,452,366 B2 | 5/2013 | Gilland |
| 8,452,394 B2 | 5/2013 | Burnes et al. |
| 8,454,552 B2 | 6/2013 | Bardy |
| 8,457,727 B2 | 6/2013 | Qu |
| 8,457,757 B2 | 6/2013 | Cauller et al. |
| 8,457,760 B2 | 6/2013 | Johnson et al. |
| 8,460,189 B2 | 6/2013 | Libbus et al. |
| 8,461,979 B2 | 6/2013 | Case, Jr. |
| 8,463,576 B2 | 6/2013 | Yuen et al. |
| 8,463,577 B2 | 6/2013 | Yuen et al. |
| 8,467,904 B2 | 6/2013 | Dariush |
| 8,469,886 B2 | 6/2013 | Brauker et al. |
| 8,473,245 B2 | 6/2013 | Ohta |
| 8,475,275 B2 | 7/2013 | Weston et al. |
| 8,475,739 B2 | 7/2013 | Holmes et al. |
| 8,478,378 B2 | 7/2013 | Lal et al. |
| 8,478,389 B1 | 7/2013 | Brockway et al. |
| 8,478,557 B2 | 7/2013 | Hayter et al. |
| 8,483,840 B2 | 7/2013 | Stevenson et al. |
| 8,484,153 B2 | 7/2013 | Mott et al. |
| 8,484,270 B2 | 7/2013 | Kurtz et al. |
| 8,485,979 B2 | 7/2013 | Giftakis et al. |
| 8,486,070 B2 | 7/2013 | Morgan et al. |
| 8,491,389 B2 | 7/2013 | Weston et al. |
| 8,493,187 B2 | 7/2013 | Rowland et al. |
| 8,494,829 B2 | 7/2013 | Teixeira |
| 8,496,657 B2 | 7/2013 | Bonutti et al. |
| RE44,408 E | 8/2013 | Lindsay |
| 8,499,476 B2 | 8/2013 | Berner, Jr. et al. |
| 8,509,893 B2 | 8/2013 | Xiao et al. |
| 8,509,913 B2 | 8/2013 | Johnson et al. |
| 8,512,242 B2 | 8/2013 | LeBoeuf et al. |
| 8,515,547 B2 | 8/2013 | Mass et al. |
| 8,515,559 B2 | 8/2013 | Roberts et al. |
| 8,521,292 B2 | 8/2013 | Wei et al. |
| 8,527,045 B2 | 9/2013 | Krause et al. |
| 8,527,064 B2 | 9/2013 | Zhang et al. |
| 8,532,779 B2 | 9/2013 | Krause et al. |
| 8,532,935 B2 | 9/2013 | Budiman |
| 8,540,632 B2 | 9/2013 | Robertson et al. |
| 8,543,185 B2 | 9/2013 | Yuen et al. |
| 8,543,199 B2 | 9/2013 | Snyder et al. |
| 8,543,351 B2 | 9/2013 | Yuen et al. |
| 8,545,436 B2 | 10/2013 | Robertson et al. |
| 8,547,248 B2 | 10/2013 | Zdeblick et al. |
| 8,548,770 B2 | 10/2013 | Yuen et al. |
| 8,554,325 B2 | 10/2013 | Molnar et al. |
| 8,554,331 B2 | 10/2013 | Gerber et al. |
| 8,557,772 B2 | 10/2013 | Popel et al. |
| 8,560,038 B2 | 10/2013 | Hayter et al. |
| 8,565,848 B2 | 10/2013 | Brister et al. |
| 8,565,886 B2 | 10/2013 | Nelson et al. |
| 8,571,808 B2 | 10/2013 | Hayter |
| 8,571,881 B2 | 10/2013 | Rousso et al. |
| 8,574,146 B2 | 11/2013 | Gillespie, Jr. et al. |
| 8,577,453 B1 | 11/2013 | Stevenson et al. |
| 8,577,465 B2 | 11/2013 | Mashiach |
| 8,577,468 B2 | 11/2013 | Mashiach et al. |
| 8,577,478 B2 | 11/2013 | Mashiach et al. |
| 8,583,227 B2 | 11/2013 | Savage et al. |
| 8,583,402 B2 | 11/2013 | Yuen et al. |
| 8,587,427 B2 | 11/2013 | LaLonde et al. |
| 8,600,681 B2 | 12/2013 | Hayter et al. |
| 8,606,355 B1 | 12/2013 | Krause |
| 8,608,535 B2 | 12/2013 | Weston et al. |
| 8,609,973 B2 | 12/2013 | D'Amours |
| 8,611,996 B2 | 12/2013 | Donofrio et al. |
| 8,612,163 B2 | 12/2013 | Hayter et al. |
| 8,615,299 B2 | 12/2013 | Goetz |
| 8,615,377 B1 | 12/2013 | Yuen et al. |
| 8,615,405 B2 | 12/2013 | Rousso et al. |
| 8,620,591 B2 | 12/2013 | Wegerich |
| 8,620,617 B2 | 12/2013 | Yuen et al. |
| 8,620,679 B2 | 12/2013 | Rousso et al. |
| 8,623,023 B2 | 1/2014 | Ritchey et al. |
| 8,629,836 B2 | 1/2014 | Liberty |
| 8,630,706 B2 | 1/2014 | Dacey, Jr. et al. |
| 8,632,463 B2 | 1/2014 | Drinan et al. |
| 8,632,465 B1 | 1/2014 | Brockway |

(56) References Cited

U.S. PATENT DOCUMENTS

| | | | |
|---|---|---|---|
| 8,639,524 B2 | 1/2014 | Solomon |
| 8,641,220 B1 | 2/2014 | Lin |
| 8,641,612 B2 | 2/2014 | Teller et al. |
| 8,644,957 B2 | 2/2014 | Mashiach |
| 8,644,967 B2 | 2/2014 | Seiler |
| 8,655,441 B2 | 2/2014 | Fletcher et al. |
| 8,656,607 B2 | 2/2014 | Ellis |
| 8,657,745 B2 | 2/2014 | Brauker et al. |
| 8,657,747 B2 | 2/2014 | Kamath et al. |
| 8,663,106 B2 | 3/2014 | Stivoric et al. |
| 8,663,109 B2 | 3/2014 | Brister et al. |
| 8,666,471 B2 | 3/2014 | Rogers et al. |
| 8,666,488 B2 | 3/2014 | Duke |
| 8,667,709 B2 | 3/2014 | Ellis |
| 8,670,953 B2 | 3/2014 | Yuen et al. |
| 8,672,845 B2 | 3/2014 | Kamath et al. |
| 8,673,194 B2 | 3/2014 | Lee et al. |
| 8,674,825 B2 | 3/2014 | Zdeblick et al. |
| 8,676,170 B2 | 3/2014 | Porrati et al. |
| 8,679,014 B2 | 3/2014 | Bennett et al. |
| 8,682,615 B2 | 3/2014 | Hayter et al. |
| 8,683,850 B2 | 4/2014 | Sheng et al. |
| 8,684,943 B2 | 4/2014 | Schmidt et al. |
| 8,686,579 B2 | 4/2014 | Barney et al. |
| 8,688,202 B2 | 4/2014 | Brockway et al. |
| 8,688,210 B2 | 4/2014 | Burnes et al. |
| 8,688,221 B2 | 4/2014 | Miesel et al. |
| 8,694,282 B2 | 4/2014 | Yuen et al. |
| 8,698,638 B2 | 4/2014 | Samuelsson et al. |
| 8,702,515 B2 | 4/2014 | Weston et al. |
| 8,706,232 B2 | 4/2014 | Su et al. |
| 8,706,233 B2 | 4/2014 | Su et al. |
| 8,706,237 B2 | 4/2014 | Giftakis et al. |
| 8,707,040 B2 | 4/2014 | Andersen |
| 8,708,821 B2 | 4/2014 | Barney et al. |
| 8,708,824 B2 | 4/2014 | Ohta et al. |
| 8,708,904 B2 | 4/2014 | Stivoric et al. |
| 8,711,094 B2 | 4/2014 | Barney et al. |
| 8,712,529 B2 | 4/2014 | Sharma et al. |
| 8,712,530 B2 | 4/2014 | Sharma et al. |
| 8,715,159 B2 | 5/2014 | Pool et al. |
| 8,715,269 B2 | 5/2014 | Wolff et al. |
| 8,718,193 B2 | 5/2014 | Arne et al. |
| 8,718,753 B2 | 5/2014 | Chon et al. |
| 8,718,776 B2 | 5/2014 | Mashiach et al. |
| 8,718,965 B2 | 5/2014 | Hayter et al. |
| 8,721,520 B2 | 5/2014 | Caira et al. |
| 8,721,643 B2 | 5/2014 | Morgan et al. |
| 8,725,244 B2 | 5/2014 | Miesel et al. |
| 8,725,253 B2 | 5/2014 | Johnson et al. |
| 8,727,995 B2 | 5/2014 | Brunke |
| 8,730,031 B2 | 5/2014 | Thompson et al. |
| 8,730,034 B2 | 5/2014 | Case, Jr. |
| 8,738,323 B2 | 5/2014 | Yuen et al. |
| 8,739,639 B2 | 6/2014 | Owings et al. |
| 8,740,751 B2 | 6/2014 | Shum |
| 8,742,623 B1 | 6/2014 | Biederman et al. |
| 8,744,587 B2 | 6/2014 | Miesel et al. |
| 8,744,803 B2 | 6/2014 | Park et al. |
| 8,744,804 B2 | 6/2014 | Messenger et al. |
| 8,747,315 B2 | 6/2014 | Brauker et al. |
| 8,750,955 B2 | 6/2014 | Brister et al. |
| 8,751,013 B2 | 6/2014 | Johnson et al. |
| 8,751,194 B2 | 6/2014 | Panther et al. |
| 8,751,320 B1 | 6/2014 | Kemist |
| 8,753,165 B2 | 6/2014 | Weston |
| 8,753,275 B2 | 6/2014 | Najafi et al. |
| 8,755,837 B2 | 6/2014 | Rhoads et al. |
| 8,755,871 B2 | 6/2014 | Weng et al. |
| 8,758,136 B2 | 6/2014 | Briggs et al. |
| 8,758,242 B2 | 6/2014 | Miesel et al. |
| 8,761,852 B2 | 6/2014 | Parthasarathy et al. |
| 8,762,101 B2 | 6/2014 | Yuen et al. |
| 8,762,102 B2 | 6/2014 | Yuen et al. |
| 8,763,261 B1 | 7/2014 | Kemist |
| 8,766,789 B2 | 7/2014 | Cosentino et al. |
| 8,766,805 B2 | 7/2014 | Alameh et al. |
| 8,768,313 B2 | 7/2014 | Rodriguez |
| 8,768,648 B2 | 7/2014 | Panther et al. |
| 8,771,222 B2 | 7/2014 | Kanderian, Jr. et al. |
| 8,774,918 B2 | 7/2014 | Donofrio et al. |
| 8,775,120 B2 | 7/2014 | Molettiere et al. |
| 8,777,924 B2 | 7/2014 | Kanderian, Jr. et al. |
| 8,781,197 B2 | 7/2014 | Wang et al. |
| 8,781,791 B2 | 7/2014 | Panther et al. |
| 8,784,425 B2 | 7/2014 | Ritchey et al. |
| 8,788,007 B2 | 7/2014 | Brauker et al. |
| 8,788,028 B2 | 7/2014 | Kumar et al. |
| 8,788,057 B2 | 7/2014 | Stevenson et al. |
| 8,790,180 B2 | 7/2014 | Barney et al. |
| 8,790,400 B2 | 7/2014 | Boyden et al. |
| 8,792,982 B2 | 7/2014 | Miesel et al. |
| 8,792,991 B2 | 7/2014 | Gerber et al. |
| 8,793,101 B2 | 7/2014 | Yuen et al. |
| 8,795,079 B2 | 8/2014 | Penzias, III |
| 8,795,260 B2 | 8/2014 | Drew |
| 8,795,359 B2 | 8/2014 | Boyden et al. |
| 8,798,773 B2 | 8/2014 | Mashiach |
| 8,801,610 B2 | 8/2014 | Brauker et al. |
| 8,805,110 B2 | 8/2014 | Rhoads et al. |
| 8,805,478 B2 | 8/2014 | Powers et al. |
| 8,805,485 B2 | 8/2014 | Sameni et al. |
| 8,805,508 B2 | 8/2014 | Gerber et al. |
| 8,805,518 B2 | 8/2014 | King et al. |
| 8,805,530 B2 | 8/2014 | John |
| 8,805,646 B2 | 8/2014 | Messenger et al. |
| 8,808,163 B2 | 8/2014 | Pool et al. |
| 8,808,373 B2 | 8/2014 | Boyden et al. |
| 8,812,259 B2 | 8/2014 | Messenger et al. |
| 8,812,260 B2 | 8/2014 | Yuen et al. |
| 8,814,688 B2 | 8/2014 | Barney et al. |
| 8,814,868 B2 | 8/2014 | Janna et al. |
| 8,818,505 B2 | 8/2014 | Bhunia et al. |
| 8,818,522 B2 | 8/2014 | Mass et al. |
| 8,818,753 B2 | 8/2014 | Yuen et al. |
| 8,821,350 B2 | 9/2014 | Maertz |
| 8,827,810 B2 | 9/2014 | Weston et al. |
| 8,827,906 B2 | 9/2014 | Yuen et al. |
| 8,834,020 B2 | 9/2014 | Abreu |
| 8,834,271 B2 | 9/2014 | Ikeda |
| 8,834,366 B2 | 9/2014 | Hayter et al. |
| 8,838,235 B2 | 9/2014 | Cowan et al. |
| 8,838,249 B2 | 9/2014 | Nycz |
| 8,840,838 B2 | 9/2014 | Holmes et al. |
| 8,842,176 B2 | 9/2014 | Schofield et al. |
| 8,843,210 B2 | 9/2014 | Simon et al. |
| 8,843,321 B2 | 9/2014 | Duke et al. |
| 8,845,536 B2 | 9/2014 | Brauker et al. |
| 8,847,766 B2 | 9/2014 | Zdeblick et al. |
| 8,849,259 B2 | 9/2014 | Rhoads et al. |
| 8,849,368 B2 | 9/2014 | Madsen et al. |
| 8,849,610 B2 | 9/2014 | Molettiere et al. |
| 8,849,682 B2 | 9/2014 | Mahajan et al. |
| 8,852,095 B2 | 10/2014 | Schlottau et al. |
| 8,852,098 B2 | 10/2014 | Teller et al. |
| 8,855,712 B2 | 10/2014 | Lord et al. |
| 8,855,785 B1 | 10/2014 | Johnson et al. |
| 8,857,078 B2 | 10/2014 | Berner, Jr. et al. |
| 8,857,934 B2 | 10/2014 | Hirayama |
| 8,858,432 B2 | 10/2014 | Robertson et al. |
| 8,868,377 B2 | 10/2014 | Yuen et al. |
| 8,870,655 B2 | 10/2014 | Ikeda |
| 8,870,736 B2 | 10/2014 | Qu |
| 8,870,742 B2 | 10/2014 | Dlugos, Jr. et al. |
| 8,870,766 B2 | 10/2014 | Stivoric et al. |
| 8,875,714 B2 | 11/2014 | Boyden et al. |
| 8,879,983 B2 | 11/2014 | Yun et al. |
| 8,880,155 B2 | 11/2014 | Mestek et al. |
| 8,882,666 B1 | 11/2014 | Goldberg et al. |
| 8,884,809 B2 | 11/2014 | Hyde et al. |
| 8,886,206 B2 | 11/2014 | Lord et al. |
| 8,888,576 B2 | 11/2014 | Briggs et al. |
| 8,892,401 B2 | 11/2014 | Yuen et al. |
| 8,900,142 B2 | 12/2014 | Old et al. |

(56) References Cited

U.S. PATENT DOCUMENTS

| | | |
|---|---|---|
| 8,901,084 B2 | 12/2014 | Genove et al. |
| 8,907,782 B2 | 12/2014 | Baker et al. |
| 8,911,486 B1 | 12/2014 | Drnek et al. |
| 8,913,011 B2 | 12/2014 | Barney et al. |
| 8,915,785 B2 | 12/2014 | Barney et al. |
| 8,915,849 B2 | 12/2014 | Brauker et al. |
| 8,918,178 B2 | 12/2014 | Simon et al. |
| 8,920,332 B2 | 12/2014 | Hong et al. |
| 8,923,970 B2 | 12/2014 | Bar-Yoseph et al. |
| 8,923,976 B2 | 12/2014 | Johanek |
| 8,926,573 B2 | 1/2015 | Smith et al. |
| 8,929,877 B2 | 1/2015 | Rhoads et al. |
| 8,929,963 B2 | 1/2015 | Lisogurski |
| 8,929,999 B2 | 1/2015 | Maschiach |
| 8,932,221 B2 | 1/2015 | Colliou et al. |
| 8,935,119 B2 | 1/2015 | Yuen |
| 8,935,123 B2 | 1/2015 | Yuen et al. |
| 8,937,594 B2 | 1/2015 | Liberty |
| 8,938,368 B2 | 1/2015 | Yuen et al. |
| 8,938,892 B2 | 1/2015 | Case, Jr. |
| 8,942,777 B2 | 1/2015 | Diab et al. |
| 8,942,953 B2 | 1/2015 | Yuen et al. |
| 8,945,017 B2 | 2/2015 | Venkatraman et al. |
| 8,945,328 B2 | 2/2015 | Longinotti-Buitoni et al. |
| 8,946,390 B2 | 2/2015 | Chahal et al. |
| 8,948,832 B2 | 2/2015 | Hong et al. |
| 8,948,834 B2 | 2/2015 | Diab et al. |
| 8,948,839 B1 | 2/2015 | Longinotti-Buitoni et al. |
| 8,954,149 B2 | 2/2015 | Shalev |
| 8,954,290 B2 | 2/2015 | Yuen et al. |
| 8,954,291 B2 | 2/2015 | Messenger et al. |
| 8,956,228 B2 | 2/2015 | Shum et al. |
| 8,956,287 B2 | 2/2015 | Zdeblick et al. |
| 8,956,288 B2 | 2/2015 | Hafezi et al. |
| 8,956,303 B2 | 2/2015 | Hong et al. |
| 8,957,777 B2 | 2/2015 | Baker et al. |
| 8,958,870 B2 | 2/2015 | Gerber et al. |
| 8,961,260 B2 | 2/2015 | Weston |
| 8,961,312 B2 | 2/2015 | Barney et al. |
| 8,961,412 B2 | 2/2015 | Hafezi et al. |
| 8,961,414 B2 | 2/2015 | Teller et al. |
| 8,965,730 B2 | 2/2015 | Yuen |
| 8,965,824 B2 | 2/2015 | Chun et al. |
| 8,968,196 B2 | 3/2015 | Teller et al. |
| 8,970,392 B2 | 3/2015 | LaLonde et al. |
| 8,971,936 B2 | 3/2015 | Derchak |
| 8,973,197 B2 | 3/2015 | Omidi |
| 8,975,372 B2 | 3/2015 | Ju et al. |
| 8,979,757 B2 | 3/2015 | Mottram et al. |
| 8,979,763 B2 | 3/2015 | Stivoric et al. |
| 8,982,150 B2 | 3/2015 | Odland et al. |
| 8,983,628 B2 | 3/2015 | Simon et al. |
| 8,983,629 B2 | 3/2015 | Simon et al. |
| 8,986,209 B2 | 3/2015 | Brauker et al. |
| 8,989,858 B2 | 3/2015 | Dacey, Jr. et al. |
| 8,989,861 B2 | 3/2015 | Su et al. |
| 8,989,867 B2 | 3/2015 | Chow et al. |
| 8,989,870 B2 | 3/2015 | Johnson et al. |
| 8,990,924 B2 | 3/2015 | Chow |
| 8,994,657 B2 | 3/2015 | Liberty et al. |
| 8,998,815 B2 | 4/2015 | Venkatraman et al. |
| 9,000,973 B2 | 4/2015 | Hyde et al. |
| 9,002,471 B2 | 4/2015 | Stevenson et al. |
| 9,005,129 B2 | 4/2015 | Venkatraman et al. |
| 9,008,724 B2 | 4/2015 | Lord |
| 9,008,762 B2 | 4/2015 | Brockway et al. |
| 9,011,248 B2 | 4/2015 | Ikeda et al. |
| 9,011,361 B2 | 4/2015 | de Juan, Jr. et al. |
| 9,014,661 B2 | 4/2015 | deCharms |
| 9,014,790 B2 | 4/2015 | Richards et al. |
| 9,014,802 B2 | 4/2015 | Dacey, Jr. et al. |
| 9,014,986 B2 | 4/2015 | Krieftewirth |
| 9,017,380 B2 | 4/2015 | Mayer et al. |
| 9,019,106 B2 | 4/2015 | Alameh et al. |
| 9,020,591 B2 | 4/2015 | Dacey, Jr. et al. |
| 9,020,592 B2 | 4/2015 | Dacey, Jr. et al. |
| 9,020,597 B2 | 4/2015 | Sharma et al. |
| 9,026,190 B2 | 5/2015 | Shenasa et al. |
| 9,026,201 B2 | 5/2015 | Zhang et al. |
| 9,026,206 B2 | 5/2015 | Krause et al. |
| 9,026,792 B2 | 5/2015 | Andersen |
| 9,029,736 B2 | 5/2015 | Lavin, Jr. |
| 9,030,335 B2 | 5/2015 | Ellis |
| 9,031,637 B2 | 5/2015 | Ritchey et al. |
| 9,031,669 B2 | 5/2015 | Zhang et al. |
| 9,031,812 B2 | 5/2015 | Roberts et al. |
| 9,033,875 B2 | 5/2015 | Teller et al. |
| 9,033,876 B2 | 5/2015 | Teller et al. |
| 9,033,920 B2 | 5/2015 | Miesel |
| 9,039,533 B2 | 5/2015 | Barney et al. |
| 9,039,614 B2 | 5/2015 | Yuen et al. |
| 9,042,971 B2 | 5/2015 | Brumback et al. |
| 9,042,988 B2 | 5/2015 | DiLorenzo |
| 9,044,149 B2 | 6/2015 | Richards et al. |
| 9,044,150 B2 | 6/2015 | Brumback et al. |
| 9,044,171 B2 | 6/2015 | Venkatraman et al. |
| 9,044,180 B2 | 6/2015 | LeBoeuf et al. |
| 9,044,209 B2 | 6/2015 | Dayton et al. |
| 9,044,612 B2 | 6/2015 | Mashiach et al. |
| 9,044,671 B2 | 6/2015 | Ikeda |
| 9,049,998 B2 | 6/2015 | Brumback et al. |
| 9,050,007 B1 | 6/2015 | Brockway et al. |
| 9,050,041 B2 | 6/2015 | Feldman et al. |
| 9,055,791 B2 | 6/2015 | Proud et al. |
| 9,055,901 B2 | 6/2015 | Brister et al. |
| 9,060,719 B2 | 6/2015 | Hayter et al. |
| 9,060,722 B2 | 6/2015 | Teixeira |
| 9,060,746 B2 | 6/2015 | Weng et al. |
| 9,061,139 B2 | 6/2015 | Stevenson et al. |
| 9,061,147 B2 | 6/2015 | Sharma et al. |
| 9,061,151 B2 | 6/2015 | Mashiach et al. |
| 9,063,529 B2 | 6/2015 | Ellis |
| 9,064,342 B2 | 6/2015 | Yuen et al. |
| 9,066,209 B2 | 6/2015 | Yuen et al. |
| 9,067,073 B2 | 6/2015 | Simms, Jr. |
| 9,072,438 B2 | 7/2015 | Brockway et al. |
| 9,072,447 B2 | 7/2015 | Chow |
| 9,072,560 B2 | 7/2015 | Doherty |
| 9,072,870 B2 | 7/2015 | Wu et al. |
| 9,077,030 B2 | 7/2015 | Norton et al. |
| 9,079,045 B2 | 7/2015 | Cowan et al. |
| 9,079,060 B2 | 7/2015 | Hong et al. |
| 9,081,534 B2 | 7/2015 | Yuen et al. |
| 9,082,011 B2 | 7/2015 | Komogortsev |
| 9,083,589 B2 | 7/2015 | Arne et al. |
| 9,089,182 B2 | 7/2015 | Schrock et al. |
| 9,095,303 B2 | 8/2015 | Osorio |
| 9,100,495 B2 | 8/2015 | Ellis |
| 9,101,260 B2 | 8/2015 | Desu-Kalyanam |
| 9,101,334 B2 | 8/2015 | Rath et al. |
| 9,103,899 B2 | 8/2015 | Hyde et al. |
| 9,104,965 B2 | 8/2015 | Fritsch et al. |
| 9,107,614 B2 | 8/2015 | Halkias et al. |
| 9,107,623 B2 | 8/2015 | Brauker et al. |
| 9,108,098 B2 | 8/2015 | Galasso et al. |
| 9,113,794 B2 | 8/2015 | Hong et al. |
| 9,113,795 B2 | 8/2015 | Hong et al. |
| 9,113,801 B2 | 8/2015 | DiLorenzo |
| 9,113,823 B2 | 8/2015 | Yuen et al. |
| 9,113,844 B2 | 8/2015 | Hollstien |
| 9,119,528 B2 | 9/2015 | Cobelli et al. |
| 9,119,529 B2 | 9/2015 | Hampapuram et al. |
| 9,119,554 B2 | 9/2015 | Zdeblick et al. |
| 9,125,548 B2 | 9/2015 | Hayter |
| 9,125,577 B2 | 9/2015 | Sameni et al. |
| 9,125,981 B2 | 9/2015 | Mann et al. |
| 9,126,825 B2 | 9/2015 | Molin et al. |
| 9,128,015 B2 | 9/2015 | Holmes et al. |
| 9,131,120 B2 | 9/2015 | Schofield et al. |
| 9,131,842 B2 | 9/2015 | Old et al. |
| 9,138,181 B2 | 9/2015 | Haisley et al. |
| 9,138,523 B2 | 9/2015 | Burnett et al. |
| 9,138,537 B2 | 9/2015 | Miesel |
| 9,142,117 B2 | 9/2015 | Muhsin et al. |

(56) References Cited

U.S. PATENT DOCUMENTS

| | | |
|---|---|---|
| 9,144,488 B2 | 9/2015 | Boyden et al. |
| 9,144,489 B2 | 9/2015 | Boyden et al. |
| 9,148,483 B1 | 9/2015 | Molettiere et al. |
| RE45,766 E | 10/2015 | Lindsay |
| 9,149,189 B2 | 10/2015 | Proud |
| 9,149,577 B2 | 10/2015 | Robertson et al. |
| 9,149,717 B2 | 10/2015 | Barney et al. |
| 9,151,834 B2 | 10/2015 | Hyde et al. |
| 9,155,885 B2 | 10/2015 | Wei et al. |
| 9,159,223 B2 | 10/2015 | Proud |
| 9,160,836 B2 | 10/2015 | Ellis |
| 9,161,693 B2 | 10/2015 | Rizwan |
| 9,162,148 B2 | 10/2015 | Barney et al. |
| 9,164,167 B2 | 10/2015 | Hyde et al. |
| 9,165,117 B2 | 10/2015 | Teller et al. |
| 9,167,991 B2 | 10/2015 | Yuen et al. |
| 9,168,001 B2 | 10/2015 | Stivoric et al. |
| 9,168,374 B2 | 10/2015 | Su |
| 9,168,419 B2 | 10/2015 | Hong et al. |
| 9,171,201 B2 | 10/2015 | Lake, II et al. |
| 9,173,574 B2 | 11/2015 | Teixeira et al. |
| 9,174,058 B2 | 11/2015 | Ellingson et al. |
| 9,185,489 B2 | 11/2015 | Gerber et al. |
| 9,186,509 B2 | 11/2015 | Nelson et al. |
| 9,186,585 B2 | 11/2015 | Briggs et al. |
| 9,187,539 B2 | 11/2015 | Popel et al. |
| 9,189,739 B2 | 11/2015 | Mott et al. |
| 9,192,328 B2 | 11/2015 | Brauker et al. |
| 9,192,329 B2 | 11/2015 | Al-Ali |
| 9,192,816 B2 | 11/2015 | Molyneux et al. |
| 9,198,478 B2 | 12/2015 | Meschter et al. |
| 9,198,604 B2 | 12/2015 | Venkatraman et al. |
| 9,198,911 B2 | 12/2015 | Christiano et al. |
| 9,201,413 B2 | 12/2015 | Hanft |
| 9,204,038 B2 | 12/2015 | Lord et al. |
| 9,204,798 B2 | 12/2015 | Proud |
| 9,204,806 B2 | 12/2015 | Stivoric et al. |
| 9,205,264 B2 | 12/2015 | Heruth et al. |
| 9,207,660 B2 | 12/2015 | Ellis |
| 9,211,185 B2 | 12/2015 | Boyden et al. |
| 9,215,290 B2 | 12/2015 | Yuen et al. |
| 9,215,910 B2 | 12/2015 | Dhillon |
| 9,218,454 B2 | 12/2015 | Kiani et al. |
| 9,220,461 B2 | 12/2015 | Samuelsson et al. |
| 9,226,663 B2 | 1/2016 | Fei |
| 9,227,128 B1 | 1/2016 | Carfagna, Jr. |
| 9,227,138 B2 | 1/2016 | Ikeda |
| 9,233,245 B2 | 1/2016 | Lamensdorf et al. |
| 9,237,012 B2 | 1/2016 | Andersen |
| 9,237,855 B2 | 1/2016 | Hong et al. |
| 9,237,858 B2 | 1/2016 | Krusor et al. |
| 9,241,635 B2 | 1/2016 | Yuen et al. |
| 9,247,911 B2 | 2/2016 | Galloway et al. |
| 9,248,291 B2 | 2/2016 | Mashiach |
| 9,248,302 B2 | 2/2016 | Mashiach et al. |
| 9,250,229 B2 | 2/2016 | Holmes |
| 9,250,716 B2 | 2/2016 | Sheng et al. |
| 9,251,960 B2 | 2/2016 | Brendel et al. |
| 9,254,092 B2 | 2/2016 | Albert et al. |
| 9,259,180 B2 | 2/2016 | McCaffrey |
| 9,261,978 B2 | 2/2016 | Liberty et al. |
| 9,265,871 B2 | 2/2016 | Jeevanandam et al. |
| 9,268,915 B2 | 2/2016 | Holmes et al. |
| 9,269,251 B2 | 2/2016 | LaLonde et al. |
| 9,270,025 B2 | 2/2016 | Robertson et al. |
| 9,271,133 B2 | 2/2016 | Rodriguez |
| RE45,905 E | 3/2016 | Ikeda et al. |
| 9,271,857 B2 | 3/2016 | Pool et al. |
| 9,272,206 B2 | 3/2016 | Weston et al. |
| 9,277,534 B2 | 3/2016 | Yun et al. |
| 9,279,734 B2 | 3/2016 | Walker |
| 9,282,894 B2 | 3/2016 | Banet et al. |
| 9,282,902 B2 | 3/2016 | Richards et al. |
| 9,282,925 B2 | 3/2016 | Kamath et al. |
| 9,288,298 B2 | 3/2016 | Choudhary et al. |
| 9,288,614 B1 | 3/2016 | Young et al. |
| 9,289,123 B2 | 3/2016 | Weibel et al. |
| 9,289,607 B2 | 3/2016 | Su et al. |
| 9,289,613 B2 | 3/2016 | Burnes et al. |
| 9,294,074 B2 | 3/2016 | Brockway |
| 9,295,403 B1 | 3/2016 | Mirov et al. |
| 9,297,709 B2 | 3/2016 | Dojan et al. |
| 9,298,282 B2 | 3/2016 | Liberty |
| 9,301,573 B2 | 4/2016 | Jasmine |
| 9,302,045 B2 | 4/2016 | Rule |
| 9,305,559 B2 | 4/2016 | Sharma et al. |
| 9,307,917 B2 | 4/2016 | Hong et al. |
| 9,308,381 B2 | 4/2016 | Mashiach et al. |
| 9,310,909 B2 | 4/2016 | Myers et al. |
| 9,317,729 B2 | 4/2016 | Krusor et al. |
| 9,317,743 B2 | 4/2016 | Datta et al. |
| 9,317,920 B2 | 4/2016 | Gluncic |
| 9,320,470 B2 | 4/2016 | Keenan et al. |
| 9,320,677 B2 | 4/2016 | Johnson et al. |
| 9,320,842 B2 | 4/2016 | Orhan et al. |
| 9,320,900 B2 | 4/2016 | DiLorenzo |
| 9,320,976 B2 | 4/2016 | Weston |
| 9,323,894 B2 | 4/2016 | Kiani |
| 9,326,566 B2 | 5/2016 | Beers et al. |
| 9,326,708 B2 | 5/2016 | Hanson et al. |
| 9,326,711 B2 | 5/2016 | Kracker et al. |
| 9,326,720 B2 | 5/2016 | McLaughlin |
| 9,326,730 B2 | 5/2016 | Boyden et al. |
| 9,327,061 B2 | 5/2016 | Govil et al. |
| 9,332,919 B2 | 5/2016 | Crockford |
| 9,333,071 B2 | 5/2016 | Boyden et al. |
| 9,333,350 B2 | 5/2016 | Rise et al. |
| 9,339,188 B2 | 5/2016 | Proud |
| 9,339,201 B2 | 5/2016 | Banet et al. |
| 9,339,202 B2 | 5/2016 | Brockway et al. |
| 9,339,203 B2 | 5/2016 | Banet et al. |
| 9,339,372 B2 | 5/2016 | Boyden et al. |
| 9,344,546 B2 | 5/2016 | Choudhary et al. |
| 9,345,404 B2 | 5/2016 | Proud |
| 9,345,879 B2 | 5/2016 | Sharma et al. |
| 9,345,892 B2 | 5/2016 | Corndorf et al. |
| 9,348,974 B2 | 5/2016 | Goetz |
| 9,351,124 B1 | 5/2016 | Shelton |
| 9,351,668 B2 | 5/2016 | Brauker et al. |
| 9,352,156 B2 | 5/2016 | Lane et al. |
| 9,356,473 B2 | 5/2016 | Ghovanloo |
| 9,357,922 B2 | 6/2016 | Proud |
| 9,358,374 B2 | 6/2016 | Dacey, Jr. et al. |
| 9,358,378 B2 | 6/2016 | Hanson et al. |
| 9,358,381 B2 | 6/2016 | Simon et al. |
| 9,358,392 B2 | 6/2016 | Mashiach |
| 9,361,572 B2 | 6/2016 | Proud et al. |
| 9,364,042 B2 | 6/2016 | Bahl et al. |
| 9,364,173 B2 | 6/2016 | Brauker et al. |
| 9,364,609 B2 | 6/2016 | Keenan et al. |
| 9,367,793 B2 | 6/2016 | Proud et al. |
| 9,369,365 B2 | 6/2016 | Molettiere et al. |
| 9,370,320 B2 | 6/2016 | Messenger et al. |
| 9,370,326 B2 | 6/2016 | McHale et al. |
| 9,370,618 B2 | 6/2016 | Mann et al. |
| 9,370,619 B2 | 6/2016 | Mann et al. |
| 9,374,279 B2 | 6/2016 | Yuen et al. |
| 9,375,047 B2 | 6/2016 | Ellis |
| 9,375,145 B2 | 6/2016 | Chin et al. |
| 9,375,171 B2 | 6/2016 | Teixeira |
| 9,380,834 B2 | 7/2016 | Rushbrook et al. |
| 9,386,360 B2 | 7/2016 | Sagan et al. |
| 9,386,924 B2 | 7/2016 | Baker et al. |
| 9,388,873 B1 | 7/2016 | Phipps et al. |
| 9,390,427 B2 | 7/2016 | Messenger et al. |
| 9,392,939 B2 | 7/2016 | Proud |
| 9,393,384 B1 | 7/2016 | Kapur et al. |
| 9,393,491 B2 | 7/2016 | Barney et al. |
| 9,393,500 B2 | 7/2016 | Barney et al. |
| 9,398,787 B2 | 7/2016 | Ellis, III |
| 9,398,854 B2 | 7/2016 | Proud |
| 9,398,856 B2 | 7/2016 | Abreu |
| 9,398,872 B2 | 7/2016 | Hayter et al. |
| 9,399,134 B2 | 7/2016 | Simon et al. |

(56) References Cited

U.S. PATENT DOCUMENTS

| | | |
|---|---|---|
| 9,400,598 B2 | 7/2016 | Pixley et al. |
| 9,401,153 B2 | 7/2016 | Sharma et al. |
| 9,402,545 B2 | 8/2016 | Baker et al. |
| 9,402,552 B2 | 8/2016 | Richards et al. |
| 9,403,009 B2 | 8/2016 | Mashiach |
| 9,403,021 B2 | 8/2016 | Dronov |
| 9,408,549 B2 | 8/2016 | Brockway et al. |
| 9,409,018 B2 | 8/2016 | Tourrel et al. |
| 9,410,691 B2 | 8/2016 | Lin |
| 9,410,857 B2 | 8/2016 | Walker |
| 9,410,979 B2 | 8/2016 | Yuen et al. |
| 9,414,641 B2 | 8/2016 | Ellis |
| 9,414,651 B2 | 8/2016 | Proud et al. |
| 9,414,758 B1 | 8/2016 | Brockway et al. |
| 9,414,775 B2 | 8/2016 | Colvin, Jr. et al. |
| 9,415,125 B2 | 8/2016 | Chen et al. |
| 9,415,163 B2 | 8/2016 | Ricotti et al. |
| 9,415,219 B2 | 8/2016 | Simon et al. |
| 9,418,390 B2 | 8/2016 | Chun et al. |
| 9,420,083 B2 | 8/2016 | Roberts et al. |
| 9,420,856 B2 | 8/2016 | Proud et al. |
| 9,420,857 B2 | 8/2016 | Proud et al. |
| 9,420,956 B2 | 8/2016 | Gopalakrishnan et al. |
| 9,420,965 B2 | 8/2016 | Brauker et al. |
| 9,421,388 B2 | 8/2016 | John |
| 9,424,508 B2 | 8/2016 | Proud et al. |
| 9,427,053 B2 | 8/2016 | Proud et al. |
| 9,427,160 B2 | 8/2016 | Proud et al. |
| 9,427,165 B2 | 8/2016 | Finlay et al. |
| 9,427,189 B2 | 8/2016 | Proud et al. |
| 9,427,190 B1 | 8/2016 | Proud |
| 9,427,581 B2 | 8/2016 | Simon et al. |
| 9,431,694 B2 | 8/2016 | Li et al. |
| 9,433,371 B2 | 9/2016 | Hafezi et al. |
| 9,433,376 B2 | 9/2016 | Estes et al. |
| 9,433,783 B2 | 9/2016 | Wei et al. |
| 9,436,903 B2 | 9/2016 | Proud et al. |
| 9,436,923 B1 | 9/2016 | Sriram et al. |
| 9,439,567 B2 | 9/2016 | Carter et al. |
| 9,439,599 B2 | 9/2016 | Thompson et al. |
| 9,440,025 B2 | 9/2016 | Kanderian, Jr. et al. |
| 9,444,503 B2 | 9/2016 | Arne et al. |
| 9,445,651 B2 | 9/2016 | Proud et al. |
| 9,445,730 B2 | 9/2016 | Snyder et al. |
| 9,445,767 B2 | 9/2016 | Abreu |
| 9,446,235 B2 | 9/2016 | Su et al. |
| 9,446,319 B2 | 9/2016 | Barney et al. |
| 9,451,886 B2 | 9/2016 | Teixeira |
| 9,452,258 B2 | 9/2016 | Dobbles et al. |
| 9,452,259 B2 | 9/2016 | Dobbles et al. |
| 9,454,644 B2 | 9/2016 | Cosentino et al. |
| 9,456,755 B2 | 10/2016 | Soykan et al. |
| 9,456,787 B2 | 10/2016 | Venkatraman et al. |
| 9,457,146 B2 | 10/2016 | Dobbles et al. |
| 9,462,856 B2 | 10/2016 | Proud et al. |
| 9,462,962 B2 | 10/2016 | Doerr |
| 9,462,979 B2 | 10/2016 | Lisogurski et al. |
| 9,463,012 B2 | 10/2016 | Bonutti et al. |
| 9,463,277 B2 | 10/2016 | Dobbles et al. |
| 9,463,325 B1 | 10/2016 | Young et al. |
| 9,463,380 B2 | 10/2016 | Weston et al. |
| 9,468,854 B2 | 10/2016 | Briggs et al. |
| 9,474,461 B2 | 10/2016 | Fisher et al. |
| 9,474,855 B2 | 10/2016 | McCann et al. |
| 9,474,888 B2 | 10/2016 | Wiley et al. |
| 9,474,962 B2 | 10/2016 | Barney et al. |
| 9,480,424 B2 | 11/2016 | Darty et al. |
| 9,483,608 B2 | 11/2016 | Hayter et al. |
| 9,486,128 B1 | 11/2016 | Hannaford et al. |
| 9,486,168 B2 | 11/2016 | Bonmassar et al. |
| 9,486,578 B2 | 11/2016 | Finan et al. |
| 9,492,084 B2 | 11/2016 | Behar et al. |
| 9,492,096 B2 | 11/2016 | Brockway et al. |
| 9,492,656 B2 | 11/2016 | Chow et al. |
| 9,492,657 B2 | 11/2016 | Gerber |
| 9,492,678 B2 | 11/2016 | Chow |
| 9,498,137 B2 | 11/2016 | Kovacs |
| 9,498,155 B2 | 11/2016 | Brauker et al. |
| 9,498,195 B2 | 11/2016 | Schutt et al. |
| 9,498,624 B2 | 11/2016 | Bar-Yoseph et al. |
| 9,498,709 B2 | 11/2016 | Ikeda |
| 9,498,728 B2 | 11/2016 | Ikeda et al. |
| 9,501,735 B2 | 11/2016 | Proud et al. |
| 9,504,291 B2 | 11/2016 | Ellis |
| 9,504,408 B2 | 11/2016 | Hong et al. |
| 9,504,425 B2 | 11/2016 | Jooste |
| 9,506,802 B2 | 11/2016 | Chu et al. |
| 9,510,788 B2 | 12/2016 | Galeev |
| 9,514,338 B1 | 12/2016 | Bromberg et al. |
| 9,517,023 B2 | 12/2016 | McMillan et al. |
| 9,517,306 B2 | 12/2016 | Morales |
| 9,520,638 B2 | 12/2016 | Baringer et al. |
| 9,521,868 B2 | 12/2016 | Cobbett et al. |
| 9,521,962 B2 | 12/2016 | LeBoeuf |
| 9,522,282 B2 | 12/2016 | Chow et al. |
| 9,522,317 B2 | 12/2016 | Bleich et al. |
| 9,526,422 B2 | 12/2016 | Proud |
| 9,526,430 B2 | 12/2016 | Srinivas et al. |
| 9,526,433 B2 | 12/2016 | Lapetina et al. |
| 9,526,650 B2 | 12/2016 | Pool et al. |
| 9,526,834 B2 | 12/2016 | Keenan et al. |
| 9,526,859 B2 | 12/2016 | Rembrand |
| 9,529,972 B2 | 12/2016 | Giftakis et al. |
| 9,530,089 B2 | 12/2016 | Proud et al. |
| 9,532,716 B2 | 1/2017 | Proud |
| 9,532,722 B2 | 1/2017 | Lamego et al. |
| 9,532,738 B2 | 1/2017 | Delbeke et al. |
| 9,533,157 B2 | 1/2017 | Chow |
| 9,538,921 B2 | 1/2017 | LeBoeuf et al. |
| 9,538,922 B2 | 1/2017 | Wang |
| 9,539,037 B2 | 1/2017 | Janna et al. |
| 9,542,685 B2 | 1/2017 | Proud et al. |
| 9,542,706 B2 | 1/2017 | Case, Jr. |
| 9,543,636 B2 | 1/2017 | Baringer et al. |
| 9,545,506 B2 | 1/2017 | Quigley |
| 9,549,585 B2 | 1/2017 | Amos et al. |
| 9,553,486 B2 | 1/2017 | Proud et al. |
| 9,554,705 B2 | 1/2017 | Huang |
| 9,554,719 B2 | 1/2017 | Banet et al. |
| 9,559,353 B2 | 1/2017 | Norton et al. |
| 9,561,367 B2 | 2/2017 | Sharma et al. |
| 9,564,777 B2 | 2/2017 | Yeh et al. |
| 9,565,512 B2 | 2/2017 | Rhoads et al. |
| 9,568,492 B2 | 2/2017 | Yuen |
| 9,569,719 B2 | 2/2017 | Proud et al. |
| 9,569,720 B2 | 2/2017 | Proud et al. |
| 9,569,771 B2 | 2/2017 | Lesavich et al. |
| 9,572,395 B2 | 2/2017 | Roser |
| 9,572,499 B2 | 2/2017 | Gopalakrishnan et al. |
| 9,572,533 B2 | 2/2017 | Venkatraman et al. |
| 9,572,935 B2 | 2/2017 | Dobbles et al. |
| 9,572,936 B2 | 2/2017 | Dobbles et al. |
| 9,572,992 B2 | 2/2017 | Shahandeh et al. |
| 9,575,570 B2 | 2/2017 | Liberty et al. |
| 9,576,236 B2 | 2/2017 | Proud et al. |
| 9,577,992 B2 | 2/2017 | Zizi et al. |
| 9,578,903 B2 | 2/2017 | Cobbett et al. |
| 9,579,020 B2 | 2/2017 | Libbus et al. |
| 9,579,048 B2 | 2/2017 | Rayner et al. |
| 9,579,060 B1 | 2/2017 | Lisy et al. |
| 9,579,422 B2 | 2/2017 | Ju et al. |
| 9,579,510 B2 | 2/2017 | Meskens |
| 9,579,516 B2 | 2/2017 | Kaib et al. |
| 9,579,568 B2 | 2/2017 | Barney et al. |
| 9,582,748 B2 | 2/2017 | Proud et al. |
| 9,582,749 B2 | 2/2017 | Proud et al. |
| 9,583,256 B2 | 2/2017 | Lapetina et al. |
| 9,585,566 B2 | 3/2017 | Samuelsson et al. |
| 9,585,606 B2 | 3/2017 | Lisogurski |
| 9,585,722 B2 | 3/2017 | Ritchey et al. |
| 9,586,004 B2 | 3/2017 | Dobbles et al. |
| 9,590,986 B2 | 3/2017 | Zizi et al. |
| 9,592,328 B2 | 3/2017 | Jeevanandam et al. |
| 9,592,379 B2 | 3/2017 | Heruth et al. |

(56) References Cited

U.S. PATENT DOCUMENTS

| | | |
|---|---|---|
| 9,592,508 B2 | 3/2017 | Holmes et al. |
| 9,595,996 B2 | 3/2017 | Yun et al. |
| 9,596,997 B1 | 3/2017 | Ritscher et al. |
| 9,597,014 B2 | 3/2017 | Venkatraman et al. |
| 9,597,023 B2 | 3/2017 | Lisogurski |
| 9,597,453 B2 | 3/2017 | Dobbles et al. |
| 9,597,505 B2 | 3/2017 | Donofrio et al. |
| 9,599,632 B2 | 3/2017 | Yuen |
| 9,600,676 B1 | 3/2017 | Farmer et al. |
| 9,603,416 B1 | 3/2017 | Walsh et al. |
| 9,603,569 B2 | 3/2017 | Mirov et al. |
| 9,603,997 B2 | 3/2017 | Humayun et al. |
| 9,610,391 B2 | 4/2017 | Vollmers et al. |
| 9,613,184 B2 | 4/2017 | Giftakis et al. |
| 9,614,337 B2 | 4/2017 | Lisogurski et al. |
| 9,615,215 B2 | 4/2017 | Yuen et al. |
| 9,615,794 B2 | 4/2017 | Kaskoun et al. |
| 9,616,225 B2 | 4/2017 | Sharma et al. |
| 9,616,334 B2 | 4/2017 | Weston et al. |
| 9,622,537 B2 | 4/2017 | Amos et al. |
| 9,622,691 B2 | 4/2017 | Budiman |
| 9,623,179 B2 | 4/2017 | Mastrototaro et al. |
| 9,623,238 B2 | 4/2017 | Sharma et al. |
| 9,623,240 B2 | 4/2017 | Simon et al. |
| 9,623,248 B2 | 4/2017 | Heruth et al. |
| 9,629,418 B2 | 4/2017 | Rushbrook et al. |
| 9,629,558 B2 | 4/2017 | Yuen et al. |
| 9,632,102 B2 | 4/2017 | Holmes et al. |
| 9,633,170 B2 | 4/2017 | Goetz |
| 9,634,921 B2 | 4/2017 | Proud et al. |
| 9,635,901 B1 | 5/2017 | Morrison et al. |
| 9,636,509 B2 | 5/2017 | Hintz |
| 9,639,170 B2 | 5/2017 | Yuen et al. |
| 9,641,239 B2 | 5/2017 | Panther et al. |
| 9,641,342 B2 | 5/2017 | Sriram et al. |
| 9,641,469 B2 | 5/2017 | Choudhary et al. |
| 9,642,414 B2 | 5/2017 | Lindsay et al. |
| 9,645,143 B2 | 5/2017 | Holmes et al. |
| 9,646,481 B2 | 5/2017 | Messenger et al. |
| 9,648,926 B2 | 5/2017 | Marks |
| 9,649,036 B2 | 5/2017 | Teixeira |
| 9,651,533 B2 | 5/2017 | Islam |
| 9,652,838 B1 | 5/2017 | Manmatha et al. |
| 9,655,405 B2 | 5/2017 | Hamill |
| 9,655,519 B2 | 5/2017 | Darty et al. |
| 9,655,548 B2 | 5/2017 | Hong et al. |
| 9,655,558 B2 | 5/2017 | Proud et al. |
| 9,655,565 B2 | 5/2017 | Hampapuram et al. |
| 9,658,066 B2 | 5/2017 | Yuen et al. |
| 9,659,484 B1 | 5/2017 | Mehta et al. |
| 9,662,015 B2 | 5/2017 | Proud et al. |
| 9,662,053 B2 | 5/2017 | Richards et al. |
| 9,662,262 B2 | 5/2017 | Hollander et al. |
| 9,662,445 B2 | 5/2017 | Parikh et al. |
| 9,664,556 B2 | 5/2017 | Chu et al. |
| 9,664,702 B2 | 5/2017 | Holmes et al. |
| 9,669,262 B2 | 6/2017 | Yuen et al. |
| 9,672,393 B1 | 6/2017 | Zhu et al. |
| 9,672,715 B2 | 6/2017 | Roberts et al. |
| 9,672,754 B2 | 6/2017 | Yuen et al. |
| 9,675,273 B2 | 6/2017 | Gluncic |
| 9,675,290 B2 | 6/2017 | Budiman et al. |
| 9,675,809 B2 | 6/2017 | Chow |
| 9,675,878 B2 | 6/2017 | Barney et al. |
| 9,680,831 B2 | 6/2017 | Jooste et al. |
| 9,681,814 B2 | 6/2017 | Galloway et al. |
| 9,681,842 B2 | 6/2017 | Zdeblick et al. |
| 9,685,802 B1 | 6/2017 | Mirov et al. |
| 9,687,194 B2 | 6/2017 | Cantwell et al. |
| 9,687,577 B2 | 6/2017 | Dobrinsky et al. |
| 9,687,658 B2 | 6/2017 | Wu et al. |
| 9,692,230 B2 | 6/2017 | Biederman et al. |
| 9,692,844 B2 | 6/2017 | Messenger et al. |
| 9,692,984 B2 | 6/2017 | Lord |
| 9,693,605 B2 | 7/2017 | Beers |
| 9,693,696 B2 | 7/2017 | Kovacs et al. |
| 9,693,777 B2 | 7/2017 | Schellin et al. |
| 9,696,199 B2 | 7/2017 | Chu et al. |
| 9,700,222 B2 | 7/2017 | Quinlan et al. |
| 9,700,223 B2 | 7/2017 | Quinlan et al. |
| 9,700,234 B2 | 7/2017 | Mickle et al. |
| 9,700,253 B2 | 7/2017 | Estes et al. |
| 9,700,806 B2 | 7/2017 | Ikeda et al. |
| 9,704,209 B2 | 7/2017 | Proud et al. |
| 9,706,956 B2 | 7/2017 | Brockway et al. |
| 9,706,957 B2 | 7/2017 | Wu et al. |
| 9,706,963 B2 | 7/2017 | Gupta et al. |
| 9,706,964 B2 | 7/2017 | Ferber et al. |
| 9,707,466 B2 | 7/2017 | Bleich et al. |
| 9,707,478 B2 | 7/2017 | Barney et al. |
| 9,709,971 B2 | 7/2017 | Ellis |
| 9,712,629 B2 | 7/2017 | Molettiere et al. |
| 9,713,445 B2 | 7/2017 | Freeman et al. |
| 9,713,701 B2 | 7/2017 | Sarkar et al. |
| 9,713,766 B2 | 7/2017 | Barney et al. |
| 9,715,012 B2 | 7/2017 | Fernandes et al. |
| 9,719,990 B2 | 8/2017 | Holmes et al. |
| 9,723,898 B2 | 8/2017 | Proud et al. |
| 9,723,986 B1 | 8/2017 | Mullin et al. |
| 9,724,098 B2 | 8/2017 | Baxter, III et al. |
| 9,724,183 B2 | 8/2017 | Mayer et al. |
| 9,724,509 B2 | 8/2017 | Su et al. |
| 9,724,510 B2 | 8/2017 | Sharma et al. |
| 9,724,511 B2 | 8/2017 | Wei et al. |
| 9,724,517 B2 | 8/2017 | Giftakis et al. |
| 9,724,521 B2 | 8/2017 | Cong et al. |
| 9,724,562 B2 | 8/2017 | Bailly et al. |
| 9,730,025 B2 | 8/2017 | Yuen et al. |
| 9,730,601 B2 | 8/2017 | Sarkar et al. |
| 9,730,619 B2 | 8/2017 | Messenger et al. |
| 9,730,625 B2 | 8/2017 | Krasnow et al. |
| 9,731,104 B2 | 8/2017 | Linden et al. |
| 9,731,194 B2 | 8/2017 | Briggs et al. |
| 9,732,322 B2 | 8/2017 | Dalton et al. |
| 9,734,304 B2 | 8/2017 | Blackadar et al. |
| 9,734,527 B2 | 8/2017 | Collier et al. |
| 9,736,603 B2 | 8/2017 | Osborne et al. |
| 9,737,249 B2 | 8/2017 | Hayter et al. |
| 9,737,263 B1 | 8/2017 | Kumar et al. |
| 9,737,797 B2 | 8/2017 | Barney et al. |
| 9,743,861 B2 | 8/2017 | Giedwoyn et al. |
| 9,747,431 B2 | 8/2017 | Chow |
| 9,749,232 B2 | 8/2017 | Sampath et al. |
| 9,750,441 B2 | 9/2017 | Brauker et al. |
| 9,750,977 B2 | 9/2017 | Yuen et al. |
| 9,752,925 B2 | 9/2017 | Chu et al. |
| 9,755,704 B2 | 9/2017 | Hviid et al. |
| 9,756,169 B2 | 9/2017 | Mehta et al. |
| 9,756,895 B2 | 9/2017 | Rice et al. |
| 9,757,040 B2 | 9/2017 | Islam |
| 9,757,124 B2 | 9/2017 | Schellin et al. |
| 9,757,302 B2 | 9/2017 | Mayer |
| 9,757,510 B2 | 9/2017 | Finan |
| 9,763,489 B2 | 9/2017 | Amos et al. |
| 9,763,490 B2 | 9/2017 | Seiler |
| 9,763,616 B2 | 9/2017 | Dugan |
| 9,764,050 B1 | 9/2017 | Almeida et al. |
| 9,766,959 B2 | 9/2017 | Faaborg et al. |
| 9,769,564 B2 | 9/2017 | Goran et al. |
| 9,770,185 B2 | 9/2017 | Wheeler et al. |
| 9,770,652 B2 | 9/2017 | Barney et al. |
| 9,774,298 B2 | 9/2017 | Kuroda et al. |
| 9,775,543 B2 | 10/2017 | Brister et al. |
| 9,775,987 B2 | 10/2017 | Donofrio et al. |
| 9,776,041 B1 | 10/2017 | Lachwani et al. |
| 9,776,042 B2 | 10/2017 | Prokhorov |
| 9,777,817 B2 | 10/2017 | Strom et al. |
| 9,778,280 B2 | 10/2017 | Yuen et al. |
| 9,779,502 B1 | 10/2017 | Lovberg et al. |
| 9,782,084 B2 | 10/2017 | Maertz |
| 9,782,125 B2 | 10/2017 | Berner, Jr. et al. |
| 9,782,132 B2 | 10/2017 | Golda et al. |
| 9,788,785 B2 | 10/2017 | LeBoeuf |
| 9,789,252 B2 | 10/2017 | Gerber et al. |

(56) References Cited

U.S. PATENT DOCUMENTS

| | | |
|---|---|---|
| 9,789,309 B2 | 10/2017 | Sharma et al. |
| 9,789,315 B2 | 10/2017 | Dacey, Jr. et al. |
| 9,795,323 B2 | 10/2017 | Yuen et al. |
| 9,795,737 B2 | 10/2017 | Finan et al. |
| 9,795,782 B2 | 10/2017 | Krusor et al. |
| 9,797,880 B2 | 10/2017 | Hayter et al. |
| 9,801,547 B2 | 10/2017 | Yuen et al. |
| 9,801,571 B2 | 10/2017 | Hayter |
| 9,801,577 B2 | 10/2017 | Budiman et al. |
| 9,804,150 B2 | 10/2017 | Hayter et al. |
| 9,804,672 B2 | 10/2017 | Anderson et al. |
| 9,808,198 B2 | 11/2017 | Takahashi et al. |
| 9,808,204 B2 | 11/2017 | LeBoeuf et al. |
| 9,810,591 B2 | 11/2017 | Walker |
| 9,810,704 B2 | 11/2017 | Holmes et al. |
| 9,811,730 B2 | 11/2017 | Komogortsev |
| 9,814,388 B2 | 11/2017 | Soro et al. |
| 9,814,400 B1 | 11/2017 | Cendrillon et al. |
| 9,814,886 B2 | 11/2017 | Zhou et al. |
| 9,814,973 B2 | 11/2017 | Barney et al. |
| 9,817,440 B2 | 11/2017 | Longinotti-Buitoni et al. |
| 9,818,092 B2 | 11/2017 | Pennanen |
| 9,820,120 B2 | 11/2017 | deCharms |
| 9,820,698 B2 | 11/2017 | Fonseca et al. |
| 9,826,903 B2 | 11/2017 | Derchak |
| 9,826,922 B2 | 11/2017 | Datta et al. |
| 9,826,940 B1 | 11/2017 | Lengerich |
| 9,826,963 B2 | 11/2017 | Scott et al. |
| 9,827,372 B2 | 11/2017 | Dobbles et al. |
| 9,830,781 B2 | 11/2017 | Mirov et al. |
| 9,833,254 B1 | 12/2017 | Barral et al. |
| 9,833,353 B2 | 12/2017 | Witt et al. |
| 9,836,896 B2 | 12/2017 | Zizi et al. |
| 9,839,422 B2 | 12/2017 | Schellin et al. |
| 9,839,423 B2 | 12/2017 | Vendely et al. |
| 9,846,231 B2 | 12/2017 | D'Angelo et al. |
| 9,847,006 B2 | 12/2017 | Asano |
| 9,847,012 B2 | 12/2017 | Zomet et al. |
| 9,848,668 B2 | 12/2017 | Smith, III |
| 9,848,789 B2 | 12/2017 | Hu et al. |
| 9,849,239 B2 | 12/2017 | Grosman et al. |
| 9,849,364 B2 | 12/2017 | Tran et al. |
| 9,852,736 B2 | 12/2017 | Sharma et al. |
| 9,853,819 B2 | 12/2017 | Truu et al. |
| 9,853,976 B2 | 12/2017 | Zizi et al. |
| 9,854,370 B2 | 12/2017 | Meskens |
| 9,854,872 B2 | 1/2018 | Bertagna et al. |
| 9,854,986 B2 | 1/2018 | Quinlan et al. |
| 9,855,433 B2 | 1/2018 | Shahandeh et al. |
| 9,855,785 B1 | 1/2018 | Nagelberg et al. |
| 9,861,165 B2 | 1/2018 | Schneider et al. |
| 9,861,286 B1 | 1/2018 | Islam |
| 9,861,887 B1 | 1/2018 | Briggs et al. |
| 9,862,222 B1 | 1/2018 | Nagelberg et al. |
| 9,863,823 B2 | 1/2018 | McMillen et al. |
| 9,864,842 B2 | 1/2018 | Hyde et al. |
| 9,868,332 B2 | 1/2018 | Anderson et al. |
| 9,869,973 B2 | 1/2018 | Raymann et al. |
| 9,872,652 B2 | 1/2018 | Salehizadeh et al. |
| 9,872,968 B2 | 1/2018 | de Zambotti et al. |
| 9,874,923 B1 | 1/2018 | Brown et al. |
| 9,876,537 B2 | 1/2018 | Zhu et al. |
| 9,877,523 B2 | 1/2018 | Ellis |
| 9,877,650 B2 | 1/2018 | Muhsin et al. |
| 9,878,096 B2 | 1/2018 | Roy et al. |
| 9,878,159 B2 | 1/2018 | Mashiach |
| 9,879,741 B2 | 1/2018 | Phipps et al. |
| 9,882,610 B1 | 1/2018 | Baker et al. |
| 9,883,800 B2 | 2/2018 | Pekander |
| 9,884,150 B2 | 2/2018 | Jho et al. |
| 9,884,456 B2 | 2/2018 | Schellin et al. |
| 9,885,698 B2 | 2/2018 | Islam |
| 9,886,845 B2 | 2/2018 | Rhoads et al. |
| 9,888,848 B2 | 2/2018 | Samuelsson et al. |
| 9,889,305 B1 | 2/2018 | Hellman et al. |
| 9,894,691 B1 | 2/2018 | Hellman et al. |
| 9,895,063 B1 | 2/2018 | Hannaford et al. |
| 9,895,301 B2 | 2/2018 | Christiano et al. |
| 9,897,985 B2 | 2/2018 | Zeltzer |
| 9,900,287 B1 | 2/2018 | Jooste et al. |
| 9,900,669 B2 | 2/2018 | Touma et al. |
| 9,901,269 B2 | 2/2018 | Hu et al. |
| 9,901,276 B2 | 2/2018 | Sarkar |
| 9,901,305 B2 | 2/2018 | Massey et al. |
| 9,901,741 B2 | 2/2018 | Chapman et al. |
| 9,905,105 B1 | 2/2018 | Ikonen et al. |
| 9,907,909 B2 | 3/2018 | Finan et al. |
| 9,913,509 B2 | 3/2018 | Case, Jr. |
| 9,913,591 B2 | 3/2018 | Lapetina et al. |
| 9,913,599 B2 | 3/2018 | Bernstein et al. |
| 9,913,617 B2 | 3/2018 | Al-Ali et al. |
| 9,913,619 B2 | 3/2018 | Budiman |
| 9,918,183 B2 | 3/2018 | Rhoads et al. |
| 9,918,646 B2 | 3/2018 | Singh Alvarado et al. |
| 9,918,716 B2 | 3/2018 | Baxter, III et al. |
| 9,919,099 B2 | 3/2018 | Tai et al. |
| 9,921,726 B1 | 3/2018 | Sculley et al. |
| 9,922,380 B2 | 3/2018 | Isaacson et al. |
| 9,922,381 B2 | 3/2018 | Isaacson et al. |
| 9,924,760 B2 | 3/2018 | Molyneux et al. |
| 9,931,040 B2 | 4/2018 | Homyk et al. |
| 9,931,578 B2 | 4/2018 | Weston |
| 9,936,763 B2 | 4/2018 | Semperlotti et al. |
| 9,936,890 B2 | 4/2018 | Sarkar et al. |
| 9,936,910 B2 | 4/2018 | Hayter et al. |
| 9,936,916 B2 | 4/2018 | Sahin |
| 9,936,919 B2 | 4/2018 | Baxi et al. |
| 9,942,304 B2 | 4/2018 | Gold |
| 9,943,247 B2 | 4/2018 | Ernst et al. |
| 9,943,267 B2 | 4/2018 | Ferber et al. |
| 9,943,269 B2 | 4/2018 | Muhsin et al. |
| 9,943,461 B1 | 4/2018 | Muench et al. |
| 9,943,697 B2 | 4/2018 | John |
| 9,943,719 B2 | 4/2018 | Smith et al. |
| 9,946,356 B2 | 4/2018 | Liberty |
| 9,950,166 B2 | 4/2018 | Mashiach et al. |
| 9,950,236 B1 | 4/2018 | Jooste et al. |
| 9,952,095 B1 | 4/2018 | Hotelling et al. |
| 9,952,240 B2 | 4/2018 | Holmes et al. |
| 9,953,041 B2 | 4/2018 | Hilsdale et al. |
| 9,955,919 B2 | 5/2018 | LeBoeuf et al. |
| 9,956,393 B2 | 5/2018 | Perez et al. |
| 9,956,470 B2 | 5/2018 | Bleich et al. |
| 9,961,963 B2 | 5/2018 | Schneider et al. |
| 9,965,059 B2 | 5/2018 | Myers et al. |
| 9,968,159 B2 | 5/2018 | Morrison et al. |
| 9,968,238 B2 | 5/2018 | Patel et al. |
| 9,968,788 B2 | 5/2018 | Ecker et al. |
| 9,974,484 B2 | 5/2018 | Kaskoun et al. |
| 9,974,705 B2 | 5/2018 | Rapoport |
| 9,975,196 B2 | 5/2018 | Zhang et al. |
| 9,977,578 B1 | 5/2018 | Pereira et al. |
| 9,980,535 B2 | 5/2018 | Bohnsack et al. |
| 9,984,549 B2 | 5/2018 | Poisner et al. |
| 9,985,825 B2 | 5/2018 | Huang |
| 9,986,771 B2 | 6/2018 | Longinotti-Buitoni et al. |
| 9,986,782 B2 | 6/2018 | Odland et al. |
| 9,986,924 B2 | 6/2018 | Rogers et al. |
| 9,987,489 B2 | 6/2018 | Goodall et al. |
| 9,987,497 B2 | 6/2018 | Kaib et al. |
| 9,991,920 B2 | 6/2018 | Sadasivam et al. |
| 9,993,207 B2 | 6/2018 | Al-Ali et al. |
| 9,993,724 B2 | 6/2018 | Barney et al. |
| 9,998,804 B2 | 6/2018 | Awiszus et al. |
| 9,999,355 B2 | 6/2018 | Kirenko |
| 9,999,728 B2 | 6/2018 | Parikh et al. |
| 2001/0035723 A1 | 11/2001 | Pelrine et al. |
| 2001/0045104 A1 | 11/2001 | Bailey, Sr. et al. |
| 2002/0001588 A1 | 1/2002 | Sinha |
| 2002/0019586 A1 | 2/2002 | Teller et al. |
| 2002/0090487 A1 | 7/2002 | Andersen et al. |
| 2002/0099282 A1 | 7/2002 | Knobbe et al. |
| 2002/0111547 A1 | 8/2002 | Knobbe et al. |
| 2002/0121979 A1 | 9/2002 | Smith |

(56) References Cited

U.S. PATENT DOCUMENTS

| | | |
|---|---|---|
| 2002/0128544 A1 | 9/2002 | Diab et al. |
| 2002/0133196 A1 | 9/2002 | Thompson |
| 2002/0177135 A1 | 11/2002 | Doung et al. |
| 2002/0177782 A1 | 11/2002 | Penner |
| 2002/0183646 A1 | 12/2002 | Stivoric et al. |
| 2003/0004403 A1 | 1/2003 | Drinan et al. |
| 2003/0018369 A1 | 1/2003 | Thompson et al. |
| 2003/0053284 A1 | 3/2003 | Stevenson et al. |
| 2003/0070324 A1 | 4/2003 | Nelson |
| 2003/0107487 A1 | 6/2003 | Korman et al. |
| 2003/0130616 A1 | 7/2003 | Steil et al. |
| 2003/0195404 A1 | 10/2003 | Knobbe et al. |
| 2003/0220579 A1 | 11/2003 | Mault |
| 2004/0002634 A1 | 1/2004 | Nihtila |
| 2004/0034289 A1 | 2/2004 | Teller et al. |
| 2004/0034295 A1 | 2/2004 | Salganicoff |
| 2004/0039243 A1 | 2/2004 | Bearnson et al. |
| 2004/0039254 A1 | 2/2004 | Stivoric et al. |
| 2004/0053290 A1 | 3/2004 | Terbrueggen et al. |
| 2004/0078067 A1 | 4/2004 | Thompson et al. |
| 2004/0133081 A1 | 7/2004 | Teller et al. |
| 2004/0147818 A1 | 7/2004 | Levy et al. |
| 2004/0152956 A1 | 8/2004 | Korman |
| 2004/0152957 A1 | 8/2004 | Stivoric et al. |
| 2004/0158194 A1 | 8/2004 | Wolff et al. |
| 2004/0176822 A1 | 9/2004 | Thompson et al. |
| 2004/0177531 A1 | 9/2004 | DiBenedetto et al. |
| 2004/0186390 A1 | 9/2004 | Ross et al. |
| 2004/0193025 A1 | 9/2004 | Steil et al. |
| 2005/0027463 A1 | 2/2005 | Goode et al. |
| 2005/0043598 A1 | 2/2005 | Goode et al. |
| 2005/0050750 A1 | 3/2005 | Whiting |
| 2005/0053757 A1 | 3/2005 | Andersen et al. |
| 2005/0060030 A1 | 3/2005 | Lashinski et al. |
| 2005/0061323 A1 | 3/2005 | Lee et al. |
| 2005/0065572 A1 | 3/2005 | Hartley et al. |
| 2005/0069162 A1 | 3/2005 | Haykin et al. |
| 2005/0075213 A1 | 4/2005 | Arick |
| 2005/0076909 A1 | 4/2005 | Stahmann et al. |
| 2005/0080322 A1 | 4/2005 | Korman |
| 2005/0091884 A1 | 5/2005 | Omstead et al. |
| 2005/0101845 A1 | 5/2005 | Nihtila |
| 2005/0115561 A1 | 6/2005 | Stahmann et al. |
| 2005/0116820 A1 | 6/2005 | Goldreich |
| 2005/0135948 A1 | 6/2005 | Olsen et al. |
| 2005/0136385 A1 | 6/2005 | Mann et al. |
| 2005/0142070 A1 | 6/2005 | Hartley et al. |
| 2005/0148828 A1 | 7/2005 | Lindsay |
| 2005/0154271 A1 | 7/2005 | Rasdal et al. |
| 2005/0165456 A1 | 7/2005 | Mann et al. |
| 2005/0181973 A1 | 8/2005 | Genove et al. |
| 2005/0182389 A1 | 8/2005 | LaPorte et al. |
| 2005/0183292 A1 | 8/2005 | DiBenedetto et al. |
| 2005/0192557 A1 | 9/2005 | Brauker et al. |
| 2005/0197677 A1 | 9/2005 | Stevenson |
| 2005/0203360 A1 | 9/2005 | Brauker et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0217142 A1 | 10/2005 | Ellis |
| 2005/0222522 A1 | 10/2005 | Heruth et al. |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0247319 A1 | 11/2005 | Berger |
| 2005/0256385 A1 | 11/2005 | Diab et al. |
| 2005/0261609 A1 | 11/2005 | Collings et al. |
| 2005/0267342 A1 | 12/2005 | Blank et al. |
| 2005/0268487 A1 | 12/2005 | Ellis |
| 2006/0020187 A1 | 1/2006 | Brister et al. |
| 2006/0020297 A1 | 1/2006 | Gerber et al. |
| 2006/0030890 A1 | 2/2006 | Cosentino et al. |
| 2006/0047283 A1 | 3/2006 | Evans et al. |
| 2006/0064030 A1 | 3/2006 | Cosentino et al. |
| 2006/0085040 A1 | 4/2006 | VanDanacker |
| 2006/0103538 A1 | 5/2006 | Daniel |
| 2006/0122474 A1 | 6/2006 | Teller et al. |
| 2006/0122864 A1 | 6/2006 | Gottesman et al. |
| 2006/0149324 A1 | 7/2006 | Mann et al. |
| 2006/0149330 A1 | 7/2006 | Mann et al. |
| 2006/0149331 A1 | 7/2006 | Mann et al. |
| 2006/0160205 A1 | 7/2006 | Blackburn et al. |
| 2006/0211942 A1 | 9/2006 | Hoctor et al. |
| 2006/0212096 A1 | 9/2006 | Stevenson |
| 2006/0222566 A1 | 10/2006 | Brauker et al. |
| 2006/0224051 A1 | 10/2006 | Teller et al. |
| 2006/0224109 A1 | 10/2006 | Steil et al. |
| 2006/0230641 A1 | 10/2006 | Vick et al. |
| 2006/0230642 A1 | 10/2006 | Vick et al. |
| 2006/0235472 A1 | 10/2006 | Goetz et al. |
| 2006/0248749 A1 | 11/2006 | Ellis |
| 2006/0248750 A1 | 11/2006 | Rosenberg |
| 2006/0253005 A1 | 11/2006 | Drinan et al. |
| 2006/0264730 A1 | 11/2006 | Stivoric et al. |
| 2006/0265024 A1 | 11/2006 | Goetz et al. |
| 2006/0265025 A1 | 11/2006 | Goetz et al. |
| 2006/0287677 A1 | 12/2006 | Shalev et al. |
| 2006/0293571 A1 | 12/2006 | Bao et al. |
| 2007/0000154 A1 | 1/2007 | DiBenedetto et al. |
| 2007/0000188 A1 | 1/2007 | Smushkovich |
| 2007/0006489 A1 | 1/2007 | Case et al. |
| 2007/0011919 A1 | 1/2007 | Case |
| 2007/0011920 A1 | 1/2007 | DiBenedetto et al. |
| 2007/0015976 A1 | 1/2007 | Miesel et al. |
| 2007/0016381 A1 | 1/2007 | Kamath et al. |
| 2007/0021269 A1 | 1/2007 | Shum |
| 2007/0021979 A1 | 1/2007 | Cosentino et al. |
| 2007/0027371 A1 | 2/2007 | Benaron et al. |
| 2007/0027385 A1 | 2/2007 | Brister et al. |
| 2007/0032706 A1 | 2/2007 | Kamath et al. |
| 2007/0039205 A1 | 2/2007 | Erb et al. |
| 2007/0039209 A1 | 2/2007 | White et al. |
| 2007/0043582 A1 | 2/2007 | Peveto et al. |
| 2007/0060800 A1 | 3/2007 | Drinan et al. |
| 2007/0088226 A1 | 4/2007 | Spence et al. |
| 2007/0088521 A1 | 4/2007 | Shmueli et al. |
| 2007/0098600 A1 | 5/2007 | Kayyem |
| 2007/0100666 A1 | 5/2007 | Stivoric et al. |
| 2007/0106138 A1 | 5/2007 | Beiski et al. |
| 2007/0106172 A1 | 5/2007 | Abreu |
| 2007/0120683 A1 | 5/2007 | Flippen et al. |
| 2007/0123758 A1 | 5/2007 | Miesel et al. |
| 2007/0123779 A1 | 5/2007 | Hoctor et al. |
| 2007/0142955 A1 | 6/2007 | Lin et al. |
| 2007/0146371 A1 | 6/2007 | Dariush |
| 2007/0154030 A1 | 7/2007 | Moses |
| 2007/0157488 A1 | 7/2007 | Guzman |
| 2007/0161919 A1 | 7/2007 | DiLorenzo |
| 2007/0162086 A1 | 7/2007 | DiLorenzo |
| 2007/0162090 A1 | 7/2007 | Penner |
| 2007/0162164 A1 | 7/2007 | Dariush |
| 2007/0167991 A1 | 7/2007 | DiLorenzo |
| 2007/0173705 A1 | 7/2007 | Teller et al. |
| 2007/0173761 A1 | 7/2007 | Kanderian et al. |
| 2007/0179562 A1 | 8/2007 | Nycz |
| 2007/0180736 A1 | 8/2007 | DiBenedetto et al. |
| 2007/0180737 A1 | 8/2007 | DiBenedetto et al. |
| 2007/0189921 A1 | 8/2007 | Duong et al. |
| 2007/0197890 A1 | 8/2007 | Boock et al. |
| 2007/0203966 A1 | 8/2007 | Brauker et al. |
| 2007/0208212 A1 | 9/2007 | DiLorenzo |
| 2007/0208245 A1 | 9/2007 | Brauker et al. |
| 2007/0219639 A1 | 9/2007 | Otto et al. |
| 2007/0239054 A1 | 10/2007 | Giftakis et al. |
| 2007/0239230 A1 | 10/2007 | Giftakis et al. |
| 2007/0247306 A1 | 10/2007 | Case |

(56) References Cited

U.S. PATENT DOCUMENTS

| | | |
|---|---|---|
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0260421 A1 | 11/2007 | Berner et al. |
| 2007/0260491 A1 | 11/2007 | Palmer et al. |
| 2007/0265508 A1 | 11/2007 | Sheikhzadeh-Nadjar et al. |
| 2007/0265704 A1 | 11/2007 | Mayer et al. |
| 2007/0270668 A1 | 11/2007 | Childre et al. |
| 2007/0271817 A1 | 11/2007 | Ellis |
| 2007/0276439 A1 | 11/2007 | Miesel et al. |
| 2007/0282196 A1 | 12/2007 | Birk et al. |
| 2007/0282562 A1 | 12/2007 | Schwartz et al. |
| 2007/0293737 A1 | 12/2007 | Heruth et al. |
| 2008/0000108 A1 | 1/2008 | Ellis |
| 2008/0004642 A1 | 1/2008 | Birk et al. |
| 2008/0005931 A1 | 1/2008 | Ellis |
| 2008/0015421 A1 | 1/2008 | Penner |
| 2008/0020012 A1 | 1/2008 | Ju et al. |
| 2008/0033254 A1 | 2/2008 | Kamath et al. |
| 2008/0048855 A1 | 2/2008 | Berger |
| 2008/0049376 A1 | 2/2008 | Stevenson et al. |
| 2008/0051667 A1 | 2/2008 | Goldreich |
| 2008/0065181 A1 | 3/2008 | Stevenson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0077440 A1 | 3/2008 | Doron |
| 2008/0091092 A1 | 4/2008 | Al-Ali |
| 2008/0097263 A1 | 4/2008 | Grigoriev et al. |
| 2008/0097496 A1 | 4/2008 | Chang et al. |
| 2008/0102096 A1 | 5/2008 | Molin et al. |
| 2008/0103534 A1 | 5/2008 | Gerber |
| 2008/0106419 A1 | 5/2008 | Sakama et al. |
| 2008/0108942 A1 | 5/2008 | Brister et al. |
| 2008/0119703 A1 | 5/2008 | Brister et al. |
| 2008/0119900 A1 | 5/2008 | DiLorenzo |
| 2008/0122657 A1 | 5/2008 | Chen |
| 2008/0129486 A1 | 6/2008 | Jeckelmann et al. |
| 2008/0131362 A1 | 6/2008 | Rousso et al. |
| 2008/0132981 A1 | 6/2008 | Gerber |
| 2008/0132982 A1 | 6/2008 | Gerber |
| 2008/0140161 A1 | 6/2008 | Goetz et al. |
| 2008/0140162 A1 | 6/2008 | Goetz et al. |
| 2008/0140163 A1 | 6/2008 | Keacher et al. |
| 2008/0161654 A1 | 7/2008 | Teller et al. |
| 2008/0161655 A1 | 7/2008 | Teller et al. |
| 2008/0167535 A1 | 7/2008 | Stivoric et al. |
| 2008/0167536 A1 | 7/2008 | Teller et al. |
| 2008/0167537 A1 | 7/2008 | Teller et al. |
| 2008/0167538 A1 | 7/2008 | Teller et al. |
| 2008/0167539 A1 | 7/2008 | Teller et al. |
| 2008/0167700 A1 | 7/2008 | Shalev et al. |
| 2008/0167741 A1 | 7/2008 | Lay et al. |
| 2008/0171919 A1 | 7/2008 | Stivoric et al. |
| 2008/0171920 A1 | 7/2008 | Teller et al. |
| 2008/0171921 A1 | 7/2008 | Teller et al. |
| 2008/0171922 A1 | 7/2008 | Teller et al. |
| 2008/0172102 A1 | 7/2008 | Shalev |
| 2008/0177355 A1 | 7/2008 | Miesel et al. |
| 2008/0180242 A1 | 7/2008 | Cottingham |
| 2008/0188796 A1 | 8/2008 | Steil et al. |
| 2008/0189194 A1 | 8/2008 | Bentvelzen |
| 2008/0195249 A1 | 8/2008 | Rousso et al. |
| 2008/0197126 A1 | 8/2008 | Bourke et al. |
| 2008/0202927 A1 | 8/2008 | Kayyem et al. |
| 2008/0207983 A1 | 8/2008 | Boyden et al. |
| 2008/0208010 A1 | 8/2008 | Boyden et al. |
| 2008/0208538 A1 | 8/2008 | Visser et al. |
| 2008/0214903 A1 | 9/2008 | Orbach |
| 2008/0234598 A1 | 9/2008 | Snyder et al. |
| 2008/0242553 A1 | 10/2008 | Kayyem |
| 2008/0243431 A1 | 10/2008 | Wai |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0254944 A1 | 10/2008 | Muri et al. |
| 2008/0260212 A1 | 10/2008 | Moskal et al. |
| 2008/0275309 A1 | 11/2008 | Stivoric et al. |
| 2008/0275349 A1 | 11/2008 | Halperin et al. |
| 2008/0287751 A1 | 11/2008 | Stivoric et al. |
| 2008/0287817 A1 | 11/2008 | Stivoric et al. |
| 2008/0288027 A1 | 11/2008 | Kroll et al. |
| 2008/0294020 A1 | 11/2008 | Sapounas |
| 2008/0294024 A1 | 11/2008 | Cosentino et al. |
| 2008/0300449 A1 | 12/2008 | Gerber et al. |
| 2008/0300470 A1 | 12/2008 | Gerber et al. |
| 2008/0300649 A1 | 12/2008 | Gerber et al. |
| 2008/0300650 A1 | 12/2008 | Gerber et al. |
| 2008/0300651 A1 | 12/2008 | Gerber et al. |
| 2008/0303728 A1 | 12/2008 | Lee et al. |
| 2008/0306357 A1 | 12/2008 | Korman |
| 2008/0312511 A1 | 12/2008 | Osler et al. |
| 2008/0314395 A1 | 12/2008 | Kovatchev et al. |
| 2009/0012372 A1 | 1/2009 | Burnett et al. |
| 2009/0012766 A1 | 1/2009 | Miyake et al. |
| 2009/0022336 A1 | 1/2009 | Visser et al. |
| 2009/0024161 A1 | 1/2009 | Bonutti et al. |
| 2009/0028957 A1 | 1/2009 | Daniloff |
| 2009/0030263 A1 | 1/2009 | Heruth et al. |
| 2009/0036951 A1 | 2/2009 | Heruth et al. |
| 2009/0040041 A1 | 2/2009 | Janetis et al. |
| 2009/0057147 A1 | 3/2009 | Kayyem |
| 2009/0058635 A1 | 3/2009 | LaLonde et al. |
| 2009/0058636 A1 | 3/2009 | Gaskill et al. |
| 2009/0062825 A1 | 3/2009 | Pool et al. |
| 2009/0062887 A1 | 3/2009 | Mass et al. |
| 2009/0063193 A1 | 3/2009 | Barton et al. |
| 2009/0069869 A1 | 3/2009 | Stouffer et al. |
| 2009/0076343 A1 | 3/2009 | James et al. |
| 2009/0076346 A1 | 3/2009 | James et al. |
| 2009/0082640 A1 | 3/2009 | Kovach et al. |
| 2009/0082641 A1 | 3/2009 | Giftakis et al. |
| 2009/0083070 A1 | 3/2009 | Giftakis et al. |
| 2009/0099626 A1 | 4/2009 | de Juan, Jr. et al. |
| 2009/0099627 A1 | 4/2009 | Molnar et al. |
| 2009/0105605 A1 | 4/2009 | Abreu |
| 2009/0105785 A1 | 4/2009 | Wei et al. |
| 2009/0112071 A1 | 4/2009 | LeBoeuf et al. |
| 2009/0112478 A1 | 4/2009 | Mueller, Jr. et al. |
| 2009/0113295 A1 | 4/2009 | Halpern et al. |
| 2009/0118599 A1 | 5/2009 | Heruth et al. |
| 2009/0118683 A1 | 5/2009 | Hanson et al. |
| 2009/0126233 A1 | 5/2009 | Rastegar et al. |
| 2009/0128487 A1 | 5/2009 | Langereis et al. |
| 2009/0131739 A1 | 5/2009 | Shalev |
| 2009/0135001 A1 | 5/2009 | Yuk |
| 2009/0138207 A1 | 5/2009 | Cosentino et al. |
| 2009/0148496 A1 | 6/2009 | Schmitz et al. |
| 2009/0149148 A1 | 6/2009 | Kurtz et al. |
| 2009/0149797 A1 | 6/2009 | Dacey, Jr. et al. |
| 2009/0149798 A1 | 6/2009 | Dacey, Jr. et al. |
| 2009/0149799 A1 | 6/2009 | Dacey, Jr. et al. |
| 2009/0149895 A1 | 6/2009 | Dacey, Jr. et al. |
| 2009/0149896 A1 | 6/2009 | Dacey, Jr. et al. |
| 2009/0149897 A1 | 6/2009 | Dacey, Jr. et al. |
| 2009/0149914 A1 | 6/2009 | Dacey, Jr. et al. |
| 2009/0151199 A1 | 6/2009 | Connor |
| 2009/0155900 A1 | 6/2009 | Vemuri et al. |
| 2009/0156309 A1 | 6/2009 | Weston et al. |
| 2009/0157147 A1 | 6/2009 | Cauller et al. |
| 2009/0157151 A1 | 6/2009 | Cauller et al. |
| 2009/0163980 A1 | 6/2009 | Stevenson |
| 2009/0163981 A1 | 6/2009 | Stevenson et al. |
| 2009/0171163 A1 | 7/2009 | Mates et al. |
| 2009/0177068 A1 | 7/2009 | Stivoric et al. |
| 2009/0178305 A1 | 7/2009 | Maxwell et al. |
| 2009/0192556 A1 | 7/2009 | Wu et al. |
| 2009/0193689 A1 | 8/2009 | Galica et al. |
| 2009/0198293 A1 | 8/2009 | Cauller et al. |
| 2009/0199429 A1 | 8/2009 | Ellis |
| 2009/0202387 A1 | 8/2009 | Dlugos, Jr. et al. |
| 2009/0204360 A1 | 8/2009 | Ridenour et al. |

(56) References Cited

U.S. PATENT DOCUMENTS

| | | |
|---|---|---|
| 2009/0206087 A1 | 8/2009 | Reinmuller |
| 2009/0222065 A1 | 9/2009 | Dlugos, Jr. et al. |
| 2009/0227862 A1 | 9/2009 | Smith et al. |
| 2009/0228078 A1 | 9/2009 | Zhang et al. |
| 2009/0234916 A1 | 9/2009 | Cosentino et al. |
| 2009/0241378 A1 | 10/2009 | Ellis |
| 2009/0254179 A1 | 10/2009 | Burnett |
| 2009/0259216 A1 | 10/2009 | Drew et al. |
| 2009/0264789 A1 | 10/2009 | Molnar et al. |
| 2009/0264955 A1 | 10/2009 | Giftakis et al. |
| 2009/0264956 A1 | 10/2009 | Rise et al. |
| 2009/0264957 A1 | 10/2009 | Giftakis et al. |
| 2009/0264967 A1 | 10/2009 | Giftakis et al. |
| 2009/0265958 A1 | 10/2009 | DiBenedetto et al. |
| 2009/0270942 A1 | 10/2009 | Heruth et al. |
| 2009/0274737 A1 | 11/2009 | Borck |
| 2009/0276002 A1 | 11/2009 | Sommer et al. |
| 2009/0276004 A1 | 11/2009 | Kronich et al. |
| 2009/0281594 A1 | 11/2009 | King et al. |
| 2009/0281597 A1 | 11/2009 | Parramon et al. |
| 2009/0284368 A1 | 11/2009 | Case, Jr. |
| 2009/0287452 A1 | 11/2009 | Stanley et al. |
| 2009/0292180 A1 | 11/2009 | Mirow |
| 2009/0299428 A1 | 12/2009 | Chow |
| 2009/0305972 A1 | 12/2009 | Chahal et al. |
| 2009/0306740 A1 | 12/2009 | Heruth et al. |
| 2009/0312622 A1 | 12/2009 | Regittnig |
| 2009/0313853 A1 | 12/2009 | Tadin |
| 2009/0326346 A1 | 12/2009 | Kracker et al. |
| 2009/0326350 A1 | 12/2009 | Kracker |
| 2009/0326356 A1 | 12/2009 | Kracker |
| 2010/0015201 A1 | 1/2010 | Borck et al. |
| 2010/0016918 A1 | 1/2010 | Mann et al. |
| 2010/0022856 A1 | 1/2010 | Cinbis et al. |
| 2010/0022861 A1 | 1/2010 | Cinbis et al. |
| 2010/0023089 A1 | 1/2010 | DiLorenzo |
| 2010/0028984 A1 | 2/2010 | Duong et al. |
| 2010/0030043 A1 | 2/2010 | Kuhn |
| 2010/0030088 A1 | 2/2010 | Carney et al. |
| 2010/0030090 A1 | 2/2010 | Zhang et al. |
| 2010/0030286 A1 | 2/2010 | Goetz et al. |
| 2010/0030289 A1 | 2/2010 | Casavant et al. |
| 2010/0030293 A1 | 2/2010 | Sarkar et al. |
| 2010/0035688 A1 | 2/2010 | Picunko |
| 2010/0036211 A1 | 2/2010 | La Rue et al. |
| 2010/0037489 A1 | 2/2010 | Berner, Jr. et al. |
| 2010/0041975 A1 | 2/2010 | Chen et al. |
| 2010/0048242 A1 | 2/2010 | Rhoads et al. |
| 2010/0049010 A1 | 2/2010 | Goldreich |
| 2010/0050478 A1 | 3/2010 | DiBenedetto et al. |
| 2010/0058462 A1 | 3/2010 | Chow |
| 2010/0063347 A1 | 3/2010 | Yomtov et al. |
| 2010/0069841 A1 | 3/2010 | Miesel |
| 2010/0082102 A1 | 4/2010 | Govil et al. |
| 2010/0090477 A1 | 4/2010 | Keating et al. |
| 2010/0094654 A1 | 4/2010 | Stewart |
| 2010/0104470 A1 | 4/2010 | McCabe |
| 2010/0106212 A1 | 4/2010 | Hedberg et al. |
| 2010/0114015 A1 | 5/2010 | Kanderian, Jr. et al. |
| 2010/0114195 A1 | 5/2010 | Burnes et al. |
| 2010/0114196 A1 | 5/2010 | Burnes et al. |
| 2010/0114197 A1 | 5/2010 | Burnes et al. |
| 2010/0114198 A1 | 5/2010 | Donofrio et al. |
| 2010/0114199 A1 | 5/2010 | Krause et al. |
| 2010/0114200 A1 | 5/2010 | Krause et al. |
| 2010/0114201 A1 | 5/2010 | Donofrio et al. |
| 2010/0114202 A1 | 5/2010 | Donofrio et al. |
| 2010/0114203 A1 | 5/2010 | Burnes et al. |
| 2010/0114204 A1 | 5/2010 | Burnes et al. |
| 2010/0114208 A1 | 5/2010 | Donofrio et al. |
| 2010/0114209 A1 | 5/2010 | Krause et al. |
| 2010/0114216 A1 | 5/2010 | Krause et al. |
| 2010/0114217 A1 | 5/2010 | Krause et al. |
| 2010/0114221 A1 | 5/2010 | Krause et al. |
| 2010/0114224 A1 | 5/2010 | Krause et al. |
| 2010/0114237 A1 | 5/2010 | Giftakis et al. |
| 2010/0114241 A1 | 5/2010 | Donofrio et al. |
| 2010/0114244 A1 | 5/2010 | Manda et al. |
| 2010/0121170 A1 | 5/2010 | Rule |
| 2010/0121215 A1 | 5/2010 | Giftakis et al. |
| 2010/0121413 A1 | 5/2010 | Willerton et al. |
| 2010/0122472 A1 | 5/2010 | Griffin et al. |
| 2010/0138379 A1 | 6/2010 | Mott et al. |
| 2010/0139672 A1 | 6/2010 | Kroll et al. |
| 2010/0143871 A1 | 6/2010 | Berger |
| 2010/0144641 A1 | 6/2010 | Popel et al. |
| 2010/0145337 A1 | 6/2010 | Janna et al. |
| 2010/0152573 A1 | 6/2010 | Ritchey et al. |
| 2010/0152815 A1 | 6/2010 | Vandanacker |
| 2010/0160014 A1 | 6/2010 | Galasso et al. |
| 2010/0160800 A1 | 6/2010 | Xi |
| 2010/0160804 A1 | 6/2010 | Qu |
| 2010/0160807 A1 | 6/2010 | Schmidt et al. |
| 2010/0160997 A1 | 6/2010 | Johnson et al. |
| 2010/0161004 A1 | 6/2010 | Najafi et al. |
| 2010/0168538 A1 | 7/2010 | Keenan et al. |
| 2010/0168607 A1 | 7/2010 | Miesel |
| 2010/0168821 A1 | 7/2010 | Johnson et al. |
| 2010/0170115 A1 | 7/2010 | Smith |
| 2010/0174155 A1 | 7/2010 | Heruth et al. |
| 2010/0174180 A1 | 7/2010 | Rousso et al. |
| 2010/0174240 A1 | 7/2010 | Wells et al. |
| 2010/0174349 A1 | 7/2010 | Stevenson et al. |
| 2010/0185064 A1 | 7/2010 | Bandic et al. |
| 2010/0185225 A1 | 7/2010 | Albrecht et al. |
| 2010/0187305 A1 | 7/2010 | Holcomb |
| 2010/0191236 A1 | 7/2010 | Johnson et al. |
| 2010/0191306 A1 | 7/2010 | Stevenson et al. |
| 2010/0194631 A1 | 8/2010 | Janetis et al. |
| 2010/0198034 A1 | 8/2010 | Thomas et al. |
| 2010/0198279 A1 | 8/2010 | Corndorf et al. |
| 2010/0198280 A1 | 8/2010 | Corndorf et al. |
| 2010/0198284 A1 | 8/2010 | Zhou et al. |
| 2010/0198291 A1 | 8/2010 | Sambelashvili et al. |
| 2010/0198308 A1 | 8/2010 | Zhou et al. |
| 2010/0210924 A1 | 8/2010 | Parthasarathy et al. |
| 2010/0217239 A1 | 8/2010 | Mann et al. |
| 2010/0217240 A1 | 8/2010 | Mann et al. |
| 2010/0217241 A1 | 8/2010 | Mann et al. |
| 2010/0217242 A1 | 8/2010 | Mann et al. |
| 2010/0217243 A1 | 8/2010 | Mann |
| 2010/0217244 A1 | 8/2010 | Mann et al. |
| 2010/0222686 A1 | 9/2010 | Fisher et al. |
| 2010/0222802 A1 | 9/2010 | Gillespie, Jr. et al. |
| 2010/0222845 A1 | 9/2010 | Goetz |
| 2010/0222846 A1 | 9/2010 | Goetz |
| 2010/0228314 A1 | 9/2010 | Goetz |
| 2010/0238019 A1 | 9/2010 | Richman et al. |
| 2010/0242303 A1 | 9/2010 | Callahan et al. |
| 2010/0245077 A1 | 9/2010 | Shmueli et al. |
| 2010/0249540 A1 | 9/2010 | Lisogurski |
| 2010/0261526 A1 | 10/2010 | Anderson et al. |
| 2010/0268040 A1 | 10/2010 | Ben-Oren et al. |
| 2010/0268477 A1 | 10/2010 | Mueller, Jr. et al. |
| 2010/0273738 A1 | 10/2010 | Valcke et al. |
| 2010/0274100 A1 | 10/2010 | Behar et al. |
| 2010/0274102 A1 | 10/2010 | Teixeira |
| 2010/0274106 A1 | 10/2010 | Heruth et al. |
| 2010/0274121 A1 | 10/2010 | Ritchey et al. |
| 2010/0280330 A1 | 11/2010 | Samuelsson et al. |
| 2010/0280334 A1 | 11/2010 | Carlson et al. |
| 2010/0280335 A1 | 11/2010 | Carlson et al. |
| 2010/0280336 A1 | 11/2010 | Giftakis et al. |
| 2010/0280574 A1 | 11/2010 | Carlson et al. |
| 2010/0280579 A1 | 11/2010 | Denison et al. |
| 2010/0285981 A1 | 11/2010 | Kayyem |
| 2010/0289971 A1 | 11/2010 | Odland et al. |
| 2010/0305545 A1 | 12/2010 | Kanderian, Jr. et al. |
| 2010/0305665 A1 | 12/2010 | Miesel et al. |
| 2010/0308974 A1 | 12/2010 | Rowland et al. |
| 2010/0311388 A1 | 12/2010 | Flippo et al. |
| 2010/0311640 A1 | 12/2010 | Genove et al. |
| 2010/0312081 A1 | 12/2010 | Benaron et al. |
| 2010/0317955 A1 | 12/2010 | Madsen et al. |

(56) References Cited

U.S. PATENT DOCUMENTS

| | | |
|---|---|---|
| 2010/0318160 A1 | 12/2010 | Stevenson et al. |
| 2010/0321163 A1 | 12/2010 | Stevenson |
| 2010/0324382 A1 | 12/2010 | Cantwell et al. |
| 2010/0324578 A1 | 12/2010 | Bardy |
| 2010/0324579 A1 | 12/2010 | Bardy |
| 2010/0324639 A1 | 12/2010 | Stevenson et al. |
| 2010/0331868 A1 | 12/2010 | Bardy |
| 2010/0331874 A1 | 12/2010 | Bardy |
| 2010/0331932 A1 | 12/2010 | Stevenson et al. |
| 2011/0003664 A1 | 1/2011 | Richard |
| 2011/0004110 A1 | 1/2011 | Shusterman |
| 2011/0022123 A1 | 1/2011 | Stancer et al. |
| 2011/0022140 A1 | 1/2011 | Stevenson et al. |
| 2011/0023343 A1 | 2/2011 | Turner et al. |
| 2011/0029043 A1 | 2/2011 | Frysz et al. |
| 2011/0029269 A1 | 2/2011 | Hayter et al. |
| 2011/0034176 A1 | 2/2011 | Lord et al. |
| 2011/0040197 A1 | 2/2011 | Welch et al. |
| 2011/0040343 A1 | 2/2011 | Johnson et al. |
| 2011/0040546 A1 | 2/2011 | Gerber et al. |
| 2011/0040547 A1 | 2/2011 | Gerber et al. |
| 2011/0043297 A1 | 2/2011 | Stevenson et al. |
| 2011/0044524 A1 | 2/2011 | Wang et al. |
| 2011/0046697 A1 | 2/2011 | Gerber et al. |
| 2011/0054270 A1 | 3/2011 | Derchak |
| 2011/0054359 A1 | 3/2011 | Sazonov et al. |
| 2011/0056093 A1 | 3/2011 | Ellis |
| 2011/0056097 A1 | 3/2011 | Ellis |
| 2011/0057037 A1 | 3/2011 | Frysz et al. |
| 2011/0061647 A1 | 3/2011 | Stahmann et al. |
| 2011/0063088 A1 | 3/2011 | Stevenson et al. |
| 2011/0066079 A1 | 3/2011 | Otto et al. |
| 2011/0074349 A1 | 3/2011 | Ghovanloo |
| 2011/0076984 A1 | 3/2011 | Flippo et al. |
| 2011/0077706 A1 | 3/2011 | Ellingson et al. |
| 2011/0082377 A1 | 4/2011 | Mahajan et al. |
| 2011/0093040 A1 | 4/2011 | Ellingson et al. |
| 2011/0093046 A1 | 4/2011 | Ellingson et al. |
| 2011/0094127 A1 | 4/2011 | Alfred |
| 2011/0098576 A1 | 4/2011 | Hollstien |
| 2011/0105860 A1 | 5/2011 | Houben et al. |
| 2011/0105873 A1 | 5/2011 | Feldman et al. |
| 2011/0105921 A1 | 5/2011 | Wang |
| 2011/0106200 A1 | 5/2011 | Ziegler |
| 2011/0106453 A1 | 5/2011 | Krieftewirth |
| 2011/0112442 A1 | 5/2011 | Meger et al. |
| 2011/0118805 A1 | 5/2011 | Wei et al. |
| 2011/0124983 A1 | 5/2011 | Kroll et al. |
| 2011/0130092 A1 | 6/2011 | Yun et al. |
| 2011/0130636 A1 | 6/2011 | Daniel et al. |
| 2011/0143811 A1 | 6/2011 | Rodriguez |
| 2011/0144463 A1 | 6/2011 | Pesach et al. |
| 2011/0144967 A1 | 6/2011 | Adirovich |
| 2011/0152632 A1 | 6/2011 | Le Neel et al. |
| 2011/0152756 A1 | 6/2011 | Drew |
| 2011/0160623 A1 | 6/2011 | Shalev |
| 2011/0160796 A1 | 6/2011 | Lane et al. |
| 2011/0172504 A1 | 7/2011 | Wegerich |
| 2011/0172545 A1 | 7/2011 | Grudic et al. |
| 2011/0179637 A1 | 7/2011 | Eberman et al. |
| 2011/0180425 A1 | 7/2011 | Kayyem |
| 2011/0183305 A1 | 7/2011 | Orbach |
| 2011/0184267 A1 | 7/2011 | Duke et al. |
| 2011/0184482 A1 | 7/2011 | Eberman et al. |
| 2011/0184483 A1 | 7/2011 | Norton et al. |
| 2011/0190570 A1 | 8/2011 | Zaimi |
| 2011/0190580 A1 | 8/2011 | Bennett et al. |
| 2011/0190581 A1 | 8/2011 | Bennett et al. |
| 2011/0190595 A1 | 8/2011 | Bennett et al. |
| 2011/0190654 A1 | 8/2011 | Hettrick et al. |
| 2011/0208012 A1 | 8/2011 | Gerber et al. |
| 2011/0208015 A1 | 8/2011 | Welch et al. |
| 2011/0212717 A1 | 9/2011 | Rhoads et al. |
| 2011/0237861 A1 | 9/2011 | Pool et al. |
| 2011/0237916 A1 | 9/2011 | Hanson et al. |
| 2011/0245633 A1 | 10/2011 | Goldberg et al. |
| 2011/0249381 A1 | 10/2011 | Diebold |
| 2011/0251516 A1 | 10/2011 | Doerr |
| 2011/0260857 A1 | 10/2011 | Hamill |
| 2011/0264034 A1 | 10/2011 | Roberts et al. |
| 2011/0264058 A1 | 10/2011 | Linden et al. |
| 2011/0273287 A1 | 11/2011 | LaLonde et al. |
| 2011/0275930 A1 | 11/2011 | Jho et al. |
| 2011/0285853 A1 | 11/2011 | Chu |
| 2011/0288600 A1 | 11/2011 | Ritchey et al. |
| 2011/0295335 A1 | 12/2011 | Sharma et al. |
| 2011/0295336 A1 | 12/2011 | Sharma et al. |
| 2011/0301436 A1 | 12/2011 | Teixeira |
| 2011/0301441 A1 | 12/2011 | Bandic et al. |
| 2011/0301662 A1 | 12/2011 | Bar-Yoseph et al. |
| 2011/0305672 A1 | 12/2011 | Dalton et al. |
| 2011/0307027 A1 | 12/2011 | Sharma et al. |
| 2011/0307028 A1 | 12/2011 | Sharma et al. |
| 2011/0314700 A1 | 12/2011 | Case, Jr. |
| 2011/0314702 A1 | 12/2011 | Berner, Jr. et al. |
| 2011/0319785 A1 | 12/2011 | Snyder et al. |
| 2012/0001751 A1 | 1/2012 | Baker et al. |
| 2012/0001920 A1 | 1/2012 | Halpern et al. |
| 2012/0003933 A1 | 1/2012 | Baker et al. |
| 2012/0008714 A1 | 1/2012 | Rizwan |
| 2012/0010543 A1 | 1/2012 | Johnson et al. |
| 2012/0022336 A1 | 1/2012 | Teixeira |
| 2012/0022340 A1 | 1/2012 | Heruth et al. |
| 2012/0022350 A1 | 1/2012 | Teixeira |
| 2012/0022384 A1 | 1/2012 | Teixeira |
| 2012/0022805 A1 | 1/2012 | Teixeira et al. |
| 2012/0022844 A1 | 1/2012 | Teixeira |
| 2012/0029586 A1 | 2/2012 | Kumar et al. |
| 2012/0053585 A1 | 3/2012 | Nycz et al. |
| 2012/0058106 A1 | 3/2012 | Chahal et al. |
| 2012/0059389 A1 | 3/2012 | Larson et al. |
| 2012/0059434 A1 | 3/2012 | Nycz |
| 2012/0065507 A1 | 3/2012 | Brunke |
| 2012/0073165 A1 | 3/2012 | McKeown |
| 2012/0083650 A1 | 4/2012 | Raven |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0086550 A1 | 4/2012 | LeBlanc et al. |
| 2012/0094649 A1 | 4/2012 | Porrati et al. |
| 2012/0095306 A1 | 4/2012 | Egozi |
| 2012/0108998 A1 | 5/2012 | Molnar et al. |
| 2012/0109237 A1 | 5/2012 | Xiao et al. |
| 2012/0116475 A1 | 5/2012 | Nelson et al. |
| 2012/0123221 A1 | 5/2012 | Windolf |
| 2012/0123232 A1 | 5/2012 | Najarian et al. |
| 2012/0130286 A1 | 5/2012 | Miesel et al. |
| 2012/0130444 A1 | 5/2012 | Wei et al. |
| 2012/0132211 A1 | 5/2012 | Halperin et al. |
| 2012/0136261 A1 | 5/2012 | Sethi et al. |
| 2012/0136413 A1 | 5/2012 | Bonde et al. |
| 2012/0144068 A1 | 6/2012 | Lay et al. |
| 2012/0149996 A1 | 6/2012 | Stivoric et al. |
| 2012/0150258 A1 | 6/2012 | Miesel et al. |
| 2012/0161901 A1 | 6/2012 | Stevenson et al. |
| 2012/0167325 A1 | 7/2012 | Omidi |
| 2012/0172652 A1 | 7/2012 | Dacey, Jr. et al. |
| 2012/0184878 A1 | 7/2012 | Najafi et al. |
| 2012/0190386 A1 | 7/2012 | Anderson |
| 2012/0197336 A1 | 8/2012 | Su |
| 2012/0197337 A1 | 8/2012 | Su et al. |
| 2012/0197338 A1 | 8/2012 | Su et al. |
| 2012/0197349 A1 | 8/2012 | Griswold et al. |
| 2012/0197350 A1 | 8/2012 | Roberts et al. |
| 2012/0203079 A1 | 8/2012 | McLaughlin |
| 2012/0203118 A1 | 8/2012 | Samuelsson et al. |
| 2012/0203131 A1 | 8/2012 | DiLorenzo |
| 2012/0220986 A1 | 8/2012 | Wolff et al. |
| 2012/0223705 A1 | 9/2012 | Lowery et al. |
| 2012/0226118 A1 | 9/2012 | Delbeke et al. |
| 2012/0226471 A1 | 9/2012 | Yuen et al. |

(56) References Cited

U.S. PATENT DOCUMENTS

| | | |
|---|---|---|
| 2012/0226472 A1 | 9/2012 | Yuen et al. |
| 2012/0232012 A1 | 9/2012 | Popel et al. |
| 2012/0234111 A1 | 9/2012 | Molyneux et al. |
| 2012/0234433 A1 | 9/2012 | Shih et al. |
| 2012/0245439 A1 | 9/2012 | Andre et al. |
| 2012/0249324 A1 | 10/2012 | Richman et al. |
| 2012/0258776 A1 | 10/2012 | Lord et al. |
| 2012/0265026 A1 | 10/2012 | Shenasa et al. |
| 2012/0265031 A1 | 10/2012 | Feldman et al. |
| 2012/0273354 A1 | 11/2012 | Orhan et al. |
| 2012/0277545 A1 | 11/2012 | Teixeira |
| 2012/0277546 A1 | 11/2012 | Soykan et al. |
| 2012/0277859 A1 | 11/2012 | Govil et al. |
| 2012/0283577 A1 | 11/2012 | LeBoeuf et al. |
| 2012/0283578 A1 | 11/2012 | LeBoeuf et al. |
| 2012/0291563 A1 | 11/2012 | Schrock et al. |
| 2012/0291564 A1 | 11/2012 | Amos et al. |
| 2012/0293326 A1 | 11/2012 | Case, Jr. |
| 2012/0296184 A1 | 11/2012 | LeBoeuf et al. |
| 2012/0296399 A1 | 11/2012 | Cauller et al. |
| 2012/0302874 A1 | 11/2012 | Hollstien |
| 2012/0311885 A1 | 12/2012 | Moreshead |
| 2012/0318781 A1 | 12/2012 | Lavin, Jr. |
| 2012/0321759 A1 | 12/2012 | Marinkovich et al. |
| 2012/0324763 A1 | 12/2012 | Ellis |
| 2012/0330112 A1 | 12/2012 | Lamego et al. |
| 2013/0006076 A1 | 1/2013 | McHale et al. |
| 2013/0008058 A1 | 1/2013 | Jasmine |
| 2013/0018239 A1 | 1/2013 | Lisogurski |
| 2013/0018668 A1 | 1/2013 | Goldberg et al. |
| 2013/0019503 A1 | 1/2013 | Vogt |
| 2013/0019694 A1 | 1/2013 | Molyneux et al. |
| 2013/0023954 A1 | 1/2013 | Meskens |
| 2013/0030255 A1 | 1/2013 | Ben |
| 2013/0030259 A1 | 1/2013 | Thomsen et al. |
| 2013/0035544 A1 | 2/2013 | Pool et al. |
| 2013/0035575 A1 | 2/2013 | Mayou et al. |
| 2013/0035740 A1 | 2/2013 | Sharma et al. |
| 2013/0035865 A1 | 2/2013 | Mayou et al. |
| 2013/0035871 A1 | 2/2013 | Mayou et al. |
| 2013/0053657 A1 | 2/2013 | Ziarno et al. |
| 2013/0053711 A1 | 2/2013 | Kotlanka et al. |
| 2013/0053913 A1 | 2/2013 | Koh et al. |
| 2013/0060098 A1 | 3/2013 | Thomsen et al. |
| 2013/0064388 A1 | 3/2013 | Jacobs |
| 2013/0067775 A1 | 3/2013 | Ellis |
| 2013/0070387 A1 | 3/2013 | Stevenson et al. |
| 2013/0072998 A1 | 3/2013 | Su et al. |
| 2013/0073254 A1 | 3/2013 | Yuen et al. |
| 2013/0073255 A1 | 3/2013 | Yuen et al. |
| 2013/0074614 A1 | 3/2013 | Holmes et al. |
| 2013/0078149 A1 | 3/2013 | Holmes et al. |
| 2013/0078244 A1 | 3/2013 | Christiano et al. |
| 2013/0078624 A1 | 3/2013 | Holmes et al. |
| 2013/0078625 A1 | 3/2013 | Holmes et al. |
| 2013/0078733 A1 | 3/2013 | Holmes et al. |
| 2013/0079236 A1 | 3/2013 | Holmes |
| 2013/0079599 A1 | 3/2013 | Holmes et al. |
| 2013/0079646 A1 | 3/2013 | Bhunia et al. |
| 2013/0079840 A1 | 3/2013 | Su et al. |
| 2013/0080113 A1 | 3/2013 | Yuen et al. |
| 2013/0082837 A1 | 4/2013 | Cosentino et al. |
| 2013/0085401 A1 | 4/2013 | Zhang et al. |
| 2013/0085408 A1 | 4/2013 | Pool |
| 2013/0085679 A1 | 4/2013 | Budiman |
| 2013/0092564 A1 | 4/2013 | Doherty |
| 2013/0096843 A1 | 4/2013 | Yuen et al. |
| 2013/0102859 A1 | 4/2013 | Schechter |
| 2013/0104288 A1 | 5/2013 | Schlottau et al. |
| 2013/0109946 A1 | 5/2013 | Shim et al. |
| 2013/0109997 A1 | 5/2013 | Linke et al. |
| 2013/0114869 A1 | 5/2013 | Hernandez Stark et al. |
| 2013/0116664 A1 | 5/2013 | Tai et al. |
| 2013/0116665 A1 | 5/2013 | Humayun et al. |
| 2013/0116666 A1 | 5/2013 | Shih et al. |
| 2013/0116667 A1 | 5/2013 | Ricotti et al. |
| 2013/0118340 A1 | 5/2013 | D'Amours |
| 2013/0124039 A1 | 5/2013 | Abreu |
| 2013/0131679 A1 | 5/2013 | Janna et al. |
| 2013/0135108 A1 | 5/2013 | Alameh et al. |
| 2013/0147622 A1 | 6/2013 | LaLonde et al. |
| 2013/0151196 A1 | 6/2013 | Yuen et al. |
| 2013/0154838 A1 | 6/2013 | Alameh et al. |
| 2013/0154851 A1 | 6/2013 | Gaskill et al. |
| 2013/0158369 A1 | 6/2013 | Yuen et al. |
| 2013/0158372 A1 | 6/2013 | Haisley et al. |
| 2013/0158473 A1 | 6/2013 | Kanderian, Jr. et al. |
| 2013/0158503 A1 | 6/2013 | Kanderian, Jr. et al. |
| 2013/0165819 A1 | 6/2013 | Tieu |
| 2013/0165901 A1 | 6/2013 | Ruchti et al. |
| 2013/0172759 A1 | 7/2013 | Melker et al. |
| 2013/0179382 A1 | 7/2013 | Fritsch et al. |
| 2013/0185003 A1 | 7/2013 | Carbeck et al. |
| 2013/0190638 A1 | 7/2013 | Chon et al. |
| 2013/0191513 A1 | 7/2013 | Kamen et al. |
| 2013/0195806 A1 | 8/2013 | Gay et al. |
| 2013/0198463 A1 | 8/2013 | Hintz |
| 2013/0213144 A1 | 8/2013 | Rice et al. |
| 2013/0213145 A1 | 8/2013 | Owings et al. |
| 2013/0213146 A1 | 8/2013 | Amos et al. |
| 2013/0213147 A1 | 8/2013 | Rice et al. |
| 2013/0217440 A1 | 8/2013 | Lord et al. |
| 2013/0217979 A1 | 8/2013 | Blackadar et al. |
| 2013/0218070 A1 | 8/2013 | Burnett et al. |
| 2013/0218232 A1 | 8/2013 | Giftakis et al. |
| 2013/0225968 A1 | 8/2013 | Auvray et al. |
| 2013/0229287 A1 | 9/2013 | Samuelsson et al. |
| 2013/0233324 A1 | 9/2013 | Witt et al. |
| 2013/0238049 A1 | 9/2013 | Simon et al. |
| 2013/0238050 A1 | 9/2013 | Simon et al. |
| 2013/0238056 A1 | 9/2013 | Poore et al. |
| 2013/0243799 A1 | 9/2013 | Chahal et al. |
| 2013/0245401 A1 | 9/2013 | Estes et al. |
| 2013/0245462 A1 | 9/2013 | Capdevila et al. |
| 2013/0245480 A1 | 9/2013 | Crockford |
| 2013/0245711 A1 | 9/2013 | Simon et al. |
| 2013/0245712 A1 | 9/2013 | Simon et al. |
| 2013/0245981 A1 | 9/2013 | Estes et al. |
| 2013/0253297 A1 | 9/2013 | Johnson et al. |
| 2013/0253334 A1 | 9/2013 | Al-Ali et al. |
| 2013/0253351 A1 | 9/2013 | Qu |
| 2013/0253380 A1 | 9/2013 | Miesel et al. |
| 2013/0253660 A1 | 9/2013 | Nycz et al. |
| 2013/0263349 A1 | 10/2013 | Roser |
| 2013/0265157 A1 | 10/2013 | Case, Jr. |
| 2013/0268029 A1 | 10/2013 | Cauller et al. |
| 2013/0268236 A1 | 10/2013 | Yuen et al. |
| 2013/0273968 A1 | 10/2013 | Rhoads et al. |
| 2013/0274584 A1 | 10/2013 | Finlay et al. |
| 2013/0274705 A1 | 10/2013 | Burnes et al. |
| 2013/0278435 A1 | 10/2013 | Ellis |
| 2013/0278436 A1 | 10/2013 | Ellis |
| 2013/0282322 A1 | 10/2013 | Hayter et al. |
| 2013/0282646 A1 | 10/2013 | Mott et al. |
| 2013/0289424 A1 | 10/2013 | Brockway et al. |
| 2013/0289446 A1 | 10/2013 | Stone et al. |
| 2013/0289529 A1 | 10/2013 | Caira et al. |
| 2013/0289659 A1 | 10/2013 | Nelson et al. |
| 2013/0289664 A1 | 10/2013 | Johanek |
| 2013/0294969 A1 | 11/2013 | Chen et al. |
| 2013/0295894 A1 | 11/2013 | Rhoads et al. |
| 2013/0296669 A1 | 11/2013 | Chen et al. |
| 2013/0296670 A1 | 11/2013 | Chen et al. |
| 2013/0297220 A1 | 11/2013 | Yuen et al. |
| 2013/0297330 A1 | 11/2013 | Kamen et al. |
| 2013/0297344 A1 | 11/2013 | Cosentino et al. |
| 2013/0303843 A1 | 11/2013 | Raven |
| 2013/0310706 A1 | 11/2013 | Stone et al. |
| 2013/0310896 A1 | 11/2013 | Mass |
| 2013/0312291 A1 | 11/2013 | Berner, Jr. et al. |
| 2013/0317580 A1 | 11/2013 | Simon et al. |
| 2013/0317584 A1 | 11/2013 | Stevenson et al. |
| 2013/0317753 A1 | 11/2013 | Kamen et al. |
| 2013/0325394 A1 | 12/2013 | Yuen et al. |

(56) References Cited

U.S. PATENT DOCUMENTS

| | | |
|---|---|---|
| 2013/0325396 A1 | 12/2013 | Yuen et al. |
| 2013/0325404 A1 | 12/2013 | Yuen et al. |
| 2013/0326912 A1 | 12/2013 | Lindsay et al. |
| 2013/0331660 A1 | 12/2013 | Al-Ali et al. |
| 2013/0331919 A1 | 12/2013 | Zhang et al. |
| 2013/0333054 A1 | 12/2013 | Duke |
| 2013/0338448 A1 | 12/2013 | Libbus et al. |
| 2013/0338494 A1 | 12/2013 | Wiley et al. |
| 2013/0338768 A1 | 12/2013 | Boyden et al. |
| 2013/0338769 A1 | 12/2013 | Boyden et al. |
| 2013/0338770 A1 | 12/2013 | Boyden et al. |
| 2013/0338771 A1 | 12/2013 | Boyden et al. |
| 2013/0338772 A1 | 12/2013 | Boyden et al. |
| 2013/0338773 A1 | 12/2013 | Boyden et al. |
| 2013/0345561 A1 | 12/2013 | Quigley |
| 2014/0005633 A1 | 1/2014 | Finan |
| 2014/0012105 A1 | 1/2014 | LeBoeuf et al. |
| 2014/0012111 A1 | 1/2014 | Snyder et al. |
| 2014/0018644 A1 | 1/2014 | Colvin, Jr. et al. |
| 2014/0025447 A1 | 1/2014 | Odland et al. |
| 2014/0031787 A1 | 1/2014 | Burnes et al. |
| 2014/0033572 A1 | 2/2014 | Steier et al. |
| 2014/0035761 A1 | 2/2014 | Burton et al. |
| 2014/0036643 A1 | 2/2014 | Messenger et al. |
| 2014/0039383 A1 | 2/2014 | Dobbles et al. |
| 2014/0039804 A1 | 2/2014 | Park et al. |
| 2014/0039839 A1 | 2/2014 | Yuen et al. |
| 2014/0039840 A1 | 2/2014 | Yuen et al. |
| 2014/0039841 A1 | 2/2014 | Yuen et al. |
| 2014/0039842 A1 | 2/2014 | Yuen et al. |
| 2014/0043149 A1 | 2/2014 | Cowan et al. |
| 2014/0045757 A1 | 2/2014 | Popel et al. |
| 2014/0046391 A1 | 2/2014 | Cowan et al. |
| 2014/0048214 A1 | 2/2014 | Dhillon |
| 2014/0049377 A1 | 2/2014 | Krusor et al. |
| 2014/0051949 A1 | 2/2014 | Old et al. |
| 2014/0051962 A1 | 2/2014 | Krusor et al. |
| 2014/0052091 A1 | 2/2014 | Dobbles et al. |
| 2014/0052092 A1 | 2/2014 | Dobbles et al. |
| 2014/0052093 A1 | 2/2014 | Dobbles et al. |
| 2014/0052094 A1 | 2/2014 | Dobbles et al. |
| 2014/0052095 A1 | 2/2014 | Dobbles et al. |
| 2014/0052790 A1 | 2/2014 | Yuen et al. |
| 2014/0056757 A1 | 2/2014 | Chen et al. |
| 2014/0058221 A1 | 2/2014 | Old et al. |
| 2014/0059897 A1 | 3/2014 | Sayed |
| 2014/0062717 A1 | 3/2014 | Mudumbai et al. |
| 2014/0062718 A1 | 3/2014 | LaLonde et al. |
| 2014/0065153 A1 | 3/2014 | Christiano et al. |
| 2014/0066844 A1 | 3/2014 | Rule |
| 2014/0066884 A1 | 3/2014 | Keenan et al. |
| 2014/0066885 A1 | 3/2014 | Keenan et al. |
| 2014/0066886 A1 | 3/2014 | Roy et al. |
| 2014/0066887 A1 | 3/2014 | Mastrototaro et al. |
| 2014/0066888 A1 | 3/2014 | Parikh et al. |
| 2014/0066889 A1 | 3/2014 | Grosman et al. |
| 2014/0066892 A1 | 3/2014 | Keenan et al. |
| 2014/0067278 A1 | 3/2014 | Yuen et al. |
| 2014/0067423 A1 | 3/2014 | Joao |
| 2014/0073043 A1 | 3/2014 | Holmes |
| 2014/0073704 A1 | 3/2014 | Ju et al. |
| 2014/0073839 A1 | 3/2014 | Yomtov et al. |
| 2014/0073969 A1 | 3/2014 | Zou et al. |
| 2014/0077956 A1 | 3/2014 | Sampath et al. |
| 2014/0080428 A1 | 3/2014 | Rhoads et al. |
| 2014/0081076 A1 | 3/2014 | Schutt et al. |
| 2014/0081100 A1 | 3/2014 | Muhsin et al. |
| 2014/0081665 A1 | 3/2014 | Holmes |
| 2014/0081667 A1 | 3/2014 | Joao |
| 2014/0082963 A1 | 3/2014 | Beers |
| 2014/0088393 A1 | 3/2014 | Bernstein et al. |
| 2014/0088664 A1 | 3/2014 | Sharma et al. |
| 2014/0088922 A1 | 3/2014 | Messenger et al. |
| 2014/0089399 A1 | 3/2014 | Chun et al. |
| 2014/0089514 A1 | 3/2014 | Messenger et al. |
| 2014/0095420 A1 | 4/2014 | Chun et al. |
| 2014/0100432 A1 | 4/2014 | Golda et al. |
| 2014/0107433 A1 | 4/2014 | Wegerich |
| 2014/0107509 A1 | 4/2014 | Banet et al. |
| 2014/0107511 A1 | 4/2014 | Banet et al. |
| 2014/0107513 A1 | 4/2014 | Banet et al. |
| 2014/0107567 A1 | 4/2014 | Goetz |
| 2014/0108020 A1 | 4/2014 | Sharma et al. |
| 2014/0114278 A1 | 4/2014 | Dobbles et al. |
| 2014/0118138 A1 | 5/2014 | Cobelli et al. |
| 2014/0118166 A1 | 5/2014 | Hampapuram et al. |
| 2014/0123838 A1 | 5/2014 | D'Amours |
| 2014/0128803 A1 | 5/2014 | Dobbles et al. |
| 2014/0130370 A1 | 5/2014 | Knudson et al. |
| 2014/0135594 A1 | 5/2014 | Yuen et al. |
| 2014/0135631 A1 | 5/2014 | Brumback et al. |
| 2014/0139405 A1 | 5/2014 | Ribble et al. |
| 2014/0142403 A1 | 5/2014 | Brumback et al. |
| 2014/0142549 A1 | 5/2014 | Su et al. |
| 2014/0142958 A1 | 5/2014 | Sharma et al. |
| 2014/0144049 A1 | 5/2014 | Ellis |
| 2014/0145915 A1 | 5/2014 | Ribble et al. |
| 2014/0156043 A1 | 6/2014 | Blackadar et al. |
| 2014/0156228 A1 | 6/2014 | Molettiere et al. |
| 2014/0163432 A1 | 6/2014 | Dacey, Jr. et al. |
| 2014/0163483 A1 | 6/2014 | Dacey, Jr. et al. |
| 2014/0163517 A1 | 6/2014 | Finan et al. |
| 2014/0163644 A1 | 6/2014 | Scott et al. |
| 2014/0163647 A1 | 6/2014 | Dacey, Jr. et al. |
| 2014/0163927 A1 | 6/2014 | Molettiere et al. |
| 2014/0164320 A1 | 6/2014 | Yuen et al. |
| 2014/0164611 A1 | 6/2014 | Molettiere et al. |
| 2014/0170735 A1 | 6/2014 | Holmes |
| 2014/0171749 A1 | 6/2014 | Chin et al. |
| 2014/0172310 A1 | 6/2014 | Chin et al. |
| 2014/0172362 A1 | 6/2014 | Burton et al. |
| 2014/0176475 A1 | 6/2014 | Myers et al. |
| 2014/0180020 A1 | 6/2014 | Stivoric et al. |
| 2014/0180021 A1 | 6/2014 | Stivoric et al. |
| 2014/0180022 A1 | 6/2014 | Stivoric et al. |
| 2014/0180023 A1 | 6/2014 | Stivoric et al. |
| 2014/0180137 A1 | 6/2014 | Stivoric et al. |
| 2014/0180240 A1 | 6/2014 | Finan et al. |
| 2014/0180358 A1 | 6/2014 | Giftakis et al. |
| 2014/0182166 A1 | 7/2014 | Ellis |
| 2014/0186238 A1 | 7/2014 | Holmes et al. |
| 2014/0188516 A1 | 7/2014 | Kamen et al. |
| 2014/0191866 A1 | 7/2014 | Yuen et al. |
| 2014/0191867 A1 | 7/2014 | Yuen et al. |
| 2014/0194701 A1 | 7/2014 | Drinan et al. |
| 2014/0200421 A1 | 7/2014 | Gilland |
| 2014/0201024 A1 | 7/2014 | Collier et al. |
| 2014/0203797 A1 | 7/2014 | Stivoric et al. |
| 2014/0206955 A1 | 7/2014 | Stivoric et al. |
| 2014/0206959 A1 | 7/2014 | Samuelsson et al. |
| 2014/0206976 A1 | 7/2014 | Thompson et al. |
| 2014/0213855 A1 | 7/2014 | Teller et al. |
| 2014/0213856 A1 | 7/2014 | Teller et al. |
| 2014/0213857 A1 | 7/2014 | Teller et al. |
| 2014/0213926 A1 | 7/2014 | Vaidyanathan |
| 2014/0213940 A1 | 7/2014 | Mayer |
| 2014/0213941 A1 | 7/2014 | Johnson et al. |
| 2014/0214502 A1 | 7/2014 | Bahl et al. |
| 2014/0221732 A1 | 8/2014 | Dayton et al. |
| 2014/0221769 A1 | 8/2014 | Teller et al. |
| 2014/0221770 A1 | 8/2014 | Teller et al. |
| 2014/0221774 A1 | 8/2014 | Teller et al. |
| 2014/0221784 A1 | 8/2014 | Pacione et al. |
| 2014/0221785 A1 | 8/2014 | Pacione et al. |
| 2014/0221787 A1 | 8/2014 | Teller et al. |
| 2014/0221788 A1 | 8/2014 | Teller et al. |
| 2014/0221789 A1 | 8/2014 | Pacione et al. |
| 2014/0221790 A1 | 8/2014 | Pacione et al. |
| 2014/0221791 A1 | 8/2014 | Pacione et al. |
| 2014/0221855 A1 | 8/2014 | McCaffrey |
| 2014/0222101 A1 | 8/2014 | Miesel et al. |
| 2014/0222106 A1 | 8/2014 | Sharma et al. |
| 2014/0222173 A1 | 8/2014 | Giedwoyn et al. |
| 2014/0222174 A1 | 8/2014 | Teller et al. |

(56) References Cited

U.S. PATENT DOCUMENTS

| | | |
|---|---|---|
| 2014/0223406 A1 | 8/2014 | Teller et al. |
| 2014/0223407 A1 | 8/2014 | Teller et al. |
| 2014/0223421 A1 | 8/2014 | Carter et al. |
| 2014/0228649 A1 | 8/2014 | Rayner et al. |
| 2014/0228911 A1 | 8/2014 | Sharma et al. |
| 2014/0232516 A1 | 8/2014 | Stivoric et al. |
| 2014/0234949 A1 | 8/2014 | Wasson et al. |
| 2014/0236105 A1 | 8/2014 | Hanson et al. |
| 2014/0236493 A1 | 8/2014 | Park et al. |
| 2014/0236536 A1 | 8/2014 | Hayter et al. |
| 2014/0236538 A1 | 8/2014 | Messenger et al. |
| 2014/0237028 A1 | 8/2014 | Messenger et al. |
| 2014/0239528 A1 | 8/2014 | Govil et al. |
| 2014/0240122 A1 | 8/2014 | Roberts et al. |
| 2014/0244395 A1 | 8/2014 | Case, Jr. |
| 2014/0245161 A1 | 8/2014 | Yuen et al. |
| 2014/0245783 A1 | 9/2014 | Proud et al. |
| 2014/0245784 A1 | 9/2014 | Proud et al. |
| 2014/0245785 A1 | 9/2014 | Proud et al. |
| 2014/0245786 A1 | 9/2014 | Proud et al. |
| 2014/0245787 A1 | 9/2014 | Proud et al. |
| 2014/0245788 A1 | 9/2014 | Proud et al. |
| 2014/0245789 A1 | 9/2014 | Proud et al. |
| 2014/0245790 A1 | 9/2014 | Proud et al. |
| 2014/0245791 A1 | 9/2014 | Proud et al. |
| 2014/0246497 A1 | 9/2014 | Proud et al. |
| 2014/0246498 A1 | 9/2014 | Proud et al. |
| 2014/0246499 A1 | 9/2014 | Proud et al. |
| 2014/0246500 A1 | 9/2014 | Proud et al. |
| 2014/0246501 A1 | 9/2014 | Proud et al. |
| 2014/0246502 A1 | 9/2014 | Proud et al. |
| 2014/0246917 A1 | 9/2014 | Proud et al. |
| 2014/0247136 A1 | 9/2014 | Proud et al. |
| 2014/0247137 A1 | 9/2014 | Proud et al. |
| 2014/0247142 A1 | 9/2014 | Proud |
| 2014/0247143 A1 | 9/2014 | Proud |
| 2014/0247144 A1 | 9/2014 | Proud |
| 2014/0247146 A1 | 9/2014 | Proud |
| 2014/0247147 A1 | 9/2014 | Proud |
| 2014/0247149 A1 | 9/2014 | Proud |
| 2014/0247150 A1 | 9/2014 | Proud |
| 2014/0247151 A1 | 9/2014 | Proud et al. |
| 2014/0247154 A1 | 9/2014 | Proud |
| 2014/0247155 A1 | 9/2014 | Proud |
| 2014/0247156 A1 | 9/2014 | Proud |
| 2014/0249379 A1 | 9/2014 | Proud |
| 2014/0249594 A1 | 9/2014 | Sharma et al. |
| 2014/0249600 A1 | 9/2014 | Heruth et al. |
| 2014/0249605 A1 | 9/2014 | Heruth et al. |
| 2014/0249760 A1 | 9/2014 | Proud et al. |
| 2014/0249774 A1 | 9/2014 | Yuen et al. |
| 2014/0249853 A1 | 9/2014 | Proud et al. |
| 2014/0250726 A1 | 9/2014 | Meschter |
| 2014/0257055 A1 | 9/2014 | Pacione et al. |
| 2014/0257058 A1 | 9/2014 | Clarysse et al. |
| 2014/0257437 A1 | 9/2014 | Simon et al. |
| 2014/0257540 A1 | 9/2014 | Pacione et al. |
| 2014/0258220 A1 | 9/2014 | Yuen et al. |
| 2014/0259798 A1 | 9/2014 | Hollander |
| 2014/0260677 A1 | 9/2014 | Dojan et al. |
| 2014/0260689 A1 | 9/2014 | Walker |
| 2014/0266939 A1 | 9/2014 | Baringer et al. |
| 2014/0273824 A1 | 9/2014 | Fenner et al. |
| 2014/0273858 A1 | 9/2014 | Panther et al. |
| 2014/0275812 A1 | 9/2014 | Stivoric et al. |
| 2014/0275813 A1 | 9/2014 | Stivoric et al. |
| 2014/0275850 A1 | 9/2014 | Venkatraman et al. |
| 2014/0275852 A1 | 9/2014 | Hong et al. |
| 2014/0275854 A1 | 9/2014 | Venkatraman et al. |
| 2014/0275886 A1 | 9/2014 | Teixeira |
| 2014/0276119 A1 | 9/2014 | Venkatraman et al. |
| 2014/0276130 A1 | 9/2014 | Mirelman et al. |
| 2014/0276192 A1 | 9/2014 | Stivoric et al. |
| 2014/0276554 A1 | 9/2014 | Finan et al. |
| 2014/0276555 A1 | 9/2014 | Morales |
| 2014/0277250 A1 | 9/2014 | Su et al. |
| 2014/0277277 A1 | 9/2014 | Gordon et al. |
| 2014/0277631 A1 | 9/2014 | Rice et al. |
| 2014/0277632 A1 | 9/2014 | Walker |
| 2014/0277658 A1 | 9/2014 | Hanft |
| 2014/0278220 A1 | 9/2014 | Yuen |
| 2014/0278229 A1 | 9/2014 | Hong et al. |
| 2014/0285311 A1 | 9/2014 | Ellis |
| 2014/0285396 A1 | 9/2014 | Lee et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0288619 A1 | 9/2014 | Johnson et al. |
| 2014/0288620 A1 | 9/2014 | DiLorenzo |
| 2014/0288647 A1 | 9/2014 | Boyden et al. |
| 2014/0295537 A1 | 10/2014 | Omidi |
| 2014/0296089 A1 | 10/2014 | Holmes et al. |
| 2014/0296658 A1 | 10/2014 | Yuen et al. |
| 2014/0296663 A1 | 10/2014 | Boyden et al. |
| 2014/0296978 A1 | 10/2014 | Boyden et al. |
| 2014/0297217 A1 | 10/2014 | Yuen |
| 2014/0297218 A1 | 10/2014 | Yuen |
| 2014/0303552 A1 | 10/2014 | Kanderian, Jr. et al. |
| 2014/0305204 A1 | 10/2014 | Hong et al. |
| 2014/0305470 A1 | 10/2014 | Desu-Kalyanam |
| 2014/0306807 A1 | 10/2014 | Rowland et al. |
| 2014/0307878 A1 | 10/2014 | Osborne et al. |
| 2014/0308661 A1 | 10/2014 | Holmes et al. |
| 2014/0309505 A1 | 10/2014 | Euliano et al. |
| 2014/0316191 A1 | 10/2014 | de Zambotti et al. |
| 2014/0316192 A1 | 10/2014 | de Zambotti et al. |
| 2014/0316305 A1 | 10/2014 | Venkatraman et al. |
| 2014/0318699 A1 | 10/2014 | Longinotti-Buitoni et al. |
| 2014/0320284 A1 | 10/2014 | Messenger et al. |
| 2014/0320331 A1 | 10/2014 | Fernandes et al. |
| 2014/0323897 A1 | 10/2014 | Brown et al. |
| 2014/0324118 A1 | 10/2014 | Simon et al. |
| 2014/0327320 A1 | 11/2014 | Muhs et al. |
| 2014/0328517 A1 | 11/2014 | Gluncic |
| 2014/0330094 A1 | 11/2014 | Pacione et al. |
| 2014/0330244 A1 | 11/2014 | Hyde et al. |
| 2014/0330256 A1 | 11/2014 | Hyde et al. |
| 2014/0330257 A1 | 11/2014 | Hyde et al. |
| 2014/0330347 A1 | 11/2014 | Simms, Jr. |
| 2014/0330357 A1 | 11/2014 | Stevenson et al. |
| 2014/0330431 A1 | 11/2014 | Hollander et al. |
| 2014/0331523 A1 | 11/2014 | Ellis |
| 2014/0336980 A1 | 11/2014 | Yuen et al. |
| 2014/0337450 A1 | 11/2014 | Choudhary et al. |
| 2014/0337451 A1 | 11/2014 | Choudhary et al. |
| 2014/0340221 A1 | 11/2014 | Yuen et al. |
| 2014/0342328 A1 | 11/2014 | Pacione et al. |
| 2014/0343370 A1 | 11/2014 | Stivoric et al. |
| 2014/0343691 A1 | 11/2014 | Guillory et al. |
| 2014/0343867 A1 | 11/2014 | Yuen et al. |
| 2014/0343892 A1 | 11/2014 | Yuen et al. |
| 2014/0350636 A1 | 11/2014 | King et al. |
| 2014/0358012 A1 | 12/2014 | Richards et al. |
| 2014/0358024 A1 | 12/2014 | Nelson et al. |
| 2014/0358196 A1 | 12/2014 | Mashiach |
| 2014/0358197 A1 | 12/2014 | Mashiach et al. |
| 2014/0361147 A1 | 12/2014 | Fei |
| 2014/0364705 A1 | 12/2014 | Parthasarathy et al. |
| 2014/0368601 A1 | 12/2014 | deCharms |
| 2014/0371556 A1 | 12/2014 | Maertz |
| 2014/0371821 A1 | 12/2014 | Mashiach et al. |
| 2014/0371824 A1 | 12/2014 | Mashiach et al. |
| 2014/0371913 A1 | 12/2014 | Zeltzer |
| 2014/0374276 A1 | 12/2014 | Guthrie et al. |
| 2014/0376336 A1 | 12/2014 | Steckner et al. |
| 2014/0378787 A1 | 12/2014 | Brumback et al. |
| 2014/0379090 A1 | 12/2014 | Diomidis et al. |
| 2015/0003047 A1 | 1/2015 | Lin |
| 2015/0005650 A1 | 1/2015 | Banet et al. |
| 2015/0005652 A1 | 1/2015 | Banet et al. |
| 2015/0005911 A1 | 1/2015 | Lee et al. |

(56) References Cited

U.S. PATENT DOCUMENTS

| | | |
|---|---|---|
| 2015/0011194 A1 | 1/2015 | Rodriguez |
| 2015/0011860 A1 | 1/2015 | Pool et al. |
| 2015/0011914 A1 | 1/2015 | Berner, Jr. et al. |
| 2015/0018660 A1 | 1/2015 | Thomson et al. |
| 2015/0018702 A1 | 1/2015 | Galloway et al. |
| 2015/0019135 A1 | 1/2015 | Kacyvenski et al. |
| 2015/0019257 A1 | 1/2015 | Doyle et al. |
| 2015/0022675 A1 | 1/2015 | Lord et al. |
| 2015/0025393 A1 | 1/2015 | Hong et al. |
| 2015/0025394 A1 | 1/2015 | Hong et al. |
| 2015/0025478 A1 | 1/2015 | Hibdon et al. |
| 2015/0031964 A1 | 1/2015 | Bly et al. |
| 2015/0031970 A1 | 1/2015 | Lain |
| 2015/0032178 A1 | 1/2015 | Simon et al. |
| 2015/0039040 A1 | 2/2015 | Cowan et al. |
| 2015/0039053 A1 | 2/2015 | Kaib et al. |
| 2015/0040282 A1 | 2/2015 | Longinotti-Buitoni et al. |
| 2015/0040428 A1 | 2/2015 | Davis et al. |
| 2015/0045634 A1 | 2/2015 | Goldberg et al. |
| 2015/0048942 A1 | 2/2015 | Bertagna et al. |
| 2015/0050888 A1 | 2/2015 | Baker et al. |
| 2015/0057595 A1 | 2/2015 | Gunn et al. |
| 2015/0057718 A1 | 2/2015 | Sharma et al. |
| 2015/0065786 A1 | 3/2015 | Jeevanandam et al. |
| 2015/0065826 A1 | 3/2015 | Mulligan et al. |
| 2015/0066124 A1 | 3/2015 | Stevenson et al. |
| 2015/0071934 A1 | 3/2015 | Christiano |
| 2015/0073498 A1 | 3/2015 | Kothandaraman |
| 2015/0073499 A1 | 3/2015 | Kothandaraman |
| 2015/0073500 A1 | 3/2015 | Kothandaraman et al. |
| 2015/0073723 A1 | 3/2015 | Mulligan et al. |
| 2015/0076909 A1 | 3/2015 | Biederman et al. |
| 2015/0077050 A1 | 3/2015 | Van Funderburk |
| 2015/0080746 A1 | 3/2015 | Bleich et al. |
| 2015/0080756 A1 | 3/2015 | Robinson et al. |
| 2015/0080982 A1 | 3/2015 | Van Funderburk |
| 2015/0080992 A1 | 3/2015 | Drnek et al. |
| 2015/0088024 A1 | 3/2015 | Sackellares et al. |
| 2015/0088226 A1 | 3/2015 | Tourrel et al. |
| 2015/0088457 A1 | 3/2015 | Yuen et al. |
| 2015/0094547 A1 | 4/2015 | Mickle et al. |
| 2015/0094552 A1 | 4/2015 | Golda et al. |
| 2015/0094914 A1 | 4/2015 | Abreu |
| 2015/0096204 A1 | 4/2015 | Case, Jr. |
| 2015/0096597 A1 | 4/2015 | Patel et al. |
| 2015/0097701 A1 | 4/2015 | Al-Ali et al. |
| 2015/0099943 A1 | 4/2015 | Russell |
| 2015/0099959 A1 | 4/2015 | Bonmassar et al. |
| 2015/0100038 A1 | 4/2015 | McCann et al. |
| 2015/0100108 A1 | 4/2015 | Vansickle et al. |
| 2015/0100109 A1 | 4/2015 | Feldman et al. |
| 2015/0100270 A1 | 4/2015 | Yuen et al. |
| 2015/0102923 A1 | 4/2015 | Messenger et al. |
| 2015/0112151 A1 | 4/2015 | Muhsin et al. |
| 2015/0112170 A1 | 4/2015 | Lee et al. |
| 2015/0113417 A1 | 4/2015 | Yuen et al. |
| 2015/0116053 A1 | 4/2015 | Stevenson et al. |
| 2015/0119728 A1 | 4/2015 | Blackadar et al. |
| 2015/0119951 A1 | 4/2015 | Nelson et al. |
| 2015/0119952 A1 | 4/2015 | Sharma et al. |
| 2015/0120496 A1 | 4/2015 | Watson |
| 2015/0122018 A1 | 5/2015 | Yuen |
| 2015/0125945 A1 | 5/2015 | Holmes et al. |
| 2015/0126822 A1 | 5/2015 | Chavan et al. |
| 2015/0129664 A1 | 5/2015 | Brar |
| 2015/0134107 A1 | 5/2015 | Hyde et al. |
| 2015/0134268 A1 | 5/2015 | Yuen et al. |
| 2015/0134345 A1 | 5/2015 | Hyde et al. |
| 2015/0134346 A1 | 5/2015 | Hyde et al. |
| 2015/0137935 A1 | 5/2015 | Ellis |
| 2015/0137997 A1 | 5/2015 | Huang |
| 2015/0141769 A1 | 5/2015 | Mulligan et al. |
| 2015/0141873 A1 | 5/2015 | Fei |
| 2015/0142074 A1 | 5/2015 | Bar-Yoseph et al. |
| 2015/0142082 A1 | 5/2015 | Simon et al. |
| 2015/0143601 A1 | 5/2015 | Longinotti-Buitoni et al. |
| 2015/0146939 A1 | 5/2015 | Datta et al. |
| 2015/0148637 A1 | 5/2015 | Golda et al. |
| 2015/0148697 A1 | 5/2015 | Burnes et al. |
| 2015/0148700 A1 | 5/2015 | Mhuircheartaigh et al. |
| 2015/0148868 A1 | 5/2015 | Shahandeh et al. |
| 2015/0149096 A1 | 5/2015 | Soykan |
| 2015/0149217 A1 | 5/2015 | Rath et al. |
| 2015/0150453 A1 | 6/2015 | Abreu |
| 2015/0150505 A1 | 6/2015 | Kaskoun et al. |
| 2015/0154364 A1 | 6/2015 | Biasi et al. |
| 2015/0156749 A1 | 6/2015 | Yun et al. |
| 2015/0157256 A1 | 6/2015 | Galeev |
| 2015/0157269 A1 | 6/2015 | Lisogurski et al. |
| 2015/0157512 A1 | 6/2015 | Abir |
| 2015/0164321 A1 | 6/2015 | Weibel et al. |
| 2015/0164322 A1 | 6/2015 | Derchak |
| 2015/0164349 A1 | 6/2015 | Gopalakrishnan et al. |
| 2015/0164376 A1 | 6/2015 | Huang |
| 2015/0164377 A1 | 6/2015 | Nathan et al. |
| 2015/0164432 A1 | 6/2015 | Gupta et al. |
| 2015/0170504 A1 | 6/2015 | Jooste |
| 2015/0173452 A1 | 6/2015 | Semperlotti et al. |
| 2015/0173628 A1 | 6/2015 | Yuen et al. |
| 2015/0173631 A1 | 6/2015 | Richards et al. |
| 2015/0173674 A1 | 6/2015 | Hayes et al. |
| 2015/0174296 A1 | 6/2015 | Ju et al. |
| 2015/0174406 A1 | 6/2015 | Lamensdorf et al. |
| 2015/0177081 A1 | 6/2015 | Steier |
| 2015/0179038 A1 | 6/2015 | Daniel et al. |
| 2015/0183828 A1 | 7/2015 | Genove et al. |
| 2015/0189062 A1 | 7/2015 | Ellis |
| 2015/0189063 A1 | 7/2015 | Ellis |
| 2015/0190053 A1 | 7/2015 | Baker et al. |
| 2015/0190636 A1 | 7/2015 | Simon et al. |
| 2015/0190637 A1 | 7/2015 | Simon et al. |
| 2015/0193612 A1 | 7/2015 | Chow |
| 2015/0194052 A1 | 7/2015 | Sagan et al. |
| 2015/0196229 A1 | 7/2015 | Old et al. |
| 2015/0196256 A1 | 7/2015 | Venkatraman et al. |
| 2015/0196378 A1 | 7/2015 | Mayer et al. |
| 2015/0196409 A1 | 7/2015 | Pool et al. |
| 2015/0201853 A1 | 7/2015 | Hong et al. |
| 2015/0201854 A1 | 7/2015 | Hong et al. |
| 2015/0206408 A1 | 7/2015 | LaLonde et al. |
| 2015/0207915 A1 | 7/2015 | Roberts et al. |
| 2015/0208943 A1 | 7/2015 | Shenasa et al. |
| 2015/0220700 A1 | 8/2015 | Chait et al. |
| 2015/0221208 A1 | 8/2015 | Knighton et al. |
| 2015/0223700 A1 | 8/2015 | Kirenko |
| 2015/0223708 A1 | 8/2015 | Richards et al. |
| 2015/0224310 A1 | 8/2015 | Sharma et al. |
| 2015/0226619 A1 | 8/2015 | Rice et al. |
| 2015/0230722 A1 | 8/2015 | Sarkar et al. |
| 2015/0230735 A1 | 8/2015 | Venkatraman et al. |
| 2015/0230761 A1 | 8/2015 | Brumback et al. |
| 2015/0231402 A1 | 8/2015 | Aghassian |
| 2015/0238097 A1 | 8/2015 | Teller et al. |
| 2015/0238277 A1 | 8/2015 | Ritchey et al. |
| 2015/0243967 A1 | 8/2015 | Norton et al. |
| 2015/0245797 A1 | 9/2015 | Teller et al. |
| 2015/0250429 A1 | 9/2015 | Hampapuram et al. |
| 2015/0254710 A1 | 9/2015 | Black et al. |
| 2015/0255858 A1 | 9/2015 | Li et al. |
| 2015/0257479 A1 | 9/2015 | Ellis |
| 2015/0258261 A1 | 9/2015 | Novack |
| 2015/0258415 A1 | 9/2015 | Trivedi et al. |
| 2015/0260514 A1 | 9/2015 | Menelas et al. |
| 2015/0265150 A1 | 9/2015 | Darty et al. |
| 2015/0265164 A1 | 9/2015 | Gopalakrishnan et al. |
| 2015/0265195 A1 | 9/2015 | Darty et al. |
| 2015/0265207 A1 | 9/2015 | Wu et al. |
| 2015/0265214 A1 | 9/2015 | De Kok et al. |
| 2015/0265217 A1 | 9/2015 | Penders et al. |
| 2015/0265903 A1 | 9/2015 | Kolen et al. |
| 2015/0269009 A1 | 9/2015 | Faaborg et al. |
| 2015/0269624 A1 | 9/2015 | Cheng et al. |
| 2015/0272511 A1 | 10/2015 | Najafi et al. |
| 2015/0278453 A1 | 10/2015 | Joao |

(56) References Cited

U.S. PATENT DOCUMENTS

| | | |
|---|---|---|
| 2015/0282711 A1 | 10/2015 | Thomas et al. |
| 2015/0282713 A1 | 10/2015 | Fei |
| 2015/0282767 A1 | 10/2015 | Stivoric et al. |
| 2015/0283365 A1 | 10/2015 | Dacey, Jr. et al. |
| 2015/0283386 A1 | 10/2015 | Chow |
| 2015/0288772 A1 | 10/2015 | Molettiere et al. |
| 2015/0289594 A1 | 10/2015 | Rushbrook et al. |
| 2015/0289595 A1 | 10/2015 | Rushbrook et al. |
| 2015/0289596 A1 | 10/2015 | Beers et al. |
| 2015/0289797 A1 | 10/2015 | Pacione et al. |
| 2015/0289798 A1 | 10/2015 | Pacione et al. |
| 2015/0289799 A1 | 10/2015 | Pacione et al. |
| 2015/0289800 A1 | 10/2015 | Pacione et al. |
| 2015/0289808 A1 | 10/2015 | Pacione et al. |
| 2015/0289809 A1 | 10/2015 | Pacione et al. |
| 2015/0289810 A1 | 10/2015 | Pacione et al. |
| 2015/0289811 A1 | 10/2015 | Pacione et al. |
| 2015/0289812 A1 | 10/2015 | Pacione et al. |
| 2015/0289820 A1 | 10/2015 | Miller et al. |
| 2015/0289911 A1 | 10/2015 | Beyar et al. |
| 2015/0294574 A1 | 10/2015 | Pacione et al. |
| 2015/0294575 A1 | 10/2015 | Pacione et al. |
| 2015/0294576 A1 | 10/2015 | Pacione et al. |
| 2015/0294583 A1 | 10/2015 | Pacione et al. |
| 2015/0294594 A1 | 10/2015 | Pacione et al. |
| 2015/0296922 A1 | 10/2015 | Rushbrook et al. |
| 2015/0297059 A1 | 10/2015 | Desu-Kalyanam |
| 2015/0297103 A1 | 10/2015 | Hu et al. |
| 2015/0297134 A1 | 10/2015 | Albert et al. |
| 2015/0297904 A1 | 10/2015 | Kavounas |
| 2015/0304797 A1 | 10/2015 | Rhoads et al. |
| 2015/0305682 A1 | 10/2015 | LeBoeuf et al. |
| 2015/0313308 A1 | 11/2015 | Rice et al. |
| 2015/0313309 A1 | 11/2015 | Darden et al. |
| 2015/0314166 A1 | 11/2015 | Hong et al. |
| 2015/0317515 A1 | 11/2015 | Lee et al. |
| 2015/0320588 A1 | 11/2015 | Connor |
| 2015/0321084 A1 | 11/2015 | Galasso et al. |
| 2015/0327989 A1 | 11/2015 | Boyden et al. |
| 2015/0331997 A1 | 11/2015 | Joao |
| 2015/0335096 A1 | 11/2015 | Semperlotti et al. |
| 2015/0335385 A1 | 11/2015 | Miao et al. |
| 2015/0335507 A1 | 11/2015 | Emmons et al. |
| 2015/0338428 A1 | 11/2015 | Holmes et al. |
| 2015/0339946 A1 | 11/2015 | Pacione et al. |
| 2015/0347689 A1 | 12/2015 | Neagle |
| 2015/0351695 A1 | 12/2015 | Cronin |
| 2015/0351698 A1 | 12/2015 | Cronin |
| 2015/0356524 A1 | 12/2015 | Pennanen |
| 2015/0356555 A1 | 12/2015 | Pennanen |
| 2015/0358525 A1 | 12/2015 | Lord |
| 2015/0359429 A1 | 12/2015 | Al-Ali et al. |
| 2015/0359457 A1 | 12/2015 | Blumenthal et al. |
| 2015/0359489 A1 | 12/2015 | Baudenbacher et al. |
| 2015/0359490 A1 | 12/2015 | Massey et al. |
| 2015/0360038 A1 | 12/2015 | Zottola et al. |
| 2015/0364018 A1 | 12/2015 | Mirov et al. |
| 2015/0364938 A1 | 12/2015 | Lapetina et al. |
| 2015/0365738 A1 | 12/2015 | Purvis et al. |
| 2015/0366746 A1 | 12/2015 | Ashby |
| 2015/0366915 A1 | 12/2015 | Gay et al. |
| 2015/0367144 A1 | 12/2015 | Flynn et al. |
| 2015/0368717 A1 | 12/2015 | Holmes et al. |
| 2015/0371516 A1 | 12/2015 | Petersen et al. |
| 2015/0374289 A1 | 12/2015 | Teller et al. |
| 2015/0374541 A1 | 12/2015 | de Juan, Jr. et al. |
| 2016/0000188 A1 | 1/2016 | Hanft |
| 2016/0000385 A1 | 1/2016 | Petersen et al. |
| 2016/0000640 A1 | 1/2016 | Lai et al. |
| 2016/0000642 A1 | 1/2016 | Zipper |
| 2016/0000984 A1 | 1/2016 | Burnett et al. |
| 2016/0001034 A1 | 1/2016 | Rembrand |
| 2016/0001071 A1 | 1/2016 | Sharma et al. |
| 2016/0003823 A1 | 1/2016 | Holmes |
| 2016/0004980 A1* | 1/2016 | Goldschmidt ........... G06N 5/04 706/11 |
| 2016/0005299 A1 | 1/2016 | Zomet et al. |
| 2016/0007890 A1 | 1/2016 | Kovatchev et al. |
| 2016/0007925 A1 | 1/2016 | Mirov et al. |
| 2016/0008632 A1 | 1/2016 | Wetmore et al. |
| 2016/0011215 A1 | 1/2016 | Holmes |
| 2016/0011225 A1 | 1/2016 | Holmes |
| 2016/0012465 A1 | 1/2016 | Sharp |
| 2016/0015280 A1 | 1/2016 | Hyde et al. |
| 2016/0015972 A1 | 1/2016 | Hyde et al. |
| 2016/0016041 A1 | 1/2016 | Giedwoyn et al. |
| 2016/0022193 A1 | 1/2016 | Rau et al. |
| 2016/0023007 A1 | 1/2016 | Stouffer et al. |
| 2016/0025760 A1 | 1/2016 | Holmes |
| 2016/0025763 A1 | 1/2016 | Holmes |
| 2016/0025854 A1 | 1/2016 | D'Angelo et al. |
| 2016/0029905 A1 | 2/2016 | Kovacs |
| 2016/0029931 A1* | 2/2016 | Salas-Boni .......... A61B 5/7203 600/365 |
| 2016/0029966 A1 | 2/2016 | Salas-Boni et al. |
| 2016/0030650 A1 | 2/2016 | Yomtov et al. |
| 2016/0030741 A1 | 2/2016 | Wei et al. |
| 2016/0030756 A1 | 2/2016 | Dronov |
| 2016/0032361 A1 | 2/2016 | Holmes et al. |
| 2016/0033544 A1 | 2/2016 | Holmes et al. |
| 2016/0034696 A1 | 2/2016 | Jooste et al. |
| 2016/0036118 A1 | 2/2016 | Baringer et al. |
| 2016/0037855 A1 | 2/2016 | Ellis |
| 2016/0038037 A1 | 2/2016 | Kovacs |
| 2016/0038038 A1 | 2/2016 | Kovacs |
| 2016/0038042 A1 | 2/2016 | Mulligan et al. |
| 2016/0038043 A1 | 2/2016 | Mulligan et al. |
| 2016/0038055 A1 | 2/2016 | Wheeler et al. |
| 2016/0038324 A1 | 2/2016 | Pool et al. |
| 2016/0038673 A1 | 2/2016 | Morales |
| 2016/0038744 A1 | 2/2016 | Ellingson et al. |
| 2016/0044993 A1 | 2/2016 | Meschter et al. |
| 2016/0047787 A1 | 2/2016 | Islam |
| 2016/0051169 A1 | 2/2016 | Hong et al. |
| 2016/0051825 A1 | 2/2016 | Ter-Petrosyan et al. |
| 2016/0054343 A1 | 2/2016 | Holmes et al. |
| 2016/0058286 A1 | 3/2016 | Joshua et al. |
| 2016/0058302 A1 | 3/2016 | Raghuram et al. |
| 2016/0058324 A1 | 3/2016 | Cao |
| 2016/0058329 A1 | 3/2016 | Srinivas et al. |
| 2016/0058331 A1 | 3/2016 | Keen et al. |
| 2016/0058332 A1 | 3/2016 | Tan et al. |
| 2016/0058333 A1 | 3/2016 | Arnold et al. |
| 2016/0058356 A1 | 3/2016 | Raghuram et al. |
| 2016/0058370 A1 | 3/2016 | Raghuram et al. |
| 2016/0058371 A1 | 3/2016 | Singh Alvarado et al. |
| 2016/0058372 A1 | 3/2016 | Raghuram et al. |
| 2016/0058375 A1 | 3/2016 | Rothkopf |
| 2016/0059010 A1 | 3/2016 | Sharma et al. |
| 2016/0059064 A1 | 3/2016 | Smith et al. |
| 2016/0066803 A1 | 3/2016 | Hu et al. |
| 2016/0066844 A1 | 3/2016 | Venkatraman et al. |
| 2016/0067584 A1 | 3/2016 | Giedwoyn et al. |
| 2016/0069919 A1 | 3/2016 | Holmes et al. |
| 2016/0069920 A1 | 3/2016 | Holmes et al. |
| 2016/0069921 A1 | 3/2016 | Holmes et al. |
| 2016/0072690 A1 | 3/2016 | Molettiere et al. |
| 2016/0073884 A1 | 3/2016 | Samuelsson et al. |
| 2016/0073914 A1 | 3/2016 | Lapetina et al. |
| 2016/0074278 A1 | 3/2016 | Muench et al. |
| 2016/0074547 A1 | 3/2016 | Dobrinsky et al. |
| 2016/0074600 A1 | 3/2016 | Miesel |
| 2016/0077015 A1 | 3/2016 | Holmes et al. |
| 2016/0078061 A1 | 3/2016 | Hilsdale et al. |
| 2016/0080166 A1 | 3/2016 | Chen et al. |
| 2016/0081418 A1 | 3/2016 | Amos et al. |
| 2016/0081435 A1 | 3/2016 | Marks |
| 2016/0081574 A1 | 3/2016 | Krusor et al. |
| 2016/0081622 A1 | 3/2016 | Abreu |
| 2016/0082187 A1 | 3/2016 | Schaible et al. |
| 2016/0084863 A1 | 3/2016 | Holmes et al. |
| 2016/0084869 A1 | 3/2016 | Yuen et al. |
| 2016/0089028 A1 | 3/2016 | Chatterjee et al. |

(56) References Cited

U.S. PATENT DOCUMENTS

| | | |
|---|---|---|
| 2016/0089575 A1 | 3/2016 | Smith et al. |
| 2016/0095550 A1 | 4/2016 | Lin et al. |
| 2016/0098723 A1 | 4/2016 | Feeney |
| 2016/0098730 A1 | 4/2016 | Feeney |
| 2016/0100801 A1 | 4/2016 | Clark et al. |
| 2016/0103123 A1 | 4/2016 | Holmes et al. |
| 2016/0106177 A1 | 4/2016 | De Laurentis |
| 2016/0113838 A1 | 4/2016 | Paydarfar et al. |
| 2016/0117951 A1 | 4/2016 | Fleischer et al. |
| 2016/0124009 A1 | 5/2016 | Wasson et al. |
| 2016/0135516 A1 | 5/2016 | Cobbett et al. |
| 2016/0135695 A1 | 5/2016 | Cobbett et al. |
| 2016/0135696 A1 | 5/2016 | Cobbett et al. |
| 2016/0135697 A1 | 5/2016 | Rinderknecht et al. |
| 2016/0135706 A1 | 5/2016 | Sullivan et al. |
| 2016/0135741 A1 | 5/2016 | Chetham et al. |
| 2016/0135742 A1 | 5/2016 | Cobbett et al. |
| 2016/0135743 A1 | 5/2016 | Cobbett et al. |
| 2016/0136882 A1 | 5/2016 | Cobbett et al. |
| 2016/0139156 A1 | 5/2016 | Lakdawala |
| 2016/0143548 A1 | 5/2016 | Al-Ali |
| 2016/0143562 A1 | 5/2016 | Ashby |
| 2016/0143584 A1 | 5/2016 | Inagaki |
| 2016/0147964 A1 | 5/2016 | Corey et al. |
| 2016/0148531 A1 | 5/2016 | Bleich et al. |
| 2016/0151603 A1 | 6/2016 | Shouldice et al. |
| 2016/0158426 A1 | 6/2016 | Jeevanandam et al. |
| 2016/0158552 A1 | 6/2016 | Heruth et al. |
| 2016/0162662 A1 | 6/2016 | Monirabbasi et al. |
| 2016/0166156 A1 | 6/2016 | Yuen et al. |
| 2016/0169880 A1 | 6/2016 | Holmes et al. |
| 2016/0169923 A1 | 6/2016 | Holmes et al. |
| 2016/0170996 A1 | 6/2016 | Frank et al. |
| 2016/0174840 A1 | 6/2016 | Udoh et al. |
| 2016/0174898 A1 | 6/2016 | Udoh et al. |
| 2016/0180440 A1 | 6/2016 | Dibenedetto et al. |
| 2016/0183818 A1 | 6/2016 | Richards et al. |
| 2016/0186140 A1 | 6/2016 | Dalton et al. |
| 2016/0188856 A1 | 6/2016 | Miki et al. |
| 2016/0191120 A1 | 6/2016 | Dobyns et al. |
| 2016/0192166 A1 | 6/2016 | deCharms |
| 2016/0192865 A1 | 7/2016 | Datta et al. |
| 2016/0193462 A1 | 7/2016 | Krusor et al. |
| 2016/0193679 A1 | 7/2016 | Zhang et al. |
| 2016/0195440 A1 | 7/2016 | Amos et al. |
| 2016/0198961 A1 | 7/2016 | Homyk et al. |
| 2016/0203522 A1 | 7/2016 | Shiffert et al. |
| 2016/0203572 A1 | 7/2016 | McConaghy et al. |
| 2016/0205450 A1 | 7/2016 | Gartseev et al. |
| 2016/0206215 A1 | 7/2016 | Takahashi et al. |
| 2016/0206922 A1 | 7/2016 | Dalebout et al. |
| 2016/0210679 A1 | 7/2016 | Rohr et al. |
| 2016/0213314 A1 | 7/2016 | Zuckerman-Stark et al. |
| 2016/0213334 A1 | 7/2016 | Oleson |
| 2016/0216286 A1 | 7/2016 | Holmes et al. |
| 2016/0216287 A1 | 7/2016 | Holmes et al. |
| 2016/0219266 A1 | 7/2016 | Lane |
| 2016/0219967 A1 | 8/2016 | Smith et al. |
| 2016/0220151 A1 | 8/2016 | Zizi et al. |
| 2016/0220186 A9 | 8/2016 | Clark et al. |
| 2016/0220198 A1 | 8/2016 | Proud |
| 2016/0224130 A1 | 8/2016 | Myers et al. |
| 2016/0224803 A1 | 8/2016 | Frank et al. |
| 2016/0227870 A1 | 8/2016 | Odland et al. |
| 2016/0227883 A1 | 8/2016 | Beers et al. |
| 2016/0228034 A1 | 8/2016 | Gluncic |
| 2016/0228052 A1 | 8/2016 | Proud |
| 2016/0231402 A1 | 8/2016 | Rothberg et al. |
| 2016/0232131 A1 | 8/2016 | Liu et al. |
| 2016/0232137 A1 | 8/2016 | Liu |
| 2016/0232201 A1 | 8/2016 | Goran et al. |
| 2016/0232244 A1 | 8/2016 | Liu et al. |
| 2016/0232726 A1 | 8/2016 | Zizi et al. |
| 2016/0232807 A1 | 8/2016 | Ghaffari et al. |
| 2016/0234143 A1 | 8/2016 | Choudhary et al. |
| 2016/0234174 A1 | 8/2016 | Zizi et al. |
| 2016/0234184 A1 | 8/2016 | Liu et al. |
| 2016/0234595 A1 | 8/2016 | Goran et al. |
| 2016/0235317 A1 | 8/2016 | Sarkar et al. |
| 2016/0235318 A1 | 8/2016 | Sarkar |
| 2016/0235352 A1 | 8/2016 | DiLorenzo |
| 2016/0235374 A1 | 8/2016 | Miller et al. |
| 2016/0238439 A1 | 8/2016 | Chu et al. |
| 2016/0238440 A1 | 8/2016 | Chu et al. |
| 2016/0238441 A1 | 8/2016 | Chu et al. |
| 2016/0238443 A1 | 8/2016 | Chu et al. |
| 2016/0238444 A1 | 8/2016 | Chu et al. |
| 2016/0239084 A1 | 8/2016 | Connor |
| 2016/0239624 A1 | 8/2016 | Short et al. |
| 2016/0240721 A1 | 8/2016 | Chu et al. |
| 2016/0241554 A1 | 8/2016 | Zizi et al. |
| 2016/0242646 A1 | 8/2016 | Obma |
| 2016/0242654 A1 | 8/2016 | Quinlan et al. |
| 2016/0242665 A1 | 8/2016 | Galloway et al. |
| 2016/0242700 A1 | 8/2016 | Ferber et al. |
| 2016/0243373 A1 | 8/2016 | Kalgren et al. |
| 2016/0252412 A1 | 9/2016 | McMillen et al. |
| 2016/0253471 A1 | 9/2016 | Volpe |
| 2016/0256095 A1 | 9/2016 | Krasnow et al. |
| 2016/0256097 A1 | 9/2016 | Manautou et al. |
| 2016/0256106 A1 | 9/2016 | Krasnow et al. |
| 2016/0256112 A1 | 9/2016 | Brockway et al. |
| 2016/0256350 A1 | 9/2016 | Johnson et al. |
| 2016/0256629 A1 | 9/2016 | Grosman et al. |
| 2016/0256697 A1 | 9/2016 | Shahandeh et al. |
| 2016/0259426 A1 | 9/2016 | Yuen et al. |
| 2016/0260311 A1 | 9/2016 | Asano |
| 2016/0261458 A1 | 9/2016 | Huang |
| 2016/0262485 A1 | 9/2016 | Walker |
| 2016/0262486 A1 | 9/2016 | Ellis |
| 2016/0262670 A1 | 9/2016 | Wasson et al. |
| 2016/0263382 A1 | 9/2016 | Heruth et al. |
| 2016/0270656 A1 | 9/2016 | Samec et al. |
| 2016/0274752 A1 | 9/2016 | Zhu et al. |
| 2016/0278638 A1 | 9/2016 | Schwartz et al. |
| 2016/0278669 A1 | 9/2016 | Messenger et al. |
| 2016/0279021 A1 | 9/2016 | Hyde et al. |
| 2016/0279022 A1 | 9/2016 | Hyde et al. |
| 2016/0279023 A1 | 9/2016 | Hyde et al. |
| 2016/0279024 A1 | 9/2016 | Hyde et al. |
| 2016/0279025 A1 | 9/2016 | Hyde et al. |
| 2016/0279410 A1 | 9/2016 | Simon et al. |
| 2016/0279435 A1 | 9/2016 | Hyde et al. |
| 2016/0283706 A1 | 9/2016 | Holmes |
| 2016/0285985 A1 | 9/2016 | Molettiere et al. |
| 2016/0287184 A1 | 10/2016 | Diebold et al. |
| 2016/0287380 A1 | 10/2016 | Shi et al. |
| 2016/0287879 A1 | 10/2016 | Denison et al. |
| 2016/0287887 A1 | 10/2016 | Wu et al. |
| 2016/0290878 A1 | 10/2016 | Severinkangas et al. |
| 2016/0293172 A1 | 10/2016 | Sharma et al. |
| 2016/0296114 A1 | 10/2016 | Finch et al. |
| 2016/0296116 A1 | 10/2016 | Baker et al. |
| 2016/0296145 A1 | 10/2016 | Bajaj et al. |
| 2016/0296169 A1 | 10/2016 | McHale et al. |
| 2016/0296759 A1 | 10/2016 | Cong et al. |
| 2016/0299021 A1 | 10/2016 | Thillainadarajah et al. |
| 2016/0300028 A1 | 10/2016 | Abell et al. |
| 2016/0300252 A1 | 10/2016 | Frank et al. |
| 2016/0302509 A1 | 10/2016 | Amos et al. |
| 2016/0302521 A1 | 10/2016 | Rennex |
| 2016/0302706 A1 | 10/2016 | Richards et al. |
| 2016/0302707 A1 | 10/2016 | Pesach et al. |
| 2016/0303313 A1 | 10/2016 | Burke et al. |
| 2016/0303371 A1 | 10/2016 | Whiting et al. |
| 2016/0306339 A1 | 10/2016 | Rushbrook et al. |
| 2016/0309829 A1 | 10/2016 | Molyneux et al. |
| 2016/0309830 A1 | 10/2016 | Rushbrook et al. |
| 2016/0309842 A1 | 10/2016 | Ellis |
| 2016/0310022 A1 | 10/2016 | Stivoric et al. |
| 2016/0310048 A1 | 10/2016 | Pang et al. |
| 2016/0310737 A1 | 10/2016 | Tourrel et al. |
| 2016/0314670 A1 | 10/2016 | Roberts et al. |
| 2016/0316849 A1 | 11/2016 | McLeod et al. |

(56) References Cited

U.S. PATENT DOCUMENTS

| | | |
|---|---|---|
| 2016/0317095 A1 | 11/2016 | Berger et al. |
| 2016/0317744 A1 | 11/2016 | Rule |
| 2016/0317797 A1 | 11/2016 | Smith et al. |
| 2016/0320381 A1 | 11/2016 | Holmes et al. |
| 2016/0321400 A1 | 11/2016 | Durrant et al. |
| 2016/0321598 A1 | 11/2016 | Baughman et al. |
| 2016/0321599 A1 | 11/2016 | Baughman et al. |
| 2016/0321654 A1 | 11/2016 | Lesavich et al. |
| 2016/0323401 A1 | 11/2016 | Messenger et al. |
| 2016/0324450 A1 | 11/2016 | Estes et al. |
| 2016/0324472 A1 | 11/2016 | Kaskoun et al. |
| 2016/0324478 A1 | 11/2016 | Goldstein |
| 2016/0324488 A1 | 11/2016 | Olsen |
| 2016/0325083 A1 | 11/2016 | Linden et al. |
| 2016/0325084 A1 | 11/2016 | Linden et al. |
| 2016/0325143 A1 | 11/2016 | Yuen et al. |
| 2016/0327476 A1 | 11/2016 | Islam |
| 2016/0331257 A1 | 11/2016 | Baumann et al. |
| 2016/0331273 A1 | 11/2016 | Armoundas |
| 2016/0331518 A1 | 11/2016 | Cable, II et al. |
| 2016/0331986 A1 | 11/2016 | Piha et al. |
| 2016/0331987 A1 | 11/2016 | Chapman et al. |
| 2016/0334087 A1 | 11/2016 | Lin |
| 2016/0334124 A1 | 11/2016 | Hou et al. |
| 2016/0335632 A1 | 11/2016 | Proud et al. |
| 2016/0335913 A1 | 11/2016 | Grant et al. |
| 2016/0337843 A1 | 11/2016 | Repka et al. |
| 2016/0341611 A1 | 11/2016 | Walker |
| 2016/0342744 A1 | 11/2016 | Joao |
| 2016/0342762 A1 | 11/2016 | Goetz |
| 2016/0342882 A1 | 11/2016 | Proud et al. |
| 2016/0345653 A1 | 12/2016 | Beers et al. |
| 2016/0345902 A1 | 12/2016 | Degreef et al. |
| 2016/0346501 A1 | 12/2016 | Hooper et al. |
| 2016/0346530 A1 | 12/2016 | Jeffery et al. |
| 2016/0346542 A1 | 12/2016 | Simon et al. |
| 2016/0346609 A1 | 12/2016 | Bailly et al. |
| 2016/0349076 A1 | 12/2016 | Campos Gallo et al. |
| 2016/0354606 A1 | 12/2016 | Dacey, Jr. et al. |
| 2016/0358063 A1 | 12/2016 | Proud et al. |
| 2016/0358155 A1 | 12/2016 | Proud et al. |
| 2016/0358156 A1 | 12/2016 | Proud et al. |
| 2016/0359222 A1 | 12/2016 | Li et al. |
| 2016/0361009 A1 | 12/2016 | Proud et al. |
| 2016/0361026 A1 | 12/2016 | Sarkar et al. |
| 2016/0361027 A1 | 12/2016 | Jang et al. |
| 2016/0366972 A1 | 12/2016 | Wilken et al. |
| 2016/0367803 A1 | 12/2016 | Wei et al. |
| 2016/0369861 A1 | 12/2016 | Phipps et al. |
| 2016/0370396 A1 | 12/2016 | Wasson et al. |
| 2016/0373161 A1 | 12/2016 | Yun et al. |
| 2016/0374171 A1 | 12/2016 | Wilken et al. |
| 2016/0374556 A1 | 12/2016 | Colvin, Jr. et al. |
| 2016/0374600 A1 | 12/2016 | Short et al. |
| 2016/0374608 A1 | 12/2016 | Dugan |
| 2016/0374618 A1 | 12/2016 | Giovangrandi |
| 2016/0374620 A1 | 12/2016 | Lisogurski et al. |
| 2016/0374625 A1 | 12/2016 | Mulligan et al. |
| 2016/0377640 A1 | 12/2016 | Balwani et al. |
| 2016/0378069 A1 | 12/2016 | Rothkopf |
| 2016/0378070 A1 | 12/2016 | Rothkopf |
| 2016/0378071 A1 | 12/2016 | Rothkopf |
| 2016/0379312 A1 | 12/2016 | Arjomand et al. |
| 2017/0000324 A1 | 1/2017 | Samec et al. |
| 2017/0000325 A1 | 1/2017 | Samec et al. |
| 2017/0000326 A1 | 1/2017 | Samec et al. |
| 2017/0000329 A1 | 1/2017 | Samec et al. |
| 2017/0000330 A1 | 1/2017 | Samec et al. |
| 2017/0000331 A1 | 1/2017 | Samec et al. |
| 2017/0000332 A1 | 1/2017 | Samec et al. |
| 2017/0000333 A1 | 1/2017 | Samec et al. |
| 2017/0000334 A1 | 1/2017 | Samec et al. |
| 2017/0000335 A1 | 1/2017 | Samec et al. |
| 2017/0000337 A1 | 1/2017 | Samec et al. |
| 2017/0000340 A1 | 1/2017 | Samec et al. |
| 2017/0000341 A1 | 1/2017 | Samec et al. |
| 2017/0000342 A1 | 1/2017 | Samec et al. |
| 2017/0000343 A1 | 1/2017 | Samec et al. |
| 2017/0000345 A1 | 1/2017 | Samec et al. |
| 2017/0000371 A1 | 1/2017 | Quinlan et al. |
| 2017/0000372 A1 | 1/2017 | Quinlan et al. |
| 2017/0000375 A1 | 1/2017 | Demas et al. |
| 2017/0000390 A1 | 1/2017 | Biederman et al. |
| 2017/0000391 A1 | 1/2017 | Wasson et al. |
| 2017/0000415 A1 | 1/2017 | Lapetina et al. |
| 2017/0000454 A1 | 1/2017 | Samec et al. |
| 2017/0000683 A1 | 1/2017 | Samec et al. |
| 2017/0000936 A1 | 1/2017 | Soykan et al. |
| 2017/0001032 A1 | 1/2017 | Samec et al. |
| 2017/0004106 A1 | 1/2017 | Joshua et al. |
| 2017/0007111 A1 | 1/2017 | Samec et al. |
| 2017/0007115 A1 | 1/2017 | Samec et al. |
| 2017/0007116 A1 | 1/2017 | Samec et al. |
| 2017/0007122 A1 | 1/2017 | Samec et al. |
| 2017/0007123 A1 | 1/2017 | Samec et al. |
| 2017/0007182 A1 | 1/2017 | Samec et al. |
| 2017/0007420 A1 | 1/2017 | Stevenson et al. |
| 2017/0007450 A1 | 1/2017 | Samec et al. |
| 2017/0007799 A1 | 1/2017 | Samec et al. |
| 2017/0007843 A1 | 1/2017 | Samec et al. |
| 2017/0010469 A1 | 1/2017 | Samec et al. |
| 2017/0010470 A1 | 1/2017 | Samec et al. |
| 2017/0017083 A1 | 1/2017 | Samec et al. |
| 2017/0017936 A1 | 1/2017 | Bisikalo et al. |
| 2017/0017954 A1 | 1/2017 | McDonough et al. |
| 2017/0017955 A1 | 1/2017 | Stern et al. |
| 2017/0020241 A1 | 1/2017 | Proud et al. |
| 2017/0020402 A1 | 1/2017 | Rogers et al. |
| 2017/0021171 A1 | 1/2017 | Perez et al. |
| 2017/0021172 A1 | 1/2017 | Perez et al. |
| 2017/0027278 A1 | 2/2017 | Roser |
| 2017/0027514 A1 | 2/2017 | Biederman et al. |
| 2017/0027515 A1 | 2/2017 | Wiser |
| 2017/0027523 A1 | 2/2017 | Venkatraman et al. |
| 2017/0027812 A1 | 2/2017 | Hyde et al. |
| 2017/0028185 A1 | 2/2017 | Wiley et al. |
| 2017/0028231 A1 | 2/2017 | Zhao et al. |
| 2017/0028622 A1 | 2/2017 | Westlind et al. |
| 2017/0031874 A1 | 2/2017 | Boudville |
| 2017/0033932 A1 | 2/2017 | Truu et al. |
| 2017/0036021 A1 | 2/2017 | Sharma et al. |
| 2017/0036031 A1 | 2/2017 | Norton et al. |
| 2017/0038401 A1 | 2/2017 | Holmes et al. |
| 2017/0038747 A1 | 2/2017 | Ellis |
| 2017/0043160 A1 | 2/2017 | Goodall et al. |
| 2017/0045862 A1 | 2/2017 | Jia et al. |
| 2017/0046652 A1 | 2/2017 | Haldenby et al. |
| 2017/0046689 A1 | 2/2017 | Lohe et al. |
| 2017/0046694 A1 | 2/2017 | Chow et al. |
| 2017/0046799 A1 | 2/2017 | Chan et al. |
| 2017/0046806 A1 | 2/2017 | Haldenby et al. |
| 2017/0048209 A1 | 2/2017 | Lohe et al. |
| 2017/0048234 A1 | 2/2017 | Lohe et al. |
| 2017/0048235 A1 | 2/2017 | Lohe et al. |
| 2017/0049352 A1 | 2/2017 | Mirov |
| 2017/0049406 A1 | 2/2017 | Lanzel et al. |
| 2017/0049946 A1 | 2/2017 | Kapur et al. |
| 2017/0053078 A1 | 2/2017 | Lanzel et al. |
| 2017/0055205 A1 | 2/2017 | Morris et al. |
| 2017/0055845 A1 | 3/2017 | Mirov et al. |
| 2017/0055851 A1 | 3/2017 | Al-Ali |
| 2017/0055880 A1 | 3/2017 | Agrawal et al. |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0056677 A1 | 3/2017 | Zhang et al. |
| 2017/0058451 A1 | 3/2017 | Smith et al. |
| 2017/0063434 A1 | 3/2017 | Hviid et al. |
| 2017/0065183 A1 | 3/2017 | Abreu |
| 2017/0065230 A1 | 3/2017 | Sinha et al. |
| 2017/0065821 A1 | 3/2017 | Brink et al. |
| 2017/0068774 A1 | 3/2017 | Cluckers et al. |
| 2017/0068970 A1 | 3/2017 | McCormack |
| 2017/0071474 A1 | 3/2017 | Islam |

(56) References Cited

U.S. PATENT DOCUMENTS

| | | |
|---|---|---|
| 2017/0071487 A1 | 3/2017 | Ritscher et al. |
| 2017/0071506 A1 | 3/2017 | Dwarika |
| 2017/0071510 A1 | 3/2017 | Delbeke et al. |
| 2017/0071545 A1 | 3/2017 | Ritscher et al. |
| 2017/0072121 A1 | 3/2017 | Yomtov et al. |
| 2017/0076068 A1 | 3/2017 | Dobbles et al. |
| 2017/0079368 A1 | 3/2017 | Amos et al. |
| 2017/0079596 A1 | 3/2017 | Teixeira |
| 2017/0080207 A1 | 3/2017 | Perez et al. |
| 2017/0083907 A1 | 3/2017 | McDonough et al. |
| 2017/0084983 A1 | 3/2017 | Baringer et al. |
| 2017/0085545 A1 | 3/2017 | Lohe et al. |
| 2017/0085555 A1 | 3/2017 | Bisikalo et al. |
| 2017/0085967 A1 | 3/2017 | Case, Jr. |
| 2017/0086519 A1 | 3/2017 | Vigano' et al. |
| 2017/0086752 A1 | 3/2017 | Baxi et al. |
| 2017/0091756 A1 | 3/2017 | Stern et al. |
| 2017/0095011 A1 | 4/2017 | Cobbett et al. |
| 2017/0095205 A1 | 4/2017 | Abreu |
| 2017/0095673 A1 | 4/2017 | Ludwig et al. |
| 2017/0095721 A1 | 4/2017 | Bleich et al. |
| 2017/0097994 A1 | 4/2017 | Karavirta |
| 2017/0098367 A1 | 4/2017 | M et al. |
| 2017/0100056 A1 | 4/2017 | Zhu et al. |
| 2017/0100214 A1 | 4/2017 | Wen |
| 2017/0103669 A1 | 4/2017 | Silveratawil et al. |
| 2017/0105474 A1 | 4/2017 | Morrison et al. |
| 2017/0105476 A1 | 4/2017 | Morrison et al. |
| 2017/0106196 A1 | 4/2017 | Ter-Petrosyan et al. |
| 2017/0109735 A1 | 4/2017 | Sheng et al. |
| 2017/0111359 A1 | 4/2017 | Zizi et al. |
| 2017/0112391 A1 | 4/2017 | Stivoric et al. |
| 2017/0112439 A1 | 4/2017 | Dubin et al. |
| 2017/0112671 A1 | 4/2017 | Goldstein |
| 2017/0113042 A1 | 4/2017 | Goodall et al. |
| 2017/0113046 A1 | 4/2017 | Fried et al. |
| 2017/0113057 A1 | 4/2017 | Goodall et al. |
| 2017/0117739 A1 | 4/2017 | Tuseth et al. |
| 2017/0118626 A1 | 4/2017 | Sadhu |
| 2017/0119261 A1 | 5/2017 | Teixeira |
| 2017/0119312 A1 | 5/2017 | Kaskoun et al. |
| 2017/0119968 A1 | 5/2017 | Keenan et al. |
| 2017/0124853 A1 | 5/2017 | Mehta et al. |
| 2017/0127929 A1 | 5/2017 | Schutt et al. |
| 2017/0127975 A1 | 5/2017 | Bozkurt |
| 2017/0127999 A1 | 5/2017 | Linders et al. |
| 2017/0128140 A1 | 5/2017 | Samuelsson et al. |
| 2017/0128722 A1 | 5/2017 | Perez |
| 2017/0128735 A1 | 5/2017 | Gustavson et al. |
| 2017/0132615 A1 | 5/2017 | Castinado et al. |
| 2017/0132630 A1 | 5/2017 | Castinado et al. |
| 2017/0133022 A1 | 5/2017 | Gurijala et al. |
| 2017/0135415 A1 | 5/2017 | Ellis |
| 2017/0135633 A1 | 5/2017 | Connor |
| 2017/0136209 A1 | 5/2017 | Burnett et al. |
| 2017/0136264 A1 | 5/2017 | Hyde et al. |
| 2017/0136265 A1 | 5/2017 | Hyde et al. |
| 2017/0136842 A1 | 5/2017 | Anderson et al. |
| 2017/0140408 A1 | 5/2017 | Wuehler |
| 2017/0143219 A1 | 5/2017 | Ciecko |
| 2017/0143233 A1 | 5/2017 | Audeh et al. |
| 2017/0143266 A1 | 5/2017 | Kovacs et al. |
| 2017/0143267 A1 | 5/2017 | Kovacs et al. |
| 2017/0143268 A1 | 5/2017 | Kovacs et al. |
| 2017/0143282 A1 | 5/2017 | Kovacs et al. |
| 2017/0146385 A1 | 5/2017 | Kovacs et al. |
| 2017/0146386 A1 | 5/2017 | Wiard et al. |
| 2017/0146387 A1 | 5/2017 | Wiard et al. |
| 2017/0146388 A1 | 5/2017 | Kovacs et al. |
| 2017/0146389 A1 | 5/2017 | Kovacs et al. |
| 2017/0146390 A1 | 5/2017 | Kovacs |
| 2017/0146391 A1 | 5/2017 | Kovacs et al. |
| 2017/0147722 A1 | 5/2017 | Greenwood |
| 2017/0147754 A1 | 5/2017 | Kovacs |
| 2017/0147803 A1 | 5/2017 | Zizi et al. |
| 2017/0147837 A1 | 5/2017 | Kovacs et al. |
| 2017/0148240 A1 | 5/2017 | Kovacs et al. |
| 2017/0149773 A1 | 5/2017 | Kovacs et al. |
| 2017/0150895 A1 | 6/2017 | Cobbett et al. |
| 2017/0152486 A1 | 6/2017 | Shen et al. |
| 2017/0156593 A1 | 6/2017 | Ferber et al. |
| 2017/0156606 A1 | 6/2017 | Ferber et al. |
| 2017/0156662 A1 | 6/2017 | Goodall et al. |
| 2017/0156663 A1 | 6/2017 | Heruth et al. |
| 2017/0157411 A1 | 6/2017 | Shahandeh et al. |
| 2017/0160398 A1 | 6/2017 | Venkatraman et al. |
| 2017/0161517 A1 | 6/2017 | Shah |
| 2017/0164850 A1 | 6/2017 | Murphy et al. |
| 2017/0164876 A1 | 6/2017 | Hyde et al. |
| 2017/0164878 A1 | 6/2017 | Connor |
| 2017/0165425 A9 | 6/2017 | Ruchti et al. |
| 2017/0165483 A1 | 6/2017 | Sharma et al. |
| 2017/0168457 A1 | 6/2017 | Sadasivam et al. |
| 2017/0169190 A1 | 6/2017 | Harma et al. |
| 2017/0169695 A1 | 6/2017 | Poisner et al. |
| 2017/0172249 A1 | 6/2017 | Kassatly et al. |
| 2017/0172522 A1 | 6/2017 | Insler et al. |
| 2017/0173216 A1 | 6/2017 | Ju et al. |
| 2017/0173262 A1 | 6/2017 | Veltz |
| 2017/0181671 A1 | 6/2017 | Varsavsky et al. |
| 2017/0181677 A1 | 6/2017 | Varsavsky et al. |
| 2017/0181700 A1* | 6/2017 | Olivier ................. A61B 5/6823 |
| 2017/0181708 A1 | 6/2017 | Orron et al. |
| 2017/0182330 A1 | 6/2017 | Schneider et al. |
| 2017/0188893 A1 | 7/2017 | Venkatraman et al. |
| 2017/0189756 A1 | 7/2017 | Brothers et al. |
| 2017/0189757 A1 | 7/2017 | Brothers et al. |
| 2017/0189815 A1 | 7/2017 | Tweedale et al. |
| 2017/0193140 A1 | 7/2017 | Brothers et al. |
| 2017/0195475 A1 | 7/2017 | Mehta et al. |
| 2017/0196455 A1 | 7/2017 | Mirov et al. |
| 2017/0196457 A1 | 7/2017 | Thakur et al. |
| 2017/0196458 A1 | 7/2017 | Ternes et al. |
| 2017/0196513 A1 | 7/2017 | Longinotti-Buitoni et al. |
| 2017/0197072 A1 | 7/2017 | Linden et al. |
| 2017/0202461 A1 | 7/2017 | Darty et al. |
| 2017/0202484 A1 | 7/2017 | Al-Shaery et al. |
| 2017/0206532 A1 | 7/2017 | Choi |
| 2017/0209053 A1 | 7/2017 | Pantelopoulos et al. |
| 2017/0209055 A1 | 7/2017 | Pantelopoulos et al. |
| 2017/0209081 A1 | 7/2017 | Davidson |
| 2017/0209666 A1 | 7/2017 | Quigley |
| 2017/0209705 A1 | 7/2017 | Faltys et al. |
| 2017/0215028 A1 | 7/2017 | Rhoads et al. |
| 2017/0215524 A1 | 8/2017 | Rushbrook et al. |
| 2017/0215729 A1 | 8/2017 | Mullin et al. |
| 2017/0215756 A1 | 8/2017 | Galloway et al. |
| 2017/0215757 A1 | 8/2017 | Gil Da Costa et al. |
| 2017/0215765 A1 | 8/2017 | Amos et al. |
| 2017/0216125 A1 | 8/2017 | Hyde et al. |
| 2017/0216610 A1 | 8/2017 | Yoder et al. |
| 2017/0216611 A1 | 8/2017 | Yoder et al. |
| 2017/0216625 A1 | 8/2017 | Pishdad et al. |
| 2017/0216627 A1 | 8/2017 | Brooks et al. |
| 2017/0221032 A1 | 8/2017 | Mazed |
| 2017/0221052 A1 | 8/2017 | Sheng et al. |
| 2017/0221463 A1 | 8/2017 | Lenhert |
| 2017/0224252 A1 | 8/2017 | Salzar et al. |
| 2017/0224260 A1 | 8/2017 | Darty et al. |
| 2017/0224268 A1 | 8/2017 | Altini et al. |
| 2017/0224291 A1 | 8/2017 | Hampapuram et al. |
| 2017/0224581 A1 | 8/2017 | Johnson et al. |
| 2017/0224990 A1 | 8/2017 | Goldwasser et al. |
| 2017/0228516 A1 | 8/2017 | Sampath et al. |
| 2017/0228627 A1 | 8/2017 | Geissler et al. |
| 2017/0228706 A1 | 8/2017 | Parziale et al. |
| 2017/0228731 A1 | 8/2017 | Sheng et al. |
| 2017/0228734 A1 | 8/2017 | Kurian |
| 2017/0230084 A1 | 8/2017 | Zhu et al. |
| 2017/0231494 A1 | 8/2017 | Pekander |
| 2017/0231495 A1 | 8/2017 | Soro et al. |
| 2017/0231569 A1 | 8/2017 | Kumar et al. |
| 2017/0231597 A1 | 8/2017 | Howard |
| 2017/0231738 A1 | 8/2017 | Severson |

(56) References Cited

U.S. PATENT DOCUMENTS

| | | |
|---|---|---|
| 2017/0232256 A1 | 8/2017 | Meskens |
| 2017/0232297 A1 | 8/2017 | Prokhorov |
| 2017/0232300 A1 | 8/2017 | Tran et al. |
| 2017/0236177 A1 | 8/2017 | Sebastian et al. |
| 2017/0236196 A1 | 8/2017 | Isaacson et al. |
| 2017/0236407 A1 | 8/2017 | Rhoads et al. |
| 2017/0237569 A1 | 8/2017 | Vandervort |
| 2017/0237570 A1 | 8/2017 | Vandervort |
| 2017/0237694 A1 | 8/2017 | Choudhary et al. |
| 2017/0238659 A1 | 8/2017 | Bohnsack et al. |
| 2017/0238814 A1 | 8/2017 | Gopalakrishnan et al. |
| 2017/0238881 A1 | 8/2017 | Cheng et al. |
| 2017/0239470 A1 | 8/2017 | Wei et al. |
| 2017/0239523 A1 | 8/2017 | Cheng et al. |
| 2017/0243056 A1 | 8/2017 | Cheng et al. |
| 2017/0243177 A1 | 8/2017 | Johnsrud et al. |
| 2017/0243208 A1 | 8/2017 | Kurian et al. |
| 2017/0243209 A1 | 8/2017 | Johnsrud et al. |
| 2017/0243212 A1 | 8/2017 | Castinado et al. |
| 2017/0243213 A1 | 8/2017 | Castinado et al. |
| 2017/0243214 A1 | 8/2017 | Johnsrud et al. |
| 2017/0243217 A1 | 8/2017 | Johnsrud et al. |
| 2017/0243222 A1 | 8/2017 | Balasubramanian |
| 2017/0243286 A1 | 8/2017 | Castinado et al. |
| 2017/0243287 A1 | 8/2017 | Johnsrud et al. |
| 2017/0243508 A1 | 8/2017 | Cheng et al. |
| 2017/0244707 A1 | 8/2017 | Johnsrud et al. |
| 2017/0244721 A1 | 8/2017 | Kurian et al. |
| 2017/0245767 A1 | 8/2017 | Ferber et al. |
| 2017/0246459 A1 | 8/2017 | Kelley et al. |
| 2017/0246521 A1 | 8/2017 | deGreef et al. |
| 2017/0248567 A1 | 8/2017 | Islam |
| 2017/0249115 A1 | 8/2017 | Yuen et al. |
| 2017/0250796 A1 | 8/2017 | Samid |
| 2017/0251232 A1 | 8/2017 | Kaib et al. |
| 2017/0251940 A1 | 9/2017 | Perschbacher et al. |
| 2017/0251974 A1 | 9/2017 | Shreim et al. |
| 2017/0251975 A1 | 9/2017 | Shreim et al. |
| 2017/0252513 A1 | 9/2017 | Buck, Jr. et al. |
| 2017/0255185 A1 | 9/2017 | Hinshaw |
| 2017/0255262 A1 | 9/2017 | Liu |
| 2017/0256000 A1 | 9/2017 | Isaacson et al. |
| 2017/0256001 A1 | 9/2017 | Isaacson et al. |
| 2017/0256003 A1 | 9/2017 | Isaacson et al. |
| 2017/0257162 A1 | 9/2017 | Panther et al. |
| 2017/0258389 A1 | 9/2017 | Howard |
| 2017/0258585 A1 | 9/2017 | Marquez et al. |
| 2017/0259072 A1 | 9/2017 | Newham et al. |
| 2017/0262015 A1 | 9/2017 | Li et al. |
| 2017/0262604 A1 | 9/2017 | Francois |
| 2017/0262862 A1 | 9/2017 | Aljawhari |
| 2017/0264338 A1 | 9/2017 | Yun et al. |
| 2017/0264693 A1 | 9/2017 | Xue et al. |
| 2017/0265578 A1 | 9/2017 | Schneider |
| 2017/0265580 A1 | 9/2017 | Schneider et al. |
| 2017/0265581 A1 | 9/2017 | Chang |
| 2017/0265582 A1 | 9/2017 | Walker et al. |
| 2017/0265583 A1 | 9/2017 | Schneider et al. |
| 2017/0265584 A1 | 9/2017 | Walker et al. |
| 2017/0265586 A1 | 9/2017 | Schneider et al. |
| 2017/0265587 A1 | 9/2017 | Walker et al. |
| 2017/0265588 A1 | 9/2017 | Walker et al. |
| 2017/0265589 A1 | 9/2017 | Walker et al. |
| 2017/0265591 A1 | 9/2017 | Schneider |
| 2017/0265592 A1 | 9/2017 | Schneider et al. |
| 2017/0265594 A1 | 9/2017 | Walker et al. |
| 2017/0265769 A1 | 9/2017 | Quinlan et al. |
| 2017/0265770 A1 | 9/2017 | Quinlan et al. |
| 2017/0266533 A1 | 9/2017 | Dalebout et al. |
| 2017/0270224 A1 | 9/2017 | Singh et al. |
| 2017/0270721 A1 | 9/2017 | Graafstra |
| 2017/0270765 A1 | 9/2017 | Roberts et al. |
| 2017/0272008 A1 | 9/2017 | Schneider |
| 2017/0272316 A1 | 9/2017 | Johnson et al. |
| 2017/0272842 A1 | 9/2017 | Touma et al. |
| 2017/0273599 A1 | 9/2017 | Reese et al. |
| 2017/0273606 A1 | 9/2017 | Estes et al. |
| 2017/0273629 A1 | 9/2017 | Yu et al. |
| 2017/0274267 A1 | 9/2017 | Blahnik |
| 2017/0281020 A1 | 10/2017 | Mulligan et al. |
| 2017/0281867 A1 | 10/2017 | Parikh et al. |
| 2017/0281927 A1 | 10/2017 | Orinski |
| 2017/0281928 A1 | 10/2017 | Orinski |
| 2017/0281957 A1 | 10/2017 | Howard |
| 2017/0282011 A1 | 10/2017 | Jang et al. |
| 2017/0283845 A1 | 10/2017 | Holmes et al. |
| 2017/0284875 A1 | 10/2017 | Walker |
| 2017/0290513 A1 | 10/2017 | O'Reilly et al. |
| 2017/0290528 A1 | 10/2017 | Ternes et al. |
| 2017/0290937 A1 | 10/2017 | Dobrinsky et al. |
| 2017/0290980 A1 | 10/2017 | Friedli et al. |
| 2017/0293266 A1 | 10/2017 | Ji |
| 2017/0295889 A1 | 10/2017 | Beers |
| 2017/0296052 A1 | 10/2017 | Behar et al. |
| 2017/0296076 A1 | 10/2017 | Mahajan et al. |
| 2017/0296107 A1 | 10/2017 | Reid et al. |
| 2017/0296139 A1 | 10/2017 | Giaya et al. |
| 2017/0296813 A1 | 10/2017 | Sharma et al. |
| 2017/0296814 A1 | 10/2017 | Sharma et al. |
| 2017/0296834 A1 | 10/2017 | Kothandaraman et al. |
| 2017/0300653 A1 | 10/2017 | Hresko et al. |
| 2017/0300741 A1 | 10/2017 | Seuss et al. |
| 2017/0300905 A1 | 10/2017 | Withrow et al. |
| 2017/0300910 A1 | 10/2017 | Bethke et al. |
| 2017/0300946 A1 | 10/2017 | Wilkinson et al. |
| 2017/0301214 A1 | 10/2017 | Chen et al. |
| 2017/0303784 A1 | 10/2017 | Huiku |
| 2017/0303786 A1 | 10/2017 | Mullin et al. |
| 2017/0303827 A1 | 10/2017 | Giedwoyn et al. |
| 2017/0304635 A1 | 10/2017 | Aghassian |
| 2017/0306539 A1 | 10/2017 | Gladish et al. |
| 2017/0308044 A1 | 10/2017 | Ellis |
| 2017/0308066 A1 | 10/2017 | Farren et al. |
| 2017/0308663 A1 | 10/2017 | Moya et al. |
| 2017/0308945 A1 | 10/2017 | Loveder et al. |
| 2017/0311878 A1 | 11/2017 | Wu et al. |
| 2017/0311897 A1 | 11/2017 | Faccioli et al. |
| 2017/0311902 A1 | 11/2017 | Ferber et al. |
| 2017/0312161 A1 | 11/2017 | Johnson et al. |
| 2017/0312165 A1 | 11/2017 | Johnson et al. |
| 2017/0312530 A1 | 11/2017 | Schilling et al. |
| 2017/0312612 A1 | 11/2017 | Bleich et al. |
| 2017/0312746 A1 | 11/2017 | Holmes et al. |
| 2017/0316182 A1 | 11/2017 | Blackadar et al. |
| 2017/0316487 A1 | 11/2017 | Mazed |
| 2017/0319119 A1 | 11/2017 | Krasnow et al. |
| 2017/0319122 A1 | 11/2017 | Wild et al. |
| 2017/0319123 A1 | 11/2017 | Voss et al. |
| 2017/0319849 A1 | 11/2017 | Su et al. |
| 2017/0324437 A1 | 11/2017 | Ruttler et al. |
| 2017/0325056 A1 | 11/2017 | Mehta et al. |
| 2017/0325524 A1 | 11/2017 | Hyde et al. |
| 2017/0325525 A1 | 11/2017 | Hyde et al. |
| 2017/0325727 A1 | 11/2017 | Buza |
| 2017/0325736 A1 | 11/2017 | Cantwell et al. |
| 2017/0326013 A1 | 11/2017 | Hyde et al. |
| 2017/0330257 A1 | 11/2017 | Collier et al. |
| 2017/0330447 A1 | 11/2017 | Mehta et al. |
| 2017/0332733 A1 | 11/2017 | Cluckers et al. |
| 2017/0332980 A1 | 11/2017 | Fifield et al. |
| 2017/0333080 A1 | 11/2017 | Roschak et al. |
| 2017/0333752 A1 | 11/2017 | Korkala et al. |
| 2017/0336781 A1 | 11/2017 | Livaccari et al. |
| 2017/0340049 A1 | 11/2017 | Rice et al. |
| 2017/0340260 A1 | 11/2017 | Chowdhury et al. |
| 2017/0340277 A1 | 11/2017 | Berner, Jr. et al. |
| 2017/0340872 A1 | 11/2017 | Hanson et al. |
| 2017/0340920 A1 | 11/2017 | Posio et al. |
| 2017/0344736 A1 | 11/2017 | Lane |
| 2017/0345105 A1 | 11/2017 | Isaacson et al. |
| 2017/0347895 A1 | 12/2017 | Wei et al. |
| 2017/0348146 A1 | 12/2017 | Drnek et al. |
| 2017/0350878 A1 | 12/2017 | Holmes et al. |
| 2017/0351891 A1 | 12/2017 | Ackley et al. |

(56) References Cited

U.S. PATENT DOCUMENTS

| | | |
|---|---|---|
| 2017/0354351 A1 | 12/2017 | Krans et al. |
| 2017/0354365 A1 | 12/2017 | Zhou |
| 2017/0354547 A1 | 12/2017 | Abir |
| 2017/0354795 A1 | 12/2017 | Blahnik et al. |
| 2017/0356770 A1 | 12/2017 | Bhatt et al. |
| 2017/0357217 A1 | 12/2017 | Raymann et al. |
| 2017/0357419 A1 | 12/2017 | Raymann et al. |
| 2017/0358041 A1 | 12/2017 | Forbes, Jr. et al. |
| 2017/0358239 A1 | 12/2017 | Arney et al. |
| 2017/0358240 A1 | 12/2017 | Blahnik et al. |
| 2017/0358242 A1 | 12/2017 | Thompson et al. |
| 2017/0360320 A1 | 12/2017 | Sarkar et al. |
| 2017/0361092 A1 | 12/2017 | Sharma et al. |
| 2017/0361162 A1 | 12/2017 | Bailly et al. |
| 2017/0363440 A1 | 12/2017 | Ahmed et al. |
| 2017/0364860 A1 | 12/2017 | Wilkinson et al. |
| 2017/0365101 A1 | 12/2017 | Samec et al. |
| 2017/0366233 A1 | 12/2017 | Hviid et al. |
| 2017/0367576 A1 | 12/2017 | Sanyal et al. |
| 2017/0367585 A1 | 12/2017 | Islam |
| 2017/0367599 A1 | 12/2017 | Sanyal et al. |
| 2017/0368158 A1 | 12/2017 | Vescovi et al. |
| 2017/0372009 A1 | 12/2017 | Sanyal et al. |
| 2017/0372026 A1 | 12/2017 | Sanyal et al. |
| 2017/0372216 A1 | 12/2017 | Awiszus et al. |
| 2017/0373849 A1 | 12/2017 | Donner et al. |
| 2017/0374436 A1 | 12/2017 | Awiszus et al. |
| 2018/0000336 A1 | 1/2018 | Gilad-Gilor et al. |
| 2018/0000345 A1 | 1/2018 | Soro et al. |
| 2018/0000347 A1 | 1/2018 | Perez et al. |
| 2018/0000414 A1 | 1/2018 | Lowet et al. |
| 2018/0001005 A1 | 1/2018 | Casas |
| 2018/0001018 A1 | 1/2018 | Burke et al. |
| 2018/0001023 A1 | 1/2018 | Gerber et al. |
| 2018/0001083 A9 | 1/2018 | Finch et al. |
| 2018/0001184 A1 | 1/2018 | Tran et al. |
| 2018/0006990 A1 | 1/2018 | Munemann |
| 2018/0007467 A1 | 1/2018 | Goran et al. |
| 2018/0008003 A1 | 1/2018 | Davis et al. |
| 2018/0008005 A1 | 1/2018 | Compton et al. |
| 2018/0008151 A1 | 1/2018 | Maertz |
| 2018/0008185 A1 | 1/2018 | Ramu et al. |
| 2018/0008191 A1 | 1/2018 | Cronin et al. |
| 2018/0008193 A1 | 1/2018 | Takahashi et al. |
| 2018/0008206 A1 | 1/2018 | Stahmann et al. |
| 2018/0008831 A1 | 1/2018 | An et al. |
| 2018/0012311 A1 | 1/2018 | Small et al. |
| 2018/0012469 A1 | 1/2018 | Tofighbakhsh |
| 2018/0013815 A1 | 1/2018 | Gold |
| 2018/0019984 A1 | 1/2018 | Isaacson et al. |
| 2018/0020764 A1 | 1/2018 | Walker |
| 2018/0021235 A1 | 1/2018 | Christiano et al. |
| 2018/0021498 A1 | 1/2018 | Yomtov et al. |
| 2018/0021510 A1 | 1/2018 | Burke et al. |
| 2018/0021564 A1 | 1/2018 | Goodall et al. |
| 2018/0021589 A1 | 1/2018 | Wu et al. |
| 2018/0027347 A1 | 1/2018 | Osborne et al. |
| 2018/0028106 A1 | 2/2018 | Leschinsky |
| 2018/0028114 A1 | 2/2018 | Cronin |
| 2018/0028122 A1 | 2/2018 | Golda et al. |
| 2018/0028275 A1 | 2/2018 | Bradley et al. |
| 2018/0028809 A1 | 2/2018 | Ziv |
| 2018/0028827 A1 | 2/2018 | Schilling et al. |
| 2018/0035898 A1 | 2/2018 | Gunderson |
| 2018/0035920 A1 | 2/2018 | Gunderson et al. |
| 2018/0035951 A1 | 2/2018 | Li |
| 2018/0035982 A1 | 2/2018 | Tholen et al. |
| 2018/0036053 A1 | 2/2018 | Toscano et al. |
| 2018/0036115 A1 | 2/2018 | Smirnov |
| 2018/0036147 A1 | 2/2018 | Gregg et al. |
| 2018/0039512 A1 | 2/2018 | Almasan et al. |
| 2018/0040258 A1 | 2/2018 | Kouache |
| 2018/0041345 A1 | 2/2018 | Maim |
| 2018/0042526 A1 | 2/2018 | Hong et al. |
| 2018/0042809 A1 | 2/2018 | Zipper |
| 2018/0043095 A1 | 2/2018 | Finan et al. |
| 2018/0043096 A1 | 2/2018 | Dobbles et al. |
| 2018/0043173 A1 | 2/2018 | Hellman et al. |
| 2018/0045745 A1 | 2/2018 | Holmes et al. |
| 2018/0047074 A1 | 2/2018 | Cronin et al. |
| 2018/0049251 A1 | 2/2018 | Hellman et al. |
| 2018/0049675 A1 | 2/2018 | Kerber |
| 2018/0050189 A1 | 2/2018 | Rump et al. |
| 2018/0050214 A1 | 2/2018 | Rump |
| 2018/0055373 A1 | 3/2018 | Kraiter et al. |
| 2018/0055376 A1 | 3/2018 | Yuen et al. |
| 2018/0055382 A1 | 3/2018 | Woodward et al. |
| 2018/0055386 A1 | 3/2018 | Zielinski et al. |
| 2018/0055500 A1 | 3/2018 | Scott et al. |
| 2018/0056071 A1 | 3/2018 | Swanson et al. |
| 2018/0059126 A1 | 3/2018 | Jones et al. |
| 2018/0060449 A1 | 3/2018 | Cronin et al. |
| 2018/0060520 A1 | 3/2018 | Degen et al. |
| 2018/0064209 A1 | 3/2018 | Hamill |
| 2018/0067516 A1 | 3/2018 | Longinotti-Buitoni et al. |
| 2018/0069899 A1 | 3/2018 | Lang et al. |
| 2018/0070877 A1 | 3/2018 | Tian |
| 2018/0071789 A1 | 3/2018 | Kingston et al. |
| 2018/0072415 A1 | 3/2018 | Cantrell et al. |
| 2018/0072416 A1 | 3/2018 | Cantrell et al. |
| 2018/0074481 A1 | 3/2018 | Kingston et al. |
| 2018/0074488 A1 | 3/2018 | Cantrell et al. |
| 2018/0074521 A1 | 3/2018 | Cantrell et al. |
| 2018/0074522 A1 | 3/2018 | Cantrell et al. |
| 2018/0074523 A1 | 3/2018 | Cantrell et al. |
| 2018/0075386 A1 | 3/2018 | Kingston et al. |
| 2018/0075406 A1 | 3/2018 | Kingston et al. |
| 2018/0075716 A1 | 3/2018 | Mirov et al. |
| 2018/0075724 A1 | 3/2018 | Steiner et al. |
| 2018/0077975 A1 | 3/2018 | Ellis |
| 2018/0078754 A1 | 3/2018 | Perez et al. |
| 2018/0078777 A1 | 3/2018 | Wu et al. |
| 2018/0078843 A1 | 3/2018 | Tran et al. |
| 2018/0081787 A1 | 3/2018 | Riddick et al. |
| 2018/0081955 A1 | 3/2018 | Gupta et al. |
| 2018/0082043 A1 | 3/2018 | Witchey et al. |
| 2018/0082295 A1 | 3/2018 | Boucard |
| 2018/0083786 A1 | 3/2018 | Dierks et al. |
| 2018/0085011 A1 | 3/2018 | Ma et al. |
| 2018/0085021 A1 | 3/2018 | Chakravarthy et al. |
| 2018/0085038 A1 | 3/2018 | Chen et al. |
| 2018/0085040 A1 | 3/2018 | Ferber et al. |
| 2018/0085572 A1 | 3/2018 | Stanslaski et al. |
| 2018/0085576 A1 | 3/2018 | Sharma et al. |
| 2018/0085580 A1 | 3/2018 | Perez et al. |
| 2018/0085585 A1 | 3/2018 | Stanslaski et al. |
| 2018/0085586 A1 | 3/2018 | Stanslaski et al. |
| 2018/0085592 A1 | 3/2018 | Yoder et al. |
| 2018/0089394 A1 | 3/2018 | Hyde et al. |
| 2018/0089627 A1 | 3/2018 | Liss |
| 2018/0089641 A1 | 3/2018 | Chan et al. |
| 2018/0089669 A1 | 3/2018 | Singh |
| 2018/0090229 A1 | 3/2018 | Sanyal et al. |
| 2018/0092551 A1 | 4/2018 | Yuen et al. |
| 2018/0092554 A1 | 4/2018 | Zhang et al. |
| 2018/0092573 A1 | 4/2018 | Datta et al. |
| 2018/0092577 A1 | 4/2018 | Kane et al. |
| 2018/0094953 A1 | 4/2018 | Colson et al. |
| 2018/0094991 A1 | 4/2018 | McMillen et al. |
| 2018/0096121 A1 | 4/2018 | Goeringer et al. |
| 2018/0096175 A1 | 4/2018 | Schmeling et al. |
| 2018/0101138 A1 | 4/2018 | Raymann et al. |
| 2018/0101655 A1 | 4/2018 | Fogelberg et al. |
| 2018/0103724 A1 | 4/2018 | Ho |
| 2018/0103863 A1 | 4/2018 | Hu et al. |
| 2018/0103874 A1 | 4/2018 | Lee et al. |
| 2018/0103879 A1 | 4/2018 | Masciotti et al. |
| 2018/0103883 A1 | 4/2018 | Darty et al. |
| 2018/0104407 A1 | 4/2018 | Dacey, Jr. et al. |
| 2018/0108024 A1 | 4/2018 | Greco et al. |
| 2018/0108440 A1 | 4/2018 | Stevens et al. |
| 2018/0110294 A1 | 4/2018 | Schneider et al. |
| 2018/0114124 A1 | 4/2018 | Cronn et al. |
| 2018/0115600 A1 | 4/2018 | Almasan et al. |

(56) References Cited

U.S. PATENT DOCUMENTS

| | | |
|---|---|---|
| 2018/0116334 A1 | 5/2018 | Andon et al. |
| 2018/0116536 A1 | 5/2018 | Katra et al. |
| 2018/0116723 A1 | 5/2018 | Hettrick et al. |
| 2018/0117346 A1 | 5/2018 | Hellman et al. |
| 2018/0117446 A1 | 5/2018 | Tran et al. |
| 2018/0117447 A1 | 5/2018 | Tran et al. |
| 2018/0120225 A1 | 5/2018 | Ditterich |
| 2018/0122211 A1 | 5/2018 | Asano |
| 2018/0123804 A1 | 5/2018 | Smith et al. |
| 2018/0124478 A1 | 5/2018 | Case, Jr. |
| 2018/0125163 A1 | 5/2018 | Bertagna et al. |
| 2018/0125689 A1 | 5/2018 | Perez et al. |
| 2018/0126053 A1 | 5/2018 | Zilbershlag |
| 2018/0126133 A1 | 5/2018 | Cully et al. |
| 2018/0126172 A1 | 5/2018 | Sarkar et al. |
| 2018/0126222 A1 | 5/2018 | Duale et al. |
| 2018/0130034 A1 | 5/2018 | Taylor et al. |
| 2018/0130050 A1 | 5/2018 | Taylor et al. |
| 2018/0130158 A1 | 5/2018 | Atkinson et al. |
| 2018/0131765 A1 | 5/2018 | Puleston et al. |
| 2018/0132032 A1 | 5/2018 | Boesen et al. |
| 2018/0132568 A1 | 5/2018 | Kim et al. |
| 2018/0132697 A1 | 5/2018 | Desu-Kalyanam |
| 2018/0132758 A1 | 5/2018 | Benford |
| 2018/0132778 A1 | 5/2018 | Dugan |
| 2018/0133583 A1 | 5/2018 | Tran et al. |
| 2018/0136486 A1 | 5/2018 | Macnamara et al. |
| 2018/0136633 A1 | 5/2018 | Small et al. |
| 2018/0137461 A1 | 5/2018 | Wilkinson et al. |
| 2018/0137506 A1 | 5/2018 | Kcl et al. |
| 2018/0137512 A1 | 5/2018 | Georgiadis et al. |
| 2018/0138022 A1 | 5/2018 | Lam et al. |
| 2018/0139057 A1 | 5/2018 | Truu et al. |
| 2018/0139518 A1 | 5/2018 | Touma et al. |
| 2018/0139799 A1 | 5/2018 | Hellman et al. |
| 2018/0140191 A1 | 5/2018 | Samuelsson et al. |
| 2018/0140198 A1 | 5/2018 | Islam |
| 2018/0140835 A1 | 5/2018 | Sharma |
| 2018/0144298 A1 | 5/2018 | Rankin |
| 2018/0144342 A1 | 5/2018 | Borandi |
| 2018/0146738 A1 | 5/2018 | Folske et al. |
| 2018/0147024 A1 | 5/2018 | Kall et al. |
| 2018/0147333 A1 | 5/2018 | Rudser |
| 2018/0147349 A1 | 5/2018 | Finan et al. |
| 2018/0147413 A1 | 5/2018 | Ter-Petrosyan et al. |
| 2018/0147449 A1 | 5/2018 | Duale et al. |
| 2018/0150816 A1 | 5/2018 | Liu et al. |
| 2018/0152972 A1 | 5/2018 | Wu et al. |
| 2018/0153404 A1 | 6/2018 | Pekander |
| 2018/0153475 A1 | 6/2018 | Massey et al. |
| 2018/0154075 A1 | 6/2018 | Jho et al. |
| 2018/0156660 A1 | 6/2018 | Turgeon et al. |
| 2018/0158036 A1 | 6/2018 | Zhou et al. |
| 2018/0158266 A1 | 6/2018 | Zizi et al. |
| 2018/0160985 A1 | 6/2018 | Willis |
| 2018/0162186 A1 | 6/2018 | Anderson et al. |
| 2018/0165738 A1 | 6/2018 | Chilukuri et al. |
| 2018/0167394 A1 | 6/2018 | High et al. |
| 2018/0168273 A1 | 6/2018 | Case, Jr. |
| 2018/0168460 A1 | 6/2018 | Morris et al. |
| 2018/0168461 A1 | 6/2018 | Morris et al. |
| 2018/0168463 A1 | 6/2018 | Morris et al. |
| 2018/0168811 A1 | 6/2018 | Ranganathan et al. |
| 2018/0168905 A1 | 6/2018 | Goodall et al. |
| 2018/0169411 A1 | 6/2018 | Goodall et al. |
| 2018/0169412 A1 | 6/2018 | Goodall et al. |
| 2018/0169421 A1 | 6/2018 | Chen et al. |
| 2018/0169474 A1 | 6/2018 | Reddy |
| 2018/0173405 A1 | 6/2018 | Pereira et al. |
| 2018/0173906 A1 | 6/2018 | Rodriguez et al. |
| 2018/0174097 A1 | 6/2018 | Liu et al. |
| 2018/0174188 A1 | 6/2018 | Wilkinson et al. |
| 2018/0174686 A1 | 6/2018 | Zaphrir et al. |
| 2018/0176017 A1 | 6/2018 | Rodriguez et al. |
| 2018/0177397 A1 | 6/2018 | Kall et al. |
| 2018/0177459 A1 | 6/2018 | Eletr et al. |
| 2018/0177963 A1 | 6/2018 | Wang et al. |
| 2018/0181806 A1 | 6/2018 | Chandrashekar et al. |
| 2018/0181909 A1 | 6/2018 | Wilkinson et al. |
| 2018/0181964 A1 | 6/2018 | Zagarese et al. |
| 2018/0182140 A1 | 6/2018 | Biradar et al. |
| 2018/0182489 A1 | 6/2018 | Harma et al. |
| 2018/0183796 A1 | 6/2018 | Smith et al. |
| 2018/0184735 A1 | 7/2018 | Longinotti-Buitoni et al. |
| 2018/0184751 A1 | 7/2018 | Molyneux et al. |
| 2018/0184901 A1 | 7/2018 | Akmandor et al. |
| 2018/0184914 A1 | 7/2018 | Goering et al. |
| 2018/0184944 A1 | 7/2018 | Bodewes et al. |
| 2018/0188704 A1 | 7/2018 | Cella et al. |
| 2018/0188714 A1 | 7/2018 | Cella et al. |
| 2018/0188715 A1 | 7/2018 | Cella et al. |
| 2018/0189452 A1 | 7/2018 | Serhani et al. |
| 2018/0189528 A1 | 7/2018 | Hanis et al. |
| 2018/0189854 A1 | 7/2018 | Gabriele et al. |
| 2018/0191503 A1 | 7/2018 | Alwar et al. |
| 2018/0191693 A1 | 7/2018 | Juels |
| 2018/0192900 A1 | 7/2018 | Wei |
| 2018/0192952 A1 | 7/2018 | Rogers et al. |
| 2018/0192953 A1 | 7/2018 | Shreim et al. |
| 2018/0198617 A1 | 7/2018 | Drouin et al. |
| 2018/0198785 A1 | 7/2018 | Zizi et al. |
| 2018/0198876 A1 | 7/2018 | Ma et al. |
| 2018/0199657 A1 | 7/2018 | Kikukawa |
| 2018/0199671 A1 | 7/2018 | Schneider et al. |
| 2018/0199673 A1 | 7/2018 | Schneider et al. |
| 2018/0199674 A1 | 7/2018 | Walker et al. |
| 2018/0200003 A1 | 7/2018 | Olson |
| 2018/0200185 A1 | 7/2018 | Labib et al. |
| 2018/0203755 A1 | 7/2018 | Das et al. |
| 2018/0203882 A1 | 7/2018 | Hilsdale et al. |
| 2018/0204034 A1 | 7/2018 | Tonnelier |
| 2018/0204111 A1 | 7/2018 | Zadeh et al. |
| 2018/0206586 A1 | 7/2018 | Akay et al. |
| 2018/0206747 A1 | 7/2018 | Rinderknecht et al. |
| 2018/0207429 A1 | 7/2018 | Reinke et al. |
| 2018/0210425 A1 | 7/2018 | Cella et al. |
| 2018/0210426 A1 | 7/2018 | Cella et al. |
| 2018/0210427 A1 | 7/2018 | Cella et al. |
| 2018/0211213 A1 | 7/2018 | Vivier |
| 2018/0211673 A1 | 7/2018 | Sharma et al. |
| 2018/0211718 A1 | 7/2018 | Heath |
| 2018/0213583 A1 | 7/2018 | Al-Ali |
| 2018/0213879 A1 | 8/2018 | Campbell |
| 2018/0214025 A1 | 8/2018 | Homyk et al. |
| 2018/0214026 A1 | 8/2018 | Goodall et al. |
| 2018/0214066 A1 | 8/2018 | Goodall et al. |
| 2018/0214080 A1 | 8/2018 | Peeters et al. |
| 2018/0214690 A1 | 8/2018 | Hodgson-Zingman et al. |
| 2018/0214694 A1 | 8/2018 | Parramon |
| 2018/0218003 A1 | 8/2018 | Banga et al. |
| 2018/0218354 A1 | 8/2018 | Kumar et al. |
| 2018/0219334 A1 | 8/2018 | Kahlman |
| 2018/0221645 A1 | 8/2018 | Medema et al. |
| 2018/0221663 A1 | 8/2018 | Saini |
| 2018/0225419 A9 | 8/2018 | Anthony et al. |
| 2018/0225649 A1 | 8/2018 | Babar et al. |
| 2018/0227354 A1 | 8/2018 | Gold |
| 2018/0228401 A1 | 8/2018 | Schwartz et al. |
| 2018/0228434 A1 | 8/2018 | Dwarika et al. |
| 2018/0228438 A1 | 8/2018 | Kaskoun et al. |
| 2018/0229674 A1 | 8/2018 | Heinrich et al. |
| 2018/0231393 A1 | 8/2018 | Czaja et al. |
| 2018/0232693 A1 | 8/2018 | Gillen et al. |
| 2018/0232730 A1 | 8/2018 | Harbour et al. |
| 2018/0232817 A1 | 8/2018 | Isaacson et al. |
| 2018/0233016 A1 | 8/2018 | Daniel et al. |
| 2018/0233028 A1 | 8/2018 | Rhoads et al. |
| 2018/0235537 A1 | 8/2018 | Whiting et al. |
| 2018/0238734 A1 | 8/2018 | Hotelling et al. |
| 2018/0240176 A1 | 8/2018 | Cronin et al. |
| 2018/0240357 A1 | 8/2018 | Trench Roca |
| 2018/0241564 A1 | 8/2018 | Peterson |
| 2018/0242691 A1 | 8/2018 | Bohnsack et al. |
| 2018/0242864 A1 | 8/2018 | Hu et al. |

(56) References Cited

U.S. PATENT DOCUMENTS

| | | |
|---|---|---|
| 2018/0242891 A1 | 8/2018 | Bernstein et al. |
| 2018/0242921 A1 | 8/2018 | Muhsin et al. |
| 2018/0242926 A1 | 8/2018 | Muhsin et al. |
| 2018/0243528 A1 | 8/2018 | Zapol et al. |
| 2018/0243541 A1 | 8/2018 | Kapur et al. |
| 2018/0243567 A1 | 8/2018 | St. Martin et al. |
| 2018/0243573 A1 | 8/2018 | Yoder et al. |
| 2018/0243577 A1 | 8/2018 | Kivi et al. |
| 2018/0247712 A1 | 8/2018 | Muhsin et al. |
| 2018/0249919 A1 | 9/2018 | Pont et al. |
| 2018/0250574 A1 | 9/2018 | Bleich et al. |
| 2018/0253073 A1 | 9/2018 | Cella et al. |
| 2018/0253074 A1 | 9/2018 | Cella et al. |
| 2018/0253075 A1 | 9/2018 | Cella et al. |
| 2018/0253430 A1 | 9/2018 | Grigorescu et al. |
| 2018/0253805 A1 | 9/2018 | Kelly et al. |
| 2018/0255374 A1 | 9/2018 | Cella et al. |
| 2018/0255375 A1 | 9/2018 | Cella et al. |
| 2018/0255376 A1 | 9/2018 | Cella et al. |
| 2018/0255377 A1 | 9/2018 | Cella et al. |
| 2018/0255378 A1 | 9/2018 | Cella et al. |
| 2018/0255379 A1 | 9/2018 | Cella et al. |
| 2018/0255380 A1 | 9/2018 | Cella et al. |
| 2018/0255381 A1 | 9/2018 | Cella et al. |
| 2018/0255382 A1 | 9/2018 | Cella et al. |
| 2018/0255383 A1 | 9/2018 | Cella et al. |
| 2018/0256076 A1 | 9/2018 | Friedman et al. |
| 2018/0256096 A1 | 9/2018 | Galeev et al. |
| 2018/0257306 A1 | 9/2018 | Mattingly et al. |
| 2018/0259976 A1 | 9/2018 | Williams et al. |
| 2018/0260530 A1 | 9/2018 | Kall et al. |
| 2018/0261066 A1 | 9/2018 | Treacy et al. |
| 2018/0261307 A1 | 9/2018 | Couse et al. |
| 2018/0262493 A1 | 9/2018 | Andrade |
| 2018/0263564 A1 | 9/2018 | Avril |
| 2018/0264347 A1 | 9/2018 | Tran et al. |
| 2018/0268237 A1 | 9/2018 | Stanimirovic et al. |
| 2018/0268360 A1 | 9/2018 | Millhouse et al. |
| 2018/0268418 A1 | 9/2018 | Tanksali |
| 2018/0268479 A1 | 9/2018 | Dowling et al. |
| 2018/0268483 A1 | 9/2018 | Jayaram et al. |
| 2018/0270549 A1 | 9/2018 | Awiszus et al. |
| 2018/0271181 A1 | 9/2018 | Ellis |
| 2018/0271211 A1 | 9/2018 | Perrault et al. |
| 2018/0271213 A1 | 9/2018 | Perrault et al. |
| 2018/0271450 A1* | 9/2018 | Kamath ............... A61B 5/1495 |
| 2018/0274996 A1 | 9/2018 | Rice et al. |
| 2018/0279713 A1 | 10/2018 | Beers et al. |
| 2018/0279901 A1 | 10/2018 | Gaudet et al. |
| 2018/0279952 A1 | 10/2018 | Orron et al. |
| 2018/0279965 A1 | 10/2018 | Pandit et al. |
| 2018/0280177 A1 | 10/2018 | Longley et al. |
| 2018/0280694 A1 | 10/2018 | Mashiach et al. |
| 2018/0284093 A1 | 10/2018 | Brown et al. |
| 2018/0284735 A1 | 10/2018 | Cella et al. |
| 2018/0284736 A1 | 10/2018 | Cella et al. |
| 2018/0284737 A1 | 10/2018 | Cella et al. |
| 2018/0284741 A1 | 10/2018 | Cella et al. |
| 2018/0284742 A1 | 10/2018 | Cella et al. |
| 2018/0284743 A1 | 10/2018 | Cella et al. |
| 2018/0284744 A1 | 10/2018 | Cella et al. |
| 2018/0284745 A1 | 10/2018 | Cella et al. |
| 2018/0284746 A1 | 10/2018 | Cella et al. |
| 2018/0284747 A1 | 10/2018 | Cella et al. |
| 2018/0284749 A1 | 10/2018 | Cella et al. |
| 2018/0284752 A1 | 10/2018 | Cella et al. |
| 2018/0284753 A1 | 10/2018 | Cella et al. |
| 2018/0284754 A1 | 10/2018 | Cella et al. |
| 2018/0284755 A1 | 10/2018 | Cella et al. |
| 2018/0284756 A1 | 10/2018 | Cella et al. |
| 2018/0284757 A1 | 10/2018 | Cella et al. |
| 2018/0284758 A1 | 10/2018 | Cella et al. |
| 2018/0285709 A1 | 10/2018 | Braunstein |
| 2018/0289166 A1 | 10/2018 | Andon et al. |
| 2018/0289275 A1 | 10/2018 | Krusor et al. |
| 2018/0289310 A1 | 10/2018 | Girouard et al. |
| 2018/0289975 A1 | 10/2018 | Kavounas |
| 2018/0289976 A1 | 10/2018 | Chapman et al. |
| 2018/0292794 A1 | 10/2018 | Ellis |
| 2018/0293430 A1 | 10/2018 | Datta et al. |
| 2018/0293577 A1 | 10/2018 | Kim et al. |
| 2018/0295667 A1 | 10/2018 | Hellman et al. |
| 2018/0295895 A1 | 10/2018 | Donohoe et al. |
| 2018/0295933 A1 | 10/2018 | Davis et al. |
| 2018/0296097 A1 | 10/2018 | Islam |
| 2018/0296098 A1 | 10/2018 | Islam |
| 2018/0296136 A1 | 10/2018 | Foxlin et al. |
| 2018/0296142 A1 | 10/2018 | Ståhl |
| 2018/0296157 A1 | 10/2018 | Bleich et al. |
| 2018/0296161 A1 | 10/2018 | Shreim et al. |
| 2018/0296847 A1 | 10/2018 | Kaib et al. |
| 2018/0299878 A1 | 10/2018 | Cella et al. |
| 2018/0300772 A1 | 10/2018 | Bushong, Jr. |
| 2018/0300919 A1 | 10/2018 | Muhsin et al. |
| 2018/0301211 A1 | 10/2018 | Pappas et al. |
| 2018/0303343 A1 | 10/2018 | Dubin et al. |
| 2018/0303356 A1 | 10/2018 | Galeev et al. |
| 2018/0303357 A1 | 10/2018 | Galeev et al. |
| 2018/0303396 A1 | 10/2018 | Wild et al. |
| 2018/0304149 A1 | 10/2018 | Galasso et al. |
| 2018/0307185 A1 | 10/2018 | Raymann et al. |
| 2018/0307854 A1 | 10/2018 | Bernau et al. |
| 2018/0307859 A1 | 10/2018 | LaFever et al. |
| 2018/0307959 A1 | 10/2018 | Pigott et al. |
| 2018/0310327 A1 | 10/2018 | Aarnio et al. |
| 2018/0310670 A1 | 11/2018 | Rovekamp, Jr. et al. |
| 2018/0310824 A1 | 11/2018 | Windolf |
| 2018/0310877 A1 | 11/2018 | Zuckerman Stark et al. |
| 2018/0310892 A1 | 11/2018 | Perschbacher et al. |
| 2018/0310964 A1 | 11/2018 | Stevenson et al. |
| 2018/0314801 A1 | 11/2018 | Janssen |
| 2018/0314868 A1 | 11/2018 | Raynesford |
| 2018/0315141 A1 | 11/2018 | Hunn et al. |
| 2018/0315285 A1 | 11/2018 | Janssen |
| 2018/0317808 A1 | 11/2018 | Wang et al. |
| 2018/0317826 A1 | 11/2018 | Muhsin et al. |
| 2018/0321666 A1 | 11/2018 | Cella et al. |
| 2018/0321667 A1 | 11/2018 | Cella et al. |
| 2018/0321672 A1 | 11/2018 | Cella et al. |
| 2018/0322164 A1 | 11/2018 | Dasari et al. |
| 2018/0322445 A1 | 11/2018 | Sayles et al. |
| 2018/0324407 A1 | 11/2018 | Peeters et al. |
| 2018/0325207 A1 | 11/2018 | Krasnow |
| 2018/0325385 A1 | 11/2018 | Deterding et al. |
| 2018/0325435 A1 | 11/2018 | Mistrorigo De Almeida |
| 2018/0325460 A1 | 11/2018 | Wegerich |
| 2018/0326142 A1 | 11/2018 | Perng et al. |
| 2018/0326286 A1 | 11/2018 | Rathi et al. |
| 2018/0326291 A1 | 11/2018 | Tran et al. |
| 2018/0329518 A1 | 11/2018 | Myers et al. |
| 2018/0330369 A1 | 11/2018 | Warner |
| 2018/0332383 A1 | 11/2018 | Boesen et al. |
| 2018/0333051 A1 | 11/2018 | Patrick-Cary |
| 2018/0333107 A1 | 11/2018 | Sada et al. |
| 2018/0333535 A1 | 11/2018 | Ruchti et al. |
| 2018/0333585 A1 | 11/2018 | Gaddam et al. |
| 2018/0333586 A1 | 11/2018 | Wasson et al. |
| 2018/0336515 A1 | 11/2018 | Mehring et al. |
| 2018/0338560 A1 | 11/2018 | Molyneux et al. |
| 2018/0338576 A1 | 11/2018 | Meschter et al. |
| 2018/0339445 A1 | 11/2018 | Loveder |
| 2018/0343977 A1 | 12/2018 | Riccomini et al. |
| 2018/0343978 A1 | 12/2018 | Stillman et al. |
| 2018/0343981 A1 | 12/2018 | Hanft |
| 2018/0344220 A1 | 12/2018 | Hayter et al. |
| 2018/0344252 A1 | 12/2018 | An et al. |
| 2018/0344255 A1 | 12/2018 | Orron et al. |
| 2018/0345006 A1 | 12/2018 | Ambrose |
| 2018/0348048 A1 | 12/2018 | Fei |
| 2018/0349893 A1 | 12/2018 | Tsai |
| 2018/0350465 A1 | 12/2018 | Corey et al. |
| 2018/0350468 A1 | 12/2018 | Friedman et al. |
| 2018/0352534 A1 | 12/2018 | Blahnik et al. |
| 2018/0353086 A1 | 12/2018 | Turner et al. |

(56) References Cited

U.S. PATENT DOCUMENTS

| | | |
|---|---|---|
| 2018/0353111 A1 | 12/2018 | Buxton et al. |
| 2018/0353139 A1 | 12/2018 | Speier et al. |
| 2018/0353219 A1 | 12/2018 | Beyar et al. |
| 2018/0357603 A1 | 12/2018 | Wilkinson et al. |
| 2018/0357725 A1 | 12/2018 | Roth et al. |
| 2018/0358117 A1 | 12/2018 | Neagle |
| 2018/0360355 A1 | 12/2018 | Chavan et al. |
| 2018/0361221 A1 | 12/2018 | Czaja et al. |
| 2018/0365633 A1 | 12/2018 | Hanis et al. |
| 2018/0368701 A1 | 12/2018 | Vule et al. |
| 2018/0368780 A1 | 12/2018 | Bruno et al. |
| 2018/0369065 A1 | 12/2018 | Siedenburg et al. |
| 2018/0369437 A1 | 12/2018 | Grossman et al. |
| 2018/0369438 A1 | 12/2018 | Grossman et al. |
| 2018/0372720 A1 | 12/2018 | Wildburger et al. |
| 2018/0374037 A1 | 12/2018 | Nazzari et al. |
| 2018/0375750 A1 | 12/2018 | Moeller |
| 2018/0375983 A1 | 12/2018 | Bai |
| 2018/0376336 A1 | 12/2018 | Turner et al. |
| 2018/0376586 A1 | 12/2018 | Longinotti-Buitoni et al. |
| 2019/0000317 A1 | 1/2019 | Muhsin et al. |
| 2019/0000400 A1 | 1/2019 | Liu et al. |
| 2019/0000656 A1 | 1/2019 | Pool et al. |
| 2019/0001128 A1 | 1/2019 | Goodall et al. |
| 2019/0005507 A1 | 1/2019 | Rodoni et al. |
| 2019/0005566 A1 | 1/2019 | Black |
| 2019/0007381 A1 | 1/2019 | Isaacson et al. |
| 2019/0007927 A1 | 1/2019 | Blahnik et al. |
| 2019/0008117 A1 | 1/2019 | Dijkstra et al. |
| 2019/0008384 A1 | 1/2019 | Brisben et al. |
| 2019/0008461 A1 | 1/2019 | Gupta et al. |
| 2019/0009019 A1 | 1/2019 | Shor et al. |
| 2019/0009094 A1* | 1/2019 | Zhang ............... A61N 1/36132 |
| 2019/0012608 A1 | 1/2019 | Teixeira |
| 2019/0012637 A1 | 1/2019 | Gillen |
| 2019/0013090 A1 | 1/2019 | Chait et al. |
| 2019/0015048 A1 | 1/2019 | Baker |
| 2019/0019144 A1 | 1/2019 | Gillen |
| 2019/0019171 A1 | 1/2019 | Silvestre |
| 2019/0019573 A1 | 1/2019 | Lake et al. |
| 2019/0025805 A1 | 1/2019 | Cella et al. |
| 2019/0025806 A1 | 1/2019 | Cella et al. |
| 2019/0025812 A1 | 1/2019 | Cella et al. |
| 2019/0025813 A1 | 1/2019 | Cella et al. |
| 2019/0026690 A1 | 1/2019 | Wappler et al. |
| 2019/0028662 A1 | 1/2019 | Kulcke et al. |
| 2019/0029598 A1 | 1/2019 | LeBoeuf et al. |
| 2019/0029599 A1 | 1/2019 | Golda et al. |
| 2019/0030350 A1 | 1/2019 | Finch et al. |
| 2019/0033845 A1 | 1/2019 | Cella et al. |
| 2019/0033846 A1 | 1/2019 | Cella et al. |
| 2019/0033847 A1 | 1/2019 | Cella et al. |
| 2019/0033848 A1 | 1/2019 | Cella et al. |
| 2019/0033849 A1 | 1/2019 | Cella et al. |
| 2019/0034536 A1 | 1/2019 | Papp et al. |
| 2019/0034605 A1 | 1/2019 | Wang et al. |
| 2019/0034808 A1 | 1/2019 | Palanichamy |
| 2019/0034888 A1 | 1/2019 | Grassadonia et al. |
| 2019/0034889 A1 | 1/2019 | Brock et al. |
| 2019/0034923 A1 | 1/2019 | Greco et al. |
| 2019/0035499 A1 | 1/2019 | Daya |
| 2019/0036886 A1 | 1/2019 | Wu et al. |
| 2019/0036887 A1 | 1/2019 | Miller |
| 2019/0037960 A1 | 2/2019 | Busbee |
| 2019/0037961 A1 | 2/2019 | Busbee et al. |
| 2019/0037969 A1 | 2/2019 | Busbee et al. |
| 2019/0038149 A1 | 2/2019 | Gopalakrishnan et al. |
| 2019/0038214 A1 | 2/2019 | Mikhail et al. |
| 2019/0038496 A1 | 2/2019 | Levesque et al. |
| 2019/0038791 A1 | 2/2019 | Gerrans et al. |
| 2019/0038831 A1 | 2/2019 | Dacey, Jr. et al. |
| 2019/0038902 A1 | 2/2019 | Kaemmerer et al. |
| 2019/0039311 A1 | 2/2019 | Busbee et al. |
| 2019/0041835 A1 | 2/2019 | Cella et al. |
| 2019/0041836 A1 | 2/2019 | Cella et al. |
| 2019/0041840 A1 | 2/2019 | Cella et al. |
| 2019/0041841 A1 | 2/2019 | Cella et al. |
| 2019/0041842 A1 | 2/2019 | Cella et al. |
| 2019/0041843 A1 | 2/2019 | Cella et al. |
| 2019/0041844 A1 | 2/2019 | Cella et al. |
| 2019/0041845 A1 | 2/2019 | Cella et al. |
| 2019/0041846 A1 | 2/2019 | Cella et al. |
| 2019/0043008 A1 | 2/2019 | Vivier |
| 2019/0043010 A1 | 2/2019 | Smith et al. |
| 2019/0044736 A1 | 2/2019 | Vandervort |
| 2019/0045877 A9 | 2/2019 | Beers et al. |
| 2019/0046038 A1 | 2/2019 | Weinstein et al. |
| 2019/0046794 A1 | 2/2019 | Goodall et al. |
| 2019/0046863 A1 | 2/2019 | Eurlings et al. |
| 2019/0049931 A1 | 2/2019 | Tschirschnitz et al. |
| 2019/0050888 A1 | 2/2019 | Elder et al. |
| 2019/0052111 A1 | 2/2019 | Wu et al. |
| 2019/0053470 A1 | 2/2019 | Singh et al. |
| 2019/0053572 A1 | 2/2019 | Patton |
| 2019/0053712 A1 | 2/2019 | Rogers et al. |
| 2019/0053758 A1 | 2/2019 | Biederman et al. |
| 2019/0053915 A1 | 2/2019 | Macke et al. |
| 2019/0054284 A1 | 2/2019 | Smith et al. |
| 2019/0056726 A1 | 2/2019 | Weldemariam et al. |
| 2019/0057454 A1 | 2/2019 | Komenda et al. |
| 2019/0059742 A1 | 2/2019 | Mudge et al. |
| 2019/0059757 A1 | 2/2019 | Balda et al. |
| 2019/0059826 A1 | 2/2019 | Hampapuram et al. |
| 2019/0060644 A1 | 2/2019 | Finch et al. |
| 2019/0061772 A1 | 2/2019 | Prinz |
| 2019/0064344 A1 | 2/2019 | Turner |
| 2019/0064791 A1 | 2/2019 | Cella et al. |
| 2019/0064792 A1 | 2/2019 | Cella et al. |
| 2019/0065733 A1 | 2/2019 | Forehand |
| 2019/0066063 A1 | 2/2019 | Jessamine |
| 2019/0068249 A1 | 2/2019 | Hviid et al. |
| 2019/0069815 A1 | 3/2019 | Burnes et al. |
| 2019/0070350 A1 | 3/2019 | Yomtov et al. |
| 2019/0072917 A1 | 3/2019 | Zeltzer |
| 2019/0072922 A1 | 3/2019 | Cella et al. |
| 2019/0072923 A1 | 3/2019 | Cella et al. |
| 2019/0072924 A1 | 3/2019 | Cella et al. |
| 2019/0072925 A1 | 3/2019 | Cella et al. |
| 2019/0072926 A1 | 3/2019 | Cella et al. |
| 2019/0072928 A1 | 3/2019 | Cella et al. |
| 2019/0073042 A1 | 3/2019 | Thapliyal |
| 2019/0073333 A1 | 3/2019 | Joshua et al. |
| 2019/0073894 A1 | 3/2019 | Mehta et al. |
| 2019/0076033 A1 | 3/2019 | Sweeney et al. |
| 2019/0076066 A1 | 3/2019 | Ajemba et al. |
| 2019/0076067 A1 | 3/2019 | Ajemba et al. |
| 2019/0076070 A1 | 3/2019 | Nogueira et al. |
| 2019/0076600 A1 | 3/2019 | Grosman et al. |
| 2019/0076643 A1 | 3/2019 | Siegle et al. |
| 2019/0077003 A1 | 3/2019 | Lennings et al. |
| 2019/0080791 A1 | 3/2019 | Wolf et al. |
| 2019/0082773 A1 | 3/2019 | Rushbrook et al. |
| 2019/0082985 A1 | 3/2019 | Hong et al. |
| 2019/0083039 A1 | 3/2019 | Shute et al. |
| 2019/0083355 A1 | 3/2019 | Zipper |
| 2019/0083784 A1 | 3/2019 | Raghunathan |
| 2019/0090585 A1 | 3/2019 | Loveder et al. |
| 2019/0090589 A1 | 3/2019 | Rushbrook et al. |
| 2019/0090764 A1 | 3/2019 | Al-Ali |
| 2019/0090820 A1 | 3/2019 | Schwenk et al. |
| 2019/0091481 A1 | 3/2019 | Gustavson et al. |
| 2019/0094374 A1 | 3/2019 | Graham et al. |
| 2019/0096534 A1 | 3/2019 | Joao |
| 2019/0099009 A1 | 4/2019 | Connor |
| 2019/0104989 A1 | 4/2019 | Breaux et al. |
| 2019/0105505 A1 | 4/2019 | Schneider et al. |
| 2019/0108427 A1 | 4/2019 | Geissler et al. |
| 2019/0110755 A1 | 4/2019 | Capodilupo et al. |
| 2019/0116896 A1 | 4/2019 | Armour et al. |
| 2019/0116915 A1 | 4/2019 | Andon et al. |
| 2019/0116935 A1 | 4/2019 | Avar et al. |
| 2019/0116937 A1 | 4/2019 | Avar et al. |
| 2019/0117068 A1 | 4/2019 | Thomson et al. |
| 2019/0117115 A1 | 4/2019 | Old et al. |

(56) References Cited

U.S. PATENT DOCUMENTS

| | | |
|---|---|---|
| 2019/0117118 A1 | 4/2019 | Amos et al. |
| 2019/0117127 A1 | 4/2019 | Keen et al. |
| 2019/0117966 A1 | 4/2019 | Kent |
| 2019/0118283 A1 | 4/2019 | Zhang et al. |
| 2019/0122523 A1 | 4/2019 | Roberts et al. |
| 2019/0125264 A1 | 5/2019 | Abreu Oramas |
| 2019/0126003 A1 | 5/2019 | Bodansky |
| 2019/0126014 A1 | 5/2019 | Kapur et al. |
| 2019/0130332 A1 | 5/2019 | Janssen |
| 2019/0132948 A1 | 5/2019 | Longinotti-Buitoni et al. |
| 2019/0133414 A1 | 5/2019 | Barnhill et al. |
| 2019/0133484 A1 | 5/2019 | Muuranto et al. |
| 2019/0134288 A1 | 5/2019 | Soykan et al. |
| 2019/0137332 A1 | 5/2019 | Chu et al. |
| 2019/0139252 A1 | 5/2019 | Zaiss et al. |
| 2019/0142283 A1 | 5/2019 | Lamego et al. |
| 2019/0146740 A1 | 5/2019 | Yuen et al. |
| 2019/0147999 A1 | 5/2019 | Aradottir et al. |
| 2019/0150748 A1 | 5/2019 | Islam |
| 2019/0150791 A1 | 5/2019 | Schwartz et al. |
| 2019/0150820 A1 | 5/2019 | Lee et al. |
| 2019/0150834 A1 | 5/2019 | Zuckerman-Stark et al. |
| 2019/0151640 A1 | 5/2019 | Weber et al. |
| 2019/0154723 A1 | 5/2019 | Kacyvenski et al. |
| 2019/0158472 A1 | 5/2019 | Juels |
| 2019/0159529 A1 | 5/2019 | Ellis |
| 2019/0159546 A1 | 5/2019 | Cohen et al. |
| 2019/0159676 A1 | 5/2019 | Murphy et al. |
| 2019/0159737 A1 | 5/2019 | Buckler et al. |
| 2019/0160213 A1 | 5/2019 | Wampler |
| 2019/0166954 A1 | 6/2019 | Walker et al. |
| 2019/0167114 A1 | 6/2019 | Islam |
| 2019/0167237 A1 | 6/2019 | Stein et al. |
| 2019/0168005 A1 | 6/2019 | Li et al. |
| 2019/0172197 A1 | 6/2019 | Buckler et al. |
| 2019/0174007 A1 | 6/2019 | Matsuura |
| 2019/0174863 A1 | 6/2019 | McClain |
| 2019/0174871 A1 | 6/2019 | Walker et al. |
| 2019/0175019 A1 | 6/2019 | Al-Ali et al. |
| 2019/0175079 A1 | 6/2019 | Nishida et al. |
| 2019/0175080 A1 | 6/2019 | Varsavsky et al. |
| 2019/0175082 A1 | 6/2019 | Varsavsky et al. |
| 2019/0175107 A1 | 6/2019 | Lu et al. |
| 2019/0175116 A1 | 6/2019 | Wijshoff et al. |
| 2019/0175411 A1 | 6/2019 | Awiszus et al. |
| 2019/0175960 A1 | 6/2019 | Awiszus et al. |
| 2019/0175961 A1 | 6/2019 | Awiszus et al. |
| 2019/0179412 A1 | 6/2019 | Penmatcha et al. |
| 2019/0180153 A1 | 6/2019 | Buckler et al. |
| 2019/0180438 A1 | 6/2019 | Buckler et al. |
| 2019/0180869 A1 | 6/2019 | Volpe |
| 2019/0183339 A1 | 6/2019 | Shah et al. |
| 2019/0183346 A1 | 6/2019 | Islam |
| 2019/0184077 A1 | 6/2019 | Novack |
| 2019/0188895 A1 | 6/2019 | Marshall et al. |
| 2019/0190862 A1 | 6/2019 | Choudhary et al. |
| 2019/0191468 A1 | 6/2019 | Wu et al. |
| 2019/0192009 A1 | 6/2019 | Reifman et al. |
| 2019/0192022 A1 | 6/2019 | Ram et al. |
| 2019/0192076 A1 | 6/2019 | McHale et al. |
| 2019/0192080 A1 | 6/2019 | Penders et al. |
| 2019/0192085 A1 | 6/2019 | Menon et al. |
| 2019/0192086 A1 | 6/2019 | Menon et al. |
| 2019/0192768 A1 | 6/2019 | Gupta et al. |
| 2019/0197073 A1 | 6/2019 | Liu et al. |
| 2019/0197861 A1 | 6/2019 | Tunnell |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201042 A1 | 7/2019 | Nott et al. |
| 2019/0201043 A1 | 7/2019 | Shelton et al. |
| 2019/0201046 A1 | 7/2019 | Shelton et al. |
| 2019/0201047 A1 | 7/2019 | Yates et al. |
| 2019/0201075 A1 | 7/2019 | Shelton et al. |
| 2019/0208295 A1 | 7/2019 | Case, Jr. |
| 2019/0208865 A1 | 7/2019 | Walker et al. |
| 2019/0209087 A1 | 7/2019 | Berner, Jr. et al. |
| 2019/0212323 A1 | 7/2019 | Gupta et al. |
| 2019/0213458 A1 | 7/2019 | DeBates et al. |
| 2019/0216350 A1 | 7/2019 | Sullivan et al. |
| 2019/0223542 A1 | 7/2019 | Folske et al. |
| 2019/0231166 A1 | 8/2019 | Anderson |
| 2019/0232592 A1 | 8/2019 | Tran et al. |
| 2019/0239309 A1 | 8/2019 | Siagian et al. |
| 2019/0244347 A1 | 8/2019 | Buckler et al. |
| 2019/0244348 A1 | 8/2019 | Buckler et al. |

OTHER PUBLICATIONS

U.S. Appl. No. 10/002,233, filed Jun. 19, 2018, Hayter et al.
U.S. Appl. No. 10/003,862, filed Jun. 19, 2018, Rowland et al.
U.S. Appl. No. 10/004,406, filed Jun. 26, 2018, Yuen et al.
U.S. Appl. No. 10/004,949, filed Jun. 26, 2018, Brothers et al.
U.S. Appl. No. 10/005,564, filed Jun. 26, 2018, Bhatia et al.
U.S. Appl. No. 10/007,758, filed Jun. 26, 2018, Al-Ali et al.
U.S. Appl. No. 10/008,090, filed Jun. 26, 2018, Yuen et al.
U.S. Appl. No. 10/010,129, filed Jul. 3, 2018, Beers et al.
U.S. Appl. No. 10/010,278, filed Jul. 3, 2018, Darty et al.
U.S. Appl. No. 10/010,753, filed Jul. 3, 2018, Brothers et al.
U.S. Appl. No. 10/010,790, filed Jul. 3, 2018, Weston et al.
U.S. Appl. No. 10/012,664, filed Jul. 3, 2018, Wasson et al.
U.S. Appl. No. 10/012,969, filed Jul. 3, 2018, Ellis.
U.S. Appl. No. 10/013,633, filed Jul. 3, 2018, Manmatha et al.
U.S. Appl. No. 10/016,015, filed Jul. 10, 2018, Ellis, III.
U.S. Appl. No. 10/016,613, filed Jul. 10, 2018, Kavounas.
U.S. Appl. No. 10/018,643, filed Jul. 10, 2018, Holmes et al.
U.S. Appl. No. 10/021,733, filed Jul. 10, 2018, Hellman et al.
U.S. Appl. No. 10/022,061, filed Jul. 17, 2018, Quinlan et al.
U.S. Appl. No. 10/022,062, filed Jul. 17, 2018, Krusor et al.
U.S. Appl. No. 10/022,613, filed Jul. 17, 2018, Tran et al.
U.S. Appl. No. 10/022,614, filed Jul. 17, 2018, Tran et al.
U.S. Appl. No. 10/022,624, filed Jul. 17, 2018, Barney et al.
U.S. Appl. No. 10/024,660, filed Jul. 17, 2018, Otis et al.
U.S. Appl. No. 10/024,740, filed Jul. 17, 2018, Rice et al.
U.S. Appl. No. 10/025,973, filed Jul. 17, 2018, Datta et al.
U.S. Appl. No. 10/026,118, filed Jul. 17, 2018, Castinado et al.
U.S. Appl. No. 10/026,410, filed Jul. 17, 2018, Gurijala et al.
U.S. Appl. No. 10/028,037, filed Jul. 17, 2018, Gartseev et al.
U.S. Appl. No. 10/028,659, filed Jul. 24, 2018, Schwartz et al.
U.S. Appl. No. 10/028,660, filed Jul. 24, 2018, Mullin et al.
U.S. Appl. No. 10/028,706, filed Jul. 24, 2018, Brockway et al.
U.S. Appl. No. 10/028,743, filed Jul. 24, 2018, Shelton, IV et al.
U.S. Appl. No. 10/029,172, filed Jul. 24, 2018, Galasso et al.
U.S. Appl. No. 10/031,002, filed Jul. 24, 2018, Hayter et al.
U.S. Appl. No. 10/032,002, filed Jul. 24, 2018, Kiani et al.
U.S. Appl. No. 10/034,512, filed Jul. 31, 2018, Rushbrook et al.
U.S. Appl. No. 10/034,625, filed Jul. 31, 2018, Schwartz et al.
U.S. Appl. No. 10/034,743, filed Jul. 31, 2018, Boyden et al.
U.S. Appl. No. 10/039,113, filed Jul. 31, 2018, Ogrinz.
U.S. Appl. No. 10/039,661, filed Aug. 7, 2018, Pool et al.
U.S. Appl. No. 10/039,928, filed Aug. 7, 2018, Hyde et al.
U.S. Appl. No. 10/043,354, filed Aug. 7, 2018, Mirov et al.
U.S. Appl. No. 10/045,117, filed Aug. 7, 2018, Boesen et al.
U.S. Appl. No. 10/045,439, filed Aug. 7, 2018, Longinotti-Buitoni et al.
U.S. Appl. No. 10/045,713, filed Aug. 14, 2018, Old et al.
U.S. Appl. No. 10/045,720, filed Aug. 14, 2018, Hayter et al.
U.S. Appl. No. 10/045,764, filed Aug. 14, 2018, Scott et al.
U.S. Appl. No. 10/045,798, filed Aug. 14, 2018, Beyar et al.
U.S. Appl. No. 10/046,113, filed Aug. 14, 2018, Ruchti et al.
U.S. Appl. No. 10/046,228, filed Aug. 14, 2018, Tran et al.
U.S. Appl. No. 10/049,187, filed Aug. 14, 2018, Chait et al.
U.S. Appl. No. 10/051,912, filed Aug. 21, 2018, Darden et al.
U.S. Appl. No. 10/052,486, filed Aug. 21, 2018, Denison et al.
U.S. Appl. No. 10/054,909, filed Aug. 21, 2018, Raymann et al.
U.S. Appl. No. 10/055,550, filed Aug. 21, 2018, Goetz.
U.S. Appl. No. 10/055,715, filed Aug. 21, 2018, Grassadonia et al.

(56) References Cited

OTHER PUBLICATIONS

U.S. Appl. No. 10/058,146, filed Aug. 28, 2018, Meschter et al.
U.S. Appl. No. 10/058,274, filed Aug. 28, 2018, Kracker.
U.S. Appl. No. 10/060,788, filed Aug. 28, 2018, Fei.
U.S. Appl. No. 10/061,911, filed Aug. 28, 2018, Zizi et al.
U.S. Appl. No. 10/064,562, filed Sep. 4, 2018, Al-Ali.
U.S. Appl. No. 10/064,624, filed Sep. 4, 2018, Shelton, IV et al.
U.S. Appl. No. 10/066,203, filed Sep. 4, 2018, Fryer et al.
U.S. Appl. No. 10/070,680, filed Sep. 11, 2018, Molyneux et al.
U.S. Appl. No. 10/070,683, filed Sep. 11, 2018, Rushbrook et al.
U.S. Appl. No. 10/070,805, filed Sep. 11, 2018, Friedman et al.
U.S. Appl. No. 10/070,992, filed Sep. 11, 2018, Pagani.
U.S. Appl. No. 10/071,285, filed Sep. 11, 2018, Smith et al.
U.S. Appl. No. 10/076,282, filed Sep. 18, 2018, LeBoeuf et al.
U.S. Appl. No. 10/076,462, filed Sep. 18, 2018, Johnson et al.
U.S. Appl. No. 10/078,839, filed Sep. 18, 2018, Mullins et al.
U.S. Appl. No. 10/080,498, filed Sep. 25, 2018, Gibson.
U.S. Appl. No. 10/080,499, filed Sep. 25, 2018, Kuhn.
U.S. Appl. No. 10/080,527, filed Sep. 25, 2018, Golda et al.
U.S. Appl. No. 10/080,530, filed Sep. 25, 2018, Cheng et al.
U.S. Appl. No. 10/085,643, filed Oct. 2, 2018, Bandic et al.
U.S. Appl. No. 10/088,356, filed Oct. 2, 2018, Chu et al.
U.S. Appl. No. 10/089,446, filed Oct. 2, 2018, Budiman.
U.S. Appl. No. 10/092,065, filed Oct. 9, 2018, Rushbrook et al.
U.S. Appl. No. 10/092,193, filed Oct. 9, 2018, Mestek et al.
U.S. Appl. No. 10/092,203, filed Oct. 9, 2018, Mirov.
U.S. Appl. No. 10/092,355, filed Oct. 9, 2018, Hannaford et al.
U.S. Appl. No. 10/092,692, filed Oct. 9, 2018, Dacey, Jr. et al.
U.S. Appl. No. 10/093,112, filed Oct. 9, 2018, Irizarry et al.
U.S. Appl. No. 10/095,649, filed Oct. 9, 2018, Joshua et al.
U.S. Appl. No. 10/095,837, filed Oct. 9, 2018, Corey et al.
U.S. Appl. No. 10/097,179, filed Oct. 9, 2018, Yang et al.
U.S. Appl. No. 10/098,546, filed Oct. 16, 2018, Islam.
U.S. Appl. No. 10/098,548, filed Oct. 16, 2018, Abreu.
U.S. Appl. No. 10/098,549, filed Oct. 16, 2018, Tan et al.
U.S. Appl. No. 10/098,558, filed Oct. 16, 2018, Huiku.
U.S. Appl. No. 10/098,810, filed Oct. 16, 2018, Muench et al.
U.S. Appl. No. 10/099,053, filed Oct. 16, 2018, Hyde et al.
U.S. Appl. No. 10/103,936, filed Oct. 16, 2018, Kurian et al.
U.S. Appl. No. 10/104,026, filed Oct. 16, 2018, Choudhary et al.
U.S. Appl. No. 10/105,080, filed Oct. 23, 2018, Kam et al.
U.S. Appl. No. 10/105,081, filed Oct. 23, 2018, Delbeke et al.
U.S. Appl. No. 10/105,100, filed Oct. 23, 2018, Biederman et al.
U.S. Appl. No. 10/105,487, filed Oct. 23, 2018, DiPierro et al.
U.S. Appl. No. 10/105,547, filed Oct. 23, 2018, Gustavson et al.
U.S. Appl. No. 10/106,222, filed Oct. 23, 2018, Teksler.
U.S. Appl. No. 10/108,785, filed Oct. 23, 2018, Kamen et al.
U.S. Appl. No. 10/108,938, filed Oct. 23, 2018, Brock et al.
U.S. Appl. No. 10/109,175, filed Oct. 23, 2018, Roberts et al.
U.S. Appl. No. 10/111,496, filed Oct. 30, 2018, Schneider et al.
U.S. Appl. No. 10/115,068, filed Oct. 30, 2018, Vivier.
U.S. Appl. No. 10/117,600, filed Nov. 6, 2018, Keen et al.
U.S. Appl. No. 10/117,606, filed Nov. 6, 2018, Feldman et al.
U.S. Appl. No. 10/117,621, filed Nov. 6, 2018, Berger et al.
U.S. Appl. No. 10/118,035, filed Nov. 6, 2018, Perez et al.
U.S. Appl. No. 10/118,041, filed Nov. 6, 2018, Goetz et al.
U.S. Appl. No. 10/119,715, filed Nov. 6, 2018, Hou et al.
U.S. Appl. No. 10/119,956, filed Nov. 6, 2018, Hayter et al.
U.S. Appl. No. 10/120,888, filed Nov. 6, 2018, Almasan et al.
U.S. Appl. No. 10/121,186, filed Nov. 6, 2018, Isaacson et al.
U.S. Appl. No. 10/122,421, filed Nov. 6, 2018, Hviid et al.
U.S. Appl. No. 10/123,098, filed Nov. 6, 2018, Case, Jr.
U.S. Appl. No. 10/123,679, filed Nov. 13, 2018, Desu-Kalyanam.
U.S. Appl. No. 10/124,179, filed Nov. 13, 2018, Norton et al.
U.S. Appl. No. 10/124,182, filed Nov. 13, 2018, Kivi et al.
U.S. Appl. No. 10/126,283, filed Nov. 13, 2018, Islam.
U.S. Appl. No. 10/126,998, filed Nov. 13, 2018, Yuen et al.
U.S. Appl. No. 10/127,247, filed Nov. 13, 2018, Arora et al.
U.S. Appl. No. 10/129,032, filed Nov. 13, 2018, Vandervort.
U.S. Appl. No. 10/130,305, filed Nov. 20, 2018, Moya et al.
U.S. Appl. No. 10/130,476, filed Nov. 20, 2018, Nycz et al.
U.S. Appl. No. 10/130,550, filed Nov. 20, 2018, Zipper.
U.S. Appl. No. 10/130,767, filed Nov. 20, 2018, Grosman et al.
U.S. Appl. No. 10/132,677, filed Nov. 20, 2018, Chu et al.
U.S. Appl. No. 10/135,076, filed Nov. 20, 2018, Liu.
U.S. Appl. No. 10/135,835, filed Nov. 20, 2018, Kandel et al.
U.S. Appl. No. 10/136,817, filed Nov. 27, 2018, Baker et al.
U.S. Appl. No. 10/136,819, filed Nov. 27, 2018, Islam.
U.S. Appl. No. 10/136,842, filed Nov. 27, 2018, Ashby.
U.S. Appl. No. 10/137,230, filed Nov. 27, 2018, Novack.
U.S. Appl. No. 10/137,365, filed Nov. 27, 2018, Ikeda.
U.S. Appl. No. 10/140,842, filed Nov. 27, 2018, Mehta et al.
U.S. Appl. No. 10/141,073, filed Nov. 27, 2018, Chin et al.
U.S. Appl. No. 10/142,312, filed Nov. 27, 2018, Johnsrud et al.
U.S. Appl. No. 10/143,395, filed Dec. 4, 2018, Chakravarthy et al.
U.S. Appl. No. 10/143,409, filed Dec. 4, 2018, Hayter.
U.S. Appl. No. 10/143,426, filed Dec. 4, 2018, Hampapuram et al.
U.S. Appl. No. 10/143,840, filed Dec. 4, 2018, Perez et al.
U.S. Appl. No. 10/143,847, filed Dec. 4, 2018, Edmonson et al.
U.S. Appl. No. 10/147,076, filed Dec. 4, 2018, Zhou et al.
U.S. Appl. No. 10/149,616, filed Dec. 11, 2018, Al-Ali et al.
U.S. Appl. No. 10/151,648, filed Dec. 11, 2018, Walker.
U.S. Appl. No. 10/152,756, filed Dec. 11, 2018, Isaacson et al..
U.S. Appl. No. 10/152,957, filed Dec. 11, 2018, Lenhert.
U.S. Appl. No. 10/153,537, filed Dec. 11, 2018, Baringer et al..
U.S. Appl. No. 10/154,129, filed Dec. 11, 2018, Repka et al..
U.S. Appl. No. 10/154,789, filed Dec. 18, 2018, Raghuram et al..
U.S. Appl. No. 10/154,922, filed Dec. 18, 2018, Perez et al..
U.S. Appl. No. 10/155,110, filed Dec. 18, 2018, Finch et al..
U.S. Appl. No. 10/155,170, filed Dec. 18, 2018, Ikeda et al..
U.S. Appl. No. 10/159,415, filed Dec. 25, 2018, Gopalakrishnan et al..
U.S. Appl. No. 10/159,897, filed Dec. 25, 2018, Penzias et al..
U.S. Appl. No. 10/160,251, filed Dec. 25, 2018, Nagelberg et al..
U.S. Appl. No. 10/163,079, filed Dec. 25, 2018, Brock et al..
U.S. Appl. No. 10/163,080, filed Dec. 25, 2018, Chow et al..
U.S. Appl. No. 10/163,314, filed Dec. 25, 2018, Tofighbakhsh.
U.S. Appl. No. 10/164,685, filed Dec. 25, 2018, Dobyns et al..
U.S. Appl. No. 10/164,952, filed Dec. 25, 2018, Vandervort.
U.S. Appl. No. 10/165,977, filed Jan. 1, 2019, Wu et al..
U.S. Appl. No. 10/166,164, filed Jan. 1, 2019, Johnson et al..
U.S. Appl. No. 10/166,333, filed Jan. 1, 2019, Friedli et al..
U.S. Appl. No. 10/168,693, filed Jan. 1, 2019, Kingston et al..
U.S. Appl. No. 10/170,135, filed Jan. 1, 2019, Pearce et al..
U.S. Appl. No. 10/172,396, filed Jan. 8, 2019, Ellis.
U.S. Appl. No. 10/172,409, filed Jan. 8, 2019, Andon.
U.S. Appl. No. 10/172,423, filed Jan. 8, 2019, Walker et al..
U.S. Appl. No. 10/172,523, filed Jan. 8, 2019, Islam.
U.S. Appl. No. 10/176,412, filed Jan. 8, 2019, Geissler et al..
U.S. Appl. No. 10/176,418, filed Jan. 8, 2019, Osborn et al.
U.S. Appl. No. 10/176,481, filed Jan. 8, 2019, Aljawhari.
U.S. Appl. No. 10/178,105, filed Jan. 8, 2019, Kurian et al.
U.S. Appl. No. 10/178,890, filed Jan. 15, 2019, Andon et al.
U.S. Appl. No. 10/178,973, filed Jan. 15, 2019, Venkatraman et al.
U.S. Appl. No. 10/179,064, filed Jan. 15, 2019, Connor.
U.S. Appl. No. 10/179,065, filed Jan. 15, 2019, Drnek et al.
U.S. Appl. No. 10/179,246, filed Jan. 15, 2019, Schneider et al.
U.S. Appl. No. 10/179,283, filed Jan. 15, 2019, Barney et al.
U.S. Appl. No. 10/182,336, filed Jan. 15, 2019, Stockton et al.
U.S. Appl. No. 10/182,608, filed Jan. 22, 2019, Smith et al.
U.S. Appl. No. 10/182,729, filed Jan. 22, 2019, Zielinski et al.
U.S. Appl. No. 10/182,744, filed Jan. 22, 2019, Amos et al.
U.S. Appl. No. 10/182,819, filed Jan. 22, 2019, Shelton, IV.
U.S. Appl. No. 10/186,760, filed Jan. 22, 2019, Heppell.
U.S. Appl. No. 10/188,173, filed Jan. 29, 2019, Walsh et al.
U.S. Appl. No. 10/188,296, filed Jan. 29, 2019, Al-Ali et al.
U.S. Appl. No. 10/188,299, filed Jan. 29, 2019, Islam.
U.S. Appl. No. 10/188,319, filed Jan. 29, 2019, Schwartz et al.
U.S. Appl. No. 10/188,334, filed Jan. 29, 2019, Budiman et al.
U.S. Appl. No. 10/188,394, filed Jan. 29, 2019, Shelton, IV et al.
U.S. Appl. No. 10/188,953, filed Jan. 29, 2019, Barney et al.
U.S. Appl. No. 10/192,198, filed Jan. 29, 2019, Nazzari et al.
U.S. Appl. No. 10/193,695, filed Jan. 29, 2019, Endress et al.

(56) References Cited

OTHER PUBLICATIONS

U.S. Appl. No. 10/194,418, filed Jan. 29, 2019, Blahnik et al.
U.S. Appl. No. 10/194,702, filed Feb. 5, 2019, Cobbett et al.
U.S. Appl. No. 10/194,714, filed Feb. 5, 2019, McGinnity et al.
U.S. Appl. No. 10/194,802, filed Feb. 5, 2019, Windolf.
U.S. Appl. No. 10/194,808, filed Feb. 5, 2019, Thompson et al.
U.S. Appl. No. 10/194,809, filed Feb. 5, 2019, Mirov et al.
U.S. Appl. No. 10/194,816, filed Feb. 5, 2019, Perschbacher et al.
U.S. Appl. No. 10/194,836, filed Feb. 5, 2019, Venkatraman et al.
U.S. Appl. No. 10/194,850, filed Feb. 5, 2019, Kovatchev et al.
U.S. Appl. No. 10/195,513, filed Feb. 5, 2019, Tran et al.
U.S. Appl. No. 10/196,596, filed Feb. 5, 2019, Glazier et al.
U.S. Appl. No. 10/200,199, filed Feb. 5, 2019, Truu et al.
U.S. Appl. No. 10/200,834, filed Feb. 5, 2019, Tran et al.
U.S. Appl. No. 10/201,283, filed Feb. 12, 2019, Islam.
U.S. Appl. No. 10/201,295, filed Feb. 12, 2019, Wasson et al.
U.S. Appl. No. 10/201,702, filed Feb. 12, 2019, Bonde et al.
U.S. Appl. No. 10/204,160, filed Feb. 12, 2019, Yelton et al.
U.S. Appl. No. 10/207,041, filed Feb. 19, 2019, Soykan et al.
U.S. Appl. No. 10/209,365, filed Feb. 19, 2019, Venkatraman et al.
U.S. Appl. No. 10/210,741, filed Feb. 19, 2019, Chen et al.
U.S. Appl. No. 10/213,113, filed Feb. 26, 2019, Islam.
U.S. Appl. No. 10/213,150, filed Feb. 26, 2019, Leschinsky.
U.S. Appl. No. 10/215,619, filed Feb. 26, 2019, Kovacs.
U.S. Appl. No. 10/218,433, filed Feb. 26, 2019, Panther et al.
U.S. Appl. No. 10/219,746, filed Mar. 5, 2019, McHale et al.
U.S. Appl. No. 10/219,754, filed Mar. 5, 2019, Lamego.
U.S. Appl. No. 10/220,217, filed Mar. 5, 2019, Chow et al.
U.S. Appl. No. 10/222,283, filed Mar. 5, 2019, Thillainadarajah et al.
U.S. Appl. No. 10/223,459, filed Mar. 5, 2019, Liu et al.
U.S. Appl. No. 10/225,085, filed Mar. 5, 2019, Drouin et al.
U.S. Appl. No. 10/226,082, filed Mar. 12, 2019, Ellis.
U.S. Appl. No. 10/226,187, filed Mar. 12, 2019, Al-Ali et al.
U.S. Appl. No. 10/226,188, filed Mar. 12, 2019, Watson et al.
U.S. Appl. No. 10/226,217, filed Mar. 12, 2019, Dubin et al.
U.S. Appl. No. 10/226,396, filed Mar. 12, 2019, Ashby.
U.S. Appl. No. 10/227,063, filed Mar. 12, 2019, Abreu.
U.S. Appl. No. 10/230,699, filed Mar. 12, 2019, Juels.
U.S. Appl. No. 10/231,666, filed Mar. 19, 2019, Zuckerman-Stark et al.
U.S. Appl. No. 10/231,784, filed Mar. 19, 2019, Hettrick et al.
U.S. Appl. No. 10/234,330, filed Mar. 19, 2019, Fei.
U.S. Appl. No. 10/234,340, filed Mar. 19, 2019, Severinkangas et al.
U.S. Appl. No. 10/234,942, filed Mar. 19, 2019, Connor.
U.S. Appl. No. 10/236,006, filed Mar. 19, 2019, Gurijala et al.
U.S. Appl. No. 10/238,978, filed Mar. 26, 2019, Ikeda et al.
U.S. Appl. No. 10/248,302, filed Apr. 2, 2019, Raymann et al.
U.S. Appl. No. 10/248,985, filed Apr. 2, 2019, Rohr et al.
U.S. Appl. No. 10/251,571, filed Apr. 9, 2019, Cendrillon et al.
U.S. Appl. No. 10/251,595, filed Apr. 9, 2019, Heruth et al.
U.S. Appl. No. 10/251,601, filed Apr. 9, 2019, Berner, Jr. et al.
U.S. Appl. No. 10/252,140, filed Apr. 9, 2019, Jooste et al.
U.S. Appl. No. 10/255,994, filed Apr. 9, 2019, Sampath et al.
U.S. Appl. No. 10/258,092, filed Apr. 16, 2019, Longinotti-Buitoni et al.
U.S. Appl. No. 10/258,288, filed Apr. 16, 2019, Penders et al.
U.S. Appl. No. 10/258,828, filed Apr. 16, 2019, Dalebout et al.
U.S. Appl. No. 10/261,069, filed Apr. 16, 2019, Hayter et al.
U.S. Appl. No. 10/264,971, filed Apr. 23, 2019, Kennedy et al.
U.S. Appl. No. 10/269,452, filed Apr. 23, 2019, Volpe.
U.S. Appl. No. 10/271,587, filed Apr. 30, 2019, Cobbett et al.
U.S. Appl. No. 10/271,792, filed Apr. 30, 2019, Inagaki.
U.S. Appl. No. 10/272,242, filed Apr. 30, 2019, Sharma et al.
U.S. Appl. No. 10/275,640, filed Apr. 30, 2019, Seuss et al.
U.S. Appl. No. 10/277,963, filed Apr. 30, 2019, Case, Jr..
U.S. Appl. No. 10/278,217, filed Apr. 30, 2019, Wu et al.
U.S. Appl. No. 10/278,624, filed May 7, 2019, Short et al.
U.S. Appl. No. 10/279,152, filed May 7, 2019, Kapur et al.
U.S. Appl. No. 10/279,200, filed May 7, 2019, Hyde et al.
U.S. Appl. No. 10/279,201, filed May 7, 2019, Hyde et al.
U.S. Appl. No. 10/284,537, filed May 7, 2019, Liu et al.
U.S. Appl. No. 10/289,098, filed May 14, 2019, Livaccari et al.
U.S. Appl. No. 10/289,806, filed May 14, 2019, Hyde et al.
U.S. Appl. No. 10/292,453, filed May 21, 2019, Bertagna et al.
U.S. Appl. No. 10/292,611, filed May 21, 2019, Katra et al.
U.S. Appl. No. 10/292,631, filed May 21, 2019, Homyk et al.
U.S. Appl. No. 10/293,158, filed May 21, 2019, Goodall et al.
U.S. Appl. No. 10/293,184, filed May 21, 2019, Pishdad et al.
U.S. Appl. No. 10/293,208, filed May 21, 2019, Bailly et al.
U.S. Appl. No. 10/293,565, filed May 21, 2019, Tran et al.
U.S. Appl. No. 10/299,693, filed May 28, 2019, Sarkar et al.
U.S. Appl. No. 10/299,722, filed May 28, 2019, Tran et al.
U.S. Appl. No. 10/299,725, filed May 28, 2019, Mirov et al.
U.S. Appl. No. 10/299,734, filed May 28, 2019, Watson et al.
U.S. Appl. No. 10/299,736, filed May 28, 2019, Najafi et al.
U.S. Appl. No. 10/300,283, filed May 28, 2019, Miesel et al.
U.S. Appl. No. 10/300,303, filed May 28, 2019, Brooks et al.
U.S. Appl. No. 10/300,374, filed May 28, 2019, Briggs et al.
U.S. Appl. No. 10/302,469, filed May 28, 2019, Bhatt et al.
U.S. Appl. No. 10/305,692, filed May 28, 2019, Peterson.
U.S. Appl. No. 10/306,726, filed May 28, 2019, Wilken et al.
U.S. Appl. No. 10/307,081, filed Jun. 4, 2019, Nino et al.
U.S. Appl. No. 10/307,101, filed Jun. 4, 2019, Miller et al.
U.S. Appl. No. 10/307,111, filed Jun. 4, 2019, Muhsin et al.
U.S. Appl. No. 10/307,671, filed Jun. 4, 2019, Barney et al.
U.S. Appl. No. 10/307,683, filed Jun. 4, 2019, Weston.
U.S. Appl. No. 10/311,451, filed Jun. 4, 2019, McCormack.
U.S. Appl. No. 10/311,696, filed Jun. 4, 2019, Janssen.
U.S. Appl. No. 10/311,706, filed Jun. 4, 2019, M et al.
U.S. Appl. No. 10/314,488, filed Jun. 11, 2019, Samuelsson et al.
U.S. Appl. No. 10/314,546, filed Jun. 11, 2019, Lisogurski et al.
U.S. Appl. No. 10/314,547, filed Jun. 11, 2019, Miller et al.
U.S. Appl. No. 10/314,928, filed Jun. 11, 2019, Dobrinsky et al.
U.S. Appl. No. 10/321,732, filed Jun. 18, 2019, Folske et al.
U.S. Appl. No. 10/325,681, filed Jun. 18, 2019, Sampath et al.
U.S. Appl. No. 10/327,672, filed Jun. 25, 2019, Giedwoyn et al.
U.S. Appl. No. 10/327,674, filed Jun. 25, 2019, Hong et al.
U.S. Appl. No. 10/327,689, filed Jun. 25, 2019, Krasnow et al.
U.S. Appl. No. 10/327,708, filed Jun. 25, 2019, Yu et al.
U.S. Appl. No. 10/327,984, filed Jun. 25, 2019, Goodall et al.
U.S. Appl. No. 10/328,228, filed Jun. 25, 2019, Zapol et al.
U.S. Appl. No. 10/328,266, filed Jun. 25, 2019, Whiting et al.
U.S. Appl. No. 10/332,315, filed Jun. 25, 2019, Samec et al.
U.S. Appl. No. 10/333,932, filed Jun. 25, 2019, Zizi et al.
U.S. Appl. No. 10/334,906, filed Jul. 2, 2019, Andon et al.
U.S. Appl. No. 10/339,352, filed Jul. 2, 2019, Ackley et al.
U.S. Appl. No. 10/339,654, filed Jul. 2, 2019, Lovberg et al.
U.S. Appl. No. 10/349,872, filed Jul. 16, 2019, Varsavsky et al.
U.S. Appl. No. 10/352,787, filed Jul. 16, 2019, McMillen et al.
U.S. Appl. No. 10/357,078, filed Jul. 23, 2019, Rice et al.
U.S. Appl. No. 10/357,210, filed Jul. 23, 2019, Zizi et al.
U.S. Appl. No. 10/358,106, filed Jul. 23, 2019, Sumiya et al.
U.S. Appl. No. 10/362,830, filed Jul. 30, 2019, Campbell.
U.S. Appl. No. 10/363,420, filed Jul. 30, 2019, Fried et al.
U.S. Appl. No. 10/369,463, filed Aug. 6, 2019, Barney et al.
U.S. Appl. No. 10/370,785, filed Aug. 6, 2019, McGinnity et al.
U.S. Appl. No. 10/376,018, filed Aug. 13, 2019, Rushbrook et al.
U.S. Appl. No. 10/760,062, filed Sep. 1, 2020, Naesby et al.

\* cited by examiner

DEVICE AND METHOD FOR MEDICAL DIAGNOSTICS

CROSS REFERENCE TO RELATED APPLICATIONS

The present application is a non-provisional of, and claims benefit of priority under 35 U.S.C. § 119(e), U.S. Provisional Patent Application No. 62/888,213, filed Aug. 16, 2019, the entirety of which is expressly incorporated herein by reference.

FIELD OF THE INVENTION

The present invention pertains to medical diagnostic devices, medical implants, and wearable devices and, more particularly, to a device and method for measurement of physiological parameters to assess changes in health or medical conditions.

BACKGROUND OF THE INVENTION

All patents, references, and other information cited herein are expressly incorporated herein by reference in their entirety.

Biological organisms are homeostatically controlled, which means that feedback or other control mechanisms are present which, tend to maintain constant (quasistatic) internal conditions over a range of external conditions. These biological systems may be complex and interrelated, but often, at their basic level, there is a response to the perturbation that returns to nominal. Physical disease or pathology may relate to a change in the nominal conditions, or a defect in the mechanisms that return the system to normal. These features imply that a second or higher-order differential equation or equivalent construct in various representational domains can model the biological system, and that a large set of such equations or constructs can model an organism. Modern medicine evolved from a time prior to automation, and mainstream practitioners and their regulatory agencies mainly rely on values and thresholds (zeroth order) for determining health. Rarely are rates (first-order) employed, except in some specialties, such as nephrology and pharmacology, when considering metabolic and excretion rates.

Thus, in modern medicine, a patient's physiological parameters may represent actionable signals. For example, blood oxygen saturation below 90% may indicate a need for immediate attention, such as oxygen supplementation. Similarly, trends may be actionable, such as increasing prostate-specific antigen (PSA). However, more complex temporal analysis is typically not performed due to lack of normalization, data sampling irregularities, etc. Perhaps more importantly, there is typically no accepted underlying theory for action based on complex temporal analysis, and rather typical actions are predicated on a level or rate only, and not higher-order considerations.

Biometrics is the technical term for body measurements and calculations. It refers to metrics related to physiological characteristics. The biometric system can be used for various purposes ranging from measurement of a physiological parameter to the assessment of any medical condition.

The proliferation of medical implants and, particularly, wearable devices, present a rich source of biometric data available for collection, analysis, and action dependent thereon.

Generally, most data come as a mixture of patterns and random noise. It is usually the objective of data analysis to separate patterns from noise. However, the data discarded as "noise" is not necessarily meaningless, and its omission from the analysis is often more as a matter of convenience than correctness. The classification of data as "noise" often depends on the choice of the filter or the knowledge of the underlying dynamics (the model). In the absence of the model, often quite meaningful data is discarded labeled as "noise."

In the general case of analog processes described by smooth differentiable functions, the pattern may be modeled as a differential equation, whereas the noise is modeled by the constants arising out of the integration of the differential equation required for this solution. In other cases, noise may be modeled as a Gaussian or other statistical process.

Let us consider, for example, the law of motion, described by the second-order differential equation, also known as the Second Law of Newton: $m \times d^2x/dt^2 = F$, where m is the mass of an object, F is the force acting on the object, and $d^2x/dt^2$ is the second derivative of the coordinate x over time t. Alternatively, this equation can be expressed as $m\ddot{x}=F$, where two dots over x signify the second derivative over time: $\ddot{x}=d^2x/dt^2$, or as $ma=F$, where a is the acceleration, $a=d^2x/dt^2$. To solve this differential equation of the second-order, we need to integrate it twice. As it is well known, integration, which is the reverse of differentiation, involves supplying constants (because a derivative of a constant is always zero). Integrating the equation twice, therefore, produces two constants not defined by the differential equation itself, that need to be constrained by choosing the initial conditions for both. Where the system being modeled is known, these initial conditions may be real and ascertainable values.

Integrating the equation of motion the first time, gives the velocity (the first derivative of the position over time) plus or minus an arbitrary constant, which is constrained by choosing the initial velocity. Integrating the equation of motion the second time, gives us the position x plus or minus an arbitrary constant, which is constrained by choosing the initial position. During differentiation, these constants disappear, revealing the pattern: $ma=F$.

In Analytical Mechanics (see en.wikipedia.org/wiki/Analytical_mechanics), the equation of motion emerges from Euler-Lagrange or Hamiltonian formalism, which ultimately links the law of motion with energy conservation. Lagrangian mechanics (see en.wikipedia.org/wiki/Lagrangian_mechanics), Hamiltonian mechanics (see en.wikipedia.org/wiki/Hamiltonian mechanics), Principle of Least Action (see en.wikipedia.org/wiki/Principle_of_least_action) are all different ways of describing evolution in time of a dynamical system in a deterministic way.

Hooke's law is a law of physics that states that the force (F) needed to extend or compress a spring by some distance x scales linearly with respect to that distance: $F_S=kx$, where k is a constant characterizing the spring's stiffness, and x is the displacement, which is small compared to the total possible deformation of the spring.

Similarly, in biology, all live organisms, cells, closed systems, and subsystems strive to maintain homeostasis. In this regard, they act as "springs" in a sense that, when displaced from the equilibrium under stress, they strive to return to equilibrium. The "elasticity" or "stiffness" of the biological system is accomplished by self-correcting mechanisms that engage in restoring the homeostasis under stress. The loss of the ability to effectively maintain homeostasis and return to equilibrium state under stress may be a sign of a disease or a result of aging. The evolution in time of physiological parameters could be modeled similarly to mechanical systems using tools of analytical mechanics. The disease process may be reflected in shortening or lengthening of the timescale, roughly corresponding to a natural frequency, and energy efficiency and overshoot, roughly corresponding to damping.

When measuring blood chemistry, an analyte sensor may be employed. The analyte sensor may be an implantable glucose sensor, such as described with reference to U.S. Pat. No. 6,001,067 and U.S. Patent Publication No. 2005/0027463; a transcutaneous glucose sensor, such as described with reference to U.S. Patent Publication No. 2006/0020187; the sensor may be configured to be implanted in a host vessel or extracorporeally, such as is described in U.S. Patent Publication No. 2007/0027385, U.S. Patent Publication No. 2008/0119703, U.S. Patent Publication No. 2008/0108942, and U.S. Patent Publication No. 2007/0197890; the continuous glucose sensor comprises a transcutaneous sensor such as described in U.S. Pat. No. 6,565,509, for example; a subcutaneous sensor such as described with reference to U.S. Pat. No. 6,579,690 or 6,484,046; a refillable subcutaneous sensor such as described with reference to U.S. Pat. No. 6,512,939; an intravascular sensor such as described with reference to U.S. Pat. No. 6,477,395; or an intravascular sensor such as described with reference to U.S. Pat. No. 6,424,847.

Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Biocompatible implants are well-known. See, U.S. Pat. Nos. and US Pub. App. Nos. 5764518; 6379669; 6567259; 7097662; 7333013; 7371825; 7414534; 7713923; 7727143; 7765005; 7780590; 7787958; 7813778; 7842092; 7876228; 7916013; 7932825; 7956162; 7966075; 7981025; 7983435; 7983763; 8000801; 8036736; 8078282; 8079518; 8081925; 8093991; 8114345; 8114964; 8192406; 8197454; 8200342; 8202260; 8207316; 8246533; 8251946; 8257729; 8269635; 8269636; 8301243; 8321032; 8323232; 8326435; 8348882; 8374697; 8389286; 8444653; 8454552; 8457757; 8457760; 8478378; 8483840; 8486070; 8496657; 8509913; 8543199; 8557772; 8574146; 8577453; 8577465; 8577468; 8577478; 8623023; 8639524; 8644957; 8666471; 8673194; 8707040; 8715159; 8718776; 8721520; 8721643; 8751013; 8784425; 8788057; 8790400; 8795260; 8795359; 8798773; 8805478; 8805530; 8808163; 8808373; 8814868; 8838249; 8849368; 8855785; 8875714; 8901084; 8911486; 8926573; 8929999; 8946390; 8975372; 8989867; 8989870; 9002471; 9011361; 9017380; 9026792; 9031637; 9044209; 9044612; 9055791; 9061139; 9061151; 9067073; 9072560; 9113844; 9125981; 9126825; 9144488; 9144489; 9149189; 9159223; 9161693; 9187539; 9198911; 9204798; 9211185; 9237012; 9248291; 9248302; 9251960; 9271857; 9288614; 9308381; 9317920; 9326720; 9326730; 9327061; 9333071; 9339188; 9339372; 9345404; 9356473; 9357922; 9358378; 9358392; 9361572; 9367793; 9370618; 9370619; 9386360; 9392939; 9398854; 9403009; 9403021; 9409018; 9414651; 9414775; 9415163; 9420856; 9420857; 9421388; 9424508; 9427053; 9427160; 9427189; 9427190; 9436903; 9445651; 9445730; 9462856; 9462962; 9463012; 9474461; 9474888; 9486168; 9492656; 9492678; 9498195; 9501735; 9514338; 9517023; 9522282; 9526422; 9526650; 9530089; 9532716; 9532738; 9539037; 9542685; 9545506; 9553486; 9564777; 9569719; 9569720; 9576236; 9579422; 9579510; 9582748; 9582749; 9585722; 9603997; 9610391; 9634921; 9636509; 9655558; 9662015; 9672393; 9675273; 9675809; 9693777; 9700234; 9704209; 9723898; 9724098; 9724183; 9731104; 9732322; 9757124; 9804672; 9826963; 9833353; 9839422; 9839423; 9854370; 9874923; 9876537; 9878159; 9884150; 9884456; 9895301; 9901276; 9918716; 9919099; 9936890; 9943697; 9950166; 9974705; 9986924; 10028659; 10028743; 10034743; 10039661; 10045764; 10045798; 10064624; 10066203; 10070992; 10105081; 10117621; 10124182; 10130476; 10164685; 10176412; 10179065; 10182819; 10186760; 10188394; 10194802; 10196596; 10220217; 20020001588; 20030053284; 20050181973; 20050197677; 20050247319; 20060047283; 20060212096; 20070027371; 20070120683; 20070154030; 20070179562; 20070219639; 20070265704; 20070282196; 20080004642; 20080020012; 20080048855; 20080049376; 20080065181; 20080097496; 20080102096; 20080106419; 20080180242; 20080207983; 20080208010; 20080234598; 20080288027; 20080303728; 20090012372; 20090024161; 20090028957; 20090062825; 20090069869; 20090099626; 20090118683; 20090148496; 20090155900; 20090157147; 20090157151; 20090163980; 20090163981; 20090198293; 20090202387; 20090206087; 20090227862; 20090254179; 20090274737; 20090281597; 20090305972; 20100015201; 20100063347; 20100082102; 20100094654; 20100139672; 20100143871; 20100144641; 20100145337; 20100152573; 20100160997; 20100161004; 20100168821; 20100174240; 20100174349; 20100191236; 20100191306; 20100217239; 20100217240; 20100217241; 20100217242; 20100217243; 20100217244; 20100222686; 20100222802; 20100261526; 20100274121; 20100311640; 20100312081; 20100317955; 20100318160; 20100321163; 20100324578; 20100324579; 20100324639; 20100331868; 20100331874; 20100331932; 20110022140; 20110023343; 20110029043; 20110040343; 20110043297; 20110057037; 20110063088; 20110066079; 20110074349; 20110098576; 20110124983; 20110130636; 20110152756; 20110237861; 20110249381; 20110251516; 20110264058; 20110275930; 20110288600; 20110305672; 20110319785; 20120008714; 20120053585; 20120058106; 20120059434; 20120123221; 20120161901; 20120190386; 20120203079; 20120223705; 20120226118; 20120232012; 20120234433; 20120277859; 20120296399; 20120302874; 20130023954; 20130030255; 20130035544; 20130053711; 20130070387; 20130078244; 20130085408; 20130092564; 20130116664; 20130116665; 20130116666; 20130116667; 20130131679; 20130195806; 20130198463; 20130233324; 20130238056; 20130243799; 20130253297; 20130253660; 20130268029; 20130289529; 20130317584; 20130338494; 20130338768; 20130338769; 20130338770; 20130338771; 20130338772; 20130338773; 20130345561; 20140012111; 20140018644; 20140045757; 20140062717; 20140065153; 20140073704; 20140073839; 20140081076; 20140163644; 20140221732; 20140236105; 20140239528; 20140245783; 20140245784; 20140245785; 20140245786; 20140245787; 20140245788; 20140245789; 20140245790; 20140245791; 20140246497; 20140246498; 20140246499; 20140246500; 20140246501; 20140246502; 20140246917; 20140247136; 20140247137; 20140247142; 20140247143; 20140247144; 20140247146; 20140247147; 20140247149; 20140247150; 20140247151; 20140247154; 20140247155; 20140247156; 20140249379; 20140249760; 20140249853; 20140273824; 20140277277; 20140285396; 20140288619; 20140288647; 20140296663; 20140296978; 20140328517; 20140330224; 20140330256; 20140330257; 20140330347; 20140330357; 20140343691; 20140358196; 20140358197; 20140371821; 20140371824; 20140376336; 20140379090; 20150011860; 20150025478; 20150057595; 20150066124; 20150071934; 20150073498; 20150073499; 20150073500;

20150077050; 20150080982; 20150080992; 20150088226; 20150094547; 20150099959; 20150100108; 20150100109; 20150116053; 20150129664; 20150174296; 20150179038; 20150183828; 20150194052; 20150196378; 20150196409; 20150221208; 20150231402; 20150238277; 20150289911; 20150327989; 20150360038; 20150365738; 20150366915; 20150367144; 20150374541; 20160023007; 20160030650; 20160030756; 20160038324; 20160051825; 20160058324; 20160186140; 20160191120; 20160220198; 20160228034; 20160228052; 20160235317; 20160235318; 20160274752; 20160278638; 20160287380; 20160303313; 20160310048; 20160310737; 20160317095; 20160317797; 20160325083; 20160325084; 20160331518; 20160335632; 20160342882; 20160358063; 20160358155; 20160358156; 20160359222; 20160361009; 20160374556; 20170007420; 20170020241; 20170020402; 20170028185; 20170056677; 20170071510; 20170072121; 20170100214; 20170106196; 20170117739; 20170127929; 20170152486; 20170173216; 20170197072; 20170209666; 20170209705; 20170216610; 20170216611; 20170228627; 20170230084; 20170231738; 20170232256; 20170258585; 20170259072; 20170270721; 20170272316; 20170281927; 20170281928; 20170281957; 20170296834; 20170304635; 20170312530; 20170316487; 20170333080; 20170340872; 20170348146; 20170368158; 20180001018; 20180008185; 20180021235; 20180021498; 20180021510; 20180028275; 20180028827; 20180036053; 20180036115; 20180050189; 20180050214; 20180055500; 20180059126; 20180060520; 20180085038; 20180085592; 20180103879; 20180126053; 20180126133; 20180138022; 20180147413; 20180154075; 20180168811; 20180184944; 20180188704; 20180188714; 20180188715; 20180192952; 20180200003; 20180200185; 20180210425; 20180210426; 20180210427; 20180214690; 20180214694; 20180221663; 20180233016; 20180243567; 20180243573; 20180243577; 20180253073; 20180253074; 20180253075; 20180255374; 20180255375; 20180255376; 20180255377; 20180255378; 20180255379; 20180255380; 20180255381; 20180255382; 20180255383; 20180280694; 20180284735; 20180284736; 20180284737; 20180284741; 20180284742; 20180284743; 20180284744; 20180284745; 20180284746; 20180284747; 20180284749; 20180284752; 20180284753; 20180284754; 20180284755; 20180284756; 20180284757; 20180284758; 20180299878; 20180310824; 20180310964; 20180321666; 20180321667; 20180321672; 20180322445; 20180353219; 20180360355; 20180372720; 20190000656; 20190025805; 20190025806; 20190025812; 20190025813; 20190033845; 20190033846; 20190033847; 20190033848; 20190033849; 20190038214; 20190038496; 20190041835; 20190041836; 20190041840; 20190041841; 20190041842; 20190041843; 20190041844; 20190041845; 20190041846; 20190053712; 20190053915; 20190054284; 20190064791; 20190064792; 20190070350; 20190072922; 20190072923; 20190072924; 20190072925; 20190072926; 20190072928;

Medical devices may communicate directly with a server or caregiver device, or indirectly through a relay or mesh network. Swarm methods may be used for the relay of messages, selection of supernodes for forwarding of messages in an ad hoc network, distributed processing of tasks, etc. Security and privacy are preferably maintained through cryptographic communications and hardware security.

The implant may have functions of other types of RF-ID tags, such as access, control, feeding and consumption management, etc. For example, a pet door, feeder, etc., may receive identification signals from the implant, and selectively authorize or react to the identification.

Various distributed ledger and blockchain technologies may be employed for data permanence, transparency, authentication, and in some cases, transfer of economic value or authority.

See, U.S. Pat. Nos. and US Pub. App. Nos.: 9014661; 9351124; 9436923; 9569771; 9641342; 9818092; 9820120; 9849364; 9853819; 9855785; 9862222; 9922380; 9922381; 9942304; 10005564; 10022613; 10022614; 10026118; 10039113; 10046228; 10055715; 10078839; 10080498; 10103936; 10108938; 10115068; 10120888; 10121186; 10127247; 10129032; 10135835; 10142312; 10147076; 10152756; 10160251; 10163079; 10163080; 10164952; 10168693; 10172409; 10176418; 10176481; 10178105; 10178890; 10192198; 10193695; 10195513; 10200199; 10200834; 10204160; 10225085; 20140368601; 20150269624; 20150356524; 20150356555; 20160012465; 20160098723; 20160098730; 20160170996; 20160192166; 20160203522; 20160203572; 20160224803; 20160300252; 20160321654; 20160379312; 20170017936; 20170017954; 20170017955; 20170028622; 20170031874; 20170033932; 20170046652; 20170046689; 20170046694; 20170046799; 20170046806; 20170048209; 20170048234; 20170048235; 20170083907; 20170085545; 20170085555; 20170091756; 20170109735; 20170132615; 20170132630; 20170140408; 20170161517; 20170173262; 20170206532; 20170221032; 20170221052; 20170228706; 20170228731; 20170228734; 20170232300; 20170236177; 20170236196; 20170237569; 20170237570; 20170243177; 20170243208; 20170243209; 20170243212; 20170243213; 20170243214; 20170243217; 20170243222; 20170243286; 20170243287; 20170244707; 20170244721; 20170250796; 20170256000; 20170256001; 20170256003; 20170262862; 20170300905; 20170300910; 20170300946; 20170316487; 20170345105; 20170358041; 20170364860; 20170373849; 20180001184; 20180006990; 20180012311; 20180013815; 20180019984; 20180039512; 20180041345; 20180069899; 20180071789; 20180072415; 20180072416; 20180074481; 20180074488; 20180074521; 20180074522; 20180074523; 20180075386; 20180075406; 20180078843; 20180081787; 20180081955; 20180082043; 20180082295; 20180083786; 20180089627; 20180089641; 20180089669; 20180094953; 20180096121; 20180096175; 20180108024; 20180115600; 20180117446; 20180117447; 20180120225; 20180123804; 20180130034; 20180130050; 20180130158; 20180131765; 20180133583; 20180136633; 20180137461; 20180137506; 20180137512; 20180139057; 20180144298; 20180144342; 20180150816; 20180158036; 20180165738; 20180167394; 20180173906; 20180174097; 20180174188; 20180176017; 20180181806; 20180181909; 20180181964; 20180182140; 20180183796; 20180189528; 20180189854; 20180191503; 20180198617; 20180198876; 20180203755; 20180204034; 20180204111; 20180211213; 20180211718; 20180218003; 20180218354; 20180225649; 20180227354; 20180232693; 20180232730; 20180232817; 20180253430; 20180253805; 20180257306; 20180259976; 20180261307; 20180262493; 20180264347; 20180268360; 20180268418; 20180268479; 20180268483; 20180284093; 20180285709; 20180293577; 20180300772; 20180307854; 20180307859; 20180307959; 20180314868; 20180315141; 20180322164; 20180324407; 20180326291; 20180330369; 20180336515; 20180349893; 20180357603; 20180357725; 20180365633; 20180369437; 20180369438; 20180374037; 20180375750; 20180376336; 20190005507; 20190005566; 20190007381; 20190008117; 20190012637; 20190019144; 20190019171; 20190026690; 20190034536; 20190034605; 20190034808; 20190034888; 20190034889; 20190034923; 20190035499; 20190036887; 20190038791; 20190043008;

20190043010; 20190044736; 20190046863; 20190049931; 20190050888; 20190053470; 20190056726; 20190057454; 20190065733; 20190066063;

There are two typical ways to approach a systems biology issue. First involves generating a descriptive or physical model of the system, i.e., a model where the components and their parameters have physical correlates, and therefore assuming the complexity of the model is sufficient, the model may be populated with measured parameters, and insights from the model will reflect on the identifiable components of the system. A second approach employs a statistical optimization process to produce an output trained to correspond to a set of inputs and corresponding actions, e.g., an artificial neural network (ANN) or deep neural network (DNN). Neural network technologies rarely implement an optimization, which represents an architecture correlated to a physical system, unless the attributes of the physical system are design constraints, and so the internal (hidden) states of the network do not correspond to real parameters and are not indicative of actual states or events. Neural networks may be trained (i.e., statistically optimized) to respond to time-domain changes, and may directly estimate derivatives, e.g., second derivatives, from time-series data.

Bishop, Chris M. "Training with noise is equivalent to Tikhonov regularization." Neural computation 7, no. 1 (1995): 108-116.

Bishop, Chris. "Exact calculation of the Hessian matrix for the multilayer perceptron." (1992): 494-501.

Buntine, Wray L., and Andreas S. Weigend. "Computing second derivatives in feed-forward networks: A review." IEEE transactions on Neural Networks 5, no. 3 (1994): 480-488.

Hirasawa, Kotaro, Masanao Ohbayashi, and Jun-ichi Murata. "Universal learning network and computation of its higher order derivatives." In Proceedings of ICNN'95-International Conference on Neural Networks, vol. 3, pp. 1273-1277. IEEE, 1995.

Hirasawa, Kotaro, Masanao Ohbayashi, Masaru Koga, and Masaaki Harada. "Forward propagation universal learning network." In Proceedings of International Conference on Neural Networks (ICNN'96), vol. 1, pp. 353-358. IEEE, 1996.

LeCun, Yann, Ido Kanter, and Sara A. Solla. "Second order properties of error surfaces: Learning time and generalization." In Advances in neural information processing systems, pp. 918-924. 1991.

Opitz, David W. "Analyzing the structure of a neural network using principal component analysis." In Proceedings of International Conference on Neural Networks (ICNN'97), vol. 1, pp. 254-259. IEEE, 1997.

Pearlmutter, Barak A. "Fast exact multiplication by the Hessian." Neural computation 6, no. 1 (1994): 147-160.

Piché, Stephen W. "The second derivative of a recurrent network." In Proceedings of 1994 IEEE International Conference on Neural Networks (ICNN'94), vol. 1, pp. 245-250. IEEE, 1994.

Popa, Cälin-Adrian. "Exact Hessian Matrix Calculation for Complex-Valued Neural Networks." In International Workshop Soft Computing Applications, pp. 439-455. Springer, Cham, 2014.

Williams, Peter M. "Bayesian regularization and pruning using a Laplace prior." Neural computation 7, no. 1 (1995): 117-143.

Therefore, while internal states of a neural network implementation typically do not correspond to physical elements emulated by the neural network, the exposed inputs, and outputs of a neural network may be trained or constrained to correspond to physical correlates, including the dynamic coefficients of a higher order differential equation or response profile. Thus, instead of purely analytic methods for defining the higher-order (e.g., order>1) derivatives, a neural network or other statistical optimization technique may be employed to extract the parameters.

Homeostasis

The characteristic of biological systems is that physiological parameters are subject to homeostasis, and thus, after a perturbation, tend to return to a nominal value. According to control theory, this return to nominal value after a perturbation requires a greater than first-degree response, i.e., a higher-order response. A first-order response can, in theory, only attenuate the perturbation, but not correct it. Thus, homeostatic mechanisms are typically higher order, or within the biological system act at a higher order.

In biology, homeostasis is the state of steady internal physical and chemical conditions maintained by living systems. This dynamic state of equilibrium is typically considered the condition of optimal functioning for the organism and includes many variables, such as body temperature and fluid balance, being kept within certain pre-set limits (homeostatic range). (Note that the basis for the optimization is complex, and therefore may not correspond to simple survival, sped, size, etc.). Other variables include the pH of extracellular fluid, the concentrations of sodium, potassium, and calcium ions, as well as that of the blood sugar level, and these need to be regulated despite changes in the environment, diet, or level of activity. Each of these variables is controlled by one or more regulators or homeostatic mechanisms, which together maintain life. See, en.wikipedia.org/wiki/Homeostasis.

Homeostasis is brought about by a natural resistance or response to change in the conditions from an "optimal" state, and equilibrium is typically maintained by many regulatory mechanisms. Homeostatic control mechanisms tend to have, according to one theory, at least three interdependent components for the variable being regulated: a receptor, a control center, and an effector. The receptor is the sensing component that monitors and responds to changes in the environment, either external or internal. Receptors include thermoreceptors and mechanoreceptors. Control centers include, for example, the respiratory center, and the renin-angiotensin system. An effector is a target acted on, to bring about the change back to the normal state. At the cellular level, receptors include nuclear receptors that bring about changes in gene expression through up-regulation or down-regulation and act in negative feedback mechanisms. An example of this is in the control of bile acids in the liver.

Some centers, such as the renin-angiotensin system, control more than one variable. When the receptor senses a stimulus, it reacts by sending action potentials to a control center. The control center sets the maintenance range—the acceptable upper and lower limits—for the particular variable, such as temperature. The control center responds to the signal by determining an appropriate response and sending signals to an effector, which can be one or more muscles, an organ, or a gland. When the signal is received and acted on, negative feedback is provided to the receptor that stops the need for further signaling.

The metabolic processes of all organisms can only take place in very specific physical and chemical environments. The conditions vary with each organism, and with whether the chemical processes take place inside the cell or in the interstitial fluid bathing the cells. The best-known homeostatic mechanisms in humans and other mammals are regulators that keep the composition of the extracellular fluid (or the "internal environment") constant, especially with regard to the temperature, pH, osmolality, and the concentrations of sodium, potassium, glucose, carbon dioxide, and oxygen. However, a great many other homeostatic mechanisms, encompassing many aspects of human physiology, control other entities in the body. Where the levels of variables are higher or lower than those needed, they are often prefixed with hyper- and hypo-, respectively, such as hyperthermia and hypothermia and hypertension and hypotension.

If a system is homeostatically controlled, it does not imply that its value is necessarily absolutely steady, i.e., that it maintains a constant value or steady-state in health. Core body temperature is, for instance, regulated by a homeostatic mechanism with temperature receptors in, amongst others, the hypothalamus of the brain. However, the set point of the regulatory pathway is regularly reset. For instance, core body temperature in humans varies during the course of the day (i.e., has a circadian rhythm), with the lowest temperatures occurring at night, and the highest in the afternoons. Other normal temperature variations include those related to the menstrual cycle. The temperature regulator's set point is reset during infections to produce a fever. Organisms are capable of adjusting somewhat to varied conditions such as temperature changes or oxygen levels at altitude, by process of acclimatization.

Homeostasis does not govern every activity in the body. For instance, the signal (be it via neurons or hormones) from the receptor or sensor to the control center is, of necessity, highly variable in order to convey information about the direction and magnitude of the detected error. Similarly, the effector's response needs to be highly adjustable to reverse the error; in fact, it should be very nearly in proportion (but in the opposite direction) to the error that is threatening the internal environment. For instance, the arterial blood pressure in mammals is homeostatically controlled and measured by stretch receptors in the walls of the aortic arch and carotid sinuses at the beginnings of the internal carotid arteries. The sensors send messages via sensory nerves to the medulla oblongata of the brain, indicating whether the blood pressure has fallen or risen, and by how much. The medulla oblongata then distributes messages via the motor or efferent nerves belonging to the autonomic nervous system to a wide variety of effector organs, whose activity is consequently changed to reverse the error in the blood pressure. Thus, where the physiological measurement is of a parameter that itself comprises a feedback signal to another core body system, the parameter may itself not be homeostatically controlled, and would not be expected to achieve a consistent value over time.

One of the effector organs for homeostasis is the heart, whose rate is stimulated to rise (tachycardia) when the arterial blood pressure falls, or to slow down (bradycardia) when the pressure rises above nominal value. Thus, the heart rate (for which there is no sensor in the body) is not homeostatically controlled but is one of the effector responses to errors in the arterial blood pressure and other parameters. Another example is the rate of sweating. This is one of the effectors in the homeostatic control of body temperature, and therefore highly variable in rough proportion to the heat load that threatens to destabilize the body's core temperature, for which there is a sensor in the hypothalamus of the brain.

Mammals regulate their core temperature using input from thermoreceptors in the hypothalamus, brain, spinal cord, internal organs, and great veins. Apart from the internal regulation of temperature, a process called allostasis can come into play that adjusts behavior to adapt to the challenge of very hot or cold extremes (and to other challenges). These adjustments may include seeking shade and reducing activity, or seeking warmer conditions and increasing activity, or huddling. When core temperature falls, the blood supply to the skin is reduced by intense vasoconstriction. The blood flow to the limbs (which have a large surface area) is similarly reduced and returned to the trunk via the deep veins that lie alongside the arteries (forming venae comitantes). This acts as a counter-current exchange system that short-circuits the warmth from the arterial blood directly into the venous blood returning into the trunk, causing minimal heat loss from the extremities in cold weather. The subcutaneous limb veins are tightly constricted, not only reducing heat loss from this source but also forcing the venous blood into the counter-current system in the depths of the limbs. The metabolic rate is increased, initially by non-shivering thermogenesis, followed by shivering thermogenesis if the earlier reactions are insufficient to correct the hypothermia.

When core temperature rises are detected by thermoreceptors, the sweat glands in the skin are stimulated via cholinergic sympathetic nerves to secrete sweat onto the skin, which, when it evaporates, cools the skin and the blood flowing through it. Panting is an alternative effector in many vertebrates, which cools the body also by the evaporation of water, but this time from the mucous membranes of the throat and mouth.

Blood sugar levels are regulated within fairly narrow limits. In mammals, the primary sensors for this are the beta cells of the pancreatic islets. The beta cells respond to a rise in the blood sugar level by secreting insulin into the blood and simultaneously inhibiting their neighboring alpha cells from secreting glucagon into the blood. This combination (high blood insulin levels, and low glucagon levels) act on effector tissues, chief of which are the liver, fat cells, and muscle cells. The liver is inhibited from producing glucose, taking it up instead, and converting it to glycogen and triglycerides. The glycogen is stored in the liver, but the triglycerides are secreted into the blood as very-low-density lipoprotein (VLDL) particles that are taken up by adipose tissue, there to be stored as fats. The fat cells take up glucose through special glucose transporters (GLUT4), whose numbers in the cell wall are increased as a direct effect of insulin acting on these cells. The glucose that enters the fat cells in this manner is converted into triglycerides (via the same metabolic pathways as are used by the liver) and then stored in those fat cells together with the VLDL-derived triglycerides that were made in the liver. Muscle cells also take glucose up through insulin-sensitive GLUT4 glucose channels and convert it into muscle glycogen.

A fall in blood glucose causes insulin secretion from the beta cells to be stopped, and glucagon to be secreted from the alpha cells into the blood. This inhibits the uptake of glucose from the blood by the liver, fats cells, and muscle. Instead, the liver is strongly stimulated to hydrolyze glycogen to release glucose (through glycogenolysis) and non-carbohydrate sources (such as lactate and de-aminated amino acids) using gluconeogenesis. The glucose thus produced is discharged into the blood, correcting the detected error (hypoglycemia). The glycogen stored in muscles remains in the muscles and is only broken down during exercise, to glucose-6-phosphate, and thence to pyruvate to be fed into the citric acid cycle or turned into lactate. It is only the lactate and the waste products of the citric acid cycle that are returned to the blood. The liver can take up only the lactate, and by the process of energy-consuming gluconeogenesis, convert it back to glucose.

Changes in the levels of oxygen, carbon dioxide, and plasma pH are sent to the respiratory center in the brainstem where they are regulated. The partial pressure of oxygen and carbon dioxide in the arterial blood is monitored by the peripheral chemoreceptors (PNS) in the carotid artery and aortic arch. A change in the partial pressure of carbon dioxide is detected as altered pH in the cerebrospinal fluid by central chemoreceptors (CNS) in the medulla oblongata of the brainstem. Information from these sets of sensors is sent to the respiratory center, which activates the effector organs—the diaphragm and other muscles of respiration. An increased level of carbon dioxide in the blood, or a decreased level of oxygen, will result in a deeper breathing pattern and increased respiratory rate to bring the blood gases back to equilibrium. Too little carbon dioxide, and, to a lesser extent, too much oxygen in the blood can temporarily halt breathing, a condition known as apnea, which freedivers use to prolong the time they can stay underwater.

The partial pressure of carbon dioxide is more of a deciding factor in the monitoring of pH. However, at high altitude (above 2500 m), the monitoring of the partial pressure of oxygen takes priority, and hyperventilation keeps the oxygen level constant. With the lower level of carbon dioxide, to keep the pH at 7.4, the kidneys secrete hydrogen ions into the blood and excrete bicarbonate into the urine. This is important in the acclimatization to high altitude.

The kidneys measure the oxygen content rather than the partial pressure of oxygen in the arterial blood. When the oxygen content of the blood is chronically low, oxygen-sensitive cells secrete erythropoietin (EPO) into the blood. The effector tissue is the red bone marrow, which produces red blood cells (RBCs, erythrocytes). The increase in RBCs leads to an increased hematocrit in the blood and the subsequent increase in hemoglobin that increases the oxygen-carrying capacity. This is the mechanism whereby high-altitude dwellers have higher hematocrits than sea-level residents, and also why persons with pulmonary insufficiency or right-to-left shunts in the heart (through which venous blood by-passes the lungs and goes directly into the systemic circulation) have similarly high hematocrits.

Regardless of the partial pressure of oxygen in the blood, the amount of oxygen that can be carried depends on the hemoglobin content. The partial pressure of oxygen may be sufficient, for example, in anemia, but the hemoglobin content will be insufficient and, subsequently, as will be the oxygen content. Given enough supply of iron, vitamin $B_{12}$, and folic acid, EPO can stimulate RBC production, and hemoglobin and oxygen content restored to normal.

The brain can regulate blood flow over a range of blood pressure values by vasoconstriction and vasodilation of the arteries. High-pressure receptors called baroreceptors in the walls of the aortic arch and carotid sinus (at the beginning of the internal carotid artery) monitor the arterial blood pressure. Rising pressure is detected when the walls of the arteries stretch due to an increase in blood volume. This causes heart muscle cells to secrete the hormone atrial natriuretic peptide (ANP) into the blood. This acts on the kidneys to inhibit the secretion of renin and aldosterone, causing the release of sodium and water into the urine, thereby reducing the blood volume. This information is then conveyed, via afferent nerve fibers, to the solitary nucleus in the medulla oblongata. From here, motor nerves belonging to the autonomic nervous system are stimulated to influence the activity of chiefly the heart and the smallest diameter arteries, called arterioles. The arterioles are the main resistance vessels in the arterial tree, and small changes in diameter cause large changes in the resistance to flow through them. When the arterial blood pressure rises, the arterioles are stimulated to dilate, making it easier for blood to leave the arteries, thus deflating them, and bringing the blood pressure down, back to normal. At the same time, the heart is stimulated via cholinergic parasympathetic nerves to beat more slowly (called bradycardia), ensuring that the inflow of blood into the arteries is reduced, thus adding to the reduction in pressure, and correction of the original error.

Low pressure in the arteries, causes the opposite reflex of constriction of the arterioles and a speeding up of the heart rate (tachycardia). If the drop in blood pressure is very rapid or excessive, the medulla oblongata stimulates the adrenal medulla, via "preganglionic" sympathetic nerves, to secrete epinephrine (adrenaline) into the blood. This hormone enhances the tachycardia and causes severe vasoconstriction of the arterioles to all but the essential organs in the body (especially the heart, lungs, and brain). These reactions usually correct the low arterial blood pressure (hypotension) very effectively.

The plasma ionized calcium ($Ca^{2+}$) concentration is very tightly controlled by a pair of homeostatic mechanisms. The sensor for the first one is situated in the parathyroid glands, where the chief cells sense the $Ca^{2+}$ level by means of specialized calcium receptors in their membranes. The sensors for the second are the parafollicular cells in the thyroid gland. The parathyroid chief cells secrete parathyroid hormone (PTH) in response to a fall in the plasma ionized calcium level; the parafollicular cells of the thyroid gland secrete calcitonin in response to a rise in the plasma ionized calcium level.

The effector organs of the first homeostatic mechanism are the bones, the kidney, and, via a hormone released into the blood by the kidney in response to high PTH levels in the blood, the duodenum, and jejunum. Parathyroid hormone (in high concentrations in the blood) causes bone resorption, releasing calcium into the plasma. This is a very rapid action that can correct threatening hypocalcemia within minutes. High PTH concentrations cause the excretion of phosphate ions via the urine. Since phosphates combine with calcium ions to form insoluble salts, a decrease in the level of phosphates in the blood releases free calcium ions into the plasma ionized calcium pool. PTH has a second action on the kidneys. It stimulates the manufacture and release, by the kidneys, of calcitriol into the blood. This steroid hormone acts on the epithelial cells of the upper small intestine, increasing their capacity to absorb calcium from the gut contents into the blood.

The second homeostatic mechanism, with its sensors in the thyroid gland, releases calcitonin into the blood when the blood ionized calcium rises. This hormone acts primarily on bone, causing the rapid removal of calcium from the blood and depositing it, in an insoluble form, in the bones.

The two homeostatic mechanisms working through PTH on the one hand, and calcitonin on the other can very rapidly correct any impending error in the plasma ionized calcium level by either removing calcium from the blood and depositing it in the skeleton, or by removing calcium from it. The skeleton acts as an extremely large calcium store (about 1 kg) compared with the plasma calcium store (about 180 mg). Longer-term regulation occurs through calcium absorption or loss from the gut.

The homeostatic mechanism which controls the plasma sodium concentration is rather complex. The sensor is situated in the juxtaglomerular apparatus of kidneys, which indirectly senses the plasma sodium concentration. Instead of measuring it directly in the blood flowing past the juxtaglomerular cells, these cells respond to the sodium concentration in the renal tubular fluid after it has already undergone a certain amount of modification in the proximal convoluted tubule and loop of Henle. These cells also respond to the rate of blood flow through the juxtaglomerular apparatus, which, under normal circumstances, is directly proportional to the arterial blood pressure, making this tissue an ancillary arterial blood pressure sensor.

In response to a lowering of the plasma sodium concentration, or to a fall in the arterial blood pressure, the juxtaglomerular cells release renin into the blood. Renin is an enzyme that cleaves a decapeptide from a plasma α-2-globulin called angiotensinogen. This decapeptide, with no known biological activity, is known as angiotensin I. However, when the blood circulates through the lungs, a pulmonary capillary endothelial enzyme called angiotensin-converting enzyme (ACE) cleaves further two amino acids from angiotensin I to form an octapeptide known as angiotensin II, which acts on the adrenal cortex, causing the release into the blood of the steroid hormone, aldosterone. Angiotensin II also acts on the smooth muscle in the walls of the arterioles causing these small diameter vessels to constrict, thereby restricting the outflow of blood from the arterial tree, causing the arterial blood pressure to rise. This, therefore, reinforces the measures described above, which defend the arterial blood pressure against changes, especially hypotension.

The angiotensin II-stimulated aldosterone released from the zona glomerulosa of the adrenal glands has an effect on particularly the epithelial cells of the distal convoluted tubules and collecting ducts of the kidneys. Here it causes the reabsorption of sodium ions from the renal tubular fluid in exchange for potassium ions that are secreted from the blood plasma into the tubular fluid to exit the body via the urine. The reabsorption of sodium ions from the renal tubular fluid halts further sodium ion losses from the body and, therefore, preventing the worsening of hyponatremia. The hyponatremia can only be corrected by the consumption of salt in the diet.

When the plasma sodium ion concentration is higher than normal (hypernatremia), the release of renin from the juxtaglomerular apparatus is halted, ceasing the production of angiotensin II, and its consequent aldosterone-release into the blood. The kidneys respond by excreting sodium ions into the urine, thereby normalizing the plasma sodium ion concentration. The low angiotensin II levels in the blood lower the arterial blood pressure as an inevitable concomitant response.

The reabsorption of sodium ions from the tubular fluid as a result of high aldosterone levels in the blood does not, of itself, cause renal tubular water to be returned to the blood from the distal convoluted tubules or collecting ducts. This is because sodium is reabsorbed in exchange for potassium and, therefore, causes only a modest change in the osmotic gradient between the blood and the tubular fluid. Furthermore, the epithelium of the distal convoluted tubules and collecting ducts is impermeable to water in the absence of antidiuretic hormone (ADH) in the blood. ADH is part of the control of fluid balance. Its levels in the blood vary with the osmolality of the plasma, which is measured in the hypothalamus of the brain. Aldosterone's action on the kidney tubules prevents sodium loss to the extracellular fluid (ECF). So, there is no change in the osmolality of the ECF and, therefore, no change in the ADH concentration of the plasma. However, low aldosterone levels cause a loss of sodium ions from the ECF, which could potentially cause a change in extracellular osmolality and therefore of ADH levels in the blood.

High potassium concentrations in the plasma cause depolarization of the zona glomerulosa cells' membranes in the outer layer of the adrenal cortex. This causes the release of aldosterone into the blood. Aldosterone acts primarily on the distal convoluted tubules and collecting ducts of the kidneys, stimulating the excretion of potassium ions into the urine. It does so, however, by activating the basolateral $Na^+/K^+$ pumps of the tubular epithelial cells. These sodium/potassium exchangers pump three sodium ions out of the cell, into the interstitial fluid and two potassium ions into the cell from the interstitial fluid. This creates an ionic concentration gradient which results in the reabsorption of sodium ($Na^+$) ions from the tubular fluid into the blood, and secreting potassium ($K^+$) ions from the blood into the urine (lumen of collecting duct).

The total amount of water in the body needs to be kept in balance. Fluid balance involves keeping the fluid volume stabilized, and also keeping the levels of electrolytes in the extracellular fluid stable. Fluid balance is maintained by the process of osmoregulation and by behavior. Osmotic pressure is detected by osmoreceptors in the median preoptic nucleus in the hypothalamus. Measurement of the plasma osmolality to give an indication of the water content of the body, relies on the fact that water losses from the body, (through unavoidable water loss through the skin which is not entirely waterproof and therefore always slightly moist, water vapor in the exhaled air, sweating, vomiting, normal feces and especially diarrhea) are all hypotonic, meaning that they are less salty than the body fluids (compare, for instance, the taste of saliva with that of tears. The latter has almost the same salt content as the extracellular fluid, whereas the former is hypotonic with respect to the plasma. Saliva does not taste salty, whereas tears are decidedly salty). Nearly all normal and abnormal losses of body water, therefore, cause the extracellular fluid to become hypertonic. Conversely, excessive fluid intake dilutes the extracellular fluid causing the hypothalamus to register hypotonic hyponatremia conditions.

When the hypothalamus detects a hypertonic extracellular environment, it causes the secretion of an antidiuretic hormone (ADH) called vasopressin, which acts on the effector organ, which in this case is the kidney. The effect of vasopressin on the kidney tubules is to reabsorb water from the distal convoluted tubules and collecting ducts, thus preventing aggravation of the water loss via the urine. The hypothalamus simultaneously stimulates the nearby thirst center causing an almost irresistible (if the hypertonicity is severe enough) urge to drink water. The cessation of urine flow prevents the hypovolemia and hypertonicity from getting worse; the drinking of water corrects the defect.

Hypo-osmolality results in very low plasma ADH levels. This results in the inhibition of water reabsorption from the kidney tubules, causing high volumes of very dilute urine to be excreted, thus getting rid of the excess water in the body.

Urinary water loss, when the body water homeostat is intact, is a compensatory water loss, correcting any water excess in the body. However, since the kidneys cannot generate water, the thirst reflex is the all-important second effector mechanism of the body water homeostat, correcting any water deficit in the body.

The plasma pH can be altered by respiratory changes in the partial pressure of carbon dioxide; or altered by metabolic changes in the carbonic acid to bicarbonate ion ratio. The bicarbonate buffer system regulates the ratio of carbonic acid to bicarbonate to be equal to 1:20, at which ratio the blood pH is 7.4 (as explained in the Henderson-Hasselbalch equation). A change in the plasma pH gives an acid-base imbalance. In acid-base homeostasis, there are two mechanisms that can help regulate the pH. Respiratory compensation a mechanism of the respiratory center, adjusts the partial pressure of carbon dioxide by changing the rate and depth of breathing, to bring the pH back to normal. The partial pressure of carbon dioxide also determines the concentration of carbonic acid and the bicarbonate buffer system can also come into play. Renal compensation can help the bicarbonate buffer system. The sensor for the plasma bicarbonate concentration is not known for certain. It is very probable that the renal tubular cells of the distal convoluted tubules are themselves sensitive to the pH of the plasma. The metabolism of these cells produces carbon dioxide, which is rapidly converted to hydrogen and bicarbonate through the action of carbonic anhydrase. When the ECF pH falls (becoming more acidic) the renal tubular cells excrete hydrogen ions into the tubular fluid to leave the body via urine. Bicarbonate ions are simultaneously secreted into the blood that decreases the carbonic acid and, consequently, raises the plasma pH. The converse happens when the plasma pH rises above normal: bicarbonate ions are excreted into the urine, and hydrogen ions released into the plasma.

When hydrogen ions are excreted into the urine, and bicarbonate into the blood, the latter combines with the excess hydrogen ions in the plasma that stimulated the kidneys to perform this operation. The resulting reaction in the plasma is the formation of carbonic acid which is in equilibrium with the plasma partial pressure of carbon dioxide. This is tightly regulated to ensure that there is no excessive build-up of carbonic acid or bicarbonate. The overall effect is, therefore, that hydrogen ions are lost in the urine when the pH of the plasma falls. The concomitant rise in the plasma bicarbonate mops up the increased hydrogen ions (caused by the fall in plasma pH) and the resulting excess carbonic acid is disposed of in the lungs as carbon dioxide. This restores the normal ratio between bicarbonate and the partial pressure of carbon dioxide and therefore the plasma pH. The converse happens when a high plasma pH stimulates the kidneys to secrete hydrogen ions into the blood and to excrete bicarbonate into the urine. The hydrogen ions combine with the excess bicarbonate ions in the plasma, once again forming an excess of carbonic acid which can be exhaled, as carbon dioxide, in the lungs, keeping the plasma bicarbonate ion concentration, the partial pressure of carbon dioxide and, therefore, the plasma pH, constant.

Cerebrospinal fluid (CSF) allows for regulation of the distribution of substances between cells of the brain and neuroendocrine factors, to which slight changes can cause problems or damage to the nervous system. For example, high glycine concentration disrupts temperature and blood pressure control, and high CSF pH causes dizziness and syncope.

Inhibitory neurons in the central nervous system play a homeostatic role in the balance of neuronal activity between excitation and inhibition. Inhibitory neurons using GABA, make compensating changes in the neuronal networks preventing runaway levels of excitation. An imbalance between excitation and inhibition is seen to be implicated in a number of neuropsychiatric disorders.

The neuroendocrine system is the mechanism by which the hypothalamus maintains homeostasis, regulating metabolism, reproduction, eating and drinking behavior, energy utilization, osmolarity, and blood pressure.

The regulation of metabolism is carried out by hypothalamic interconnections to other glands.[64] Three endocrine glands of the hypothalamic-pituitary-gonadal axis (HPG axis) often work together and have important regulatory functions. Two other regulatory endocrine axes are the hypothalamic-pituitary-adrenal axis (HPA axis) and the hypothalamic-pituitary-thyroid axis (HPT axis).

The liver also has many regulatory functions of the metabolism. An important function is the production and control of bile acids. Too much bile acid can be toxic to cells, and its synthesis can be inhibited by activation of FXR a nuclear receptor.

At the cellular level, homeostasis is carried out by several mechanisms, including transcriptional regulation that can alter the activity of genes in response to changes.

The amount of energy taken in through nutrition needs to match the amount of energy used. To achieve energy, homeostasis appetite is regulated by two hormones, ghrelin, and leptin. Ghrelin stimulates hunger, and the intake of food and leptin acts to signal satiety (fullness).

Many diseases are the result of a homeostatic failure. Almost any homeostatic component can malfunction either as a result of an inherited defect, an inborn error of metabolism, or an acquired disease. Some homeostatic mechanisms have inbuilt redundancies, which ensures that life is not immediately threatened if a component malfunctions; but sometimes a homeostatic malfunction can result in serious disease, which can be fatal if not treated.

A well-known example of a homeostatic failure is shown in type 1 diabetes mellitus. In this case, blood sugar regulation is unable to function because the beta cells of the pancreatic islets are destroyed and cannot produce the necessary insulin. The blood sugar rises in a condition known as hyperglycemia.

The plasma ionized calcium homeostasis can be disrupted by the constant, unchanging, over-production of parathyroid hormone by a parathyroid adenoma resulting in the typically features of hyperparathyroidism, namely high plasma ionized $Ca^{2+}$ levels and the resorption of bone, which can lead to spontaneous fractures. The abnormally high plasma ionized calcium concentrations cause conformational changes in many cell-surface proteins (especially ion channels and hormone or neurotransmitter receptors) giving rise to lethargy, muscle weakness, anorexia, constipation, and labile emotions.

Roughly 60% of the mass of the body is water, and despite wide variation in the amount of water taken in each day, body water content remains incredibly stable. Such precise control of body water and solute concentrations is a function of several hormones acting on both the kidneys and vascular system, but the antidiuretic hormone ADH plays a key role in this process. The body water homeostasis can be compromised by the inability to secrete ADH in response to even the normal daily water losses via the exhaled air, the feces, and insensible sweating. On receiving a zero blood ADH signal, the kidneys produce huge unchanging volumes of very dilute urine, causing dehydration and death if not treated.

Caloric burn-rate is newly-discovered homeostasis kept nearly constant regardless of the physical activities of the person. Studies show that traditional hunter-gatherers, who lead physically hard lives, burn the same number of calories as the sedentary population in the U.S. with access to modern conveniences. Human energy expenditure is tightly constrained. See "The Exercise Paradox," Scientific American 316, 2, 26-31 (February 2017) (doi:10.1038/scientificamerican0217-26). As organisms age, the efficiency of their control systems becomes reduced. The inefficiencies gradually result in an unstable internal environment that increases the risk of illness, and leads to the physical changes associated with aging. Various chronic diseases are kept under control by homeostatic compensation, which masks a problem by compensating for it in another way. However, the compensating mechanisms eventually wear out or are disrupted by a new complicating factor (such as the advent of a concurrent acute viral infection), which sends the body reeling through a new cascade of events. Such decompensation unmasks the underlying disease, worsening its symptoms. Common examples include decompensated heart failure, kidney failure, and liver failure.

Other biological systems have characteristics of interest that may be measured. For example, excitability of muscles, neurons, and other tissues is dependent on ion balance as well as membrane receptors. In some cases, symptoms may directly arise from a homeostatic effect, while in others, a homeostatically-controlled system may be assessed to provide information about the variables that control that system, and to infer corresponding effects on biological systems that are less readily interrogated. For example, an electrical stimulation of a particular voluntary muscle may provide direct information on excitability, that may be related to toxic effects, ion imbalances, exercise, and the like, for that muscle. However, the same causes of alteration in the excitability of a voluntary muscle may be global for the organism, and thus a muscle excitability test may provide information about the state of inaccessible muscles, as well as other tissues that have similar characteristics or are effected by the same perturbations. Likewise, peripheral edema may reflect various causes, such as ion imbalances, serum albumin, lymphatic blockage, etc.

Predictive homeostasis is an anticipatory response to an expected challenge in the future, such as the stimulation of insulin secretion by gut hormones which enter the blood in response to a meal. This insulin secretion occurs before the blood sugar level rises, lowering the blood sugar level in anticipation of a large influx into the blood of glucose resulting from the digestion of carbohydrates in the gut. Such anticipatory reactions are open-loop systems which are based, essentially, on "guesswork" and are not self-correcting. Anticipatory responses always require a closed-loop negative feedback system to correct the 'over-shoots' and 'under-shoots,' to which the anticipatory systems are prone.

REFERENCES

Alberts, Bruce (2002). Molecular biology of the cell (4th ed.). New York [u.a.]: Garland. pp. 1292-1293. ISBN 978-0-8153-4072-0.

Alon, Uri. "An Introduction to Systems Biology: Design Principles of Biological Circuits." Chapman and Hall/CRC (2006).

Andersen, Kim E., and Malene Højbjerre. "A population-based Bayesian approach to the minimal model of glucose and insulin homeostasis." Statistics in Medicine 24, no. 15 (2005): 2381-2400.

Andrews, Burton W., and Pablo A. Iglesias. "Control engineering and systems biology." In Mathematical Methods for Robust and Nonlinear Control, pp. 267-288. Springer, London, 2007.

Antonelli, Peter L., and Vlastimil Křivan. "Fuzzy differential inclusions as substitutes for stochastic differential equations in population biology." Open Systems & Information Dynamics 1, no. 2 (1992): 217-232.

Armstrong C M, Cota G (March 1999). "Calcium block of Na+ channels and its effect on closing rate". Proceedings of the National Academy of Sciences of the United States of America. 96(7): 4154-7. Bibcode:1999 PNAS . . . 96.4154A. doi:10.1073/pnas.96.7.4154. PMC 22436. PMID 10097179.

Aronoff, Stephen L.; Berkowitz, Kathy; Shreiner, Barb; Want, Laura (1 Jul. 2004). "Glucose Metabolism and Regulation: Beyond Insulin and Glucagon". Diabetes Spectrum. 17 (3): 183-190. doi:10.2337/diaspect.17.3.183. ISSN 1040-9165.

Bauer J H, Gauntner W C (March 1979). "Effect of potassium chloride on plasma renin activity and plasma aldosterone during sodium restriction in normal man". Kidney Int. 15 (3): 286-93. doi:10.1038/ki.1979.37. PMID 513492.

Bhagavan, N. V. (2002). Medical biochemistry (4th ed.). Academic Press. p. 499. ISBN 978-0-12-095440-7.

Boron W F, Boulpaep E L (2009). Medical physiology: a cellular and molecular approach (2nd Int. ed.). Philadelphia, PA: Saunders/Elsevier. ISBN 9781416031154.

Bose, Biplab. "Systems biology: A biologist's viewpoint." Progress in biophysics and molecular biology 113, no. 3 (2013): 358-368.

Brini M, Ottolini D, Call T, Carafoli E (2013). "Chapter 4. Calcium in Health and Disease". In Sigel A, Helmut R K (eds.). Interrelations between Essential Metal Ions and Human Diseases. Metal Ions in Life Sciences. 13. Springer. pp. 81-137. doi:10.1007/978-94-007-7500-8_4. ISBN 978-94-007-7499-5. PMID 24470090.

Campbell, Neil A. (1990). Biology (2nd ed.). Redwood City, California: The Benjamin/Cummings Publishing Company. pp. 897-898. ISBN 978-0-8053-1800-5.

Cannon, W. B. (1926). "Physiological regulation of normal states: some tentative postulates concerning biological homeostatics". In A. Pettit (ed.). A Charles Riches amis, ses collègues, ses élèves (in French). Paris: Les Éditions Médicales. p. 91.

Cannon, W. B. (1932). The Wisdom of the Body. New York: W. W. Norton. pp. 177-201.

Chifman, J., A. Kniss, P. Neupane, I. Williams, B. Leung, Z. Deng, P. Mendes et al. "The core control system of intracellular iron homeostasis: a mathematical model." Journal of theoretical biology 300 (2012): 91-99.

Conrad, Matthias, Christian Hubold, Bernd Fischer, and Achim Peters. "Modeling the hypothalamus-pituitary-adrenal system: homeostasis by interacting positive and negative feedback." Journal of biological physics 35, no. 2 (2009): 149-162.

De Gaetano, Andrea, Domenico Di Martino, Alfredo Germani, and Costanzo Manes. "Mathematical models and state observation of the glucose-insulin homeostasis." In IFIP Conference on System Modeling and Optimization, pp. 281-294. Springer, Boston, MA, 2003.

DiStefano III, Joseph. "Dynamic Systems Biology Modeling and Simulation." Academic Press (2015).

El-Shal, Shendy M. "Digital modelling and robust control of the glucose homeostasis system." International Journal of Systems Science 20, no. 4 (1989): 575-586.

El-Shal, Shendy M. "Microcomputer-based robust digital control for the glucoregulatory system." International journal of systems science 22, no. 7 (1991): 1279-1293.

El-Shal, Shendy M., and Magdi S. Mahmoud. "Microcomputer-based robust control for slow time-delay processes: pole placement approach." International Journal of Systems Science 20, no. 12 (1989): 2395-2401.

Ferrillo, Franco, Stefania Donadio, Fabrizio De Carli Phy, Sergio Garbarino, and Lino Nobili. "A model-based approach to homeostatic and ultradian aspects of nocturnal sleep structure in narcolepsy." Sleep 30, no. 2 (2007): 157-165.

Fisher J W, Koury S, Ducey T, Mendel S (1996). "Erythropoietin production by interstitial cells of hypoxic monkey kidneys". British Journal of Haematology. 95 (1): 27-32. doi:10.1046/j.1365-2141.1996.d01-1864.x. PMID 8857934.

Fitzsimmons, M. D., M. M. Roberts, T. G. Sherman, and A. G. Robinson. "Models of neurohypophyseal homeostasis." American Journal of Physiology-Regulatory, Integrative and Comparative Physiology 262, no. 6 (1992): R1121-R1130.

Flores, C E; Mendez, P (2014). "Shaping inhibition: activity dependent structural plasticity of GABAergic synapses". Frontiers in Cellular Neuroscience. 8: 327. doi:10.3389/fncel.2014.00327. PMC 4209871. PMID 25386117.

Flouris, A D (January 2011). "Functional architecture of behavioural thermoregulation". European Journal of Applied Physiology. 111 (1): 1-8. doi:10.1007/s00421-010-1602-8. PMID 20711785.

Garmel, Gus M. (2012). "Fever in adults". In Mahadevan, S.V.; Garmel, Gus M. (eds.). An introduction to clinical emergency medicine (2nd ed.). Cambridge: Cambridge University Press. p. 375. ISBN 978-0521747769.

Germain, Ronald N. "Maintaining system homeostasis: the third law of Newtonian immunology." Nature immunology 13, no. 10 (2012): 902.

Gilroy, Anne M.; MacPherson, Brian R.; Ross, Lawrence M. (2008). Atlas of Anatomy. Stuttgart: Thieme Medical Publishers. pp. 318, 349. ISBN 978-1-60406-062-1.

Golubitsky, Martin, and Ian Stewart. "Homeostasis with multiple inputs." SIAM Journal on Applied Dynamical Systems 17, no. 2 (2018): 1816-1832.

Gordon, Betts, J. Anatomy and physiology. DeSaix, Peter, Johnson, Eddie., Johnson, Jody E., Korol, Oksana., Kruse, Dean H., Poe, Brandon. Houston, Texas p. 9. ISBN 9781947172043. OCLC 1001472383.

Hall, John (2011). Guyton and Hall textbook of medical physiology (12th ed.). Philadelphia, Pa.: Saunders/bicher. pp. 4-9. ISBN 9781416045748.

Harris, N Stuart; Nelson, Sara W (16 Apr. 2008). "Altitude Illness-Cerebral Syndromes". EMedicine Specialties>Emergency Medicine>Environmental.

Harrison, T. R. Principles of Internal Medicine (3rd ed.). New York: McGraw-Hill Book Company. pp. 170, 571-579.

Hendrickx, Diana M., Huub C J Hoefsloot, Margriet M W B Hendriks, Daniël J. Vis, André B. Canelas, Bas Teusink, and Age K. Smilde. "Inferring differences in the distribution of reaction rates across conditions." Molecular BioSystems 8, no. 9 (2012): 2415-2423.

Hodkinson, Duncan J., Owen O'daly, Patricia A. Zunszain, Carmine M. Pariante, Vitaly Lazurenko, Fernando O. Zelaya, Matthew A. Howard, and Steven C R Williams. "Circadian and homeostatic modulation of functional connectivity and regional cerebral blood flow in humans under normal entrained conditions." Journal of Cerebral Blood Flow & Metabolism 34, no. 9 (2014): 1493-1499.

Hu C, Rusin C G, Tan Z, Guagliardo N A, Barrett P Q (June 2012). "Zona glomerulosa cells of the mouse adrenal cortex are intrinsic electrical oscillators". J Clin Invest. 122 (6): 2046-2053. doi:10.1172/JC161996. PMC 3966877. PMID 22546854.

Ingalls, Brian P., Tau-Mu Yi, and Pablo A. Iglesias. "12 Using Control Theory to Study Biology." System Modeling in Cellular Biology (2004): 243.

Ingalls Brian P. "Mathematical Modeling in Systems Biology: An Introduction." The MIT Press (2013).

Jelkmann, W. (2007). "Erythropoietin after a century of research: younger than ever". European Journal of Haematology. 78 (3): 183-205. doi:10.1111/j.1600-0609.2007.00818.x. PMID 17253966.

Kalaany, N Y; Mangelsdorf, D J (2006). "LXRS and FXR: the yin and yang of cholesterol and fat metabolism". Annual Review of Physiology. 68: 159-91. doi:10.1146/annurev.physiol.68.033104.152158. PMID 16460270.

Khan Academy. "Homeostasis". Khan Academy.

Kluge, Matthew J. (2015). Fever: Its Biology, Evolution, and Function. Princeton University Press. p. 57. ISBN 9781400869831.

Koeslag, J. H.; Saunders, P. T.; Wessels, J. A. (1997). "Glucose homeostasis with infinite gain: further lessons from the Daisyworld parable?". Journal of Endocrinology. 134: 187-192.

Koeslag, Johan H.; Saunders, Peter T.; Terblanche, Elmarie (2003). "Topical Review: A reappraisal of the blood glucose homeostat which comprehensively explains the type 2 diabetes-syndrome X complex". Journal of Physiology. 549 (Pt 2): 333-346. doi:10.1113/jphysiol.2002.037895. PMC 2342944. PMID 12717005.

Koeslag, Johan H.; Saunders, Peter T.; Wessels, Jabus A. (1999). "The chromogranins and counter-regulatory hormones: do they make homeostatic sense?". Journal of Physiology. 517 (3): 643-649. doi:10.1111/j.1469-7793.1999.0643s.x. PMC 2269385. PMID 10358106.

LeDuc, Philip R., William C. Messner, and John P. Wikswo. "How do control-based approaches enter into biology?." Annual Review of Biomedical Engineering 13 (2011): 369-396.

Linas S L, Peterson L N, Anderson R J, Aisenbrey G A, Simon F R, Berl T (June 1979). "Mechanism of renal potassium conservation in the rat". Kidney International. 15 (6): 601-11. doi:10.1038/ki.1979.79. PMID 222934.

Longo, Giuseppe; Montévil, Maël (2014). Perspectives on Organisms. Lecture Notes in Morphogenesis. Springer. doi:10.1007/978-3-642-35938-5. ISBN 978-3-642-35937-8.

Lovelock, James (1991). Healing Gaia: Practical Medicine for the Planet. New York: Harmony Books. ISBN 978-0-517-57848-3.

Lutaif, N. A., R. Palazzo Jr, and J. A. R. Gontijo. "Early detection of metabolic and energy disorders by thermal time series stochastic complexity analysis." Brazilian Journal of Medical and Biological Research 47, no. 1 (2014): 70-79.

Mamontov, Eugen. "Modelling homeorhesis by ordinary differential equations." Mathematical and computer modelling 45, no. 5-6 (2007): 694-707.

Mansour, N. E., and D. A. Linkens. "Pole-assignment self-tuning control of blood pressure in postoperative patients: a simulation study." In IEE Proceedings D (Control Theory and Applications), vol. 136, no. 1, pp. 1-11. IET Digital Library, 1989.

Marder, Eve, and Astrid A. Prinz. "Modeling stability in neuron and network function: the role of activity in homeostasis." Bioessays 24, no. 12 (2002): 1145-1154.

Marieb E N, Hoehn K N (2009). Essentials of Human Anatomy & Physiology (9th ed.). San Francisco: Pearson/Benjamin Cummings. ISBN 978-0321513427.

Martin, Elizabeth (2008). A dictionary of biology (6th ed.). Oxford: Oxford University Press. pp. 315-316. ISBN 978-0-19-920462-5.

Mavelli, Fabio, and Pasquale Stano. "Kinetic models for autopoietic chemical systems: the role of fluctuations in a homeostatic regime." Physical Biology 7, no. 1 (2010): 016010.

Milsum, J. H. (1966). Biological control systems analysis. New York: McGraw-Hill.

Mohler, R. "Biological modeling with variable compartmental structure." IEEE Transactions on Automatic Control 19, no. 6 (1974): 922-926.

Ni, Xiao Yu, Tormod Drengstig, and Peter Ruoff. "The control of the controller: molecular mechanisms for robust perfect adaptation and temperature compensation." Biophysical journal 97, no. 5 (2009): 1244-1253.

Norwich, Kenneth H., and Raymond Reiter. "Homeostatic control of thyroxin concentration expressed by a set of linear differential equations." The Bulletin of mathematical biophysics 27, no. 2 (1965): 133.

Palmer, L G; Frindt, G (2000). "Aldosterone and potassium secretion by the cortical collecting duct". Kidney International. 57 (4): 1324-8. doi:10.1046/j.1523-1755.2000.00970.x. PMID 10760062.

Pattaranit, Ratchada, and Hugo Antonius Van Den Berg. "Mathematical models of energy homeostasis." Journal of The Royal Society Interface 5, no. 27 (2008): 1119-1135.

Peacock, Andrew J (17 Oct. 1998). "Oxygen at high altitude". British Medical Journal. 317 (7165): 1063-1066. doi:10.1136/bmj.317.7165.1063. PMC 1114067. PMID 9774298.

Peters, Achim, Matthias Conrad, Christian Hubold, Ulrich Schweiger, Bernd Fischer, and Horst Lorenz Fehm. "The principle of homeostasis in the hypothalamus-pituitary-adrenal system: new insight from positive feedback." American Journal of Physiology-Regulatory, Integrative and Comparative Physiology 293, no. 1 (2007): R83-R98.

Peterson, Mark C., and Matthew M. Riggs. "A physiologically based mathematical model of integrated calcium homeostasis and bone remodeling." Bone 46, no. 1 (2010): 49-63.

Pocock, Gillian; Richards, Christopher D. (2006). Human physiology: the basis of medicine (3rd ed.). Oxford: Oxford University Press. ISBN 978-0-19-856878-0.

Poh, C. L., L. C. Cui, and R. I. Kitney. "Modeling biological systems in Laplace Domain for Synthetic Biology Design." In World Congress on Medical Physics and Biomedical Engineering, Sep. 7-12, 2009, Munich, Germany, pp. 1377-1380. Springer, Berlin, Heidelberg, 2009.

Preston, Richard A.; Materson, B. J.; Reda, D. J.; Williams, D. W.; Hamburger, R. J.; Cushman, W. C.; Anderson, R. J. (1998). "JAMA Article January 2012". JAMA. 280 (13): 1168-72. doi:10.1001/jama.280.13.1168. PMID 9777817.

Purves, Dale (2011). Neuroscience (5th ed.). Sunderland, Mass.: Sinauer. p. 458. ISBN 978-0-87893-695-3.

Rasmussen, Howard. "Cellular calcium homeostasis and the calcium messenger system." In Seminars in liver disease, vol. 5, no. 02, pp. 110-121. Thieme Medical Publishers, Inc., 1985.

Riggs, D. S. (1970). Control theory and physiological feedback mechanisms. Baltimore: Williams & Wilkins.

Rucker, R. (1987). Mind tools: the mathematics of information. Harmondsworth: Penguin Books. pp. 25-30.

Ruoff, Peter. "General homeostasis in period- and temperature-compensated chemical clock mutants formed by random selection conditions." Naturwissenschaften 81, no. 10 (1994): 456-459.

Sakka, L.; Coll, G.; Chazal, J. (December 2011). "Anatomy and physiology of cerebrospinal fluid". European Annals of Otorhinolaryngology, Head and Neck Diseases. 128 (6): 309-316. doi:10.1016/j.anorl.2011.03.002. PMID 22100360.

Saladin, Kenneth (2012). Anatomy and Physiology (6th ed.). McGraw Hill. pp. 519-20.

Schmidt-Nielsen K (1981). "Countercurrent systems in animals". Scientific American. 244 (5): 118-28. Bibcode: 1981SciAm.244e.118S. doi:10.1038/scientificamerican0581-118. PMID 7233149.

Shannon, Claude E.; Weaver, Warren (1963). The mathematical theory of communication (4th print. ed.). Urbana: University of Illinois Press. ISBN 978-0252725487.

Sievanen, H. "Hormonal influences on the muscle-bone feedback system: a perspective." Journal of Musculoskeletal and Neuronal Interactions 5, no. 3 (2005): 255.

Singh, Prabhleen, and Scott C. Thomson. "Renal homeostasis and tubuloglomerular feedback." Current opinion in nephrology and hypertension 19, no. 1 (2010): 59-64.

Smith, Gerard P. (2008). "Unacknowledged contributions of Pavlov and Barcroft to Cannon's theory of homeostasis". Appetite. 51 (3): 428-432. doi:10.1016/j.appet.2008.07.003.

Smith, James M D, James A. Maas, Philip C. Garnsworthy, Markus R. Owen, Stephen Coombes, Tahir S. Pillay, David A. Barrett, and Michael E. Symonds. "Mathematical modeling of glucose homeostasis and its relationship with energy balance and body fat." Obesity 17, no. 4 (2009): 632.

Spencer, Laci (2015). Flotation: A Guide for Sensory Deprivation, Relaxation, & Isolation Tanks. Lulu.com. p. 29. ISBN 978-1329173750.

Spencer, Laci (29 May 2015). Flotation: A Guide for Sensory Deprivation, Relaxation, & Isolation Tanks. Lulu.com. ISBN 9781329173750.

Spyer, K M; Gourine, A V (12 Sep. 2009). "Chemosensory pathways in the brainstem controlling cardiorespiratory activity". Philosophical Transactions of the Royal Society of London. Series B, Biological Sciences. 364 (1529): 2603-10. doi:10.1098/rstb.2009.0082. PMC 2865116. PMID 19651660.

Standring, Susan (7 Aug. 2015). Gray's anatomy: the anatomical basis of clinical practice. (41st ed.). pp. 141, 151-152. ISBN 9780702068515. OCLC 920806541.

Stryer, Lubert (1995). "Vitamin D is derived from cholesterol by the ring-splitting action of light.". In: Biochemistry (4th ed.). New York: W.H. Freeman and Company. p. 707. ISBN 0 7167 2009 4.

Stryer, Lubert (1995). Biochemistry (4th ed.). New York: W.H. Freeman and Company. pp. 164, 773-774. ISBN 0 7167 2009 4.

Stuart, I. R. (2011). Human physiology (12th ed.). New York: McGraw-Hill. p. 667.

Slitterlin, Thomas, Simone Huber, Hartmut Dickhaus, and Niels Grabe. "Modeling multi-cellular behavior in epidermal tissue homeostasis via finite state machines in multi-agent systems." Bioinformatics 25, no. 16 (2009): 2057-2063.

Swedan, Nadya Gabriele (2001). Women's Sports Medicine and Rehabilitation. Lippincott Williams & Wilkins. p. 149. ISBN 978-0-8342-1731-7.

Talmage, D. W., and R. V. Talmage. "Calcium homeostasis: how bone solubility relates to all aspects of bone physiology." Journal of Musculoskeletal and Neuronal Interactions 7, no. 2 (2007): 108.
Tansey, Etain A.; Johnson, Christopher D (2015). "Recent advances in thermoregulation". Advances in Physiology Education. 39 (3): 139-148. doi:10.1152/advan.00126.2014. ISSN 1043-4046. PMID 26330029.
Thomas, S. Randall, Pierre Baconnier, Julie Fontecave, Jean-Pierre Francoise, Francois Guillaud, Patrick Hannaert, Alfredo Hernandez, et al. "SAPHIR: a physiome core model of body fluid homeostasis and blood pressure regulation." Philosophical Transactions of the Royal Society A: Mathematical, Physical and Engineering Sciences 366, no. 1878 (2008): 3175-3197.
Thorsen, Kristian, Oleg Agafonov, Christina H. Selstø, Ingunn W. Jolma, Xiao Y. Ni, Tormod Drengstig, and Peter Ruoff. "Robust concentration and frequency control in oscillatory homeostats." PloS one 9, no. 9 (2014): e107766.
Toni, R (2004). "The neuroendocrine system: organization and homeostatic role". Journal of Endocrinological Investigation. 27 (6 Suppl): 35-47. PMID 15481802.
Tortora, Gerard J.; Anagnostakos, Nicholas P. (1987). Principles of Anatomy and Physiology (Fifth ed.). New York: Harper & Row, Publishers. ISBN 978-0-06-350729-6.
Um, Ji Won (13 Nov. 2017). "Roles of Glial Cells in Sculpting Inhibitory Synapses and Neural Circuits". Frontiers in Molecular Neuroscience. 10: 381. doi:10.3389/fnmol.2017.00381. PMC 5694142. PMID 29180953.
Watson, Edmund M., Michael J. Chappell, F. Ducrozet, S. M. Poucher, and James W T Yates. "A new general glucose homeostatic model using a proportional-integral-derivative controller." Computer methods and programs in biomedicine 102, no. 2 (2011): 119-129.
Weschler, Toni (2002). Taking Charge of Your Fertility. New York: HarperCollins. pp. 52, 316, 361-362. ISBN 978-0-06-093764-5.
West, Bruce J (2006). Where Medicine Went Wrong: Rediscovering the Path to Complexity. Studies of Nonlinear Phenomena in Life Science. 11. New Jersey: World Scientific. doi:10.1142/6175. ISBN 978-981-256-883-0.
Williams G H, Dluhy R G (2008). "Chapter 336: Disorders of the Adrenal Cortex". In Loscalzo J, Fauci A S, Braunwald E, Kasper D L, Hauser S L, Longo D L (eds.). Harrison's principles of internal medicine. New York: McGraw-Hill Medical. ISBN 978-0-07-146633-2.
Williams, Peter L.; Warwick, Roger; Dyson, Mary; Bannister, Lawrence H. (1989). Gray's Anatomy (Thirty-seventh ed.). Edinburgh: Churchill Livingstone. pp. 691-692, 791, 10011-10012. ISBN 0443 041776.
Withers, P. C. "Comparative physiology." Saunders College, Fort Worth (1992).
Young, Andrew J; Reeves, John T. (2002). "Human Adaptation to High Terrestrial Altitude" (PDF). Medical Aspects of Harsh Environments. 2. Borden Institute, Washington, D C. CiteSeerX 10.1.1.175.3270.
Zion, Michal, and Sara Klein. "Conceptual understanding of homeostasis." International Journal of Biology Education 2 (2015): 1-27.
Zorea, Aharon (2014). Steroids (Health and Medical Issues Today). Westport, CT: Greenwood Press. p. 10. ISBN 978-1440802997.

It is typically assumed that the underlying function describing the physiological parameter of interest over time is, or can be described by, a smooth function. This assumption is well justified, except, perhaps, as applied to electrically excitable cells when sampled well below the Nyquist rate of their action potentials. Few things in biology are quantized, and most natural biological processes are continuous analog processes that are described by smooth differentiable functions.

For example, whether we are interested in the function describing change of the body temperature (T) over time (t), T(t), or the function describing changing the level of the glucose (G) in blood, G(t), all these functions are smooth and differentiable in a sense that there is at least a first $f'=df/dt$ and second derivative $f''=d^2f/dt^2$ of these functions over time. However, in most cases, it is not possible to monitor these parameters continuously, and sampling of the physiological data is discrete. Further, compression of the data will often discretize the information, even if it is initially in a continuous form. Thus, sampled physiological data subject to analysis typically is present as a time series.

While periodic sampling facilitates the analysis, this is not required in all cases. In periodically sampled data, a parameter of interest is sampled at fixed periods spaced by a predetermined time interval, $\Delta t_i$, at times $t \in \{0, \Delta t_1, \Delta t_2, \ldots, \Delta t_n\}$.

In some cases, sampling may not always occur at precise and predictable times, i.e., the sampling interval is irregular.

There are different methods of approximating the "acceleration," i.e., the second-order rate of change in a parameter over time. For example, the first and the second derivatives of a continuous function, which has true first and second derivatives may be determined, $f'=df/dt$ and $f''=d^2f/dt^2$. It is not possible to directly differentiate discrete sampled values. One possible solution is to fit the discrete data into a continuous function that can be differentiated, which can be accomplished by interpolation, smoothing, or any other curve-fitting technique, such as, for example, spline interpolation, polynomial interpolation or polynomial regression; using trigonometric, Gaussian, Lorentzian, Voigt and related function; ordinary and total least squares, etc.

Interpolation is a technique which is used for constructing new data points within the range of discrete data points of the discrete data retrieved from the sampling of a smooth function, which makes it a simple function and allows for the regular differentiation by taking the first and the second derivative of the interpolated function. Interpolation requires an inherent presumption that the data is oversampled, i.e., significant changes do not occur between samples, and so all significant data is captured by the samples.

Of course, the process of starting from sampled data, and interpolating, only to extract values, may be inefficient. Rather, direct analysis of the sampled data is preferred and may be more accurate, since the smoothing functions may lose information and introduce a presumption about the state of the signal between samples that is unwarranted. In many cases, the sampled data is sufficiently oversampled with respect to the physiological process that a curve may be optimally fit to a segment of the line, and the shape of the optimally fit segment will define the first and second derivatives. In other cases, the data is undersampled, and a large amount of variance will be due to physiological changes between samples. In that case, a statistical analysis is more appropriate, and short-term dynamics may be difficult to analyze. Finally, sampling may occur at a rate near a natural cycle frequency or harmonic of the underlying physiological changes, unless the sampling is synchronized with the process, and that analysis recognizes that the values between sampled datapoints are oscillatory. In the more general case, it may also difficult to analyze the data subject to aliasing, though, over longer periods, data patterns may be extracted.

There are numerous techniques for interpolating data. Approximation and interpolation differ in the sense that in approximation, all the points of the basic figure need not be located on the created figure called an approximation curve segment, whereas all the points of the basic figure are located on the created figure called interpolation curve segment.

In discrete calculus (a.k.a. finite differences), the discrete derivative of a function $f(n)$, denoted $\Delta_n f(n)$, is defined to be $f(n+1)-f(n)$. In a finite difference approximation, the first backward derivative is defined as:

$$x'_t = \frac{x_t - x_{t-1}}{\Delta t}$$

The first forward derivative is defined as:

$$x'_t = \frac{x_{t+1} - x_t}{\Delta t}$$

The first centered derivative is defined as:

$$x'_t = \frac{x_{t+1} - x_{t-1}}{2\Delta t}.$$

The second derivative is defined as:

$$x''_t = \frac{x_{t+1} - 2x_t + x_{t-1}}{(\Delta t)^2}.$$

It is preferable to use centered finite differences, when possible because it is an approximation of order 2:

$$\left| \dot{x}_t - \frac{x_{t+1} - x_{t-1}}{2\Delta t} \right| = O(\Delta t)^2$$

where $\dot{x}$ denotes the actual derivative of x at t. We assume here that there is an underlying smooth function $x(\bullet)$ such that $x_t = x(t)$, i.e., the data is a result of sampling from a smooth process. These formulae are derived by computing a simple function that interpolates the data (for example, a polynomial or a spline), and then differentiating that function. Thus, this approach is equivalent to the interpolation (curve-fitting) and subsequent differentiation of the resulting function.

Other methods in numerical differentiation include the five-point stencil, which gives a better approximation for the second derivative of a function $f(x)$ in one dimension:

$$f'' \approx \frac{-f(x+2h) + 16f(x+h) - 30f(x) + 16f(x-h) - f(x-2h)}{12h^2}$$

Further, statistical methods include noise reduction techniques. Various digital filters (e.g., such as Savitzky-Golay Filter) may be applied for smoothing the data.

An alternative to interpolation is to employ an alternate mathematical function, the z-transform. The z-transform converts a discrete-time signal, which is a sequence of real or complex numbers, into a complex frequency-domain representation. It can be considered as a discrete-time equivalent of the Laplace transform. See, en.wikipedia.org/wiki/Z-transform.

A linear system can be represented in the complex frequency domain (s-domain, where $s=\sigma+j\omega$) using the Laplace Transform $X(s)$, where the direct transform is:

$$L\{x(t)\} = X(s) = \int_{t=0}^{\infty} x(t)\varepsilon^{-st} dt$$

and $x(t)$ is assumed zero for $t \leq 0$.

The Inversion integral is a contour integral in the complex plane:

$$L^{-1}\{X(s)\} = x(t) = \frac{1}{2\pi j} \int_{s-\sigma-j\infty}^{\sigma+j\infty} X(s)\varepsilon^{st} ds$$

where $\sigma$ is chosen such that the contour integral converges.

If we assume that x(t) is ideally sampled, where: $x_n = x(n*T_s) = x(t)|_{t=n*T_s}$, and $y_n = y(n*T_s) = y(t)|_{t=n*T_s}$, this equivalent system may be analyzed using standard analog tools to establish the z-Transform. Substituting the Sampled version of x(t) into the definition of the Laplace Transform we get $L\{x(t,T_s)\} = X_T(s) = \int_{t=0}^{\infty} x(t,T_s)\varepsilon^{-st} dt$ But, $$x(t, T_s) = \sum_{n=0}^{\infty} x(t) * p(t - n * T_s)$$

(For $x(t)=0$ when $t<0$). Therefore:

$$X_T(s) = \int_{t=0}^{\infty} \left[ \sum_{n=0}^{\infty} x(n * T_s) * \delta(t - n^* T_s) \right] \varepsilon^{-st} dt$$

Now interchanging the order of integration and summation and using the sifting property of $\delta$-functions:

$$X_T(s) = \sum_{n=0}^{\infty} x(n * T_s) \int_{t=0}^{\infty} \delta(t - n * T_s)\varepsilon^{-st} dt$$

$$X_T(s) = \sum_{n=0}^{\infty} x(n * T_s)\varepsilon^{-nT_s s}$$

(We are assuming that the first sample occurs at $t=0+$) if we now adjust our nomenclature by letting: $z = \varepsilon^{sT}$, $x(n*Ts) = x_n$, and $$X(z) = X_T(s)|_{z=\varepsilon^{sT}}$$

$$X(z) = \sum_{n=0}^{\infty} x_n z^{-n},$$

which is the direct z-transform (one-sided; it assumes $x_n = 0$ for $n<0$).

The inversion integral is:

$$x_n = \frac{1}{2\pi j}\oint_c X(z)z^{n-1}dz$$

(This is a contour integral in the complex z-plane; The use of this integral can be avoided as tables can be used to invert the transform.)

To prove that these form a transform pair, we can substitute one into the other.

$$x_k = \frac{1}{2\pi j}\oint_c \left[\sum_{n=0}^{\infty} x_n z^{-n}\right] z^{k-1} dz$$

Now interchanging the order of summation and integration (valid if the contour followed stays in the region of convergence):

$$x_k = \frac{1}{2\pi j}\sum_{n=0}^{\infty} x_n \oint_c z^{k-n-1} dz$$

If "C" encloses the origin (that's where the pole is), the Cauchy Integral theorem says:

$$\oint_c z^{k-n-1} dz = \begin{smallmatrix} 0 \text{ for } n\neq k \\ 2\pi j \text{ for } n=k \end{smallmatrix},$$

and we get $x_k = x_k$ Q.E.D.

The Z transform provides a frequency domain version of a discrete-time signal. Discrete-time signals are sequences, and the Z transform is defined by $$\{h_k\} \xleftrightarrow{Z\ transform} H(z) = \sum_{-\infty}^{\infty} h_k z^{-k}. \tag{1}$$

Consider, for example, the elementary Z transform pair $$h_k = a^k u_k \xleftrightarrow{Z} H(z) = \frac{1}{1-az^{-1}}, \tag{2}$$

where $u_k$ is the unit step-function. The time-domain sequence $h_k$ and the frequency function $H(z)$ are alternate ways of describing the same signal. In the time domain, $h_k$ is exponential. In the frequency domain, $H(z)$ is rational or, by definition, the ratio of two polynomials. For discrete-time applications, we will use the representation $$H(z) = z^{\nu}\frac{B(z)}{A(z)}, \tag{3}$$

where $B(z) = b_0 + b_1 z^{-1} + \ldots + b_m z^{-m}$, $A(z) = 1 + a_1 z^{-1} + a_2 z^{-2} + \ldots + a_n z^{-n}$, and $\nu$ is an integer. The representation is unique if we demand that the end coefficients $b_0$, $b_m$, and $a_n$ are not zero.

The poles of $H(z)$ are the roots of the denominator polynomial $A(z)$. At a pole, $H(z)$ becomes infinite. The zeros of $H(z)$ are the roots of the numerator polynomial $B(z)$. At a zero, $H(z)$ is zero. A pole-zero plot of $H(z)$ simply places the poles (using the symbol x) and the zeros (using the symbol o) on the complex plane. For stability, it is necessary that the poles of $H(z)$ be inside the unit disk, or in other words, have an absolute value less than one. The complex frequency response is computed by evaluating $H(z)$ on the unit circle $z=e^{j\theta}$, $0 \leq \theta < 2\pi$.

The choice of the letter 'h' for the above signal is commonly used for filters. In the time domain, $h_k$ is the unit pulse response sequence of the filter. In the frequency domain, $H(z)$ is the transfer function of the filter. If we set $z=e^{j\theta}$, then we get the complex frequency response function $H(e^{j\theta})$. In fact, with $z=e^{j\theta}$ the Z transform becomes the DTFT, or Discrete Time Fourier Transform:

$$\{h_k\} \xleftrightarrow{DTFT} H(e^{j\theta}) = \sum_{-\infty}^{\infty} h_k e^{-jk\theta}. \tag{4}$$

This transform has the inversion rule $$h_k = \int_{-\pi}^{\pi} H(e^{j\theta}) e^{jk\theta} \frac{d\theta}{2\pi}. \tag{5}$$

Laplace transforms use the s plane, and frequency response is computed on the imaginary axis $s=j\omega$. The Z transform uses the z plane, and the frequency response is computed on the unit circle $z=e^{j\theta}$. The Laplace transform is appropriate for continuous-time systems, while the Z transform is appropriate for discrete-time systems.

Suppose that we start with continuous-time signals, and sample them to get discrete-time signals. Let the sampling frequency be $f_s$, and the sampling period be $t_s = 1/f_s = 2\pi/\omega_s$. Consider a signal $x(t)$ with Laplace transform $$X(s) = \int_{-\infty}^{\infty} x(t) e^{-st} dt, \tag{6}$$

and let $y_k = x(kt_s)$ be the discrete-time signal obtained by sampling $x(t)$. The Z Transform of the sequence of samples is $$Y(z) = \sum_{k=-\infty}^{\infty} y_k z^{-k}. \tag{7}$$

This sum approximates the integral in equation (6), if we set $$z = e^{st_s}. \tag{8}$$

This relation maps the s plane into the z plane. Using equation (8) in equation (7), we get $$t_s Y(e^{st_s}) = t_s \sum_{k=-\infty}^{\infty} y_k z^{-k} = \sum_{k=-\infty}^{\infty} x(kt_s) e^{-skt_s} t_s \approx \int_{-\infty}^{\infty} x(t) e^{-st} dt = X(s). \tag{9}$$

Therefore, the Z transform of y can approximate the Laplace Transform of x, and the DTFT of y can approximate the Fourier Transform of x, as in the following table:

TABLE 1

| Laplace Transform/ Z Transform | $X(s) \approx t_s Y(z)$ | provided $z = e^{st_s}$, and $|\text{imag}(s)| < \omega_s/2$ |
| --- | --- | --- |
| Fourier Transform/ DTFT | $X(j\omega) \approx t_s Y(e^{j\theta})$ | provided $\theta = \omega t_s = 2\pi\omega/\omega_s$, and $|\omega| < \omega_s/2$, or $|\theta| < \pi$ |

The approximation has its limits because going around the unit circle is a periodic motion. The DTFT $Y(e^{j\theta})$ is $2\pi$ periodic in $\theta = \omega t_s = 2\pi\omega/\omega_s$ and the approximation to $X(j\omega)$ is therefore periodic with period $\omega_s$. Because of symmetry about zero, this means that the approximation is good only to the half sampling frequency $\omega_s/2$, i.e., the Nyquist rate. In digital signal processing, bandwidth is limited. For greater bandwidth, one must sample faster.

There is a precise formula which relates $Y(e^{j\theta})$ and $X(j\omega)$, when $y_k = x(kt_s)$, as opposed to the approximation that we have already mentioned. Whenever one samples in the time domain, then there will be aliasing in the frequency domain. The formula is this:

$$y_k = x(kt_s) \stackrel{DTFT}{\longleftrightarrow} Y(e^{j\omega t_s}) = \frac{1}{t_s} \sum_{n=-\infty}^{\infty} X(j\omega - jn\omega_s) \quad (10)$$

(sampling in time) ⟷ (aliasing in frequency).

When $X(j\omega)$ is bandlimited to $|\omega| < \omega_s/2$, the formula $X(j\omega) = t_s \cdot Y(e^{j\omega \cdot t_s})$ will hold exactly for $|\omega| < \omega_s/2$. (This is the sampling theorem.)

If B(z) has degree equal to that of A(z), and if A(z) does not have repeated roots, then the Z transform pair for $H(z) = B(z)/A(z)$ is $$h_k = b_0 \delta_k + \left[ \sum_{m=1}^{n} \gamma_m \alpha_m^{k-1} \right] u_{k-1} \stackrel{Z}{\longleftrightarrow} H(z) = \quad (11)$$

$$b_0 + \sum_{m=1}^{n} \frac{\gamma_m}{z - \alpha_m} = b_0 + z^{-1} \sum_{m=1}^{n} \frac{\gamma_m}{1 - \alpha_m z^{-1}}.$$

The right-hand side of the above is a partial fraction expansion, of H(z). Under the conditions specified, the parameters $b_0, \gamma_1, \gamma_2, \ldots, \gamma_m, \alpha_1, \alpha_2, \ldots, \alpha_m$ can be computed.

Therefore, it is apparent that typical z-transform calculations assume periodic sampling, and the generally published analyses do not address aperiodic sampling. Further, one cannot simply interpolate the sampled signal to reduce the sampling imprecision below an error threshold, since the frequency characteristics of the function will be altered by the synthetic sampling, depending on the interpolation method. If one presumes that the sampling occurs well above the Nyquist rate, then perhaps the sampling time jitter may be ignored with small loss of accuracy, but if the underlying signal is not fully bandlimited, a simple interpolation, smoothing, or the like, is both theoretically and practically improper.

For the discrete variable case, the z-Transform of x[n] is given by $$X(z) = \sum_{n=-\infty}^{\infty} x[n] z^{-n}$$

On differentiating both sides with respect to z, and then multiplying both sides by −z, we get $$-z \frac{d}{dz} X(z) = \sum_{n=-\infty}^{\infty} (nx[n]) z^{-n},$$

provided it exists. This can be thought of as taking the z-Transform of nx[n]. Hence, we observe that if $$x[n] \stackrel{z}{\leftrightarrow} X(z)$$

with ROC as 'R', then $$nx[n] \stackrel{z}{\leftrightarrow} -z \frac{d}{dz} X(z)$$

with ROC as 'R'.

Similarly, we can proceed further by differentiating again and again.

If $$x[n] \stackrel{z}{\leftrightarrow} X(z)$$

with ROC=R, then, because of $$x[n - n_0] \stackrel{z}{\leftrightarrow} z^{-n_0} X(z)$$

with ROC=R except for the possible addition or deletion of the origin or infinity the multiplication by $z^{-n_0}$ for $n_0 > 0$ poles will be introduced at z=0, which may cancel corresponding zeroes of X(z) at z=0. In this case, the ROC for $z^{-n_0} X(z)$ equals the ROC of X(z) but with the origin deleted. Similarly, if $n_0 < 0$, z=∞ may get deleted.

It is noted that the fact that the more rigorous z-transform method does not provide a simple basis for the analysis of an aperiodically sampled discrete-time sample, the simpler method(s) inherently reflect this defect.

Differential Equations.

In a differential equation, the "order" refers to the order of the highest derivative. A linear ordinary differential equation (ODE) can be put into the following form:

$$f_n(x) \frac{d^n y}{dx^n} + f_{n-1}(x) \frac{d^{n-1} y}{dx^{n-1}} + \ldots + f_1(x) \frac{dy}{dx} + f_0(x) y = F(x)$$

A characteristic of linear systems is superposition, and therefore functions of orthogonal variables may be separated, i.e., a solution of an equation of form $f(y)dy + g(x)dx = 0$ is of form $\int f(y)dy + \int g(x)dx = C$ for example, $$q(x_i - x)dt = Vdx \Rightarrow \int \frac{dx}{x_i - x} - \int \frac{q}{V} dt = C \Rightarrow \ln(x - x_i) + \frac{q}{V} t = C$$

$$\Rightarrow x - x_i = Ke^{-\frac{q}{V}t} \Rightarrow \text{if } x(0) = x_0, K = x_0 - x_i \Rightarrow x = x_i + (x_0 - x_i)e^{-\frac{q}{V}t}$$

Homogeneous equations are of form:

$$\frac{dy}{dx} = f\left(\frac{y}{x}\right),$$

and may be solved as follows:
Let $$u = \frac{y}{x} \Rightarrow \frac{dy}{dx} = u + x\frac{du}{dx}$$

Substitute and separate u and x and then integrate:

$$\int \frac{dx}{x} = \int \frac{du}{f(u) - u} + C,$$

and substitute $u=y/x$ to obtain the general solution.

While the present technology typically addresses second-order differential responses, it is not so limited. $n^{th}$-order linear homogeneous equations with constant coefficients have the form:

$$A_n \frac{d^n y}{dx^n} + A_{n-1} \frac{d^{n-1} y}{dx^{n-1}} + \ldots + A_1 \frac{dy}{dx} + A_0 y = 0$$

$$A_n, A_{n-1}, \ldots, A_1, A_0$$

are constants. These may be solved by constructing an auxiliary equation: $A_n r^n + A_{n-1} r^{n-1} + \ldots + A_1 r + A_0 = 0$, and the auxiliary equation solved, e.g., for each distinct real root $(r_a)$: $y_a = C_a \exp(r_a x)$; for each set of repeat (m times) real roots $(r_b)$:

$$y_b = (C_{b1} + C_{b2}x + \ldots + C_{bm}x^{m-1})\exp(r_b x) = \left[\sum_{i=1}^{m-1} C_{bi} x^{i-1}\right] \exp(r_b x);$$

For each pair of Complex roots $(a \pm jb)$: $y_c = (C_c \sin bx + C'_c \cos bx)\exp(ax)$, with general solution: $y = \Sigma y_a + \Sigma y_b + \Sigma y_c$.

An $n^{th}$ order linear nonhomogeneous equation with constant coefficients has the form:

$$A_n \frac{d^n y}{dx^n} + A_{n-1} \frac{d^{n-1} y}{dx^{n-1}} + \ldots + A_1 \frac{dy}{dx} + A_0 y = f(x)$$

$$A_n, A_{n-1}, \ldots, A_1, A_0$$

are constants, and may be solved using known methods if the initial conditions are known.

The $n^{th}$ order linear nonhomogeneous equation may be transformed into the Laplace domain:

$$A_n\left[s^n Y(s) - \sum_{k=0}^{n-1} s^{n-1-k} Y^{(k)}(0)\right] + A_{n-1}\left[s^{n-1} Y(s) - \sum_{k=0}^{n-2} s^{n-2-k} Y^{(k)}(0)\right] + \ldots,$$

$$A_2[s^2 Y(s) - sY(0) - Y'(0)] + A_1[sY(s) - Y(0)] + A_0 Y(s) = F(s)$$

which may then be solved as an algebraic equation in the s-domain for Y(s), which may then be transformed back to the time domain to obtain the solution y(t).

$2^{nd}$ order linear equations may be expressed in the form: $y'' + p(x)y' + q(x)y = 0$ or $$\frac{d^2 y}{dx^2} + p(x)\frac{dy}{dx} + q(x)y = 0,$$

with linearly independent solutions $y_1 = y_1(x)$ and $y_2 = y_2(x)$. Then, $y(x) = c_1 y_1(x) + c_2 y_2(x)$ is the general solution in the sense that every solution can be obtained by choosing appropriate values for the arbitrary constants $c_1$ and $c_2$.

If the coefficients are constants, $$\text{i.e., } \frac{d^2 y}{dx^2} + p\frac{dy}{dx} + qy = 0$$

where p and q are constants, or $$a\frac{d^2 y}{dx^2} + b\frac{dy}{dx} + cy = 0$$

where a, b, and c are constants; replacing $$\frac{d^2 y}{dx^2}$$

with $m^2$, $$\frac{dy}{dx}$$

with $m^1$, and y with $m^0$ will result in $am^2 + bm + c = 0$, which is called the "auxiliary quadratic equation". The general solution of the $2^{nd}$-order linear differential equation depends on the roots of the auxiliary quadratic equation $am^2 + bm + c = 0$ such that if $b^2 - 4ac > 0$ (2 distinct real roots $m_1$ and $m_2$), then $y = c_1 e^{m_1 x} + c_2 e^{m_2 x}$. If $b^2 - 4ac = 0$ (1 real repeated root $m_1 = m_2 (= m)$), then $y = c_1 e^{mx} + c_2 x e^{mx}$. If $b^2 - 4ac < 0$ (2 complex roots $m_1 = \alpha + \beta i$ and $m_2 = \alpha - \beta i$), then $y = e^{\alpha x}(c_1 \cos \beta x + c_2 \sin \beta x)$. Considering $$\frac{d^2 y}{dx^2} + p\frac{dy}{dx} + qy = r(x),$$

where p and q are constants and r(x) is a continuous function, the general solution of $y'' + py' + qy = r(x)$ is $y(x) = c_1 y_1(x) + c_2 y_2(x) + y_p(x)$, where $c_1 y_1(x) + c_2 y_2(x)$ is the general solution of the homogeneous equation $y'' + py' + qy = 0$, and $y_p(x)$ is any solution of $y'' + py' + qy = r(x)$.

Thus, assuming that the homeostatic mechanisms have governing physics that correspond to differential equations, a rich body of analysis is available to determine the structure of the equation, and the parameters of the equations, such as by measurement of physical states. The techniques include continuous and discrete-time, analog and digital amplitude, and various transform domains of analysis.

Determination of System Parameters

The step response can be used to measure several key parameters for a physical system. First, any pure delays in the system time shift the output relative to the input. For first-order systems, the time constant can be calculated. For second-order systems, we can measure the damped natural frequency $\omega_d$ and damping ratio $\zeta$ as follows. First, measure the amplitude and time to peak of the first one or two consecutive cycles. The reduction from the initial cycle amplitude $X_o$ to the last cycle amplitude $X_n$ for the n cycles is measured.

The following relationship is associated with the logarithmic decrement for under-damped second-order systems:

$$\frac{\zeta}{\sqrt{1-\zeta^2}} = \frac{1}{2\pi n}\ln\left(\frac{X_o}{X_n}\right)$$

For small $\zeta$ this becomes $$\zeta = \frac{1}{2\pi n}\ln\left(\frac{X_o}{X_n}\right)$$

$\zeta$ may be solved by first estimating and/or trial and error. Divide the number of cycles, n, by the time taken to complete them ($t_n$-$t_o$). Convert the resulting frequency in Hz to radians/sec. This damped frequency, $\omega_d$, is related to the natural frequency, $\omega_n$, according to:

$$\omega_n = \frac{\omega_d}{\sqrt{1-\zeta^2}},$$

which becomes $\omega_n = \omega_d$ for lightly damped systems.

The frequency response of a linear system is the output response to sinusoidal inputs. The output response is at the same frequency as the input with differing magnitude and phase. The frequency response characteristics of linear systems may be understood using a Bode plot of magnitude ($M_{dB}$=20 $\log_{10}$ M) and phase (deg) versus log frequency. Typically, the gain is fairly constant up to the corner frequency $f_c$. Above the corner frequency, the amplitude rolls off with a slope of −20 dB/decade. The resonant peak at $f=f_n$ gets larger with smaller damping ratio. The gain is constant below the resonant frequency and rolls off with a slope of −40 dB/decade above the resonant frequency. The frequency response of a second-order system without stiffness and damping (pure inertia) has a gain, which rolls off with a constant −40 dB/dec, and the phase is constant at 180 deg. $\tau$, damping ratios $\zeta$, and undamped natural frequencies $\omega_n$ can be determined from experimental measurements.

Statistical Models

As stated above, discrete physiological data obtained by sampling the physiological parameter represents a time series. Models for time series data can have many forms and represent different stochastic processes. Three broad classes of modelling are the autoregressive (AR) models, the integrated (I) models, and the moving average (MA) models. These three classes depend linearly on previous data points. Combinations of these approaches produce autoregressive moving average (ARMA) and autoregressive integrated moving average (ARIMA) models. The autoregressive fractionally integrated moving average (ARFIMA) model generalizes the three models: AR, I, and MA. Extensions of these classes to deal with vector-valued data are known as multivariate time-series models, and sometimes the preceding acronyms are extended by including an initial "V" for "vector," as in VAR for vector autoregression. An additional set of extensions of these models is available for use where the observed time-series is driven by some "forcing" time-series (which may not have a causal effect on the observed series): the distinction from the multivariate case is that the forcing series may be deterministic or under the experimenter's control. For these models, the acronyms are extended with a final "X" for "exogenous."

Non-linear dependence of the level of a series on previous data points is of interest, partly because of the possibility of producing a chaotic time series. However, more importantly, empirical investigations can indicate the advantage of using predictions derived from non-linear models, over hose from linear models, as in nonlinear autoregressive exogenous models.

Among other types of non-linear time series models, there are models to represent the changes of variance over time (heteroskedasticity). These models represent autoregressive conditional heteroskedasticity (ARCH), and the collection comprises a wide variety of representation (GARCH, TARCH, EGARCH, FIGARCH, CGARCH, etc.). Here changes in variability are related to, or predicted by, recent past values of the observed series. This is in contrast to other possible representations of locally varying variability, where the variability might be modelled as being driven by a separate time-varying process, as in a doubly stochastic model.

In recent work on model-free analyses, wavelet-transform-based methods (for example, locally stationary wavelets and wavelet decomposed neural networks) have gained favor. Multiscale (often referred to as multiresolution) techniques decompose a given time series, attempting to illustrate time dependence at multiple scales. Markov switching multifractal (MSMF) techniques are used for modelling volatility evolution.

A Hidden Markov model (HMM) is a statistical Markov model in which the system being modelled is assumed to be a Markov process with unobserved (hidden) states. An HMM can be considered as the simplest dynamic Bayesian network.

Tools for investigating time-series data include: consideration of the autocorrelation function and the spectral density function (also cross-correlation functions and cross-spectral density functions); scaled cross- and auto-correlation functions to remove contributions of slow components; performing a Fourier transform to investigate the series in the frequency domain; use of a filter to remove unwanted noise; Principal Component Analysis (PCI), Independent Component Analysis (ICA), or empirical orthogonal function analysis, singular spectrum analysis; "structural" models: General State Space Models, Unobserved Components Models; Machine Learning: Artificial neural networks, Support vector machine, Fuzzy logic, Gaussian process, Hidden Markov model; Queueing theory analysis; Control chart, Shewhart individuals control chart, CUSUM chart, EWMA chart; Detrended fluctuation analysis; Dynamic time warping; Cross-correlation; Dynamic Bayesian network; Time-frequency analysis techniques: Fast Fourier transform, Continuous wavelet transform, Short-time Fourier transform, Chirplet transform, Fractional Fourier transform; Chaotic analysis: Correlation dimension, Recurrence plots, Recurrence quantification analysis, Lyapunov exponents, Entropy encoding. See en.wikipedia.org/wiki/Time_series #Models.

Nyquist Stability Criterion

The Nyquist stability criterion is useful because it allows us to gain insight into the stability of a closed-loop plant based on properties of an open-loop plant. Consider a simple closed-loop feedback system with forward gain G(s) and feedback gain of 1, u is a reference command, y is the output. It may be readily shown that the closed-loop transfer function H(s) may be expressed $$\frac{y}{u} = H(s) = \frac{G(s)}{1 + G(s)}.$$

It is convenient to break G(s) into a numerator and denominator $$G(s) = \frac{n(s)}{d(s)}$$

whereupon H(s) may be expressed $$H(s) = \frac{n(s)}{n(s) + d(s)}.$$

It is also readily shown that $$1 + G(s) = \frac{d(s) + n(s)}{d(s)}.$$

Let us define $N_{cwe}$ as the number of clockwise (CW) encirclements of the origin by the Nyquist contour of 1+G(s). $N_{cwe} = N_z - N_p$. Since we are dealing with 1+G(s), the number of zeros encircled will be the number of zeros of n(s)+d (s) in the right half-plane, or in other words, the number of zeros is the number of unstable closed-loop poles, which we will denote $N_{uclp}$. Thus $N_z = N_{uclp}$. The number of poles circled by the Nyquist contour is the number of zeros of d(s) enclosed by the Nyquist contour, but these are the unstable poles of the open-loop transfer function. Thus $N_p = N_{uolp}$, where $N_{uolp}$ denotes the number of unstable open-loop poles. The number of unstable closed-loop poles may be expressed $N_{uclp} = N_{cwe} + N_{uolp}$. Since $N_{cwe}$ is the number of clockwise encirclements of the origin by the Nyquist evaluation of 1+G (s), and 1+G(s) is just G(s) shifted by 1, $N_{cwe}$ is also equal to the number of clockwise encirclements of −1 by the Nyquist evaluation of G(s). This leads to the Nyquist Immittance Criterion: The number of unstable closed-loop poles is equal to the number of unstable open-loop poles plus the number of clockwise encirclements of −1 by the contour evaluation of G(s) over the Nyquist contour.

Thus, suppose we have knowledge of the open-loop transfer function G(s), and we know the number of unstable open-loop poles $N_{uolp}$. Then, we can perform a Nyquist evaluation of G(s) and count the number of clockwise encirclements. Thus, we may use Nyquist theory to predict the stability of the closed-loop system based on properties of the open-loop plant G(s). The path for the Nyquist contour starts at $s=-j\omega_{max}$, proceeds upward along the $j\omega_{max}$ axis through s=0 until $s=j\omega_{max}$ and then proceed in a circular arc of radius $|s|=\omega_{max}$ through $s=\omega_{max}$, and then back to $s=-j\omega_{max}$. This path is denoted $P_N$. By allowing $\omega_{max} \to \infty$, this path encompasses the entire right half plane. The Nyquist Immittance Criterion provides at a source-load system is stable provided that the Nyquist evaluation of $Z_s Y_l$ does not encircle −1, where $Z_s$ is the source impedance, and $Y_l$ is the load admittance. As a test for stability, the Nyquist Immittance Criterion can be directly applied. Various stability criteria all have interpretations in the s-plane, and in each case, each Stability Criterion forms a boundary in the s-plane; if the Nyquist evaluation of $Z_s Y_l$ does not cross this boundary, then −1 cannot be encircled and therefore the system must be stable. The Middlebrook Criterion consists of a circle of radius 1/GM in the s-plane where GM denotes the gain margin. If the Nyquist plot of $Z_s Y_l$ is always within the circle, then encirclements of the −1 point cannot occur, provided the gain margin is greater than 1. For a given $Z_s$, the range of allowable $Y_l$ is readily established; in particular $$|Y_l| < \frac{1}{|Z_z|GM}.$$

For a frequency s=jω, it is convenient to denote the real and imaginary part of N(jω) as $N_r$ and $N_i$, respectively, whereupon it can be shown that the upper half of the Nyquist contour may be expressed as $$|N_i| = |rC - L/R| \left( \frac{-N_r - r/R}{LC} \right)^{1/2}.$$

It is also convenient to designate an arbitrary stability criterion by a parameterized curve in the s-plane given by $M_r(x)+jM_i(x)$ where x is an independent variable. It is apparent that the slope $d|N_i|/d(-N_r) \to 0$ as $-N_r \to \infty$ for all values of parameter r, C, L, and R. As a result, the Nyquist contour will violate any stability criterion which has a non-zero slope $d|M_i|/d(-M_r)$ as $-M_r \infty$.

Various types of devices to measure physiological parameters are known, especially wearable and implantable devices. See: U.S. Pat. Nos. and US Pub. App. Nos. 6453195; 6595929; 6675049; 6817979; 7020508; 7044911; 7108659; 7167743; 7261690; 7273457; 7285090; 7291114; 7313440; 7330760; 7366572; 7395113; 7407484; 7447545; 7463142; 7491181; 7542803; 7561919; 7577475; 7590453; 7590455; 7598878; 7610094; 7616991; 7623919; 7630755; 7641619; 7695512; 7697994; 7717848; 7761261; 7765012; 7775993; 7782192; 7787946; 7792583; 7801591; 7805196; 7819909; 7825794; 7848819; 7881798; 7885712; 7904149; 7908000; 7908013; 7953488; 7959567; 7970470; 7978062; 8005539; 8010189; 8021299; 8032224; 8033999; 8038613; 8055330; 8055334; 8055348; 8078278; 8086250; 8086302; 8114021; 8115618; 8121691; 8121694; 8135473; 8137269; 8140161; 8152710; 8157731; 8160695; 8160702; 8165691; 8165893; 8172459; 8174378; 8174395; 8180446; 8180447; 8185181; 8190253; 8204590; 8204597; 8214045; 8217946; 8233976; 8246563; 8249708; 8251061; 8251903; 8260412; 8260422; 8265723; 8265771; 8270938; 8271072; 8273032; 8287520; 8290596; 8295933; 8301219; 8306610; 8308661; 8310336; 8321003; 8328420; 8332038; 8335568; 8337431; 8355783; 8359095; 8373556; 8376943; 8395498; 8396554;

8398546; 8406893; 8410940; 8412352; 8417311; 8419650; 8428744; 8435186; 8435738; 8436810; 8438038; 8447265; 8447401; 8447403; 8447404; 8452366; 8452394; 8457727; 8460189; 8475739; 8485979; 8493187; 8509893; 8512242; 8515547; 8515559; 8521292; 8527045; 8527064; 8532779; 8540632; 8545436; 8547248; 8554325; 8554331; 8565886; 8571881; 8583227; 8587427; 8606355; 8611996; 8615299; 8615377; 8615405; 8620591; 8620617; 8620679; 8630706; 8632463; 8641612; 8655441; 8663106; 8666488; 8674825; 8676170; 8679014; 8688210; 8688221; 8694282; 8698638; 8706232; 8706233; 8706237; 8708904; 8712529; 8712530; 8715269; 8718193; 8725244; 8725253; 8730031; 8738323; 8742623; 8744587; 8744803; 8744804; 8751194; 8755871; 8758242; 8761852; 8762101; 8762102; 8766789; 8766805; 8768648; 8774918; 8775120; 8781791; 8788028; 8792982; 8792991; 8793101; 8805508; 8805518; 8805646; 8812259; 8812260; 8818505; 8818522; 8818753; 8821350; 8827906; 8834020; 8838235; 8840838; 8847766; 8849610; 8849682; 8852095; 8852098; 8858432; 8870736; 8870742; 8870766; 8879983; 8880155; 8882666; 8884809; 8892401; 8907782; 8920332; 8923970; 8923976; 8929963; 8932221; 8935119; 8935123; 8938368; 8942953; 8945017; 8945328; 8948832; 8948839; 8954149; 8954290; 8954291; 8956287; 8956288; 8956303; 8957777; 8958870; 8961412; 8961414; 8965730; 8965824; 8968196; 8970392; 8971936; 8979757; 8979763; 8989858; 8989861; 8990924; 8998815; 9000973; 9005129; 9014790; 9014802; 9019106; 9020591; 9020592; 9020597; 9026190; 9026201; 9026206; 9031669; 9031812; 9033875; 9033876; 9033920; 9039614; 9042971; 9044149; 9044150; 9044171; 9044180; 9049998; 9050041; 9060746; 9061147; 9064342; 9066209; 9072447; 9072870; 9077030; 9079045; 9079060; 9081534; 9083589; 9101334; 9103899; 9108098; 9113794; 9113795; 9119554; 9128015; 9138181; 9138523; 9138537; 9142117; 9148483; 9149577; 9151834; 9155885; 9164167; 9165117; 9168001; 9168374; 9168419; 9171201; 9174058; 9185489; 9186509; 9192329; 9198604; 9204806; 9205264; 9215290; 9218454; 9220461; 9226663; 9227128; 9233245; 9237855; 9237858; 9241635; 9247911; 9250229; 9254092; 9259180; 9265871; 9268915; 9269251; 9270025; 9277534; 9282894; 9282902; 9288298; 9288614; 9289123; 9289607; 9289613; 9295403; 9302045; 9307917; 9310909; 9317729; 9320677; 9320842; 9323894; 9326708; 9326711; 9332919; 9333350; 9339201; 9339203; 9344546; 9345879; 9345892; 9348974; 9352156; 9358374; 9369365; 9370320; 9370326; 9374279; 9375145; 9386924; 9390427; 9393384; 9398856; 9402545; 9402552; 9410979; 9415125; 9418390; 9420083; 9420956; 9427165; 9427581; 9431694; 9433371; 9433783; 9439567; 9439599; 9444503; 9445767; 9446235; 9454644; 9456755; 9456787; 9462979; 9463325; 9480424; 9486128; 9492084; 9492657; 9498137; 9498624; 9504408; 9504425; 9506802; 9510788; 9520638; 9521868; 9521962; 9522317; 9526433; 9526859; 9529972; 9532722; 9533157; 9538921; 9538922; 9543636; 9554705; 9554719; 9559353; 9561367; 9568492; 9572499; 9572533; 9572992; 9578903; 9579020; 9579048; 9579060; 9579516; 9583256; 9585566; 9585606; 9592328; 9592379; 9592508; 9595996; 9596997; 9597014; 9597023; 9597505; 9599632; 9600676; 9603569; 9613184; 9614337; 9615215; 9615794; 9616225; 9622691; 9623238; 9623248; 9632102; 9633170; 9639170; 9641239; 9641469; 9645143; 9646481; 9651533; 9655519; 9655548; 9658066; 9659484; 9662053; 9664556; 9664702; 9669262; 9672393; 9672715; 9672754; 9680831; 9681814; 9681842; 9685802; 9687658; 9692230; 9692844; 9693696; 9696199; 9700222; 9700223; 9706957; 9707466; 9712629; 9713445; 9713701; 9719990; 9723986; 9724509; 9724510; 9724511; 9724517; 9724521; 9724562; 9730025; 9730601; 9730619; 9730625; 9734304; 9736603; 9747431; 9749232; 9750977; 9752925; 9755704; 9756169; 9757040; 9763616; 9766959; 9769564; 9770185; 9775987; 9776042; 9778280; 9782084; 9782132; 9788785; 9789252; 9789309; 9789315; 9795323; 9795782; 9801547; 9808198; 9808204; 9810704; 9814388; 9814400; 9814886; 9817440; 9820698; 9826903; 9826940; 9830781; 9833254; 9847012; 9848789; 9854986; 9855433; 9861286; 9864842; 9868332; 9869973; 9872968; 9876537; 9877650; 9882610; 9883800; 9885698; 9888848; 9889305; 9894691; 9895063; 9900287; 9901269; 9901305; 9901741; 9905105; 9913591; 9913617; 9913619; 9921726; 9931040; 9936916; 9936919; 9943269; 9943461; 9943719; 9950236; 9952095; 9952240; 9953041; 9955919; 9956393; 9956470; 9965059; 9968788; 9974484; 9977578; 9985825; 9986771; 9987489; 9987497; 9991920; 9993207; 9998804; 9999355; RE44408; RE45766; 10003862; 10004406; 10004949; 10007758; 10008090; 10010278; 10010753; 10012664; 10016613; 10018643; 10021733; 10022061; 10022062; 10028037; 10028659; 10028660; 10029172; 10032002; 10034625; 10039928; 10043354; 10045117; 10045439; 10052486; 10054909; 10055550; 10058274; 10060788; 10064562; 10070805; 10071285; 10076282; 10076462; 10080499; 10080527; 10080530; 10085643; 10088356; 10092193; 10092203; 10092355; 10092692; 10095649; 10095837; 10098546; 10098548; 10098558; 10098810; 10099053; 10104026; 10105080; 10105100; 10105487; 10105547; 10108785; 10109175; 10117600; 10117606; 10118035; 10118041; 10119715; 10122421; 10124179; 10126283; 10126998; 10130305; 10130550; 10132677; 10135076; 10136817; 10136819; 10137230; 10140842; 10141073; 10143395; 10143840; 10143847; 10149616; 10152957; 10153537; 10154129; 10154922; 10155110; 10159415; 10163314; 10165977; 10166164; 10166333; 10172523; 10176412; 10178973; 10179064; 10179246; 10182336; 10182729; 10188296; 10188299; 10194418; 10194702; 10194808; 10194809; 10194816; 10194836; 10201283; 10201295; 10201702; 10207041; 10209365; 10210741; 10213113; 10213150; 10215619; 10218433; 10219746; 10219754; 10223459; 10226187; 10226188; 10226217; 10226396; 10227063; 10230699; 10231666; 10231784; 10234330; 10248302; 10251571; 10251595; 10252140; 10255994; 10258092; 10258288; 10258828; 10264971; 10269452; 10271587; 10271792; 10272242; 10278624; 10278624; 10279152; 10279200; 10279201; 10284537; 10289806; 10292611; 10292631; 10293158; 10293208; 10299693; 10299725; 10299734; 10299736; 10300283; 10302469; 10305692; 10307101; 10307111; 10311696; 10311706; 10314488; 10314546; 10314547; 10325681; 10327674; 10327689; 10327984; 10328228; 10328266; 20020019586; 20020133196; 20020177782; 20020183646; 20030004403; 20030018369; 20030107487; 20030220579; 20040002634; 20040034289; 20040039254; 20040078067; 20040133081; 20040147818; 20040152956; 20040152957; 20040158194; 20040176822; 20040186390; 20050060030; 20050061323; 20050065572; 20050075213; 20050076909; 20050080322; 20050101845; 20050115561; 20050116820; 20050136385; 20050142070; 20050148828; 20050165456; 20050182389; 20050209511; 20050209512; 20050209513; 20050209643; 20050209644; 20050209645; 20050215847; 20050215947; 20050216064; 20050222522; 20050222643; 20050234514; 20050234518; 20050245988; 20060020297; 20060030890; 20060064030; 20060085040; 20060122474; 20060122864; 20060149324; 20060149330; 20060149331; 20060224051; 20060235472; 20060253005; 20060224730; 20060265024; 20060265025; 20060287677; 20060293571; 20070015976; 20070021979; 20070060800; 20070088521; 20070100666; 20070106138; 20070106172; 20070123758; 20070162090; 20070173705; 20070239054;

20070239230; 20070249968; 20070250121; 20070250134; 20070255118; 20070260491; 20070265508; 20070276439; 20070293737; 20080015421; 20080051667; 20080071150; 20080071324; 20080071326; 20080071327; 20080077440; 20080091092; 20080103534; 20080129486; 20080131362; 20080132981; 20080132982; 20080140161; 20080140162; 20080140163; 20080161654; 20080161655; 20080167535; 20080167536; 20080167537; 20080167538; 20080167539; 20080167700; 20080171919; 20080171920; 20080171921; 20080171922; 20080172102; 20080177355; 20080195249; 20080214903; 20080249806; 20080250340; 20080250341; 20080275309; 20080275349; 20080287751; 20080287817; 20080294020; 20080294024; 20080300449; 20080300470; 20080300649; 20080300650; 20080300651; 20080306357; 20080312511; 20090030263; 20090036951; 20090040041; 20090058635; 20090058636; 20090062887; 20090063193; 20090076343; 20090076346; 20090082640; 20090082641; 20090083070; 20090099627; 20090105605; 20090105785; 20090112071; 20090113295; 20090118599; 20090128487; 20090131739; 20090138207; 20090149797; 20090149798; 20090149799; 20090149895; 20090149896; 20090149897; 20090149914; 20090156309; 20090171163; 20090177068; 20090192556; 20090222065; 20090228078; 20090234916; 20090259216; 20090264789; 20090264955; 20090264956; 20090264957; 20090264967; 20090270942; 20090276002; 20090276004; 20090281594; 20090292180; 20090299428; 20090306740; 20090312622; 20090326346; 20090326350; 20090326356; 20100016918; 20100022856; 20100022861; 20100030043; 20100030088; 20100030090; 20100030286; 20100030289; 20100030293; 20100036211; 20100041975; 20100049010; 20100058462; 20100069841; 20100106212; 20100114195; 20100114196; 20100114197; 20100114198; 20100114199; 20100114200; 20100114201; 20100114202; 20100114203; 20100114204; 20100114208; 20100114209; 20100114216; 20100114217; 20100114221; 20100114224; 20100114237; 20100114241; 20100114244; 20100121170; 20100121215; 20100121413; 20100152815; 20100160014; 20100160800; 20100160804; 20100168607; 20100174155; 20100174180; 20100185064; 20100185225; 20100194631; 20100198034; 20100198279; 20100198280; 20100198284; 20100198291; 20100198308; 20100210924; 20100222845; 20100222846; 20100228314; 20100238019; 20100245077; 20100249540; 20100268040; 20100273738; 20100274100; 20100274106; 20100280330; 20100280334; 20100280335; 20100280336; 20100280574; 20100280579; 20100305665; 20100308974; 20100311388; 20110003664; 20110022123; 20110040197; 20110040546; 20110040547; 20110046697; 20110054270; 20110061647; 20110076984; 20110077706; 20110082377; 20110093040; 20110093046; 20110105860; 20110105873; 20110105921; 20110106200; 20110112442; 20110118805; 20110130092; 20110144463; 20110144967; 20110152632; 20110160623; 20110160796; 20110172504; 20110172545; 20110179637; 20110183305; 20110184482; 20110184483; 20110190570; 20110190580; 20110190581; 20110190595; 20110190654; 20110208012; 20110208015; 20110237916; 20110245633; 20110264034; 20110273287; 20110295335; 20110295336; 20110301441; 20110301662; 20110307027; 20110307028; 20120001751; 20120001920; 20120003933; 20120010543; 20120022340; 20120029586; 20120059389; 20120083650; 20120094649; 20120095306; 20120108998; 20120109237; 20120116475; 20120123232; 20120130286; 20120130444; 20120132211; 20120136261; 20120136413; 20120149996; 20120150258; 20120172652; 20120197336; 20120197337; 20120197338; 20120197349; 20120197350; 20120203118; 20120220986; 20120245439; 20120249324; 20120265026; 20120265031; 20120273354; 20120277546; 20120283577; 20120283578; 20120296184; 20120321759; 20120330112; 20130006076; 20130018239; 20130018668; 20130030259; 20130035575; 20130035740; 20130035865; 20130035871; 20130053657; 20130053913; 20130060098; 20130072998; 20130074614; 20130078149; 20130078624; 20130078625; 20130078733; 20130079236; 20130079599; 20130079646; 20130079840; 20130082837; 20130085401; 20130085679; 20130102859; 20130104288; 20130109997; 20130124039; 20130135108; 20130147622; 20130154838; 20130154851; 20130158372; 20130165819; 20130172759; 20130191513; 20130217979; 20130218070; 20130218232; 20130225968; 20130229287; 20130245480; 20130253334; 20130253351; 20130253380; 20130274584; 20130274705; 20130289446; 20130289659; 20130289664; 20130294969; 20130296669; 20130296670; 20130297330; 20130297344; 20130303843; 20130310706; 20130310896; 20130317753; 20130325394; 20130325396; 20130325404; 20130331660; 20130331919; 20130333054; 20130338448; 20140012105; 20140031787; 20140035761; 20140036643; 20140039804; 20140039839; 20140039840; 20140039841; 20140039842; 20140043149; 20140046391; 20140049377; 20140051962; 20140052790; 20140056757; 20140062718; 20140066844; 20140067423; 20140073043; 20140073969; 20140077956; 20140081100; 20140081665; 20140081667; 20140088664; 20140088922; 20140089399; 20140089514; 20140095420; 20140100432; 20140107433; 20140107509; 20140107511; 20140107513; 20140107567; 20140135594; 20140135631; 20140139405; 20140142403; 20140142549; 20140145915; 20140156043; 20140156228; 20140163432; 20140163483; 20140163647; 20140163927; 20140164320; 20140164611; 20140170735; 20140171749; 20140172310; 20140172362; 20140176475; 20140180020; 20140180021; 20140180022; 20140180023; 20140180137; 20140180358; 20140186238; 20140188516; 20140191866; 20140191867; 20140194701; 20140200421; 20140203797; 20140206955; 20140206959; 20140206976; 20140213855; 20140213856; 20140213857; 20140213926; 20140213941; 20140221769; 20140221770; 20140221774; 20140221784; 20140221785; 20140221787; 20140221788; 20140221789; 20140221790; 20140221791; 20140221855; 20140222101; 20140222106; 20140222174; 20140223406; 20140223407; 20140223421; 20140228649; 20140228911; 20140232516; 20140234949; 20140236493; 20140236538; 20140237028; 20140240122; 20140245161; 20140249594; 20140249600; 20140249605; 20140249774; 20140257055; 20140257058; 20140257540; 20140258220; 20140266939; 20140273858; 20140275812; 20140275813; 20140275850; 20140275852; 20140275854; 20140276119; 20140276130; 20140276192; 20140277250; 20140278220; 20140278229; 20140288390; 20140288391; 20140288392; 20140288435; 20140288436; 20140288438; 20140296089; 20140296658; 20140297217; 20140297218; 20140305204; 20140306807; 20140307878; 20140308661; 20140309505; 20140316191; 20140316192; 20140316305; 20140318699; 20140320284; 20140324118; 20140330094; 20140336980; 20140337450; 20140337451; 20140340221; 20140342328; 20140343370; 20140343892; 20140350636; 20140358012; 20140358024; 20140361147; 20140364705; 20140371556; 20140374276; 20140378787; 20150005650; 20150005652; 20150005911; 20150018660; 20150018702; 20150019135; 20150019257; 20150025393; 20150025394; 20150031964; 20150031970; 20150039040; 20150039053; 20150040282; 20150045634; 20150050888; 20150057718; 20150065786; 20150065826; 20150073723; 20150076909; 20150080746; 20150088457; 20150094552; 20150094914; 20150097701; 20150099943; 20150100270; 20150102923; 20150112151; 20150112170; 20150113417; 20150119728; 20150119951; 20150119952; 20150122018; 20150125945; 20150126822; 20150134107; 20150134345; 20150134346;

20150137997; 20150141769; 20150141873; 20150142074; 20150142082; 20150143601; 20150148637; 20150148697; 20150148868; 20150149096; 20150149217; 20150150453; 20150150505; 20150154364; 20150156749; 20150157256; 20150157269; 20150157512; 20150164321; 20150164322; 20150164349; 20150164376; 20150170504; 20150173628; 20150173631; 20150173674; 20150174406; 20150190053; 20150193612; 20150196256; 20150201853; 20150201854; 20150206408; 20150207915; 20150208943; 20150223700; 20150223708; 20150224310; 20150230722; 20150230735; 20150230761; 20150238097; 20150243967; 20150245797; 20150255858; 20150258261; 20150258415; 20150265150; 20150265164; 20150265195; 20150265207; 20150265214; 20150265217; 20150265903; 20150269009; 20150272511; 20150278453; 20150282711; 20150282713; 20150282767; 20150283365; 20150283386; 20150288772; 20150289797; 20150289798; 20150289799; 20150289800; 20150289808; 20150289809; 20150289810; 20150289811; 20150289812; 20150289820; 20150294574; 20150294575; 20150294576; 20150294583; 20150294594; 20150297103; 20150297134; 20150297904; 20150305682; 20150314166; 20150317515; 20150320588; 20150321084; 20150331997; 20150335385; 20150335507; 20150338428; 20150339946; 20150347689; 20150351695; 20150351698; 20150359429; 20150359489; 20150359490; 20150364018; 20150364938; 20150366746; 20150368717; 20150371516; 20150374289; 20160000385; 20160000640; 20160000642; 20160000984; 20160001034; 20160001071; 20160003823; 20160005299; 20160007925; 20160008632; 20160011215; 20160011225; 20160015280; 20160015972; 20160022193; 20160025760; 20160025763; 20160029905; 20160030741; 20160032361; 20160033544; 20160034696; 20160036118; 20160038037; 20160038038; 20160038042; 20160038043; 20160038055; 20160038744; 20160047787; 20160051169; 20160054343; 20160058286; 20160058331; 20160058375; 20160059010; 20160059064; 20160066803; 20160066844; 20160069919; 20160069920; 20160069921; 20160072690; 20160073884; 20160073914; 20160074278; 20160074600; 20160077015; 20160078061; 20160080166; 20160081574; 20160081622; 20160082187; 20160084863; 20160084869; 20160089028; 20160089575; 20160095550; 20160103123; 20160117951; 20160124009; 20160135516; 20160135695; 20160135696; 20160135697; 20160135741; 20160135742; 20160135743; 20160136882; 20160139156; 20160143548; 20160143584; 20160147964; 20160148531; 20160151603; 20160158426; 20160158552; 20160169880; 20160169923; 20160174840; 20160174898; 20160183818; 20160193462; 20160198961; 20160205450; 20160206215; 20160206922; 20160213314; 20160213334; 20160216286; 20160216287; 20160224130; 20160231402; 20160232131; 20160232137; 20160232201; 20160232244; 20160232807; 20160234143; 20160234184; 20160234595; 20160235374; 20160238439; 20160238440; 20160238441; 20160238443; 20160238444; 20160239624; 20160240721; 20160242646; 20160242654; 20160242665; 20160243373; 20160253471; 20160256095; 20160256097; 20160256106; 20160256350; 20160256697; 20160259426; 20160261458; 20160262670; 20160263382; 20160270656; 20160278638; 20160278669; 20160279021; 20160279022; 20160279023; 20160279024; 20160279025; 20160279435; 20160283706; 20160285985; 20160287879; 20160287887; 20160296114; 20160296116; 20160296145; 20160296169; 20160296759; 20160300028; 20160302706; 20160302707; 20160303371; 20160310022; 20160310048; 20160314670; 20160317744; 20160320381; 20160321400; 20160321598; 20160321599; 20160323401; 20160324472; 20160324478; 20160324488; 20160325143; 20160327476; 20160331257; 20160331273; 20160331986; 20160331987; 20160334124; 20160337843; 20160342744; 20160342762; 20160346501; 20160346530; 20160346542; 20160346609; 20160354606; 20160361026; 20160361027; 20160367803; 20160370396; 20160373161; 20160374600; 20160374608; 20160374618; 20160374620; 20160374625; 20160377640; 20160378069; 20160378070; 20160378071; 20170000324; 20170000325; 20170000326; 20170000329; 20170000330; 20170000331; 20170000332; 20170000333; 20170000334; 20170000335; 20170000337; 20170000340; 20170000341; 20170000342; 20170000343; 20170000345; 20170000371; 20170000372; 20170000375; 20170000390; 20170000391; 20170000415; 20170000454; 20170000683; 20170000936; 20170001032; 20170004106; 20170007111; 20170007115; 20170007116; 20170007122; 20170007123; 20170007182; 20170007450; 20170007799; 20170007843; 20170010469; 20170010470; 20170017083; 20170021171; 20170021172; 20170027514; 20170027515; 20170027523; 20170027812; 20170028231; 20170036021; 20170036031; 20170038401; 20170043160; 20170045862; 20170049352; 20170049406; 20170049946; 20170053078; 20170055205; 20170055845; 20170055851; 20170055882; 20170055887; 20170055896; 20170063434; 20170065183; 20170065821; 20170071474; 20170071487; 20170071506; 20170071545; 20170080207; 20170084983; 20170086675; 20170086752; 20170095011; 20170095205; 20170095673; 20170095721; 20170097994; 20170098367; 20170100056; 20170103669; 20170112391; 20170112439; 20170112671; 20170113042; 20170113057; 20170118626; 20170119312; 20170124853; 20170127975; 20170128140; 20170128722; 20170128735; 20170135633; 20170136209; 20170136264; 20170136265; 20170136842; 20170143219; 20170143233; 20170143266; 20170143267; 20170143268; 20170143282; 20170146385; 20170146386; 20170146387; 20170146388; 20170146389; 20170146390; 20170146391; 20170147754; 20170147837; 20170148240; 20170149773; 20170150895; 20170156662; 20170156663; 20170157411; 20170160398; 20170164850; 20170164876; 20170164878; 20170165483; 20170168457; 20170169190; 20170172522; 20170181708; 20170182330; 20170188893; 20170189756; 20170189757; 20170189815; 20170193140; 20170195475; 20170196455; 20170196457; 20170196458; 20170196513; 20170202461; 20170202484; 20170209053; 20170209055; 20170209081; 20170215729; 20170215756; 20170215757; 20170216125; 20170221463; 20170224252; 20170224260; 20170224268; 20170224581; 20170224990; 20170228516; 20170228627; 20170230084; 20170231494; 20170231495; 20170231597; 20170232297; 20170237694; 20170238814; 20170238881; 20170239470; 20170239523; 20170243056; 20170243508; 20170246459; 20170248567; 20170249115; 20170251232; 20170251940; 20170251974; 20170251975; 20170255262; 20170257162; 20170258389; 20170258585; 20170262015; 20170262604; 20170264338; 20170264693; 20170265769; 20170265770; 20170266533; 20170270765; 20170273629; 20170274267; 20170281020; 20170282011; 20170283845; 20170290513; 20170290528; 20170290980; 20170293266; 20170296052; 20170296076; 20170296107; 20170296139; 20170296813; 20170296814; 20170300653; 20170301214; 20170303784; 20170303786; 20170308663; 20170311878; 20170312161; 20170312165; 20170312612; 20170312746; 20170316182; 20170319119; 20170319122; 20170319123; 20170319849; 20170324437; 20170325056; 20170325524; 20170325525; 20170325727; 20170326013; 20170330447; 20170332980; 20170333752; 20170340920; 20170344736; 20170347895; 20170350878; 20170354351; 20170354365; 20170354547; 20170354795; 20170356770; 20170357217; 20170357419; 20170358239; 20170358240; 20170358242; 20170360320; 20170361092; 20170361162; 20170366233; 20170367576; 20170367585; 20170367599; 20170372009;

20170372026; 20170372216; 20170374436; 20180000336; 20180000345; 20180000347; 20180000414; 20180001005; 20180001023; 20180001083; 20180007467; 20180008151; 20180008191; 20180008193; 20180008206; 20180008831; 20180012469; 20180021564; 20180021589; 20180027347; 20180028106; 20180028114; 20180028122; 20180028809; 20180035898; 20180035920; 20180035982; 20180040258; 20180042526; 20180042809; 20180043173; 20180045745; 20180047074; 20180049251; 20180049675; 20180055373; 20180055382; 20180055386; 20180056071; 20180060449; 20180067516; 20180075716; 20180075724; 20180078754; 20180078777; 20180085011; 20180085021; 20180085572; 20180085576; 20180085580; 20180085585; 20180085586; 20180089394; 20180090229; 20180092551; 20180092554; 20180092577; 20180101138; 20180101655; 20180103863; 20180103874; 20180103883; 20180104407; 20180108440; 20180114124; 20180116536; 20180116723; 20180117346; 20180125689; 20180126172; 20180126222; 20180132032; 20180132778; 20180139799; 20180140191; 20180140198; 20180140835; 20180147024; 20180147333; 20180147449; 20180152972; 20180153404; 20180153475; 20180156660; 20180162186; 20180168460; 20180168461; 20180168463; 20180168905; 20180169411; 20180169412; 20180169421; 20180173405; 20180174686; 20180177397; 20180177459; 20180182489; 20180184735; 20180184901; 20180184914; 20180189452; 20180191693; 20180192953; 20180203882; 20180206747; 20180207429; 20180213583; 20180214025; 20180214026; 20180214066; 20180214080; 20180219334; 20180221645; 20180225419; 20180228434; 20180228438; 20180229674; 20180235537; 20180238734; 20180240176; 20180240357; 20180241564; 20180242864; 20180242921; 20180242926; 20180243528; 20180243541; 20180247712; 20180249919; 20180250574; 20180256076; 20180256096; 20180260530; 20180261066; 20180270549; 20180279901; 20180279952; 20180279965; 20180280177; 20180289166; 20180289275; 20180289310; 20180289975; 20180289976; 20180295667; 20180295895; 20180296097; 20180296098; 20180296136; 20180296157; 20180296161; 20180296847; 20180300919; 20180301211; 20180303343; 20180303356; 20180303357; 20180303396; 20180304149; 20180307185; 20180310327; 20180310877; 20180310892; 20180314801; 20180315285; 20180317826; 20180325385; 20180325435; 20180325460; 20180326142; 20180329518; 20180332383; 20180333107; 20180333585; 20180333586; 20180334252; 20180344255; 20180345006; 20180348048; 20180350465; 20180352534; 20180353086; 20180353111; 20180358117; 20180368701; 20180368780; 20180369065; 20180375983; 20180376586; 20190000317; 20190000400; 20190001128; 20190007927; 20190008384; 20190008461; 20190009019; 20190015048; 20190019573; 20190028662; 20190029598; 20190029599; 20190030350; 20190036886; 20190038149; 20190038831; 20190038902; 20190046038; 20190046794; 20190053758; 20190059742; 20190059757; 20190060644; 20190061772; 20190064344; 20190068249; 20190069815; 20190073042; 20190073333; 20190073894; 20190076033; 20190076066; 20190076067; 20190076070; 20190076643; 20190077003; 20190080791; 20190082985; 20190083039; 20190083355; 20190083784; 20190090764; 20190090820; 20190091481; 20190096534; 20190099009; 20190105505; 20190108427; 20190110755; 20190116896; 20190117068; 20190117127; 20190117966; 20190122523; 20190125264; 20190126003; 20190126014; 20190130332; 20190132948; 20190133484; 20190134288; 20190137332; 20190142283; 20190146740; 20190147999; 20190150748; 20190150820; 20190150834; 20190151640; 20190154723; 20190158472; 20190159676; 20190160213; 20190167114; 20190167237; 20190168005; 20190174007; 20190175019; 20190175116; 20190175411; 20190175960; 20190175961; 20190179412; 20190180869; 20190183339; 20190183346; 20190184077; 20190190862; 20190191468; 20190192022; 20190192076; 20190192080; 20190192085; 20190192086; 20190192768; 20190197073; and 20190197861.

A new type of biometric "device" is a biometric tattoo. A team of scientists in Germany has developed permanent dermal sensors that can be applied as artistic tattoos. As detailed in the journal Angewandte Chemie, a colorimetric analytic formulation was injected into the skin instead of tattoo ink. See, Yetisen, Ali Kemal, Rosalia Moreddu, Sarah Seifi, Nan Jiang, Katia Vega, Xingchen Dong, Jie Dong et al. "Dermal Tattoo Biosensors for Colorimetric Metabolite Detection." Angewandte Chemie (2019). See also, Graziano, Gabriella. "Functional tattoos." Nature Reviews Chemistry (2019): 1; Russell, Ryan J., Michael V. Pishko, Christopher C. Gefrides, Michael J. McShane, and Gerard L. Cote. "A fluorescence-based glucose biosensor using concanavalin A and dextran encapsulated in a poly (ethylene glycol) hydrogel." Analytical Chemistry 71, no. 15 (1999): 3126-3132. The pigmented skin areas varied their color when blood pH or other health indicators changed. The researchers identified and adapted three colorimetric chemical sensors that produce a color change in response to biomarkers. The first sensor was a pH indicator consisting of the dyes methyl red, bromothymol blue, and phenolphthalein. If injected into a model skin patch, the resulting tattoo turned from yellow to blue if the pH was adjusted from five to nine. The other two sensors probed the levels of glucose and albumin.

Wearable devices may be improved according to the present invention by configuring them to calculate the second derivative of the physiological parameters they are designed to measure.

SUMMARY OF THE INVENTION

Most dynamic processes in nature may be described by the second-order differential equations or corresponding equations of other systems. These equations typically correspond to physical elements or parameters of systems that can be measured, predicted, diagnosed, and controlled. The present invention provides systems and methods for the analysis of biological systems in real-time or near real-time, for predictive analytics, diagnosis, and intervention.

Once the homeostatically-controlled systems (at least at the highest level) are considered with respect to second-order differential equations, a large body of available mathematical and engineering theory becomes immediately relevant to the analysis, predictive modelling, warning, and ultimately interventional strategies to be applied. The prior art tends to look at organisms and their systems with respect to zeroth or first-order principles, and the analysis and treatment applied based on a state, or perhaps a linear trajectory (rate). When considering second-order differential effects, each homeostatically-controlled subsystem may be considered a damped oscillator, though in most normal cases (excluding overtly cyclic processes), these are overdamped with little or no overshoot. As such, the consideration of the oscillatory nature has been ignored or considered too esoteric for practical application.

In fact, once the biological systems are properly dynamically modelled, consideration of stability criteria, secondary and tertiary effects of an intervention, or withholding intervention is facilitated. In general, for any complex biological system, only a very small number of relevant parameters may be measured, over a limited period of time, and over a limited range of conditions or contexts, and on a broader scale, on a limited population. However, in many cases, the biology is sufficiently understood such that a second-order (or higher) differential equation may be constructed, which models the system of the species (and subtype). Over the conditions or context of monitoring, the individual-specific parameters and "constants" may then be derived from a limited stream of data, thus producing a predictive model for an individual. Once a predictive model is elaborated, further data may be used to assess the quality of the model, and also to determine a change in the homeostatic state of the organism or system, i.e., a requirement to modify an otherwise accurate model. Further, an accurate model has predictive value in terms of understanding the future states of the organism or system, both in the absence and presence of intervention or change of external conditions or context.

Of particular note is that by explicitly modelling homeostatic mechanisms, the present and future stability of the state of the organism or system may be determined or predicted, and deviations from normal or predicted states for the individual attributed meaning. The prior art does not typically apply engineering-style stability analysis to biological systems, and thus fails to identify stability criteria, and how intervention(s) or proposed intervention(s) impacts these criteria. In homeostatically-controlled biological systems, a proposed goal is (in the general case) to return the system to a state where the homeostatic mechanisms maintain a stable and appropriate state of the system and organism. On the other hand, in selected cases, the issue is the opposite—the homeostatic mechanisms themselves achieve an unstable process or inappropriate state, and the goal is to defeat the improper homeostasis and/or reset its "setpoint" or guiding parameters.

For example, "chronic disease" is an inappropriate state of the organism which is relatively stable (in a colloquial sense) over time, and which appears stable from a systems analysis perspective—an "acute illness" is one where the homeostatic mechanisms have failed to sufficiently maintain the organism in a proper state. In order to monitor a chronic illness according to the present technology, one should identify the impacted systems and their interaction with other systems, and model the chronic disease as an underlying model taking into account the biological systems over the range including the "operating point" represented by the disease state and, perhaps, the operating point of the biological systems with the chronic disease defects remediated (which may be drawn from population statistics).

According to the invention, in a chronic disease state, the homeostatic controls over the biological systems may be aberrant, and therefore merely treating the symptoms to return the organism to a state wherein the measurement parameters are within the normal range may be insufficient, since the setpoint of the homeostatic mechanisms may remain displaced from the normal state. Therefore, guided by the model, and intervention may be affected that seeks to alter the setpoint, and not merely treat the symptoms of the chronic disease. By employing a higher-order dynamical model, the amount of undercompensation or overcompensation may be optimized.

On the other hand, in acute disease, remediation of symptoms may be sufficient, as the underlying homeostatic mechanisms may be fully operational. The technology may also distinguish between acute and chronic diseases, and distinguish between the underlying pathology and homeostatic compensatory mechanisms which may be intact. Because the underlying biophysics are different between an acute disease, which represents a perturbation from a normal state, and a chronic disease, which represents a set of compensatory responses that lead to a revised state different from normal but stable or semi-stable, the present technology may assist in diagnosis, distinguishing between acute and chronic phases, and assist in proposing therapy, monitoring therapy, and gauging return to health.

A particular advantage of the higher-order dynamic model is that it can predict not only a need for therapy or therapeutic intervention (or lack of need), but also the amount of therapy required with respect to an immediate response, and a delayed or rebound effect. It can determine the impact of normal activity, environment, food, or drink on the physiological state, emotional and psychological impacts, and include these factors in a time-sensitive analysis. It can further distinguish between normal responses, in contradistinction to improper responses. Typically, within physiological tolerance, simple levels (zeroth order) or rates (first-order) will not be thresholds for diagnosis or therapeutic intervention, and rather the dynamic context will also be considered. These models are typically individualized, and therefore will intrinsically account for differences between individuals.

This technology may have a particular application in new drug development, where the therapeutic index (a ratio that compares the toxic vs. effective drug's concentration) is low. In such cases, a drug may fail a clinical trial if non-dynamically optimized protocols are employed. However, by analyzing and compensating for the dynamics of the patient, a therapeutic index may be achieved, which permits safe and effective use. Thus, a style of personalized medicine is provided with an adaptive protocol dependent on patient responses and predicted patient responses, but also addressing change in patient state over the course of therapy or intervention.

By employing the tools of systems dynamics, stability criteria may be determined, and a determination made whether the patient or subject meets the stability criteria, is at risk of not meeting the stability criteria, and employing or suggesting therapy when warranted to avoid unstable states, and constraining therapy or intervention that could lead to unstable states. An unstable state is one that leads to failure of the homeostatic mechanism, an undesired homeostatic response, or significant secondary effects outside a particular biological system affected by the pathology, for example, in addition to traditional notions of system stability.

In a typical second-order dynamic system, a model is provided represented by a differential equation which, in analogy to mechanical systems, has a first-term representing a temporal scale (e.g., natural frequency), and a second term representing energy loss (damping). When such a model applies, the biological system may be assessed with respect to changes in the temporal scale (shorter or longer), and energy loss (too much, too little). Of course, cases with aberrations in both time and energy may be apparent, and cases where the model itself requires restructuring, i.e., the form of the differential equation is unsatisfactory.

The present technology is not limited to assessing poor health conditions and may be applied to the training of athletes, and other non-pathological states. For example, in sports, mechanical efficiency may be a critical determinant of performance. By measuring the dynamics of an athlete and considering the task, steps may be taken to increase performance. For example, footwear of a runner has a mass, thickness, compression, damping, lateral stability (asymmetric), etc. A gait model of the athlete may be acquired, which proposes optimal footwear, for example, in terms of damping of ground impact and timing of energy recovery.

The gait model may detect changes in the athlete over time, such as fatigue, water balance, etc., and propose changes in the footwear to compensate. In some cases, the footwear itself is adaptive, and the sensors and gait model may be embedded into the footwear.

See, U.S. Pat. Nos. and US Pub. App. Nos. 4660242; 4679269; 4829932; 4866802; 5216594; 5373651; 5615111; 5642096; 5720200; 5794361; 6230501; 6563423; 6768246; 6788200; 6833039; 6843578; 6865825; 7010869; 7059070; 7107706; 7188439; 7204041; 7219449; 7225565; 7265666; 7334350; 7395614; 7404263; 7409256; 7426873; 7493230; 7497037; 7506460; 7562468; 7579946; 7607243; 7614166; 7631382; 7671599; 7676960; 7676961; 7707742; 7735351; 7758523; 7793430; 7794101; 7816632; 7890055; 7930131; 8015732; 8028443; 8056268; 8103802; 8127470; 8141276; 8186081; 8205356; 8234798; 8250782; 8258941; 8261468; 8277741; 8291614; 8388347; 8421822; 8461979; 8499476; 8609973; 8641220; 8644967; 8656607; 8667709; 8730034; 8739639; 8740751; 8751320; 8753275; 8763261; 8857078; 8938892; 8956228; 8973197; 8982150; 9029736; 9030335; 9063529; 9089182; 9100495; 9101260; 9160836; 9192816; 9198478; 9201413; 9207660; 9215910; 9279734; 9297709; 9301573; 9326566; 9364042; 9375047; 9380834; 9388873; 9398787; 9410691; 9410857; 9414641; 9504291; 9542706; 9549585; 9572395; 9603416; 9622537; 9629418; 9635901; 9642414; 9648926; 9652838; 9655405; 9662262; 9687577; 9693605; 9709971; 9715012; 9734527; 9737263; 9743861; 9756895; 9757302; 9763489; 9763490; 9764050; 9776041; 9782125; 9810591; 9846231; 9847006; 9848668; 9854872; 9861165; 9863823; 9877523; 9879741; 9913509; 9924760; 9936763; 9961963; 9968159; 9968238; 9980535; 9984549; 9986782; RE40879; RE41087; RE41102; RE41122; 10010129; 10012969; 10013633; 10016015; 10024660; 10024740; 10034512; 10051912; 10058146; 10070680; 10070683; 10092065; 10093112; 10106222; 10111496; 10123098; 10123679; 10136842; 10151648; 10170135; 10172396; 10172409; 10172423; 10178890; 10182608; 10182744; 10188173; 10188319; 10194714; 10222283; 10226082; 10234340; 10248985; 10251601; 10277963; 10289098; 10292453; 10293565; 10299722; 10306726; 10307081; 10311451; 10314928; 10321732; 10327672; 10334906; 10339352; 10352787; 10357078; 10362830; 10370785; 10376018; 20010035723; 20010045104; 20020090487; 20020121979; 20030070324; 20040177531; 20050050750; 20050053757; 20050091884; 20050183292; 20050217142; 20050261609; 20050268487; 20060103538; 20060230641; 20060230642; 20060248749; 20060248750; 20070000154; 20070000188; 20070006489; 20070011919; 20070011920; 20070021269; 20070039205; 20070039209; 20070043582; 20070142955; 20070157488; 20070180736; 20070180737; 20070247306; 20070260421; 20070271817; 20070282562; 20080000108; 20080005931; 20080097263; 20080122657; 20080167741; 20080189194; 20080197126; 20080243431; 20080254944; 20090126233; 20090135001; 20090151199; 20090178305; 20090193689; 20090199429; 20090204360; 20090241378; 20090265958; 20090284368; 20090287452; 20090313853; 20100035688; 20100037489; 20100050478; 20100090477; 20100104470; 20100122472; 20100170115; 20100187305; 20100242303; 20100289971; 20110054359; 20110056093; 20110056097; 20110094127; 20110260857; 20110285853; 20110314700; 20110314702; 20120073165; 20120086550; 20120144068; 20120167325; 20120184878; 20120234111; 20120291563; 20120291564; 20120293326; 20120311885; 20120318781; 20120324763; 20130008058; 20130019503; 20130019694; 20130064388; 20130067775; 20130114869; 20130118340; 20130185003; 20130213144; 20130213145; 20130213146; 20130213147; 20130263349; 20130265157; 20130278435; 20130278436; 20130312291; 20130326912; 20140025447; 20140033572; 20140048214; 20140059897; 20140082963; 20140123838; 20140130370; 20140144049; 20140182166; 20140201024; 20140213940; 20140214502; 20140222173; 20140244395; 20140250726; 20140259798; 20140260677; 20140260689; 20140277631; 20140277632; 20140277658; 20140285311; 20140295537; 20140305470; 20140320331; 20140327320; 20140330431; 20140331523; 20150003047; 20150011914; 20150040428; 20150048942; 20150096204; 20150096597; 20150120496; 20150137935; 20150173452; 20150177081; 20150189062; 20150189063; 20150226619; 20150254710; 20150257479; 20150260514; 20150289594; 20150289595; 20150289596; 20150296922; 20150297059; 20150313308; 20150313309; 20150335096; 20150359457; 20160000188; 20160016041; 20160025854; 20160037855; 20160044993; 20160067584; 20160074547; 20160081418; 20160081435; 20160100801; 20160106177; 20160143562; 20160180440; 20160188856; 20160195440; 20160210679; 20160219266; 20160219967; 20160220186; 20160227870; 20160227883; 20160252412; 20160260311; 20160262485; 20160262486; 20160290878; 20160299021; 20160302509; 20160302521; 20160306339; 20160309829; 20160309830; 20160309842; 20160316849; 20160334087; 20160335913; 20160341611; 20160345653; 20160345902; 20160349076; 20160366972; 20160369861; 20160374171; 20170027278; 20170038747; 20170055880; 20170058451; 20170068774; 20170068970; 20170079368; 20170085967; 20170105474; 20170105476; 20170127999; 20170135415; 20170169695; 20170172249; 20170215524; 20170215765; 20170231569; 20170238659; 20170246521; 20170255185; 20170265578; 20170265580; 20170265581; 20170265582; 20170265583; 20170265584; 20170265586; 20170265587; 20170265588; 20170265589; 20170265591; 20170265592; 20170265594; 20170270224; 20170272008; 20170273599; 20170284875; 20170290937; 20170295889; 20170303827; 20170306539; 20170308044; 20170308066; 20170308945; 20170330257; 20170332733; 20170336781; 20170340049; 20170340277; 20170351891; 20170363440; 20180008003; 20180008005; 20180020764; 20180064209; 20180070877; 20180077975; 20180094991; 20180103724; 20180110294; 20180116334; 20180122211; 20180124478; 20180125163; 20180132568; 20180132697; 20180132758; 20180146738; 20180168273; 20180169474; 20180184751; 20180199657; 20180199671; 20180199673; 20180199674; 20180206586; 20180213879; 20180228401; 20180231393; 20180242691; 20180263564; 20180271181; 20180271211; 20180271213; 20180274996; 20180279713; 20180292794; 20180295933; 20180310670; 20180325207; 20180326286; 20180338560; 20180338576; 20180339445; 20180343977; 20180343978; 20180343981; 20180361221; 20190037960; 20190037961; 20190037969; 20190039311; 20190045877; 20190052111; 20190053572; 20190082773; 20190090585; 20190090589; 20190094374; 20190116915; 20190116935; 20190116937; 20190117118; 20190133414; 20190139252; 20190150791; 20190159529; 20190159546; 20190166954; 20190174863; 20190174871; 20190175107; 20190208295; 20190208865; 20190209087; 20190213458; 20190223542; 20190231166; 20190232592; and 20190239309.

The Kalman filter is a recursive solution to the discrete-data linear filtering problem. The Kalman filter gives an estimate of the state of a dynamic system from noisy measurements. It gives a recursive minimum variance estimate of the state of the system. To be able to apply the Kalman filter to give an estimate of a state in a space, a discrete-time state-space model is needed. This consists of a state equation and a measurement equation. The state equation is given by: $x_k = A_k x_{k-1} + B_k u_k \varepsilon_k$, wherein $x_k$ is an n-dimensional state vector, which is to be estimated; $A_k$ is an n-dimensional known system matrix; $B_k$ is an n by m-dimensional known input matrix; $u_k$ is an optional m-dimensional input vector; and $\varepsilon_k$ represents the process noise. Because the variable $u_k$ is optional, it can be left out of the equation, and a new state equation that can be simplified into: $x_k = A_k x_{k-1} + \varepsilon_k$. The measurement equation is given by: $y_k = C_k x_k + \delta_k$, wherein $y_k$ is a p-dimensional measurement vector; $x_k$ is an n-dimensional state vector which is to be estimated; $C_k$ is a p by n-dimensional known measurement matrix; and $\delta_k$ represents the measurement error. The variables $\varepsilon_k$ and $\delta_k$ are assumed to have zero cross-correlation and are white.

Furthermore $\varepsilon_k$ and $\delta_k$ each has a covariance matrix ($Q_k$ and $R_k$ respectively) and has normal probability distributions: $p(\varepsilon_k) \sim N(0, Q_k)$ $p(\delta_k) \sim N(0, R_k)$. The system matrix $A_k$ and measurement matrix $C_k$ may change with each measurement or time-step. Both of the covariance matrices $Q_k$ and $R_k$ may also be time-variant.

With Kalman filters, the initial state is known and is represented by the state vector $x_0$. To be able to predict the state of the system at a time $k_1$, the previous estimate $\hat{x}_o$ is needed. Because the prediction makes use of the old estimate, before incorporating the new measurements found at the time $k_1$, this estimate will be called an "a priori" estimate. The a priori estimate is represented by $\hat{x}_1^-$ here the hat denotes that it is an estimate, and the upper minus denotes that it is a previous estimate. So, to calculate the a priori estimate, the following equation can be formed: $\hat{x}_{k+1}^- = A\hat{x}_k$. In other words, to obtain a new estimate, multiply the last collected estimate $\hat{x}_k$ with A, the system matrix.

Furthermore, it is also needed to change the error covariance matrix $P_k^-$, which is associated with the a priori estimate with every new time step. The equation showing how to calculate a new value for $P_k^-$ is: $P_{k+1}^- = AP_k A^T + Q$. Depending on the size of Q, the random process noise covariance matrix has a significant effect on the error covariance matrix. The value of Q is normally obtained before using it in the process that is to be estimated. However, this may be difficult. Q has to simulate process noise for the process to be estimated.

Given an a priori estimate $\hat{x}_k^-$, what is then needed is an updated estimate $\hat{x}_k$; this is called the a posteriori estimate, which is obtained by combining the noisy measurement $y_k$ with the a priori estimate, using $\hat{x}_k = \hat{x}_k^- + K_k(y_k - C\hat{x}_k^-)$. As can be seen, the a posteriori estimate $\hat{x}_k$ can be obtained by combining the a priori estimate $\hat{x}_k^-$ with the weighted difference between the actual measurement $y_k$ and the measurement prediction $C\hat{x}_k^-$. The difference $(y_k - C\hat{x}_k^-)$ is called the residual, and reflects the discrepancy between the actual measurement $y_k$ and the measurement that was predicted. If the residual is zero, then it appears that the prediction of the value of the next measurement and the actual measurement are the same.

The Kalman gain $K_k$ is a matrix that aims to minimize the a posteriori error covariance matrix, calculated by $K_k = P_k^- C^T (C P_k^- C^T + R)^{-1}$. From this, it can be seen that when the measurement error covariance matrix R reaches zero, the Kalman gain will weigh the residual more heavily:

$$\lim_{R_k \to 0} K_k = C^{-1}.$$

If this is the case, the actual measurement $y_k$ is more trustworthy. At the same time, the predicted measurement $C\hat{x}_k^-$ is less trustworthy. If, however, the a priori estimate error covariance matrix $P_k^-$ reaches zero, the Kalman gain will weigh the residual less heavily:

$$\lim_{P_k^- \to 0} K_k = 0.$$

When this occurs, when covariance matrix $P_k^-$ approaches zero, the actual measurement is less trustworthy, and $C\hat{x}_k^-$ is more trustworthy. The last update equation is the error covariance update equation, given by: $P_k = (I - K_k C) P_k^-$. The error covariance matrix $P_k$ gives a statistical measure of the uncertainty in $x_k$, it is a measure of the dispersion of $x_k$ around $\hat{x}_k$.

The Kalman filter estimates a certain process by using a form of feedback control. First it estimates the state of the system at a given time and afterward receives feedback from incoming measurements. In other words, first, it predicts what the state of the system will be and, after receiving new measurements from sensors, these predictions will be corrected.

After obtaining new a priori estimates, the next step is to use the measurement update equations to calculate a posteriori estimates. First, the Kalman gain has to be calculated to see how much the residual will be weighed. When the Kalman gain is known, it is possible to obtain a new a posteriori state estimate. To be able to calculate the new state, the new measurement is compared to predicted measurement, multiplied by the Kalman gain, and combined with the a priori state estimate. The final step is obtaining an a posteriori error covariance estimate.

The Kalman filter has a recursive nature. In every cycle of the process, i.e., after each time and measurement update pair, the previous a posteriori estimates are used to calculate the new a priori estimates and from them the new a posteriori estimates.

The Kalman filter represents a higher-order model of the system and may be used in conjunction with the present technology. See, en.wikipedia.org/wiki/Kalman filter. By incorporating statistical uncertainty of measurements into the model, false alarms may be suppressed, and higher quality predictions made.

Noisy sensor data, approximations in the equations that describe the system evolution, and external factors that are not accounted for all place limits on how well it is possible to determine the system's state. Kalman filter deals effectively with the uncertainty due to noisy sensor data and, to some extent, also with random external factors. Kalman filter produces an estimate of the state of the system as an average of the system's predicted state and the new measurement using a weighted average. The purpose of the weights is that values with better (i.e., smaller) estimated uncertainty are "trusted" more. The weights are calculated from the covariance, a measure of the estimated uncertainty of the prediction of the system's state. The result of the weighted average is a new state estimate that lies between the predicted and measured state and has a better-estimated uncertainty than either alone. This process is repeated at every time step, with the new estimate and its covariance informing the prediction used in the following iteration. This means that Kalman filter works recursively and requires only the last "best guess," rather than the entire history, of a system's state to calculate a new state.

The relative certainty of the measurements and current state estimate is an important consideration, and it is common to discuss the response of the filter in terms of Kalman filter's gain. The Kalman gain is the relative weight given to the measurements and current state estimate and can be "tuned" to achieve particular performance. With a high gain, the filter places more weight on the most recent measurements, and thus follows them more responsively. With a low gain, the filter follows the model predictions more closely. At the extremes, a high gain close to one will result in a more jumpy estimated trajectory, while low gain close to zero will smooth out noise but decrease the responsiveness.

When performing the actual calculations for the filter, the state estimate and covariances are coded into matrices to handle the multiple dimensions involved in a single set of calculations. This allows for a representation of linear relationships between different state variables (such as position, velocity, and acceleration) in any of the transition models or covariances.

See U.S. Patent and Pub. App. Nos. 4589078; 4763282; 5341229; 5626140; 5629848; 5850352; 6157850; 6236872; 6558351; 6572545; 6575905; 6949066; 7070398; 7149320; 7172897; 7215986; 7231254; 7267665; 7280870; 7312087; 7354420; 7392079; 7402153; 7414611; 7489298; 7489299; 7519406; 7519512; 7535456; 7621876; 7623928; 7716008; 7774155; 7783442; 7806886; 7853329; 7859540; 7860676; 7877224; 7927216; 7930035; 7931535; 7942745; 7974696; 7996158; 8041536; 8072424; 8089458; 8103471; 8123696; 8137195; 8157651; 8160273; 8160669; 8164567; 8169406; 8180591; 8180592; 8184097; 8216139; 8226493; 8233958; 8233959; 8237657; 8239166; 8248367; 8251906; 8257259; 8260393; 8260558; 8265725; 8267786; 8275437; 8280475; 8282549; 8290561; 8306766; 8308563; 8311749; 8311769; 8311770; 8313379; 8321149; 8348886; 8348923; 8359545; 8368648; 8373659; 8374667; 8384668; 8385971; 8386004; 8386008; 8388530; 8388544; 8396557; 8407022; 8409003; 8430753; 8433395; 8437980; 8444560; 8463576; 8463577; 8467904; 8469886; 8473245; 8475275; 8478389; 8478557; 8484153; 8484270; 8491389; 8494829; 8532935; 8543185; 8543351; 8548770; 8560038; 8565848; 8571808; 8583402; 8600681; 8608535; 8612163; 8629836; 8632465; 8657745; 8657747; 8663109; 8670953; 8672845; 8682615; 8683850; 8684943; 8686579; 8688202; 8702515; 8708821; 8708824; 8711094; 8718753; 8718965; 8727995; 8747315; 8750955; 8753165; 8755837; 8758136; 8768313; 8771222; 8777924; 8781197; 8788007; 8790180; 8795079; 8801610; 8805110; 8805485; 8814688; 8827810; 8834271; 8834366; 8842176; 8843210; 8843321; 8845536; 8849259; 8855712; 8868377; 8870655; 8886206; 8888576; 8900142; 8913011; 8915785; 8915849; 8918178; 8929877; 8937594; 8942777; 8945017; 8948834; 8961260; 8961312; 8983628; 8983629; 8986209; 8994657; 8998815; 9005129; 9008724; 9008762; 9011248; 9014986; 9039533; 9042988; 9044671; 9050007; 9055901; 9060719; 9060722; 9072438; 9082011; 9095303; 9104965; 9107614; 9107623; 9113801; 9113823; 9119528; 9119529; 9125548; 9125577; 9131120; 9131842; 9149717; 9162148; 9167991; 9173574; 9186585; 9189739; 9192328; 9204038; 9227138; 9250716; 9261978; 9271133; 9272206; 9282925; 9294074; 9298282; 9305559; 9317743; 9320470; 9320900; 9320976; 9339202; 9351668; 9358381; 9364173; 9364609; 9375171; 9393491; 9393500; 9398872; 9399134; 9400598; 9401153; 9408549; 9414758; 9415219; 9420965; 9433376; 9440025; 9446319; 9451886; 9452258; 9452259; 9456787; 9457146; 9463277; 9463380; 9468854; 9474855; 9474962; 9483608; 9486578; 9492096; 9498155; 9498709; 9498728; 9517306; 9526430; 9526834; 9565512; 9572935; 9572936; 9575570; 9577992; 9579568; 9586004; 9590986; 9597453; 9616334; 9623179; 9623240; 9629558; 9649036; 9655565; 9662445; 9675290; 9675878; 9687194; 9692984; 9700253; 9700806; 9706956; 9706963; 9706964; 9707478; 9713766; 9731194; 9737249; 9737797; 9750441; 9757510; 9770652; 9775543; 9779502; 9795737; 9797880; 9801571; 9801577; 9804150; 9811730; 9814973; 9826922; 9827372; 9836896; 9849239; 9852736; 9853976; 9861887; 9868332; 9872652; 9878096; 9886845; 9897985; 9900669; 9907909; 9913599; 9918183; 9918646; 9931578; 9936910; 9943247; 9943267; 9946356; 9975196; 9993724; 9999728; RE45905; 10002233; 10010790; 10022624; 10025973; 10026410; 10028706; 10031002; 10045713; 10045720; 10046113; 10049187; 10061911; 10089446; 10098549; 10119956; 10130767; 10137365; 10143409; 10143426; 10154789; 10155170; 10159897; 10178973; 10179283; 10188334; 10188953; 10194850; 10234942; 10236006; 10238978; 10261069; 10275640; 10293184; 10300303; 10300374; 10307671; 10307683; 10327708; 10332315; 10333932; 10339654; 10349872; 10357210; 10363420; 10369463; 20020099282; 20020111547; 20020128544; 20020177135; 20030130616; 20030195404; 20040034295; 20040039243; 20040053290; 20040193025; 20050069162; 20050135948; 20050240242; 20050256385; 20050267342; 20060160205; 20060211942; 20060224109; 20070088226; 20070098600; 20070123779; 20070146371; 20070161919; 20070162086; 20070162164; 20070167991; 20070173761; 20070189921; 20070208212; 20070270668; 20080119900; 20080188796; 20080202927; 20080208538; 20080242553; 20080260212; 20080314395; 20090012766; 20090022336; 20090057147; 20090112478; 20090149148; 20100023089; 20100028984; 20100048242; 20100114015; 20100138379; 20100160807; 20100168538; 20100268477; 20100274102; 20100285981; 20100305545; 20100324382; 20110004110; 20110029269; 20110034176; 20110044524; 20110106453; 20110143811; 20110180425; 20110184267; 20110212717; 20110301436; 20120022336; 20120022350; 20120022384; 20120022805; 20120022844; 20120065507; 20120083705; 20120083714; 20120083715; 20120083716; 20120084053; 20120084054; 20120203131; 20120226471; 20120226472; 20120258776; 20120277545; 20130073254; 20130073255; 20130080113; 20130096843; 20130109946; 20130151196; 20130158369; 20130158473; 20130158503; 20130165901; 20130179382; 20130190638; 20130217440; 20130238049; 20130238050; 20130245401; 20130245462; 20130245711; 20130245712; 20130245981; 20130268236; 20130273968; 20130282322; 20130282646; 20130289424; 20130295894; 20130297220; 20130317580; 20140005633; 20140039383; 20140051949; 20140052091; 20140052092; 20140052093; 20140052094; 20140052095; 20140058221; 20140066884; 20140066885; 20140066886; 20140066887; 20140066888; 20140066889; 20140066892; 20140067278; 20140080428; 20140088393; 20140108020; 20140114278; 20140118138; 20140118166; 20140128803; 20140142958; 20140163517; 20140180240; 20140236536; 20140257437; 20140275854; 20140275886; 20140276119; 20140276554; 20140276555; 20140288436; 20140288438; 20140288620; 20140303552; 20140323897; 20140343867; 20140371913; 20150011194; 20150022675; 20150032178; 20150080756; 20150088024; 20150100038; 20150134268; 20150146939; 20150148700; 20150164377; 20150164432; 20150190636; 20150190637; 20150196229; 20150196256; 20150220700; 20150250429; 20150304797; 20150358525; 20160007890; 20160029931; 20160029966; 20160038673; 20160058302; 20160058329; 20160058332; 20160058333; 20160058356; 20160058370; 20160058371; 20160058372; 20160113838; 20160135706; 20160162662; 20160166156; 20160192865; 20160193679; 20160220151; 20160232726; 20160234174; 20160235352; 20160239084;

20160241554; 20160242700; 20160256112; 20160256629; 20160279410; 20160287184; 20160293172; 20160324450; 20170027523; 20170065230; 20170076068; 20170079596; 20170111359; 20170113046; 20170119261; 20170119968; 20170133022; 20170135633; 20170136842; 20170147722; 20170147803; 20170156593; 20170156606; 20170165425; 20170181671; 20170181677; 20170209055; 20170215028; 20170216625; 20170216627; 20170224291; 20170236407; 20170245767; 20170252513; 20170272842; 20170273606; 20170281867; 20170300741; 20170311897; 20170311902; 20170325736; 20170340260; 20170365101; 20180035951; 20180036147; 20180043095; 20180043096; 20180055376; 20180085011; 20180085040; 20180092573; 20180136486; 20180139518; 20180147349; 20180158266; 20180160985; 20180162186; 20180177963; 20180192900; 20180198785; 20180211673; 20180233028; 20180242891; 20180268237; 20180293430; 20180296142; 20180317808; 20180333051; 20180333535; 20180344220; 20180350468; 20180353139; 20190012608; 20190013090; 20190059826; 20190072917; 20190076600; 20190104989; 20190117115; 20190118283; 20190159737; 20190172197; 20190175079; 20190175080; 20190175082; 20190180153; 20190180438; 20190188895; 20190192009; 20190201037; 20190201038; 20190201039; 20190201040; 20190201042; 20190201043; 20190201046; 20190201047; 20190201075; 20190212323; 20190216350; 20190244347; and 20190244348.

Four use cases are considered, though the technology is not so limited. In the first use case, a system within a normal organism is modelled by its dynamic response parameters, e.g., the equation form and parameters of a higher-order dynamic response equation. This model is derived from organismal biology and sensor measurements of the individual. The biological system in the individual is monitored for deviation of the organism from the model, with analysis to determine whether the perturbation is due to a change in the organism from the model, which may be indicative of pathology, or a stimulus that excites the normal physical mechanisms.

The second use case is where the individual has, or is suspected of having, pathology, and the system and method are applied to assist in the diagnosis and proactive monitoring. This use case differs from the normal individual, in that the system model cannot a priori be predicted to correspond to the general population. Given the homeostatic nature of the system, deviations in sensed physiological parameters may represent aberrant physical systems, aberrant stimuli, or both. In this case, where pathology is diagnosed or suspected, a particular motivation for the technology is to determine a change in the state of the individual, or responses that, though within the normal homeostatic process, are nevertheless actionable.

The third use case involves athletes and performance-oriented individuals, who are intentionally exposing themselves or enduring extreme stimuli. In this case, the underlying system is presumed "normal" or in good or high fitness, but the biological system is being externally stressed, such as by exercise, altitude, dehydration, hypoxia, lactic acidosis, etc. In these cases, often the motivation for the application of the technology is to improve performance given the nature of the task. For example, a marathon runner or bike in a race wishes to finish the race quickest, while adopting acceptable risk. How much liquid should be consumed, when, what type, what temperature? What is the target heart rate? What is the optimum gait pattern, pedaling rate, gear, etc.?

The fourth use case involves healthy adults in their senior years. In this case, while the aging is not in and of itself is considered a pathology, nevertheless, the "elasticity" of the systems is diminished, self-regulatory mechanisms in charge of maintaining homeostasis of different systems become progressively sluggish (or aged) generally leading to an extension of the recovery time needed to bring the system under stress back to normal state. In this case, where pathology is not diagnosed but is expected as a result of unexpected stress, such as a fall or a viral infection, a particular motivation for the technology is to determine the degree of loss of "elasticity," i.e., loss of efficiency of self-regulatory mechanisms in their ability to restore homeostasis.

In each of these systems, the homeostatic system within the individual is modeled with a dynamic equation and/or statistical model, based on actual sensor data from the individual, and the parameters of the dynamic equation serve as inputs or outputs. A consistency analysis is performed where feasible, based, for example, on partially redundant sensor data and/or population statistics. The sensor data from the individual are principally analyzed as state variables within the model, to predict errors in predictiveness of the model, as well as predicted state of the individual. For example, while the present technology proposes to supplement level and rate parameters with acceleration/higher-order dynamic parameters for assessment of health or physiological status, the level and rate may remain as important data; for example, levels of glucose, sodium, calcium, temperature, osmolarity, heart rate, etc. remain important limiting criteria, with useful thresholds. Including dynamic characteristics in the analysis also permits earlier prediction of likely excursions beyond tolerable limits, and also the prediction of acceptable deviations even if extreme, for example. Analyzing the model itself (distinct from the full state of the individual) also permits assessment and, for example, would assist in chronic therapies and health programs.

The use of mathematical derivatives also separates the dynamic pattern from initial conditions noise. Whatever physiological parameter is being considered, discovering its acceleration, i.e., the second derivative over time, reveals the dynamic of the system—the "force" that is acting on the system, causing the system to "accelerate" the evolution of the given parameter over time. In this context, the derivatization tends to normalize members of the population, since, while individual operating points may vary, in large part the underlying mechanisms are the same for different individuals of the same species, and eliminating the initial conditions from consideration facilitates comparison of the dynamics of the underlying system.

If we consider a homeostatically-regulated physiological system, then the value of that system may be normal, while the underlying physiological system is stressed. Thus, measurement of the level alone will only reveal perturbation once the homeostatic ability is overcome or defective, while underlying influences may be obscured. Further, measurement of feedback variables may reveal perturbation even where the controlled variable is in a normal range. For example, the accelerating value of Prostate-Specific Antigen (PSA) may indicate an early stage of malignant disease of the prostate, while the value may still be within the normal range. If one considers the slope or trend of the velocity of change, one must also consider within the homeostatically controlled system what the limit of the trend is, which then requires defining an interval of interest, since the trend may not be enduring.

However, when one looks at the second derivative of any variable within the system, the control dynamics of the system emerge. As one looks to even higher derivatives, these tend to be dominated by noise, and even sharp changes in a third derivative are not necessarily correlated with physiologically important events related to health.

Thus, the present invention relates to the extraction and analysis of dynamic variations in physiological parameters reflecting the effects of self-regulatory feedback loops within the system. In a continuous system, the dynamic variation corresponds to the second derivative, while in other systems, the corresponding concept may be adopted as the dynamic process which restores the system to a predetermined state. Note that simple first-order feedback will reduce error, but not restore the system, while homeostatic systems may fully or even overcompensate for perturbations, requiring a higher-order control. These systems have a time characteristic within their dynamics, with a response delay, and in some cases, a predictive response.

When analyzing such systems, the level and change rate of the parameter are not irrelevant, but can often be considered using traditional analysis. However, with higher-order analysis, the level and rate may be better interpreted in a broader, dynamic context. For example, hyperthermia may be quite abnormal, but if the dynamic physiological response to the hyperthermia is sufficient, the temperature alone may not represent the best basis for determining the action. On the other hand, subacute hyperthermia with a poor dynamic homeostatic response may be cause for alarm. Similarly, the issues are the same for most, if not all, homeostatically controlled variables and also the effector variables, especially if correlations with the controlled variables are considered, and alternate hypotheses analyzed and excluded. Thus, the analysis of the second-order dynamic system has fundamental distinctions from level and rate analyses, since it is better mapped to the underlying physiology, and the physiological defects that correspond to disease as differentiated from natural (and not pathological) responses.

Modern medicine often treats symptoms that represent natural responses, and thus can actually defeat the body's ability to restore itself, and therefore weaken the systems or the organism. Likewise, modern medicine tends to withhold treatment of subclinical symptoms, considering early intervention to correspond to overtreatment. Such medical decisions are often made based on the static snapshot of a particular system, which may be a poor representation of the underlying dynamics of a live organism. However, by extracting the underlying dynamics of the physiological systems, pathology and homeostatic responses may be better distinguished, with therapy targeted and titrated based on the pathology to avoid interference with normal and helpful natural responses.

On the other hand, in some cases, natural responses may be harmful; for example, autoimmune and inflammation responses, and, therefore, early intervention once these are detected may preempt symptoms.

One goal of the present invention is to detect and employ a second derivative (or discrete and/or statistical analogs thereof) or (at least) second-order differential equation of one or more physiological parameters, to better forecast the evolution of physiological states or symptoms and underlying disease, distinguish actionable patient states, and guide therapeutic intervention or withholding thereof.

According to the aspects illustrated herein, the invention includes a method of forecasting change in the physiological parameters of the human (or animal) body, based on an analysis of the second derivative and, more generally, higher-order (order>1) dynamic responses. In cases where multiple sensed parameters are available, statistical techniques may be employed, at various orders of dynamic evaluation, to produce more sensitive or earlier, accurate or precise, more reliable, or otherwise improved information upon which to alert a patient or health care provider of a need to change or consider changing therapy.

As noted above, the analysis need not be in a continuous-time, analog domain, or a discrete-time digital data domain (time series), and may be in a hybrid domain or other domain. Various parameters may be considered, using statistical techniques, or other combination techniques to increase the quality of diagnosis or treatment.

This technology may be used, for example, to detecting a change in patient status that may require medical attention, or on the other hand, a relaxation of strict medical constraints or treatment regime.

This technology may also be used to estimate the biological age of a particular organ, system, or subject as a measure of biological systems to return to homeostasis after stress, which depends on the effectiveness of self-regulatory feedback mechanisms. This biological age may have predictive value to assess future health and progression of chronic disease. The biological age, in turn, may be used to titrate therapy or assess test results.

The method, for example, may employ a traditional second derivative of a continuous function reconstructed through curve-fitting, or periodically oversampled smooth time function representing a physiological parameter. The method may also employ finite differences and other similar techniques of discrete analysis. However, the method may also encompass signals which are aperiodically sampled at discrete time intervals, or otherwise fail to meet definitions for a smooth, continuously differentiable function.

For example, a glucose measurement of a patient may be taken every 5 minutes, with a sampling duration of 10 seconds, and a time imprecision of measurement of 10 seconds (+/−5 seconds). In fact, the underlying blood glucose levels may vary with a half-life of 15 minutes for IV glucose. (Hahn, Robert G., and Thomas Nyström. "Plasma volume expansion resulting from intravenous glucose tolerance test." Computational and mathematical methods in medicine 2011 (2011), www.hindawi.com/journals/cmmm/2011/965075/.) As a result, the blood glucose level is oversampled, and, therefore, a curve may be optimally fitted to, e.g., 5 data points (−20 minutes, −15 minutes, −10 minutes, −5 minutes, 0 minutes), with a weighting of more recent times over prior times. The second derivative (or second-order finite difference) is calculated for the terminal value as a basis for determining a prospective need for insulin, glucose, or fructose.

The present technology also preferably normalizes the signal, applying statistical analysis to the higher-order difference resulting from the signal, predicting timing offset and the effect on the higher-order difference, and employing an absolute level of the physiological parameter sensitivity in the analysis. For example, when considering a parameter in which elevation over baseline is problematic, an alert threshold for the higher-order difference is suppressed near the baseline and becomes more sensitive as the normalized value of the signal increases. If the parameter has known dynamics, a physical model reflecting those dynamics may be employed to create an expectation according to the model or, in the absence of the established model, to a hypothesis. So long as the expectation agrees with the hypothesis, a predicate for the hypothesis is validated. When a deviation of the expectation of the higher-order difference of the signal occurs, the underlying hypothesis should be investigated and the cause of deviation considered. Depending on the urgency of the detection of a change in status, a statistical temporal analysis of the signal, signal difference, and higher-order difference over-time, may be analyzed to filter unattributed variance, e.g., noise.

In cases where an immediate response to a change in the patient's state is required, a statistical temporal analysis may only be backward-looking, and the system must remain sensitive to immediate changes.

The methods of calculating the diagnostic values are provided, and hence, medical devices and implants and other wearable biometric devices can be made using this technology. The devices need not be wearable, and in some cases, remote sensing such as imaging/video, radar, lidar, sonar, or another remote or non-contact physiological sensing may be employed.

The present technology considers homeostatically controlled biological systems through the tools of dynamic system analysis and therefore addresses their implied stability and instability criteria, fragility, and interconnection with other dynamic systems. Therefore, a measurement of a biological parameter over time is considered with respect to its dynamic impact on and reflection of the health of the organism, with application toward diagnosis and prognosis, on the one hand, and predicting the need for and optimization of treatment, on the other hand. By considering the state of the biological system and various stability criteria, in view of the natural homeostatic mechanisms available (and consideration of any defects in the natural mechanisms), treatment may be applied to supplement the natural mechanism, in the general case, such as strengthening and/or augmenting self-regulatory mechanisms and feedback loops or overriding that mechanism where an aberrant response occurs (such as in autoimmune response) or where therapy requires overcoming that mechanism. By considering the dynamic response of the system and the organism, the correct treatment may be applied over time, in the case of therapeutic use, or prediction of system and health state accurately made in the case of monitoring.

It is posited that the second derivative of a physiological parameter in a biological system presents an important diagnostic and predictive value. The present invention provides for a method and a device for periodic sampling of physiological parameters and approximating the second derivative over time of the collected data to use for therapeutic, diagnostic, and predictive purposes. The physiological parameter of interest may be measured under a presumption that it is a smooth function over time, which has at least a first derivative and a second derivative over time.

An obvious and intuitive way of dealing with discrete data resulting from sampling a smooth process is to interpolate the data on a simple (e.g., polynomial) function, which allows the application of regular differentiation by taking the first and second derivative of the interpolated function. However, when automated processors are employed, this intuitive approach is not necessary, and more direct calculations may be applied.

In one preferred embodiment, the present invention discloses a method of diagnosis using biometric devices periodically taking a sample of a biological specimen, measuring a level of at least one physiological parameter of the sample, and then storing a value representing the level of said at least one physiological parameter in a non-transient long-term memory. The method further comprises ascertaining a change over time (first derivative) of said at least one physiological parameter and then ascertaining a rate of change (second derivative) of said at least one physiological parameter.

In another preferred embodiment, the present invention discloses a method of retrieving data representing the level of at least one physiological parameter over a period of time, ascertaining a change over time of said at least one physiological parameter by approximating a first derivative of the level over time by calculating finite differences and ascertaining the rate of change of said at least one physiological parameter by approximating a second derivative of the level over time by calculating the second finite difference, wherein the finite difference can be, for example, a forward finite difference, a backward finite difference, or, a center finite difference.

In a preferred embodiment, the present invention discloses a method of diagnostics comprising steps of measuring a level of at least one physiological parameter in a subject (human or animal), approximating the first derivative and the second derivative of said at least one physiological parameter over time, to determine a health hazard or risk and sending an alert to the subject or a healthcare provider quantitatively dependent on the health hazard or risk.

In a preferred embodiment, the present invention discloses a biometric device for measuring at least one physiological parameter in a subject (human or animal) comprising a housing at least partially containing the device, at least one sensor for measuring said at least one physiological parameter, a non-volatile memory operatively connected to said at least one sensor and an automatic processor operatively connected to said at least one sensor, where the processor is configured to calculate at least one second-order temporal parameter of said at least one physiological parameter, the second-order parameter being, for example, a second derivative, a second-order equation, or the like. The biometric device may be an implantable or a wearable device. Alternatively, the biometric device may be external to the body of the subject and obtain a measurement of said at least one physiological parameter remotely, such as, for example, using a laser beam for optical tomography and/or spectroscopy, a camera or video camera, a radar, lidar, or sonar sensor, electrophysiological sensors, microphone, inertial or absolute position sensors, or other types of sensors.

In a preferred embodiment, a biometric device is provided for measuring at least one physiological parameter, comprising a communication module configured to send an alert to a person and/or a healthcare provider, dependent on a deviation of the measured at least one physiological parameter from that predicted by an at least second-order model of the person. For example, the alert may be sent when the future value of said at least one physiological parameter, computed using a value of the physiological parameter, its first derivative, and the second derivative, is predicted to will exceed a predetermined or adaptively determined threshold value indicating an abnormal condition or a medical condition, for example at any future time, within a predetermined time interval, or an adaptively determined interval. The device may calculate reliability of a prediction, and weight the expected excursion of the value of the physiological parameter from its nominal value (i.e., health risk if the prediction is accurate), and the statistical likelihood that predicted the excursion would occur. For example, a low risk of a large excursion may justify an alert, while a modest risk of a small excursion may not warrant an alert.

Clearly, a high risk of a large excursion justifies an alert, and a predicted lack of excursion does not justify an alert.

A biometric device may be provided for measuring at least one physiological parameter in a person, further comprising at least one actuator configured to perform an action when an at least second-order model of the biological system of the person associated with said at least one physiological parameter predicts an aberration corresponding to a health risk, which may be, for example, that the second derivative exceeds a predetermined threshold value or if the future value of said at least one physiological parameter computed using the absolute value, the first derivative and the second derivative will exceed a predetermined threshold value.

A biometric device may be further provided for measuring at least one physiological parameter in a person, further comprising a lab-on-a-chip configured to test a plurality of physiological parameters, and a controller configured to control the lab-on-a-chip (or lab on paper) and read outputs therefrom. The controller may be an FPGA, or traditional microprocessor with peripheral input-output interfaces.

It is, therefore, an object to provide an apparatus for analyzing a biological system, comprising: an input port configured to receive quantitative information reflecting at least one physiological parameter of the biological system over time; a processor configured to: perform a dynamic analysis on said at least one physiological parameter dependent on at least one derivative of the second-order of said at least one physiological parameter of the biological system; predict a future state of said at least one physiological parameter or of the biological system based on the dynamic analysis; analyze the predicted future state according to at least one decision criterion; and an output port configured to generate at least one alert selectively dependent on the analysis.

The physiological parameter may be selected from at least one of a heart rate, a cardiac stroke volume, a blood pressure, a respiratory rate, respiratory volume, and a body temperature.

The apparatus may be an implantable device or a wearable device,

The quantitative information may be derived from at least one of a motion sensor, a proximity sensor, a barometric sensor, a pressure sensor, a thermometer, a galvanic skin sensor, a photoplethysmography sensor, an electroencephalogram sensor, an electromyogram sensor, a blood flow sensor, a bio-impedance sensor, an altimeter, optical sensor, and a ultraviolet light sensor.

The processor may be further configured to communicate with an online server.

The apparatus may further comprise at least one actuator responsive to the analysis of the predicted future state.

The processor may comprise an FPGA.

The apparatus may further comprise a lab-on-a-chip configured to test a plurality of said at least one physiological parameter. The apparatus may further comprise a lab-on-a-paper.

It is also an object to provide a method for measuring at least one physiological parameter of a user and sending an alert to the user and a healthcare provider indicating abnormal health condition of the user, the method comprising: sampling a biological process; measuring a value of the sampled biological process; storing the measured value in a nonvolatile memory; determining parameters of a dynamic model equation of at least second-order predictive of the biological process; determining a deviation of the biological process from a prediction based on the dynamic model; and applying a decision criterion to the determined deviation; producing an output selectively dependent on the applied decision criterion.

The biological process may be a process selective from the group consisting of a neurological process, a muscular process, a skeletal process, a digestive process, a cardiac process, a respiratory process, a renal process, a dermal process, a reproductive organ process, a hemodynamic process, an electrochemical process, a blood chemistry process, and a vascular process.

Said at least one physiological parameter may be selected from the group consisting of at least one of a heart rate, a cardiac stroke volume, a blood pressure, a respiratory rate, respiratory volume, and a body temperature The decision criterion may be a threshold value determined according to the normal range of the physiological parameter for a healthy body condition.

The output may comprise an alert sent wirelessly in the form of a message or text, an alert that may be displayed on display proximate to the user, an alert sent to a remote the health care provider for the user, or an alert communicated through an online server.

It is a further object to provide a method for measuring at least one physiological parameter of a user and sending an alert to the user and a healthcare provider indicating abnormal health condition of the user, the method comprising: determining at least one physiological parameter by a sensor; storing a value representing the determined at least one physiological parameter in a non-volatile memory; ascertaining an at least second-order predictive model for said at least one physiological parameter and storing the at least second-order predictive model in a non-transitory storage database; determining a consistency of the at least second-order predictive model with the user; determining a predicted deviation of the user from a reliable at least second-order predictive model; and issuing an alert based on a predicted deviation and reliability of occurrence of the predicted deviation.

It is a still further object to provide a biometric device for forecasting at least one physiological parameter in a subject, the device comprising: at least one probe configured to measure said at least one physiological parameter; a non-volatile memory configured to store values of said at least one physiological parameter; a processor operatively coupled with the non-volatile memory and configured to: determine an initial value of said at least one physiological parameter at a given time to; determine an initial value of a first derivative of said at least one physiological parameter at the time to; approximate a first derivative of said at least one physiological parameter over time; approximate a second derivative of said at least one physiological parameter over time; compute the future value of said at least one physiological parameter at a future time $t_1$; compare the computed future value of said at least one physiological parameter at the future time $t_1$ with a predetermined threshold value; and an output operatively coupled to the processor configured to generate at least one signal if the computed future value of said at least one physiological parameter at the future time $t_1$ is equal or greater than the predetermined threshold value.

The biometric device may be one of a wearable device, an implanted device, and a remote device.

The subject may be one of a human subject and an animal subject.

Said at least one physiological parameter may be regulated by a homeostatic system. Said at least one physiological parameter may be an effector of a homeostatic system.

The first derivative and the second derivative are approximated by fitting a smooth curve on a dataset of values of said at least one physiological parameter; and taking respectively first and second derivatives over time of the smooth curve. The first derivative and the second derivative are approximated by computing a first finite difference and the second-order finite difference, wherein the finite difference may be one of a backward derivative, a forward derivative, and a centered derivative.

The future time $t_1$ may be the time for which a future value of said at least one physiological parameter needs to be predicted.

The threshold value may be a critical value indicating the mortal danger of the subject, a critical value indicating an irreversible change in a biological system upon which the homeostasis cannot be naturally reversed, a critical value exceeding a homeostatic range, indicating a need for medical intervention, or a value of concern indicating likely disease.

The biometric device may further comprise the actuator operatively coupled to the output; the actuator configured to be triggered by the signal. The actuator may be configured to deliver one of a pharmacological agent and an electric stimulus.

It is another object to provide a system for analyzing at least one physiological parameter of a user and sending an alert to the user and a healthcare provider indicating the medical condition of the user, the biometric device comprising: a housing containing the biometric device; a non-volatile memory operatively connected to said at least one sensor; said at least one sensor configured to measure at least one physiological parameter; a processing module operatively connected to the non-volatile memory, wherein the processing circuitry comprises: a measuring module configured to receive and store the measured physiological parameter in the non-volatile memory; a calculation module configured to determine a first derivative and a second derivative of said at least one physiological parameter; a determination module configured to determine a threshold level of said at least one physiological parameter; a configurable analysis module configured to compare a value dependent on at least the second derivative with the determined threshold level; and a communication module, configured to generate the alert to the user and to the health care provider if the value exceeds the threshold level.

It is also an object to provide a method of forecasting an evolution in time of at least one physiological parameter in a subject, the method comprising: sampling values of said at least one physiological parameter over a period of time; creating a dataset of values of the sampled values; approximating a first derivative of said at least one physiological parameter from the dataset of values; approximating a second derivative of said at least one physiological parameter from the dataset of values; and using at least the second derivative of said at least one physiological parameter to forecast the value of said at least one physiological parameter beyond the time period.

The subject may be one of a human subject and an animal subject.

The sampling values of said at least one physiological parameter over the period of time may be a periodic sampling or an aperiodic sampling.

The period of time may be longer than, shorter than, or approximate a natural period of fluctuation of said at least one physiological parameter.

The dataset of values may be organized in a relational database, wherein the table of the values of said at least one physiological parameter may be linked with a table of time points at which each of the values was sampled, a table of objective physiological data for the subject representing time points within a time range at which the values of said at least one physiological parameter were sampled, a table of subjective health data for the subject representing time points within a time range at which the values of said at least one physiological parameter were sampled, a table of physiological data other subjects that that from which the values of said at least one physiological parameter were sampled, or a table of physiological data the subject acquired over a time range different from that from which the values of said at least one physiological parameter were sampled.

The method may further comprise fitting a curve on values of the dataset, wherein approximating the first derivative of said at least one physiological parameter may be done by taking the first derivative of the curve, and approximating the second derivative of said at least one physiological parameter may be done by taking the second derivative of the curve. The curve may be fitted to include each value of the dataset or may be fitted to exclude at least one value of the dataset. The curve may be fit by a statistical process responsive to a curve-fitting error. The curve may be fit by an artificial neural network. The curve may be a Bezier curve.

Approximating the first derivative of said at least one physiological parameter may be done by calculating a first-order finite difference on the dataset. The first-order finite difference may be one of a forward finite difference, a backward finite difference, and a centered finite difference. Approximating the first derivative of said at least one physiological parameter may be done by calculating a second-order finite difference on the dataset. The second-order finite difference may be a five-point stencil.

The method may further comprise setting at least one threshold level of the forecasted value, and producing an output dependent on a relationship of the forecasted value and said at least one threshold level of the forecasted value.

The method may further comprise evaluating a function dependent on at least the second derivative with respect to at least one threshold level.

The method may further comprise issuing an alert dependent on the evaluation.

Said at least one physiological parameter may be measured in the subject by a biometric device having a sensor, the method further comprising: measuring the values of said at least one physiological parameter with the sensor; storing the measured values in a non-transient memory; maintaining the dataset of the values in the non-transient memory of the device; approximating the first derivative and the second derivative with an automated processor, and storing the first derivative and the second derivative in the non-transient memory of the device; and outputting at least the value of the second derivative from the biometric device.

A further object provides a method of diagnosing a physiological status of a biological system in a subject, the method comprising: sampling a plurality of values of at least one physiological parameter over a period of time representing the physiological status; storing the plurality of values of said at least one physiological parameter in a database; approximating an at least second-order equation modelling the physiological status of the biological system in the subject over time; and using at least the second-order equation and successive values of said at least one physiological parameter to diagnose the physiological status of the biological system in the subject.

The diagnosis of the physiological status may be selected from the group consisting of a healthy steady-state, an unhealthy steady state, an unstable state. The healthy steady-state may indicate the diagnosis of the healthy biological system, the unhealthy steady state indicates a chronic disease of the biological system, and the unstable state indicates an acute condition. The diagnosis may be one of an acute condition and a chronic disease, and the method further comprises the step of sending an alert with the diagnosis to the subject and/or a healthcare provider for the subject.

A still further object provides a method of monitoring health of a subject, comprising: acquiring data representing a health-responsive parameter; filtering the data with a statistical filter to produce a differentiable output; providing an at least second-order predictive model, the model comprising a statistical decision boundary with respect to both probability of the existence of a future state and a predicted severity of the predicted future state; determining an output, based on the statistical decision boundary of the at least second-order predictive model, and a time-series of the data.

The statistical filter may comprise a Kalman filter.

The at least second-order predictive model may comprise at least one second-order differential equation.

The statistical decision boundary may comprise an empirically-determined prognosis algorithm, dependent on normalized population data for the subject, an artificial neural network trained based on clinical data, an expert-defined set of rules, or an adaptively-determined algorithm, dependent on at least prior data from the subject.

The data representing a health-responsive parameter may be acquired through a non-contact sensor, a contact sensor, an electrophysiological sensor, a chemical sensor, a cardiac sensor, a sensor through a wireless communication link, or an implantable sensor.

The at least second-order predictive model may be adaptively updated.

The data representing a health-responsive parameter may comprise a plurality of different health-responsive parameters.

The data representing a health-responsive parameter may be acquired periodically or aperiodically.

The data representing the health-responsive parameter may comprise a plurality of different health-responsive parameters. The subject may have a chronic illness for which the at least second-order predictive model differs in form from normal members of the subject's species. The subject may have an acute illness for which the at least second-order predictive model may be in common form with normal members of the subject's species.

The method may further comprise acquiring data from the subject to establish initial conditions for the at least second-order predictive model.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Referring now more particularly to the drawings, advantageous features of a biometric device like the device has been described that works on an efficient procedure to measure different physiological parameters and generate an alert indicating abnormal body conditions with embodying the principles of the present invention.

Figure 1:
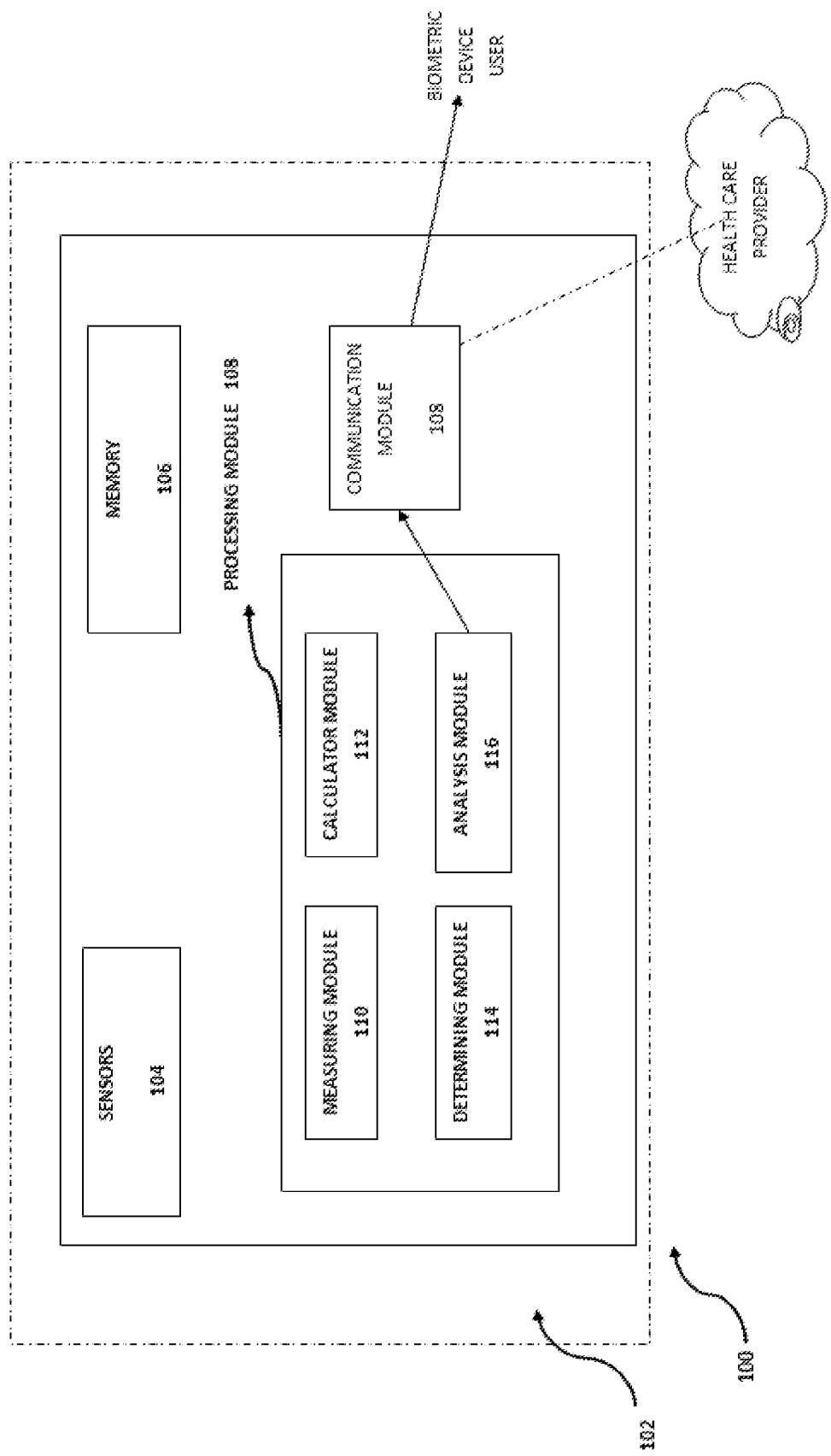
FIG. 1 illustrates a biometric device that is in accordance with at least one of the various embodiments.

FIG. 1 presents a schematic illustration of a biometric device (100) in accordance with one of the embodiments of the present invention. The biometric device (100) may be wearable or implantable. This device provides data or analysis for a health care provider or a simple user of the device. The biometric device (100) further comprises a housing (102) for at least partially containing the biometric device. A non-volatile memory (106) or non-transitory storage media may be present for storing data related to the measurement of at least one physiological parameter. A sensor (104) for measuring at least one physiological parameter is provided, either internal or external to the device. The sensor (104) may be any suitable known physiological parameters sensor or a sensor for sensing a derivative or indirect value associated with a physiological parameter.

For example, and without limitation, the sensor may be selected from a motion sensor, a proximity sensor, a barometric sensor, a pressure sensor, a thermometer, a galvanic skin sensor, a pulse oximeter, an ion or solute sensor, an electrochemical and/or enzyme-linked electrochemical sensor, a spectrophotometric or spectrofluorometric sensor, an NMR or ESR sensor, a photoplethysmography sensor, an electrocardiogram sensor, an electroencephalogram sensor, an electromyogram sensor, a blood flow sensor, a bio-impedance sensor, an altimeter sensor, optical sensor, an infrared sensor, or an ultraviolet light sensor.

The biometric device (100) may further comprise or communicate with an external processing module (108) operatively connected to the non-volatile memory (106) for executing a series of steps to execute an algorithm for analyzing or preliminarily analyzing data from the sensor.

The processing module comprises a measuring module (110) configured for storing and receiving the measured physiological parameter in the non-volatile memory, an analysis module (112) designed to determine higher-order dynamic characteristics (e.g., a first derivative and a second derivative) of said at least one physiological parameter, a configurable analysis module (116) to determine whether the higher-order dynamic characteristic (e.g., second-order formulation) conforms with the predetermined or adaptively determined criteria, a communication module (118), to selectively communicate a message dependent on the higher-order dynamic characteristic, e.g., to generate an alert signal to the user and/or to the health care provider. The health care provider may be a doctor, surgeon, or any medical specialist who is located at a remote location and is connected to the device (100) directly or by means of an online server.

The analysis may provide a weighted analysis with discounting of values of past physiological sensor readings, and/or provide a suite of calculations taking into consideration all or some of the past data. For example, an analysis emphasizing the last parameter received will be single-ended, while a retrospective analysis of the prior 10 or 100 data points may be effectively double-ended. While this double-ended analysis will produce a delayed result, its use may improve interpretation of the most recent data point(s), and therefore reduce false positive and false negative messages.

The biometric device (100) measures at least one physiological parameter, and an abnormal condition is determined or predicted based on the analysis algorithm. The basic methodology employed by a processing module (108) is to ascertain the dynamics of the underlying homeostatic system involving at least one physiological parameter. The physiological parameter may be cardiovascular, metabolic, thermal, electrolyte balance, musculoskeletal, neurological, digestive, renal, etc.

Figure 2:
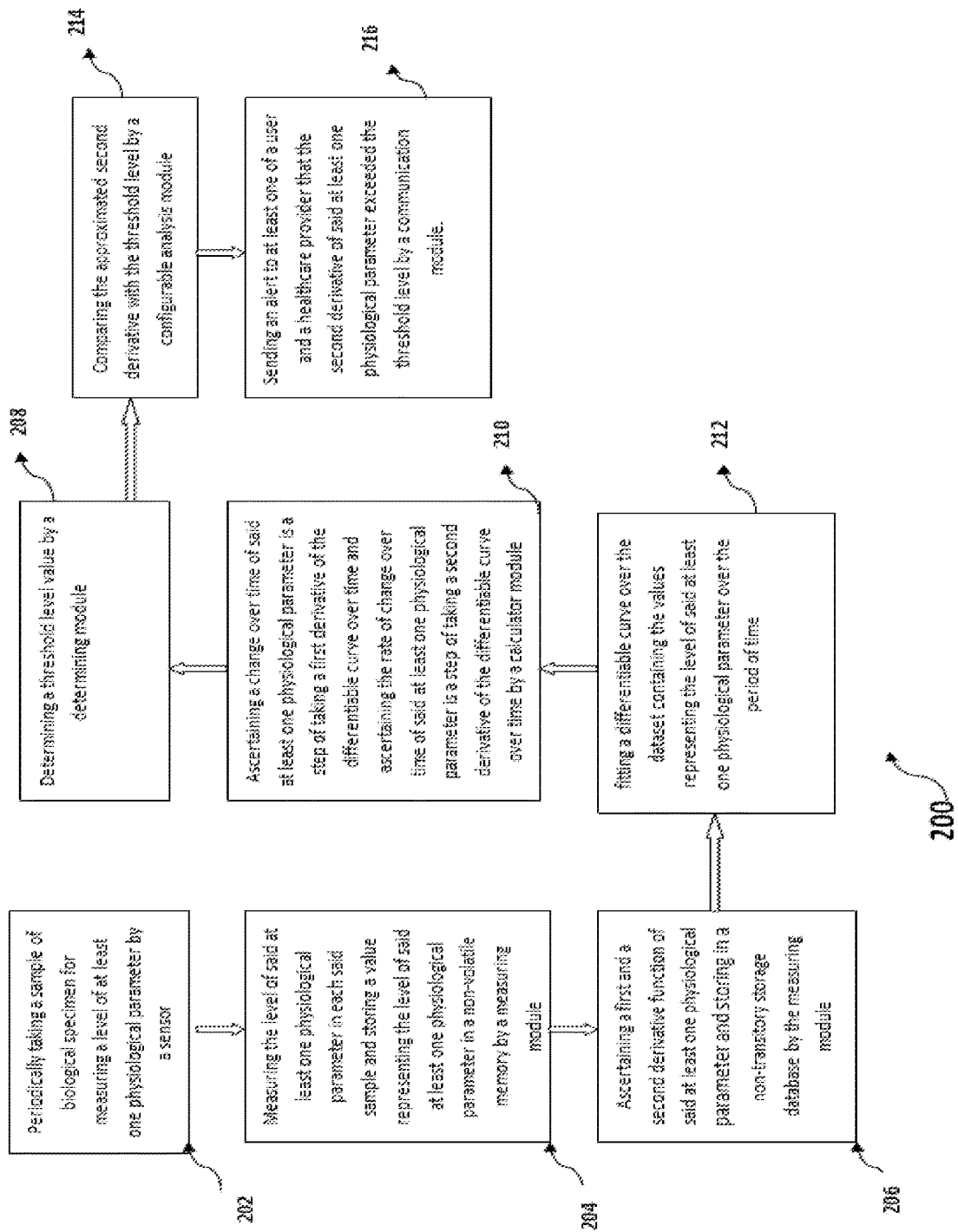
FIG. 2 is a flowchart showing a process for a method of diagnostic and generating alert in case of medical condition in accordance with one of the embodiments of the invention.
Figure 3:
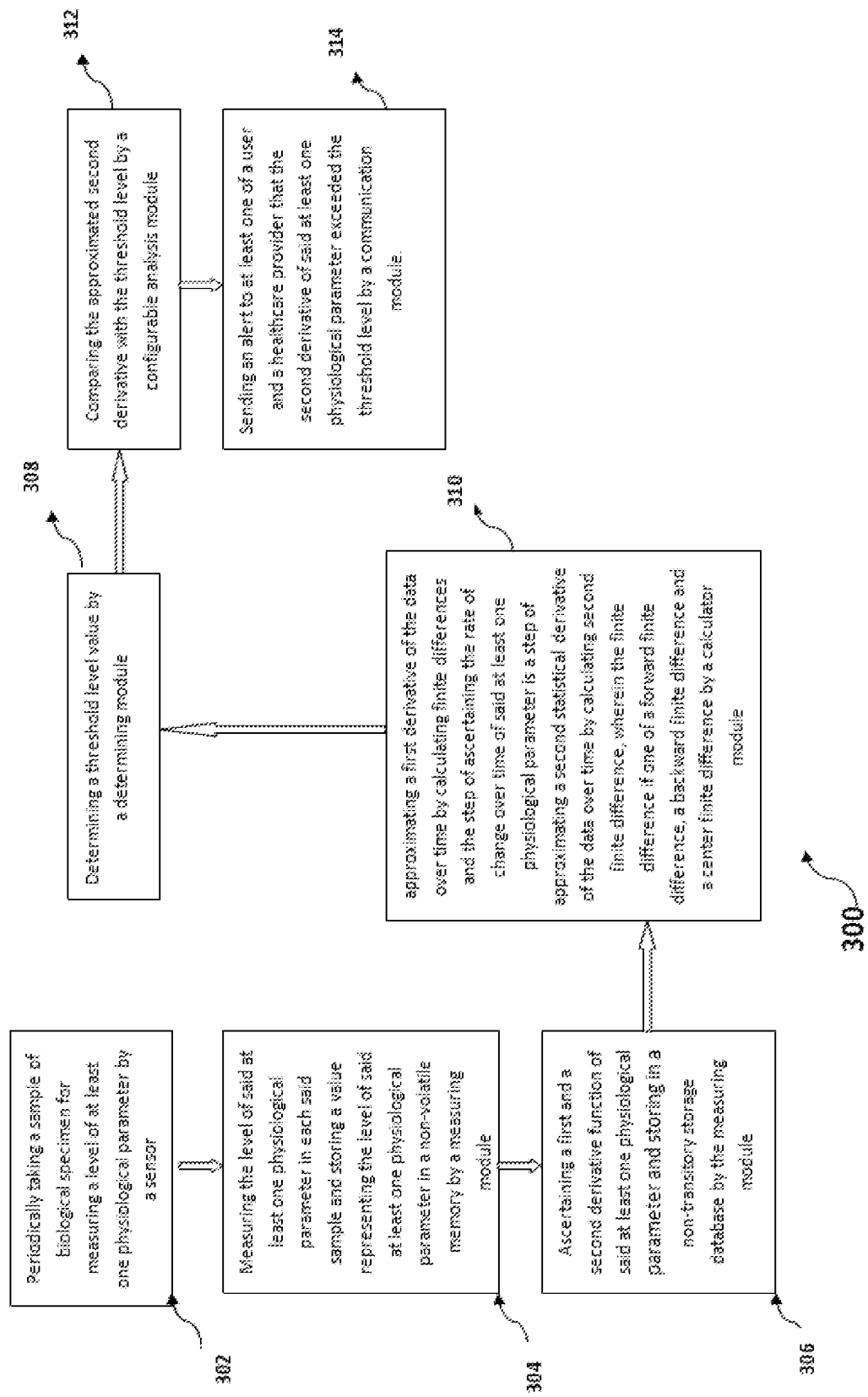
FIG. 3 illustrates a flowchart showing a process for a method of diagnostic and generating alert in case of medical condition in accordance with another embodiment of the invention.

FIG. 2 and FIG. 3 illustrate flowcharts for a process for diagnosing and generating an alert in case of an abnormal condition of a user's health. FIG. 2 discloses a series of steps (200) of measuring physiological parameters using a biometric device (100). The steps include periodically taking a sample of biological specimen for measuring a level of at least one physiological parameter by a sensor at (202), measuring the level of said at least one physiological parameter in each sample and storing a value representing the level of said at least one physiological parameter in a non-volatile memory by a measuring module at (204), ascertaining a higher order dynamic response function of said at least one physiological parameter, determining if the higher order dynamic response function is actionable with respect to a medical or physiological criterion, and generating a message in dependence on the determining and storing data representing the physiological parameter in a memory by the measuring module at (206), fitting a differentiable curve over the dataset containing the values representing the level of said at least one physiological parameter over the period of time (212), ascertaining a change over time of said at least one physiological parameter is a step of taking a first derivative of the differentiable curve over time and ascertaining the rate of change over time of said at least one physiological parameter is a step of taking a second derivative of the differentiable curve over time by a calculator module (210), determining a threshold level value by a determining module (208), comparing the approximated second derivative with the threshold level by a configurable analysis module (214), sending an alert to at least one of a user and a healthcare provider that the second derivative of said at least one physiological parameter exceeded the threshold level by a communication module (216). As discussed above, rather than analyzing the second derivative per se, an equation or model of at least second-order may be analyzed, with actionable conditions determined, not based on a fixed threshold, but rather on a deviation from the model prediction.

FIG. 3 discloses a series of steps (300) for measuring physiological parameters using a biometric device with the application of a different mathematical approach (100). The steps include periodically taking a sample of biological specimen for measuring a level of at least one physiological parameter by a sensor at (302), measuring the level of said at least one physiological parameter in each sample and storing a value representing the level of said at least one physiological parameter in a non-volatile memory by a measuring module at (304), ascertaining a first and a second derivative function of said at least one physiological parameter and storing in a non-transitory storage database by the measuring module at (306), approximating a first derivative of the data over time by calculating finite differences and the step of ascertaining the rate of change over time of said at least one physiological parameter is a step of approximating a second statistical derivative of the data over time by calculating second finite difference, wherein the finite difference if one of a forward finite difference, a backward finite difference and a center finite difference by a calculator module (310), determining a threshold level value by a determining module (308), comparing the first and second derivative function with a reference function a configurable analysis module (312), sending an alert to at least one of a user and a healthcare provider that the first and second derivative of said at least one physiological parameter deviates from the reference function by a communication module (314).

Figure 4:
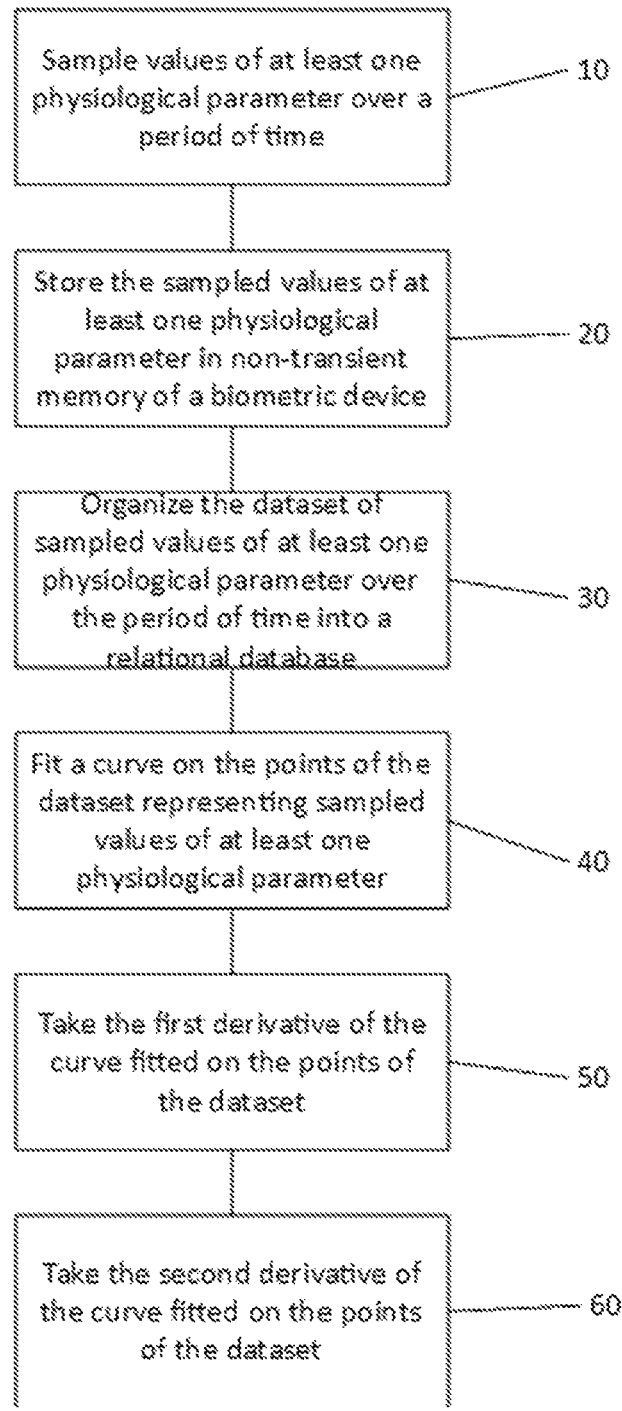
FIGS. 4-9 show flowcharts of processes according to various embodiments of the invention.

FIG. 4 shows a flowchart of a process, wherein sample values of at least one physiological parameter over a period of time 10. The sampled values of at least one physiological parameter are stored in non-transient memory of a biometric device 20. The dataset of sampled values of at least one physiological parameter over the period of time is organized into a relational database 30. A curve is fit on the points of the dataset representing sampled values of at least one physiological parameter 40. The first derivative 50 and the second derivative 60 are taken of the curve fitted on the points of the dataset.

Figure 5:
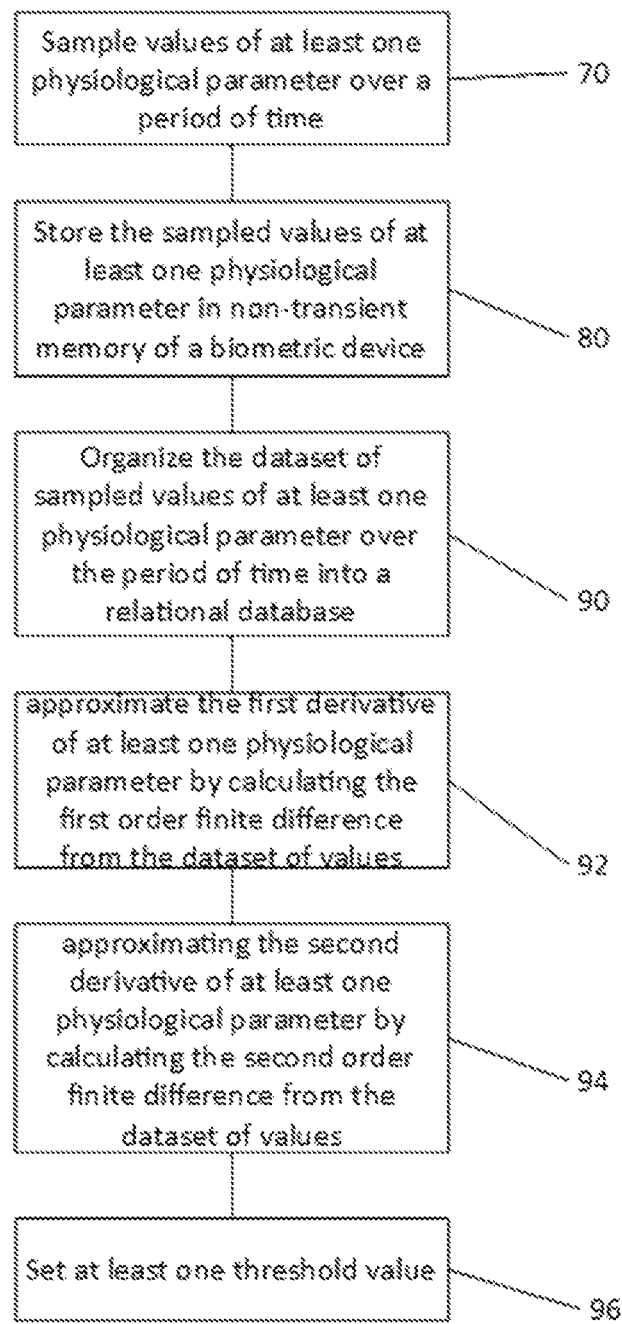

FIG. 5 shows a flowchart of a method in which values of at least one physiological parameter over a period of time are sampled 70. The sampled values of said at least one physiological parameter are stored in non-transient memory of a biometric device 80. The dataset of sampled values of at least one physiological parameter over the period of time is organized into a relational database 90. The first derivative of said at least one physiological parameter is approximated by calculating the first-order finite difference from the dataset of values 92. The second derivative of said at least one physiological parameter is approximated by calculating the second-order finite difference from the dataset of values 94. At least one threshold value is set 96.

Figure 6:
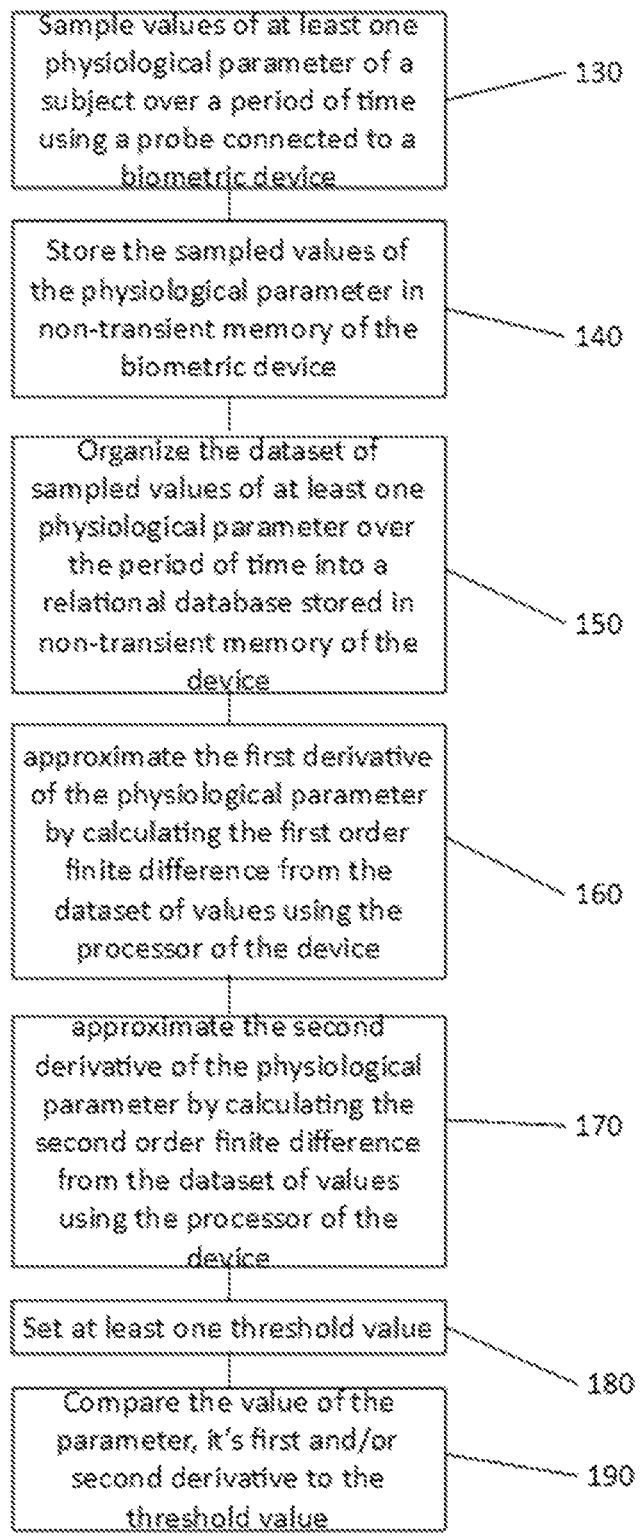

FIG. 6 shows a flowchart of a method in which values of at least one physiological parameter of a subject are sampled over a period of time using a probe connected to a biometric device 130. The sampled values of the physiological parameter are stored in non-transient memory of the biometric device 140. The dataset of sampled values of said at least one physiological parameter over the period of time is organized into a relational database stored in non-transient memory of the device 150. The first derivative of the physiological parameter is approximated by calculating the first-order finite difference from the dataset of values using the processor of the device 160. The second derivative of the physiological parameter is approximated by calculating the second-order finite difference from the dataset of values using the processor of the device 170. At least one threshold value is set 180. The value of the parameter, it's first and/or second derivative is compared to the threshold value 190.

Figure 7:
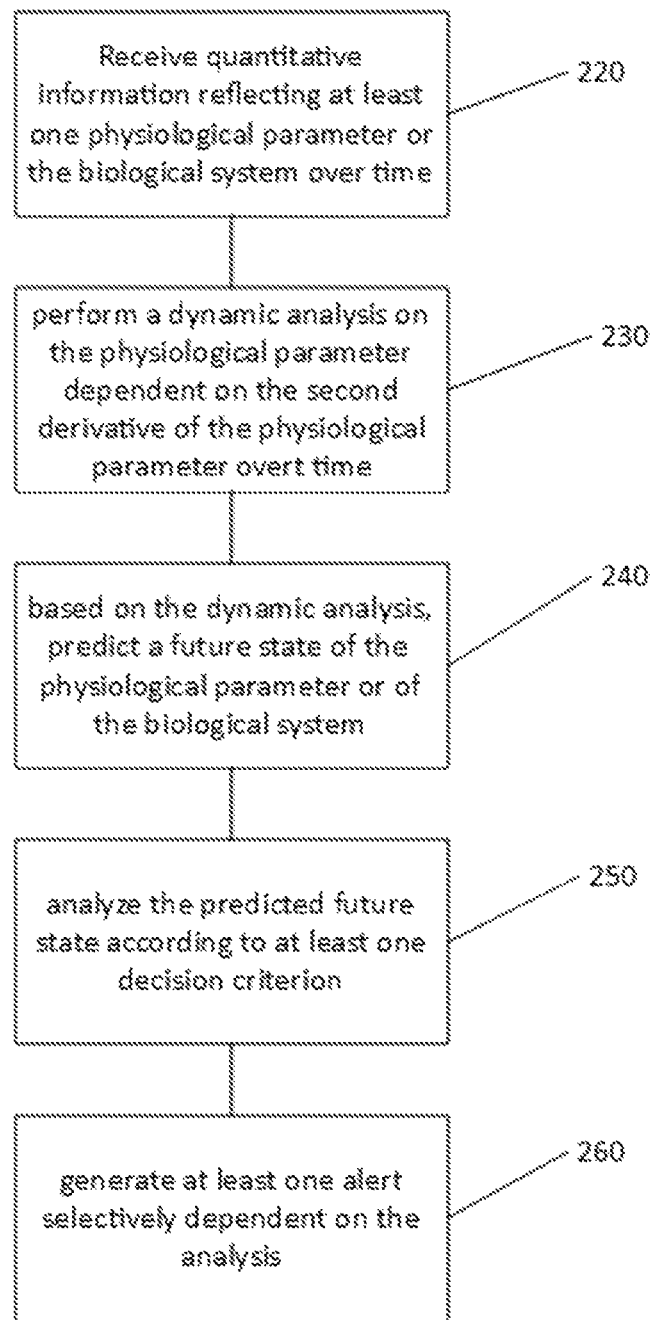

FIG. 7 shows a flowchart of a further method, in which quantitative information reflecting at least one physiological parameter or the biological system is received over time 220. A dynamic analysis is performed on the physiological parameter dependent on the second derivative of the physiological parameter over time 230. Based on the dynamic analysis, a future state of the physiological parameter or the biological system is predicted 240. The predicted future state is analyzed according to at least one decision criterion 250. At least one alert may be selectively generated dependent on the analysis 260.

Figure 8:
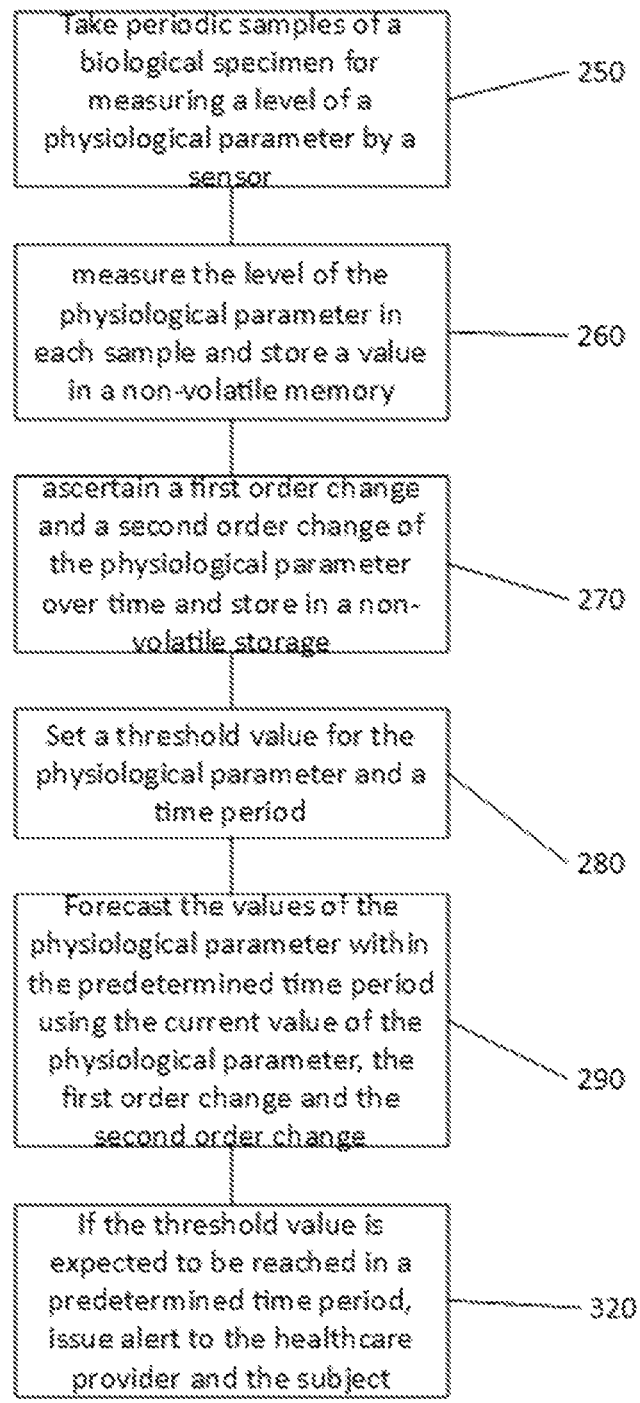

FIG. 8 shows a flowchart of a still further method, in which periodic samples of a biological specimen are taken for measuring a level of a physiological parameter by a sensor 250. The level of the physiological parameter in each sample is measured, and a value stored in a non-volatile memory 260. A first-order change (i.e., "velocity") and a second-order change (i.e., "acceleration") of the physiological parameter is ascertained over time and stored in a non-volatile storage 270. A threshold value is set for the physiological parameter and a time period 280. The values of the physiological parameter within the predetermined time period are forecasted using the current value of the physiological parameter, the first-order change and the second-order change 290. If the threshold value is expected to be reached in a predetermined time period, an alert is issued to the healthcare provider and the subject 320.

Figure 9:
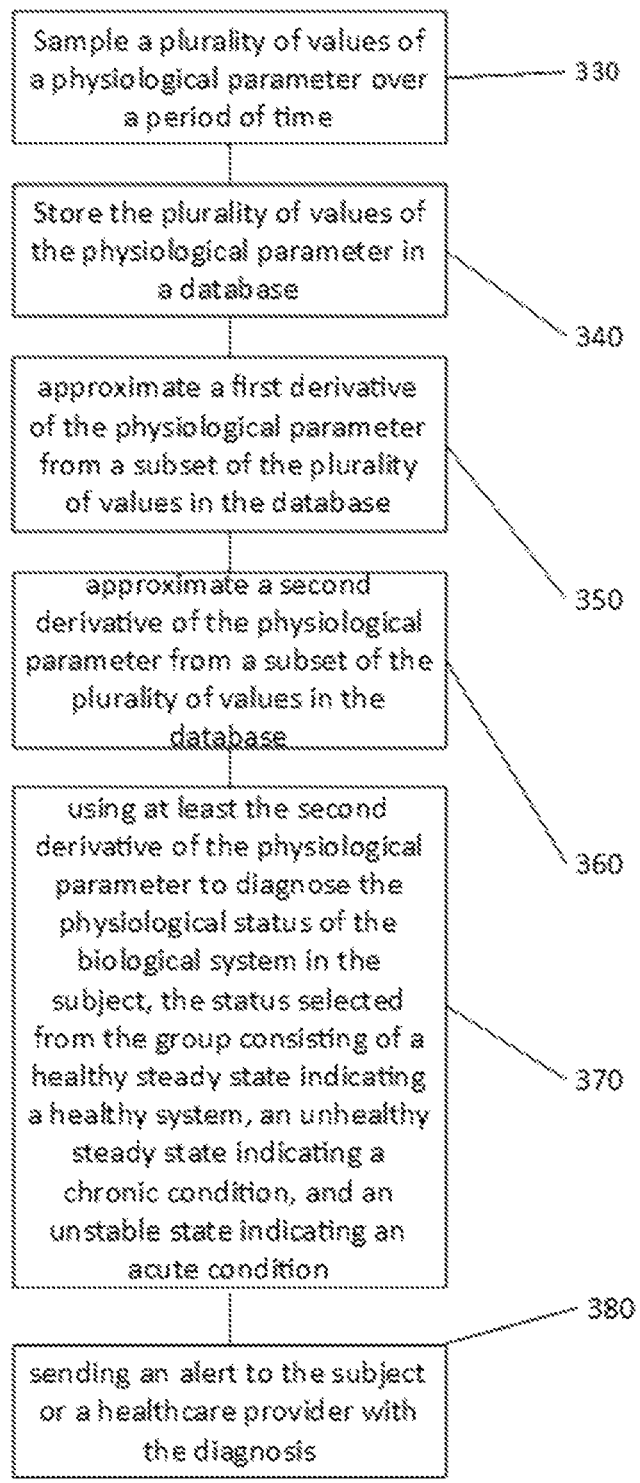

FIG. 9 shows another flowchart of a method, in which a plurality of values of a physiological parameter is sampled over a period of time 330. The plurality of values of the physiological parameter is stored in a database 340. A first derivative of the physiological parameter is approximated from a subset of the plurality of values in the database 350. A second derivative of the physiological parameter is approximated from a subset of the plurality of values in the database 360. At least the second derivative of the physiological parameter is used to diagnose the physiological status of the biological system in the subject, the status being selected from the group consisting of a healthy steady-state indicating a healthy system, an unhealthy steady-state indicating a chronic condition, and an unstable state indicating an acute condition 370. An alert is sent to the subject or a healthcare provider with the diagnosis 380.

As mentioned, there remains the foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood, however, that even though numerous characteristics and advantages of the present invention have been set forth in the foregoing description, together with details of the structure and function of the invention, the disclosure is illustrative only. Changes may be made in the details, especially in matters of shape, size, and arrangement of parts, a specific mathematical or statistical algorithm within the principles of the invention to the full extent indicated by the broad general meaning of the terms in which the appended claims are expressed.

What is claimed is:

1. An apparatus for measuring at least one physiological parameter describing a state of a homeostatically controlled system of a user subject to a process selected from the group consisting of a thermal process, a neurological process, a muscular process, a skeletal process, a digestive process, a cardiac process, a respiratory process, a renal process, a dermal process, a reproductive organ process, a hemodynamic process, an electrochemical process, a blood chemistry process, and a vascular process, comprising:
   an input port configured to receive a signal generated by a sensor corresponding to the at least one physiological parameter;
   a non-volatile memory configured to store a sequence of values representing the at least one physiological parameter over time;
   at least one processor configured to:
      store the sequence values in the non-volatile memory;
      determine a statistical uncertainty of a prior estimate of the sequence of values;
      perform a dynamic analysis of the homeostatically controlled system, based on the stored sequence of values, with a Kalman filter based on an adaptive at least second-order predictive model for said at least one physiological parameter, employing a discrete time change in rate of change of the at least one physiological parameter of the biological system and the determined statistical uncertainty;
      predict a future state of the homeostatically controlled system dependent on the dynamic analysis and the signal, with the adaptive at least second order predictive model;
      update the adaptive at least second order predictive model dependent on the dynamic analysis; and
      determine an inability of the homeostatically controlled system of the user to maintain homeostasis, based on the predicted future state of the homeostatically controlled system and the dynamic analysis;
   automatically issuing an alert selectively dependent on the deviation of the homeostatically controlled system of the user from homeostasis; and
   at least one actuator responsive to the predicted future state and the determined inability of the homeostatically controlled system of the user to maintain homeostasis, configured to alter the at least one physiological parameter.

2. The apparatus according to claim 1, wherein the at least one physiological parameter is selected from at least one of a heart rate, a cardiac stroke volume, a blood pressure, a respiratory rate, respiratory volume, and a body temperature.

3. The apparatus according to claim 1, wherein the apparatus is an implantable device.

4. The apparatus according to claim 1, wherein the apparatus is wearable.

5. The apparatus according to claim 1, wherein the physiological parameter is derived from at least one of a motion sensor, a pressure sensor, a thermometer, a galvanic skin sensor, a photoplethysmography sensor, an electroencephalogram sensor, an electromyogram sensor, a blood flow sensor, a bio-impedance sensor, and an optical sensor.

6. The apparatus according to claim 1, wherein the at least one automated processor is further configured to communicate with an online server.

7. The apparatus according to claim 1, wherein the adaptive at least second order predictive model comprises a Kalman filter.

8. The apparatus according to claim 1, wherein the at least one automated processor is further configured to:
   sample values of said at least one physiological parameter of the biological system over a period of time;
   create a dataset of the sequence of values;
   statistically analyze the dataset comprising the determination of the statistical uncertainty of the prior estimate as an error covariance matrix;

determine a discrete time rate of change as an approximation of a first derivative of said at least one physiological parameter from the dataset of values;

determine the discrete time change in rate of change as an approximation of at least one derivative of at least second order of said at least one physiological parameter from the dataset of values; and use at least the discrete time rate of change, the discrete time change in rate of change and the error covariance matrix to predict the future state of said at least one physiological parameter beyond the time period.

9. The apparatus according to claim 7, wherein the at least one automated processor is further configured to tune the Kalman filter by adjusting a Kalman gain, encode a time-varying state estimate matrix and a time-varying covariance matrix.

10. The apparatus according to claim 8, wherein the dataset of values is organized in a relational database, wherein the table of the values of said at least one physiological parameter is linked with a table of subjective health data representing time points within a time range at which the values of said at least one physiological parameter were sampled.

11. The method of claim 8, wherein the dataset of values is organized in a relational database, wherein the table of the values of said at least one physiological parameter is linked with a first table of physiological data from other users of the same type as that from which the values of said at least one physiological parameter were sampled and a second table of physiological data acquired over a time range different from that from which the values of said at least one physiological parameter were sampled.

12. The method of claim 1, wherein the adaptive at least second order predictive model comprises a recursive discrete data linear filter which is configured to determine a minimum variance of a state of the at least one physiological parameter based on a state equation and a measurement equation, employing an a priori estimate of a prior system state and an a posteriori estimate of a current system state, and to update the error covariance matrix.

13. The apparatus according to claim 8, wherein the at least one automated processor is further configured to fit a curve on values of the dataset by a statistical process responsive to a curve-fitting error, wherein:

the approximation of the first derivative of said at least one physiological parameter is done by taking the first derivative of the curve; and the approximation of the at least one derivative of at least second order of said at least one physiological parameter is done by taking the second derivative of the curve.

14. The apparatus according to claim 1, wherein the at least one automated processor is configured to perform a z-transform on the sequence of values to determine a frequency domain version.

15. The apparatus according to claim 1, wherein the adaptive at least second order predictive model comprises an artificial neural network.

16. The apparatus according to claim 8, wherein the at least one automated processor is further configured to set at least one threshold level of the predicted future state, and to produce an output dependent on a relationship of the predicted state and said at least one threshold level of the predicted state.

17. The apparatus according to claim 1, wherein: the apparatus is wearable; and the physiological parameter is derived from at least one of a motion or inertial sensor.

* * * * *